US011453900B2

(12) United States Patent
Heidtman et al.

(10) Patent No.: US 11,453,900 B2
(45) Date of Patent: Sep. 27, 2022

(54) ALPHA (1,3) FUCOSYLTRANSFERASES FOR USE IN THE PRODUCTION OF FUCOSYLATED OLIGOSACCHARIDES

(71) Applicant: Glycosyn LLC, Woburn, MA (US)

(72) Inventors: Matthew Ian Heidtman, Brighton, MA (US); Massimo Merighi, Somerville, MA (US); John M. McCoy, Reading, MA (US)

(73) Assignee: GLYCOSYN LLC, Waltham, MA (US)

( * ) Notice: Subject to any disclaimer, the term of this patent is extended or adjusted under 35 U.S.C. 154(b) by 0 days.

(21) Appl. No.: 15/509,820

(22) PCT Filed: Sep. 9, 2015

(86) PCT No.: PCT/US2015/049257
§ 371 (c)(1),
(2) Date: Mar. 8, 2017

(87) PCT Pub. No.: WO2016/040531
PCT Pub. Date: Mar. 17, 2016

(65) Prior Publication Data
US 2017/0306373 A1    Oct. 26, 2017

Related U.S. Application Data

(60) Provisional application No. 62/047,851, filed on Sep. 9, 2014.

(51) Int. Cl.
| C12P 19/18 | (2006.01) |
| C07H 3/06 | (2006.01) |
| C12N 9/10 | (2006.01) |
| C07H 5/06 | (2006.01) |
| C12P 19/26 | (2006.01) |

(52) U.S. Cl.
CPC ............ C12P 19/18 (2013.01); C07H 3/06 (2013.01); C07H 5/06 (2013.01); C12N 9/1051 (2013.01); C12P 19/26 (2013.01); C12Y 204/01065 (2013.01)

(58) Field of Classification Search
CPC .. C12P 19/18; C07H 5/06; C07H 3/06; C12Y 204/01065; C12N 9/1051
See application file for complete search history.

(56) References Cited

U.S. PATENT DOCUMENTS

| 7,326,770 | B2 | 2/2008 | Simala-Grant et al. | |
| 7,524,655 | B2 | 4/2009 | Johnson et al. | |
| 2007/0148728 | A1 | 6/2007 | Johnson et al. | |
| 2012/0208181 | A1* | 8/2012 | Merighi | C12N 9/00 435/6.1 |
| 2013/0217068 | A1* | 8/2013 | Parkot | C12N 9/1051 435/69.1 |
| 2014/0031541 | A1 | 1/2014 | Heidtman et al. | |

FOREIGN PATENT DOCUMENTS

| EP | 2439264 A1 | 4/2012 |
| JP | 2009-523173 A | 6/2009 |
| JP | 2012-532195 A | 12/2012 |
| JP | 2013541952 A | 11/2013 |
| JP | 2014506474 A | 3/2014 |
| WO | WO 0134645 A2 | 5/2001 |
| WO | 2007087468 A2 | 8/2007 |
| WO | 2011005681 A1 | 1/2011 |
| WO | WO 2012049083 A2 | 4/2012 |
| WO | 2012112777 A2 | 8/2012 |
| WO | WO 2012127410 A1 | 9/2012 |
| WO | WO 2012158517 A1 | 11/2012 |
| WO | WO 2013087884 A1 | 6/2013 |
| WO | WO 2014018596 A2 | 1/2014 |
| WO | WO 2016040531 A1 | 3/2016 |

OTHER PUBLICATIONS

Earl et al. The genome sequence of bacteroides nordii CL02T12C05. EMBL/GenBank/DDBJ databases. Jan. 2012.*
National Center for Biotechnology Information "zk37b03.s1 Soares_pregnant_uterus_NbHPU *Homo sapiens* cDNA clone IMAGE:484973 3' similar to GB:M33680 CD81 Antigen (Human), mRNA sequence", GenBank Accession No. AA037698.1, Jan. 28, 2011, 2 pages.
National Center for Biotechnology Information "alpha-1,2-fucosyltransferase [Helicobacter pylori]", GenBank Accession No. AAD29869.1, May 4, 1999, 1 page.
National Center for Biotechnology Information "conserved hypothetical protein [Helicobacter hepaticus ATCC 51449]", GenBank Accession No. AAP76669.1, Jan. 31, 2014, 1 page.
National Center for Biotechnology Information "alpha-1,3-fucosyltransferase [Helicobacter hepaticus ATCC 51449]", GenBank Accession No. AAP78373.1, Jan. 31, 2014, 1 page.
National Center for Biotechnology Information "hypothetical protein Amuc_0760 [Akkermansia muciniphila ATCC BAA-835]", GenBank Accession No. ACD04596.1, Dec. 11, 2013, 1 page.
National Center for Biotechnology Information "WbgL [*Escherichia coli*]", GenBank Accession No. ADN43847.1, Sep. 25, 2010, 1 page.
National Center for Biotechnology Information "*Bacteroides* sp. HPS0048 acKdP-supercont1.1.C14, whole genome shotgun sequence", GenBank Accession No. AGEU01000014.1, Apr. 23, 2013, 38 pages.
National Center for Biotechnology Information "family 10 protein [Moumouvirus goulette]", GenBank Accession No. AGF85027.1, Feb. 25, 2013, 1 page.
National Center for Biotechnology Information "Bacteroides nordii CL02T12C05 cont1.8, whole genome shotgun sequence", GenBank Accession No. AGXS01000008.1, Jun. 25, 2012, 42 pages.
National I Center for Biotechnology Information "Helicobacter Pylori Strain DSM 6709 Alpha-1, 4 Fucosyltransferas (FfucTIII) gene, Complete CDS", GenBank Accession No. AY450598.1, Oct. 25, 2005, 13 pages.

(Continued)

*Primary Examiner* — Lynn Y Fan
(74) *Attorney, Agent, or Firm* — Mintz Levin Cohn Ferris Glovsky and Popeo, P.C.; Ingrid A. Beattie

(57) ABSTRACT

The invention relates to methods and compositions for the production of fucosylated oligosaccharides.

23 Claims, 24 Drawing Sheets

Specification includes a Sequence Listing.

(56) References Cited

OTHER PUBLICATIONS

National Center for Biotechnology Information "Predicted Glycosyl Transferas ([Escherichia coli Str. K-12 Substr. W3110)", GenBank Accession No. BAA15898.1, Oct. 7, 2016, 13 pages.
National Center for Biotechnology Information "Colanic Acid Exporter [Escherichia coli str. K-12 Substr. W3110)", GenBank Accession No. BAA15899.1, Oct. 7, 2016, 13 pages.
National Center for Biotechnology Information "Predicted UDP-Glucoselipid Carrier Transferase (Escherichia coli str. K-12 substr W3110)", GenBank Accession No. BAA15900.1, Nov. 20, 2008, 13 pages.
National Center for Biotechnology Information "Predicted Glycosyl Transferase (Escherichia coli str. K-12 substr. W3110]", GenBank Accession No. BAA15906.1, Oct. 7, 2016, 12 pages.
National Center for Biotechnology Information "Predicted Acyl Transferase (Escherichia coli str. K-12 substr. W3110)", GenBank Accession No. BAA15910.1, Nov. 20, 2008, 13 pages.
National Center for Biotechnology Information "Predicted Acyl Transferase (Escherichia coli str. K-12 substr. W3110)", GenBank Accession No. BAA15911.1, Oct. 7, 2016, 13 pages.
National Center for Biotechnology Information "Predicted Glycosyl Transferase (Escherichia coli str. K-12 substr. W3110]", GenBank Accession No. BAA15912.1, Oct. 7, 2016, 13 pages.
National Center for Biotechnology Information "Proiein-Tyrosine kinase (Escherichia coli str. K-12 substr. W3110)", GenBank Accession No. BAA15913.1, Oct. 7, 2016, 13 pages.
National Center for Biotechnology Information "wbfL [Vibrio cholerae]", GenBank Accession No. BAA33600.1, Oct. 16, 1999, 1 page.
National Center for Biotechnology Information "Predicted Glycosyl Transferase (Escherichia coli str. K-12 substr. W3110)", GenBank Accession No. BAE76572.1, Oct. 7, 2016, 13 pages.
National Center for Biotechnology Information "Predicted Colanic Acid Polymerase (Escherichia coli str. K-12 substr. W3110]", GenBank Accession No. BAE76573.1, Oct. 7, 2016, 13 pages.
National Center for Biotechnology Information "Predicted Glycosyl Transferase (Escherichia coli str. K-12 substr. W3110]", GenBank Accession No. BAE76574.1, Oct. 7, 2016, 13 pages.
National Center for Biotechnology Information "Protein-Tyrosine Phosphatase (Escherichia coli str. K-12 substr. W3110]", GenBank Accession No. BAE76575.1, Oct. 7, 2016, 13 pages.
National Center for Biotechnology Information "Lipoprotein Required for Capsular Polysaccharide Translocation through the Outer Membrane (Escherichia coli str. K-12 substr. W3110)", GenBank Accession No. BAE76576.1, Oct. 7, 2016, 13 pages.
National Center for Biotechnology Information "O-antigen Translocase (Escherichia coli str. K-12 substr. W3110)", GenBank Accession No. BAE77506.1, Oct. 7, 2016, 13 pages.
National Center for Biotechnology Information "Bacteroides reticulotermitis JCM 10512 DNA, contig: contig00004, whole genome shotgun sequence", GenBank Accession No. BAIV01000004. 1, Sep. 15, 2015, 84 pages.
National Center for Biotechnology Information "putative LPS biosynthesis related glycosyltransferase [Bacteroides fragilis NCTC 9343]", GenBank Accession No. CAH09151.1, Feb. 6, 2015, 2 pages.
National Center for Biotechnology Information "putative fucosyltransferase [Bacteroides fragilis NCTC 9343]", GenBank Accession No. CAH09495.1, Feb. 6, 2015, 2 pages.
National Center for Biotechnology Information "DNA Sequence 01 rcsB Gene which is Regulator Gene of Capsule Polysaccharide Systhesis Gene (CPS Gene)" GenBank Accession No. E04821.1, Nov. 4, 2005, 2 pages.
National Center for Biotechnology Information "hypothetical protein HMPREF2087_01375, partial [Helicobacter canis NCTC 12740]", GenBank Accession No. ETD25547.1, Dec. 10, 2013, 2 pages.
National Center for Biotechnology Information "hypothetical protein HMPREF2087_01719 [Helicobacter canis NCTC 12740]", GenBank Accession No. ETD25885.1, Dec. 10, 2013, 2 pages.

National Center for Biotechnology Information "hypothetical protein HMPREF2087_01720 [Helicobacter canis NCTC 12740]", GenBank Accession No. ETD25886.1, Dec. 10, 2013, 2 pages.
National Center for Biotechnology Information "alpha (1,3)-Fucosyltransferase [Helicobacter fennelliae MRY12-0050]", GenBank Accession No. GAD18300.1, Sep. 15, 2015, 2 pages.
National Center for Biotechnology Information "E. coli ATP-dependent Protease La (Ion) Gene, Complete CDS", GenBank Accession No. L20572.1, Mar. 17, 1994, 2 pages.
National Center for Biotechnology Information "Escherichia coli Capsular Polysaccharide Regulator (rcsA) Gene, Complete CDS", GenBank Accession No. M58003.1, Dec. 6, 1995, 2 pages.
National Center for Biotechnology Information "Kluyveromyces Lactis Beta-D-Galactosidase (LAC4) Gene, Complete CDS", GenBank Accession No. M84410.1, Apr. 27, 1993, 2 pages.
National Center for Biotechnology Information "fucosyltransferase [Helicobacter pylori 26695]", GenBank Accession No. NP_207177.1, Aug. 2, 2016, 2 pages.
National Center for Biotechnology Information "Glycosyltransferase [Helicobacter Pylori 26695]", GenBank Accession No. NP_207619.1, Aug. 2, 2016, 2 pages.
National Center for Biotechnology Information "Lacto-N-Neotetraose Biosynthesis Glycosyl Transferase Lgtb [Neisseria Meningitidis MC58]", GenBank Accession No. NP_274922.1, Aug. 3, 2016, 2 pages.
National Center for Biotechnology Information "Lacto-N-Neotetraose Biosynthesis Glycosyl Transferase [Neisseria Meningitidis MC58]", GenBank Accession No. NP_274923.1, Aug. 3, 2016, 2 pages.
National Center for Biotechnology Information "E. coli lacY Gene (Codes for Lactose Permease)", GenBank Accession No. V00295.1, Jul. 26, 2016, 3 pages.
National Center for Biotechnology Information "Multispecies: hypothetical protein [Clostridiales]", GenBank Accession No. WP_002570751.1, Sep. 4, 2018, 1 page.
National Center for Biotechnology Information "Alpha1,2fucosyltransferase [[Clostridium] Bolteae]", GenBank Accession No. WP_002570768.1, Dec. 9, 2016, 1 page.
National Center for Biotechnology Information "alpha-1,3-fucosyl transferase [Helicobacter cinaedi]", GenBank Accession No. WP_002956732.1, May 26, 2013, 1 page.
National Center for Biotechnology Information "hypothetical protein [Helicobacter bilis]", GenBank Accession No. WP_004086382.1, May 13, 2013, 1 page.
National Center for Biotechnology Information "alpha-1,2-fucosyltransferase [Bacteroides caccae]", GenBank Accession No. WP_005675707.1, Dec. 9, 2016, 1 page.
National Center for Biotechnology Information "hypothetical protein [Bacteroides salyersiae]", GenBank Accession No. WP_005934126.1, Jun. 4, 2013, 1 page.
National Center for Biotechnology Information "putative LPS biosynthesis related glycosyltransferase [Gillisia limnaea]", GenBank Accession No. WP_006987752.1, Jun. 4, 2013, 1 page.
National Center for Biotechnology Information "glycosyl transferase [Bacteroides nordii]", GenBank Accession No. WP_007483358.1, Dec. 7, 2015, 1 page.
National Center for Biotechnology Information "hypothetical protein [Parabacteroides goldsteinii]", GenBank Accession No. WP_007657871.1, Jun. 5, 2013, 1 page.
National Center for Biotechnology Information "hypothetical protein [[Clostridium] citroniae]", GenBank Accession No. WP_007869439.1, Jun. 5, 2013, 1 page.
National Center for Biotechnology Information "Alpha-1,2-Fucosyltransferase [Parabacteroides Johnsonii]", GenBank Accession No. WP_008155883.1, Dec. 9, 2016, 1 page.
National Center for Biotechnology Information "alpha (1,3)-fucosyltransferase [Algoriphagus machipongonensis]", GenBank Accession No. WP_008200114.1, Jun. 5, 2013, 1 page.
National Center for Biotechnology Information "Multispecies: Alpha-1,2-Fucosyltransferase [Clostridiales]", GenBank Accession No. WP_009251343.1, Apr. 19, 2017, 1 page.

(56) References Cited

OTHER PUBLICATIONS

National Center for Biotechnology Information "Multispecies: hypothetical protein [Parabacteroides]", GenBank Accession No. WP_010803436.1, May 13, 2013, 1 page.
National Center for Biotechnology Information "hypothetical protein, partial [*Flavobacterium* sp. ACAM 123]", GenBank Accession No. WP_016989022.1, Jun. 27, 2013, 1 page.
National Center for Biotechnology Information "hypothetical protein [*Flavobacterium* sp. ACAM 123]", GenBank Accession No. WP_016991062.1, Jun. 27, 2013, 1 page.
National Center for Biotechnology Information "hypothetical protein [Yoonia vestfoldensis]", GenBank Accession No. WP_019955165.1, Jun. 30, 2013, 1 page.
National Center for Biotechnology Information "hypothetical protein [Verrucomicrobia bacterium SCGC AAA300-K03]", GenBank Accession No. WP_019977713.1, Jun. 30, 2013, 1 page.
National Center for Biotechnology Information "hypothetical protein [Verrucomicrobia bacterium SCGC AAA300-N18]", GenBank Accession No. WP_020152244.1, Jun. 30, 2013, 1 page.
National Center for Biotechnology Information "fucosyltransferase, partial [Helicobacter pylori]", GenBank Accession No. WP_020982055.1, Sep. 3, 2013, 1 page.
National Center for Biotechnology Information "hypothetical protein [Helicobacter rappini]", GenBank Accession No. WP_020995419.1, Mar. 2, 2018, 1 page.
National Center for Biotechnology Information "Multispecies: Alpha1,2fucosyltransferase [*Escherichia*]", GenBank Accession No. WP_021554465.1, Mar. 9, 2018, 1 page.
National Center for Biotechnology Information "Alpha1,2fucosyltransferase [*Tannerella* Sp. CAG:118]", GenBank Accession No. WP_021929367.1, Dec. 9, 2016, 1 page.
National Center for Biotechnology Information "hypothetical protein [*Tannerella* sp. CAG:118]", GenBank Accession No. WP_021930564.1, Mar. 25, 2015, 1 page.
National Center for Biotechnology Information "Alpha1,2fucosyltransferase [*Bacteroides* Sp. Cag:633]", GenBank Accession No. WP_022161880.1, Dec. 9, 2016, 1 page.
National Center for Biotechnology Information "hypothetical protein [*Akkermansia* sp. CAG:344]", GenBank Accession No. WP_022396409.1, Jan. 22, 2015, 1 page.
National Center for Biotechnology Information "hypothetical protein [*Prevotella* sp. CAG:873]", GenBank Accession No. WP_022453039.1, Mar. 25, 2015, 1 page.
National Center for Biotechnology Information "Alpha1,2fucosyltransferase [*Prevotella* Sp. Cag:891]", GenBank Accession No. WP_022481266.1, Dec. 9, 2016, 1 page.
National Center for Biotechnology Information "glycosyl transferase [Butyrivibrio fibrisolvens]", GenBank Accession No. WP_022753767.1, Dec. 8, 2015, 1 page.
National Center for Biotechnology Information "glycosyl transferase [*Butyrivibrio* sp. NC2007]", GenBank Accession No. WP_022768256.1, Dec. 8, 2015, 1 page.
National Center for Biotechnology Information "Alpha1,2fucosyltransferase [*Butyrivibrio* Sp. Ae2015]", GenBank Accession No. WP_022772718.1, Oct. 22, 2013, 1 page.
National Center for Biotechnology Information "glycosyl transferase [*Butyrivibrio* sp. AE2015]", GenBank Accession No. WP_022772782.1, Dec. 8, 2015, 1 page.
National Center for Biotechnology Information "hypothetical protein [*Butyrivibrio* sp. AE3009]", GenBank Accession No. WP_022777675.1, Oct. 22, 2013, 1 page.
National Center for Biotechnology Information "hypothetical protein [Lachnospiraceae bacterium NK4A136]", GenBank Accession No. WP_022781173.1, Oct. 22, 2013, 1 page.
National Center for Biotechnology Information "glycosyl transferase [Lachnospiraceae bacterium NK4A136]", GenBank Accession No. WP_022781636.1, Dec. 8, 2015, 1 page.
National Center for Biotechnology Information "glycosyl transferase [Lachnospiraceae bacterium NK4A179]", GenBank Accession No. WP_022783468.1, Dec. 8, 2015, 1 page.

National Center for Biotechnology Information "Alpha1,2fucosyltransferase [*Salmonella enterica*]", GenBank Accession No. WP_023214330.1, Oct. 30, 2013, 1 page.
National Center for Biotechnology Information "putative LPS biosynthesis related glycosyltransferase [Bacteroides fragilis NCTC 9343]", GenBank Accession No. YP_213065.1, Dec. 17, 2014, 2 pages.
National Center for Biotechnology Information "putative fucosyltransferase [Bacteroides fragilis NCTC 9343]", GenBank Accession No. YP_213404.1, Dec. 17, 2014, 2 pages.
National Center for Biotechnology Information "LPS biosynthesis related glycosyltransferase [Anaeromyxobacter dehalogenans 2CP-C]", GenBank Accession No. YP_466262.1, Dec. 17, 2014, 2 pages.
National Center for Biotechnology Information "Alpha-(1,3)-fucosyltransferase [Rickettsia bellii RML369-C]", GenBank Accession No. YP_537673.1, Dec. 17, 2014, 1 page.
National Center for Biotechnology Information "Glycosyl Transferase Family Protein [Bacteroides Vulgatus ATCC 8482]", GenBank Accession No. YP_001300461.1, Jan. 26, 2012, 1 page.
National Center for Biotechnology Information "hypothetical protein Amuc_0760 [Akkermansia muciniphila ATCC BAA-835]", GenBank Accession No. YP_001877377.1, Dec. 17, 2014, 2 pages.
National Center for Biotechnology Information "Lipopolysaccharide Biosynthesis Protein [Helicobacter Pylori P12]", GenBank Accession No. YP_002301261.1, Dec. 17, 2014, 1 page.
National Center for Biotechnology Information "Glycosyl Transferase Family Protein [Methanosphaerula Palustris E19c]", GenBank Accession No. YP_002467213.1, Dec. 16, 2014, 1 page.
National Center for Biotechnology Information "LPS biosynthesis glycosyltransferase [Anaeromyxobacter dehalogenans 2CP-1]", GenBank Accession No. YP_002493655.1, Dec. 17, 2014, 2 pages.
National Center for Biotechnology Information "glycosyl transferase [Methanobrevibacter ruminantium M1]", GenBank Accession No. YP_003424269.1, Dec. 17, 2014, 1 page.
National Center for Biotechnology Information "alpha-(1,3)-fucosyltransferase [*Azospirillum* sp. B510]", GenBank Accession No. YP_003447891.1, Dec. 17, 2014, 2 pages.
National Center for Biotechnology Information "Alpha1,2fucosyltransferase [Helicobacter Mustelae 12198]", GenBank Accession No. YP_003517185.1, Dec. 17, 2014, 1 page.
National Center for Biotechnology Information "alpha-1,3-fucosyltransferase [Coraliomargarita akajimensis DSM 45221]", GenBank Accession No. YP_003549734.1, Dec. 17, 2014, 2 pages.
National Center for Biotechnology Information "Glycosyltransferase Family 11 [Prevotella Melaninogenica ATCC 25845]", GenBank Accession No. YP_003814512.1, Dec. 17, 2014, 1 page.
National Center for Biotechnology Information "alpha (1,3)-fucosyltransferase [Helicobacter bizzozeronii CIII-1]", GenBank Accession No. YP_004607881.1, Dec. 17, 2014, 1 page.
National Center for Biotechnology Information "putative glycosyltransferase (plasmid) [Azospirillum brasilense Sp245]", GenBank Accession No. YP_004985483.1, Dec. 17, 2014, 2 pages.
Albermann, et al., "Synthesis of the Milk Oligosaccharide 2'-Fucosyllactose Using Recombinant Bacterial Enzymes", Carbohydrate Research, Sep. 2001, 334(2):97-103.
Altschul, et al., "Basic Local Alignment Search Tool", Journal of Molecular Biology, Oct. 1990, 215(3):403-410.
Altschul, et al., "Gapped BLAST and PSI-BLAST: a New Generation of Protein Database Search Programs", Nucleic Acids Research, Sep. 1, 1997, 25(17):3389-3402.
Amonsen, et al., "Human Parainfluenza Viruses hPIV1 and hPIV3 Bind Oligosaccharides with 2-3-Linked Sialic Acids That Are Distinct from Those Bound by H5 Avian Influenza Virus Hemagglutinin", Journal of Virology, Sep. 2007, 81(15):8341-8345.
Appelmelk, et al., "Phase Variation in Helicobacter Pylori Lipopolysaccharide", Infection and Immunity, Jan. 1998, 66(1):70-76.
Asakuma, et al., "Physiology of Consumption of Human Milk Oligosaccharides by Infant Gut-associated Bifidobacteria", The Journal of Biological Chemistry, Oct. 7, 2011, 286(40):34583-34592.
Bachmann, et al., "Pedigrees of Some Mutant Strains of *Escherichia coli* K-12", Bacteriological Reviews, 1972, 36(4):525-557.

(56) References Cited

OTHER PUBLICATIONS

Belfort, et al., "Characterization of the *Escherichia coli* thyA Gene and its Amplified Thymidylate Synthase Product", Proceedings of the National Academy of Sciences, May 1983, 80(7):1858-1861.
Bettler, et al., "The Living Factory: In vivo Production of N-Acetyl-lactosamine Containing Carbohydrates in *E. coli*", Glycoconjugate Journal, Mar. 1999, 16(3):205-212.
Blank, et al., "Human Milk Oligosaccharides and Lewis Blood Group: Individual High-Throughput Sample Profiling to Enhance Conclusions From Functional Studies1,2", Advances in Nutrition, May 1, 2012, 3(3):440S-449S.
Bode, et al., "Recent Advances on Structure, Metabolism, and Function of Human Milk Oligosaccharides", The Journal of Nutrition, 2006, 136(8):2127-2130.
Bode, et al., "Structure-Function Relationships of Human Milk Oligosaccharides", Advances in Nutrition, May 1, 2012, 3(3):383S-391S.
Breton, et al., "Conserved Structural Features in Eukaryotic and Prokaryotic Fucosyltransferases", Glycobiology, Jan. 1998, 8(1):87-94.
Charlwood, et al., "A Detailed Analysis of Neutral and Acidic Carbohydrates in Human Milk", Analytical Biochemistry, 1999, 273(2):261-277.
Chaturvedi, et al., "Fucosylated Human Milk Oligosaccharides Vary Between Individuals and Over the Course of Lactation", Glycobiology, Jun. 2001, 11(5):365-372.
Chaturvedi, et al., "Survival of Human Milk Oligosaccharides in the Intestine of Infants", Advances in Experimental Medicine and Biology, 2001, 501:315-323.
Couceiro, et al., "Influenza Virus Strains Selectively Recognize Sialyloligosaccharides on Human Respiratory Epithelium; The Role of the Host Cell in Selection of Hemagglutinin Receptor Specificity", Virus Research, Aug. 1993, 29(2):155-165.
Court, et al., "Genetic Engineering Using Homologous Recombination", Annual Review of Genetics, 2002, 36:361-388.
Coyne, et al., "Human Symbionts Use a Host-Like Pathway for Surface Fucosylation", Science, Mar. 18, 2005, 307(5716):1778-1781.
Crout, et al., "Glycosidases and Glycosyl Transferases in Glycoside and Oligosaccharide Synthesis", Current Opinion in Chemical Biology, Feb. 1998, 2(1):98-111.
Danchin, Antoine, "Cells need safety valves", BioEssays, 2009, 31(7):769-773.
Dumon, et al., "Assessment of the Two Helicobacter pylori α-1,3-Fucosyltransferase Ortholog Genes for the Large-Scale Synthesis of LewisX Human Milk Oligosaccharides by Metabolically Engineered *Escherichia coli*", Biotechnology Progress, 2004, 20(2):412-419.
Dumon, et al., "In Vivo Fucosylation of Lacto-N-Neotetraose and Lacto-N-Neohexaose by Heterologous Expression of Helicobacter Pylori α-1,3 Fucosyltransferase in Engineered *Escherichia coli*", Glycoconjugate Journal, Jun. 2001, 18(6):465-474.
Dumon, et al., "Production of Lewis x Tetrasaccharides by Metabolically Engineered *E.Coli*", ChemBiochem, 2006, 7(2):359-365.
Endo, et al., "Large-scale Production of CMP-NeuAc and Sialylated Oligosaccharides Through Bacterial Coupling", Applied Microbiology and Biotechnology, Mar. 2000, 53(3):257-261.
Endo, et al., "Large-Scale Production of N-Acetyllactosamine Through Bacterial Coupling", Carbohydrate Research, Mar. 1999, 316(1-4):179-183.
Endo, et al., "Large-Scale Production of Oligosaccharides Using Engineered Bacteria", Current Opinion in Structural Biology, Oct. 1, 2000, 10(5):536-541.
Endo, et al., "Large-scale Production of the Carbohydrate Portion of the sialyl-Tn Epitope, α-Neup5Ac-(2→6)-D-GalpNAc, Through Bacterial Coupling", Carbohydrate Research, Feb. 28, 2001, 330(4):439-443.
Flowers, Harold M., "Chemical Synthesis of Oligosaccharides", Methods in Enzymology, 1978, 50:93-121.
Garcia, et al., "Comparison and Calibration of Different Reporters for Quantitative Analysis of Gene Expression", Biophysical Journal, Aug. 2011, 101:535-544.
Garrido, et al., "A Molecular Basis for Bifidobacterial Enrichment in the Infant Gastrointestinal Tract1-3", Advances in Nutrition, May 1, 2012, 3(3):415S-421S.
Gnoth, et al., "Human Milk Oligosaccharides Are Minimally Digested In Vitro", Journal of Nutrition, Dec. 2000, 130(12):3014-3020.
Gottesman, et al., "Regulation of Capsular Polysaccharide Synthesis in *Escherichia coli* K12", Molecular Microbiology, Jul. 1991, 5(7):1599-1606.
Hamosh, M., "Bioactive Factors in Human Milk", Pediatric Clinics of North America, 2001, 48(1):69-86.
Huang, et al., "Noroviruses Bind to Human ABO, Lewis, and Secretor Histo—Blood Group Antigens: Identification of 4 Distinct Specific Patterns", The Journal of Infectious Diseases, Jul. 1, 2003, 188(1):19-31.
Johnson, Karl F., "Synthesis of Oligosaccharides by Bacterial Enzymes", Glycoconjugate Journal, 1999, 16(2):141-146.
Koeller, et al., "Synthesis of Complex Carbohydrates and Glycoconjugates: Enzyme-Based and Programmable One-Pot Strategies", Chemical Reviews, Dec. 13, 2000, 100(12):4465-4494.
Koizumi, et al., "Large-Scale Production of UDP-Galactose and Globotriose by Coupling Metabolically Engineered Bacteria", Nature Biotechnology, Sep. 1998, 16(9):847-850.
Kuhlenschmidt, et al., "Sialic Acid Dependence and Independence of Group A Rotaviruses", Advances in Experimental Medicine and Biology, 1999, 473:309-317.
Kunz, et al., "Oligosaccharides in Human Milk: Structural, Functional, and Metabolic Aspects", Annual Review of Nutrition, 2000, 20:699-722.
Lavallie, et al., "A Thioredoxin Gene Fusion Expression System That Circumvents Inclusion Body Formation in the *E. coli* Cytoplasm", Nature Biotechnology, 1993, 11:187-193.
Lavallie, et al., "Thioredoxin as a Fusion Partner for Production of Soluble Recombinant Proteins in *Escherichia coli*", Methods in Enzymology, 2000, 326:322-340.
Li, et al., "Characterization of a Novel α1,2-Fucosyltransferase of *Escherichia coli* O128:B12 and Functional Investigation of its Common Motif", Biochemistry, Jan. 8, 2008, 47(1):378-387.
Ma, et al., "C-terminal Amino Acid of Helicobacter Pylor α1, 3/4 Fucosyltransferases Determine Type 1 and Type 11 Transfer", Journal of Chemical Biology, Jun. 13, 2003, 278(24):21893-21900.
Ma, et al., "Fucosylation in Prokaryotes and Eukaryotes", Glycobiology, Dec. 2006, 16(12):158R-184R.
Mahdavi, et al., "Helicobacter pylori SabA Adhesin in Persistent Infection and Chronic Inflammation", Science, Jul. 26, 2002, 297(5581):573-578.
Marcobal, et al., "Consumption of Human Milk Oligosaccharides by Gut-Related Microbes", Journal of Agricultural and Food Chemistry, May 2010, 58(9):5334-5340.
Martin, et al., "Lewis X Biosynthesis in Helicobacter pylori: Molecular Cloning of an α (1,3)-Fucosyltransferase Gene", The Journal of Biological Chemistry, Aug. 22, 1997, 272(34):21349-21356.
Martín-Sosa, et al., "Sialyloligosaccharides in Human and Bovine Milk and in Infant Formulas: Variations with the Progression of Lactation", Journal of Dairy Science, Jan. 2003, 86(1):52-59.
Mieschendahl, et al., "A Novel Prophage Independent TRP Regulated Lambda PL Expression System", Nature Biotechnology, 1986, 4(9):802-808.
Morrow, et al., "Human Milk Oligosaccharide Blood Group Epitopes and Innate Immune Protection against Campylobacter and Calicivirus Diarrhea in Breastfed Infants", Advances in Experimental Medicine and Biology, Jan. 1, 2004, 554:443-446.
Morrow, et al., "Human Milk Oligosaccharides are Associated with Protection Against Diarrhea in Breast-Fed Infants", The Journal of Pediatrics, Sep. 2004, 145(3):297-303.
Newburg, David S, "Bioactive Components of Human Milk: Evolution, Efficiency, and Protection", Advances in Experimental Medicine and Biology, 2001, 501(1):3-10.
Newburg, David S, "Human Milk Glycoconjugates that Inhibit Pathogens", Current Medicinal Chemistry, 1999, 6(2):117-127.

(56) References Cited

OTHER PUBLICATIONS

Newburg, David S., "Oligosaccharides in Human Milk and Bacterial Colonization", Journal of Pediatric Gastroenterology and Nutrition, 2000, 30(Suppl. 2):S8-S17.
Newburg, et al., "Human Milk Glycans Protect Infants Against Enteric Pathogens", Annual Review of Nutrition, Aug. 2005, 25:37-58.
Newburg, et al., "Protection of the Neonate by the Innate Immune System of Developing Gut and of Human Milk", Pediatric Research, 2007, 61:2-8.
Ninonuevo, et al., "A Strategy for Annotating the Human Milk Glycome", Journal of Agricultural and Food Chemistry, Oct. 4, 2006, 54(20):7471-7480.
Palcic, Monika M, "Biocatalytic Synthesis of Oligosaccharides", Current Opinion in Biotechnology, 1999, 10(6):616-624.
Parkkinen, et al., "Isolation of Sialyl Oligosaccharides and Sialyl Oligosaccharide Phosphates from Bovine Colostrum and Human Urine", Methods in Enzymology, 1987, 138:289-300.
Rabbani, et al., "Molecular Cloning and Functional Expression of a Novel Helicobacter Pylori Alpha-1,4 Fucosyltransferase", Glycobiology, Nov. 2005, 15(11):1076-1083.
Rasko, et al., "Cloning and Characterization of the Alpha(1,3/4) Fucosyltransferase of Helicobacter Pylori", Journal of Biological Chemistry, Feb. 2000, 275(7):4988-4994.
Rudloff, et al., "Milk Oligosaccharides and Metabolism in Infants", Advances in Nutrition, May 1, 2012, 3(3):398S-340S.
Ruffing, et al., "Metabolic Engineering of Microbes for Oligosaccharide and Polysaccharide Synthesis", Microbial Cell Factories, Jul. 21, 2006, 5(25):9 pages.
Ruiz-Palacios, et al., "Campylobacter jejuni Binds Intestinal H(O) Antigen (Fucα1, 2Galβ1, 4GlcNAc), and Fucosyloligosaccharides of Human Milk Inhibit its Binding and Infection", Journal of Biological Chemistry, 2003, 278(16):14112-14120.
Rydell, et al., "Human Noroviruses Recognize Sialyl Lewis x Neoglycoprotein", Glycobiology, 2009, 19(3):309-320.
Sanger, et al., "Nucleotide Sequence of Bacteriophage λ DNA", Journal of Molecular Biology, Dec. 25, 1982, 162(4):729-773.
Scharfman, et al., "Sialyl-Lex and Sulfo-Sialyl-Lex Determinants are Receptors for P. aeruginosa", Glycoconjugate Journal, Oct. 2000, 17(10):735-740.
Seeberger, Peter H., "Automated Carbohydrate Synthesis to Drive Chemical Glycomics", Chemical Communications, 2003, Issue 10:1115-1121.
Sela, et al., "*Bifidobacterium longum* subsp. infantis ATCC 15697 a-Fucosidases are Active on Fucosylated Human Milk Oligosaccharides", Applied and Environmental Microbiology, Feb. 2012, 78(3):795-803.
Sharon, N., "Carbohydrates as Future Anti-Adhesion Drugs for Infectious Diseases", Biochimica et Biophysica Acta, 2006, 1760(4):527-537.
Shen, et al., "Resolution of Structural Isomers of Sialylated Oligosaccharides by Capillary Electrophoresis", Journal of Chromatography A, Jul. 6, 2001, 921(2):315-321.
Stein, et al., "Cloning Genes for Proline Biosynthesis from Neisseria Gonorrhoeae: Identification by Interspecific Complementation of *Escherichia coli* Mutants", Journal of Bacteriology, May 1984, 158(2):696-700.
Stevenson, et al., "Organization of the *Escherichia coli* K-12 Gene Cluster Responsible for Production of the Extracellular Polysaccharide Colanic Acid", Journal of Bacteriology, Aug. 1996, 178(16):4885-4893.
Sun, et al., "Structure and Mechanism of Helicobacter pylori Fucosyltransferase. A Basis for Lipopolysaccharide Variation and Inhibitor Design", Journal of Biological Chemistry, Mar. 30, 2007, 282(13):9973-9982.
Ward, et al., "In Vitro Fermentability of Human Milk Oligosaccharides by Several Strains of Bifidobacteria", Mol. Nutr. Food Research, 2007, 51(11):1398-1405.
Warren, et al., "Comparison of Oligosaccharides in Milk Specimens from Humans and Twelve Other Species", Advances in Experimental Medicine and Biology, 2001, 501:325-332.
Wolfe, et al., "Nucleotide Sequence and Analysis of the Pura Gene Encoding Adenylosuccinate Synthetase of *Escherichia coli* K12", The Journal of Biological Chemistry, Dec. 15, 1988, 263(35):19147-19153.
Wymer, et al., "Enzyme-Catalyzed Synthesis of Carbohydrates", Current Opinion in Chemical Biology, Feb. 1, 2000, 4(Issue 1):110-119.
Yu, et al., "The Principal Fucosylated Oligosaccharides of Human Milk Exhibit Prebiotic Properties on Cultured Infant Microbiota", Glycobiology, 2012, 23(2):169-177.
Zhang, et al., "Helicobacter hepaticus Hh0072 Gene Encodes a Novel α1-3-Fucosyltransferase Belonging to CAZy GT11 Family", Glycobiology, 2010, 20(9):1077-1088.

* cited by examiner

FIG. 1  Synthetic routes for neutral hMOS

FIG. 5
A
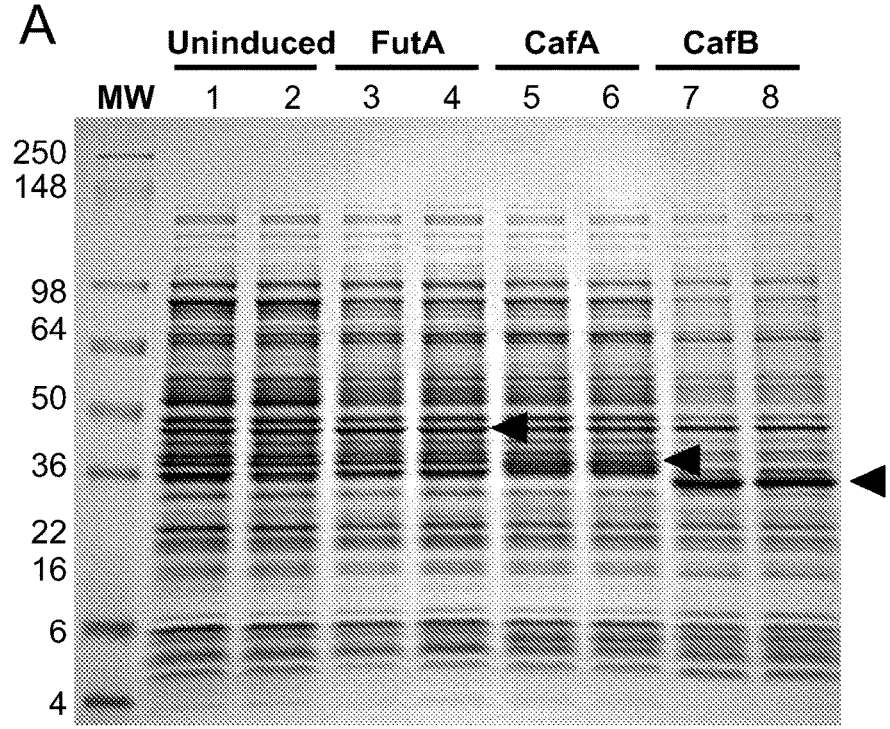
B
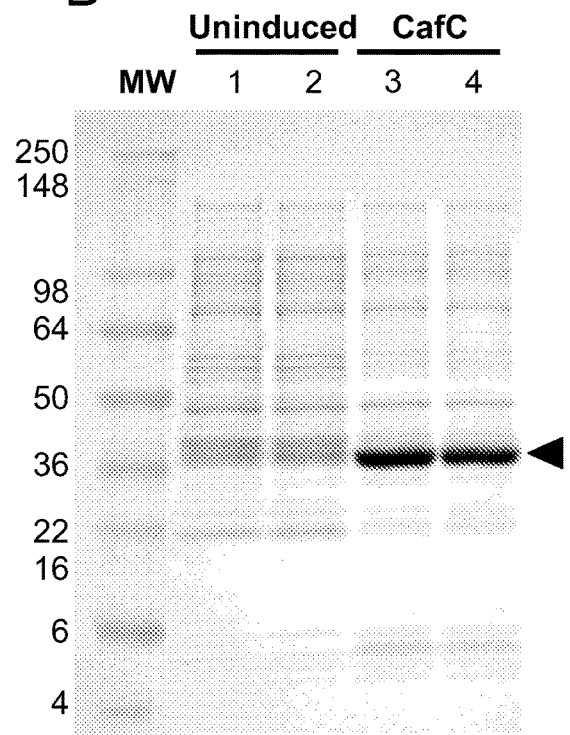
C
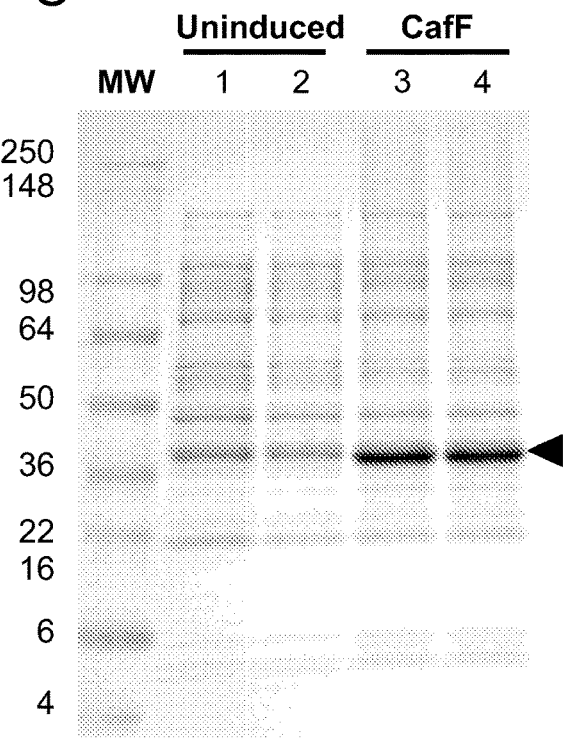

FIG. 6  12 α(1,3)-fucosyltransferase candidates: roller tube 3-FL biosynthesis (in E638 F'402+)
5ml induced cultures @ 30°C: IMC/amp$^{150}$/trp$^{200}$/0.5%lac Lac (Lactose) = Galβ1-4Glc
LNnT (Lacto-N-neotetraose) = Galβ1-4GlcNAcβ1-3Galβ1-4Glc
LNF III (Lacto-N-fucopentaose) = Galβ1-4(Fucα1,3)GlcNAcβ1-3Galβ1-4Glc
LNnH (Lacto-N-neohexaose) = Galβ1-4GlcNAcβ1-3Galβ1-4GlcNAcβ1-3Galβ1-4Glc

FIG. 18 (continued)

```
                                       180            200            220              240
                                        |              |              |                |
Helicobacter pylori FutA    ALKKPSHHFK ENHPNLCAVV NDESDLLKRG FASFVASNAN A--PMRNAFY DALNSIEPVT GGGSVRNTLG YK-----V 223
Bacteroides nordii CafC     -VLN------ ---------- ---------- FCSFVVSNAK GA-PERERFF QLLSEYKQVD SGGRYKNNVC GP-----V 159
Akkermansia muciniphila CafF ---------- ---------- ---LLASKTG FCNFIYANRK SH-PNRDAMF HKLSAFRFVN SLGPHLNNTP GDGHRAEDWY 176
Tannerella sp. CafN         -VLK------ ---------- ---------- FCSYVVSNNI GA-PERSRFF HLLSEYKKVD SGGWENNVG  GP-----V 159
Lachnospiraceae bacterium CafO YLAK------ ---------- ---------- FCNYVISNPY AA-PERDLMI DALEKYMPVD SGGRYRNNVG GP-----V 164
Butyrivibrio sp. CafL       D--N------ ---------- ---------- FCNFVYSNGR NAIPERDSFF ADLSKYKQVD SGGRHLNNIG GP-----V 155
Bacteroides salyersiae CafQ -IKG------ ---------- ---------- FCSFVVSNCF AN-DTRAIFY ELLNQYKYIA SGGRYKNNIG GA-----I 162
Helicobacter canis CafV     VVRN------ ---------- ---------- FCNFVVTNGK GD-PYREKVF HALCAYKRVD SAGKFLNNVG AR-----V 172
Helicobacter canis CafU     LLAS------ ---------- ---------- FCNFVVSNGN AD-PYREQVF YALNAYKRVD SGGRYLNNIG GS-----V 167
Consensus                   -XXX------ ---------- ---------- FCNFVVSNGK AA-PERXXFF HALSAYKXVD SGGRYLNNVG GP-----V 260            280            3000             320
                                        |              |              |                |
Helicobacter pylori FutA    GNKSEFLSQY KFNLCFENSQ GYGYVTEKIL DAYFSHTIPI YWGSPSVAKD F------NP KSFVNVHDFN NFDEAIDYIK 296
Bacteroides nordii CafC     PDKTAFIKDY KFNIAFENSM CDGYTTEKIM EPMLVNSVPI YWGNKLIDRD F------NP DSFINVSSYS SLEEAVEHIV 232
Akkermansia muciniphila CafF ASSIRMKKPY KFSIAFENAW YPGYTSEKIV TSMLAGTIPI YWGNPDISRE F------NS ASFINCHDFP TLDDAAAYVK 249
Tannerella sp. CafN         PNKLDFIKDY KFNIAFENSM YDGYTTEKIM EPMLVNSLPI YWGNRLINKD F------NP ASFINVSDFP SLEAAVEHIV 232
Lachnospiraceae bacterium CafO ADKVEFASHY RFSMAFENSA MSGYTTEKIF DGFAACTIPI YWGSDRIKEE F------NP ESFVSARDFE NFDQVVARVK 237
Butyrivibrio sp. CafL       DDKREFQKQY KFSIAFENAV SRGYTTEKII QAFSAGTIPI YYGNPLVAKE F------NS KAFINCHEYR SFDEVIEKVK 228
Bacteroides salyersiae CafQ KDKTFLSKY  KFNIAFENCS HDGYATEKIV EAFAAGVVPI YYGDPRIAED F------NP KAFINAHDYQ SFEEMVERIK 235
Helicobacter canis CafV     KDKFAFQSEC RFSLCFENSS TPGYLTEKLI QAAAAQTIPI YWGDPLATKP LFDGGGGINA KAFINAHEFA NIASLVRHIE 252
Helicobacter canis CafU     ADKFAFQSEC RFSLCFENSS TPGYLTEKLI QAAAAQTIPI YWGDTLATKP LFDGGGGINA KAFINAHSFS SLESLIAHIA 247
Consensus                   ADKFXFQSXY KFSIAFENSS XXGYTTEKII XAXAAGTIPI YWGNPLIAKD F------NP KSFINAHDFX SXXEAVEHIK
```

FIG. 19

| | | | |
|---|---|---|---|
| Bacteroides nordii CafC | RK-FCSFVVSNAKGA-PERERFFQLLSEYKQVDSGGRYKNNVGGP------ | ------VPDKTAFIKDYKFNIAFENSMCDGYTTEKIMEPMLVNSVPIYWG | 87 |
| Tannerella sp. CafN | RK-FCSYVVSNNIGA-PERSRFFHLLSEYKKVDSGGRWENNVGGP------ | ------VPNKLDFIKDYKFNIAFENSMYDGYTTEKIMEPMLVNSLPIYWG | 87 |
| Butyrivibrio sp. CafL | KK-FCNFVYSNGRNAIPERDSFFADLSKYKQVDSGGRHLNNIGGP------ | ------VDDKREFQKQYKFSIAFENAVSRGYTTEKIIQAFSAGTIPIYYG | 88 |
| Bacteroides salyersiae CafQ | RG-FCSFVVSNCFAN-DTRAIFYELLNQYKYIASGGRYKNNIGA------- | ------IKDKKTFLSKYKFNIAFENCSHDGYATEKIVEAFAAGVVPIYYG | 87 |
| Lachnospiraceae bacterium CafO | KK-FCNYVISNPYAA-PERDLMIDALEKYMPVDSGGRYRNNVGGP------ | ------VADKVEFASHYRFSMAFENSAMSGYTTEKIFDGFAACTIPIYWG | 87 |
| Helicobacter canis CafU | KSRFCNFVVSNGNAD-PYREQVFYALNAYKRVDSGGRYLNNIGGS------ | ------VADKFAFQSECRFSLCFENSSTPGYLIEKLIQAAAAQTIPIYWG | 88 |
| Helicobacter canis CafV | KKRFCNFVVTNGKGD-PYREKVFHALCAYKRVDSAGKFLNNVGAR------ | ------VKDKFAFQSECRFSLCFENSSTPGYLTEKLIQAAAAQTIPIYWG | 88 |
| Helicobacter pylori FutA | KRGFASFVASNANA--PMRNAFYDALNSIEPVTGGGSVRNTLGYK------ | ------VGNKSEFLSQYKFNLCFENSQGYGYVTEKILDAYFSHTIPIYWG | 87 |
| Akkermansia muciniphila CafF | KTGFCNFIYANRKSH-PNRDAMFHKLSAFRFVNSLGPHLNNTPGDGHRAEDWYASSIRMKKPYKFSIAFENAWYPGYTSEKIVTSMLAGTIPIYWG | 95 |
| Consensus | KK-FCNFVVSNGKAA-PER..FFHALSAYK.VDSGGRYLNNVGGP------ | ------VADKF.FQS.YKFSIAFENSS..GYTTEKII.A.AAGTIPIYWG | |

FIG. 20

| | 1 | 2 | 3 | 4 | 5 | 6 | 7 | 8 | 9 |
|---|---|---|---|---|---|---|---|---|---|
| Bacteroides nordii CafC | 1 | | 85.06 | 60.23 | 57.47 | 55.17 | 51.14 | 50.00 | 43.18 | 40.00 |
| Tannerella sp. CafN | 2 | 85.06 | | 56.82 | 51.72 | 54.02 | 45.45 | 45.45 | 42.05 | 40.00 |
| Butyrivibrio sp. CafL | 3 | 60.23 | 56.82 | | 52.27 | 61.36 | 58.43 | 53.93 | 43.82 | 47.92 |
| Bacteroides salyersiae CafQ | 4 | 57.47 | 51.72 | 52.27 | | 47.13 | 50.00 | 42.05 | 43.18 | 32.63 |
| Lachnospiraceae bacterium CafO | 5 | 55.17 | 54.02 | 61.36 | 47.13 | | 57.95 | 52.27 | 48.86 | 40.00 |
| Helicobacter canis CafU | 6 | 51.14 | 45.45 | 58.43 | 50.00 | 57.95 | | 84.09 | 47.73 | 38.95 |
| Helicobacter canis CafV | 7 | 50.00 | 45.45 | 53.93 | 42.05 | 52.27 | 84.09 | | 42.05 | 38.95 |
| Helicobacter pylori FutA | 8 | 43.18 | 42.05 | 43.82 | 43.18 | 48.86 | 47.73 | 42.05 | | 31.58 |
| Akkermansia muciniphila CafF | 9 | 40.00 | 40.00 | 47.92 | 32.63 | 40.00 | 38.95 | 38.95 | 31.58 | |

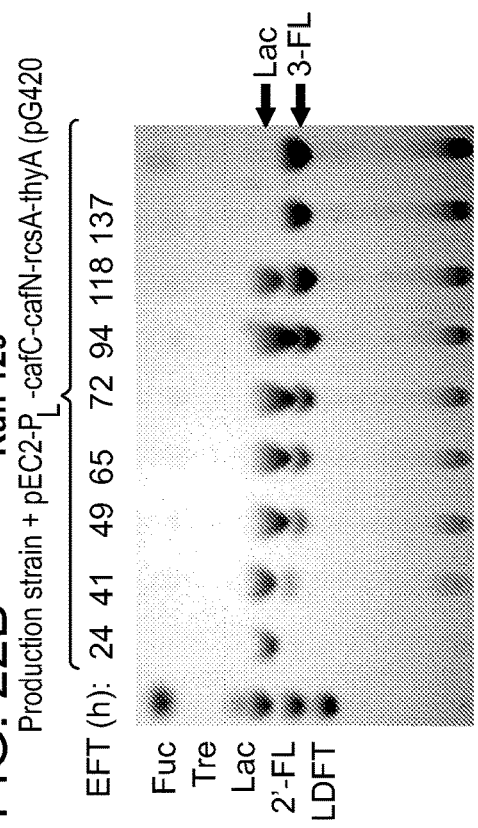
FIG. 22A Run 126
Production strain + pEC2-P$_L$-cafC-rcsA-thyA (pG366)
3-FL yield (HPLC): ~7.5 g/L
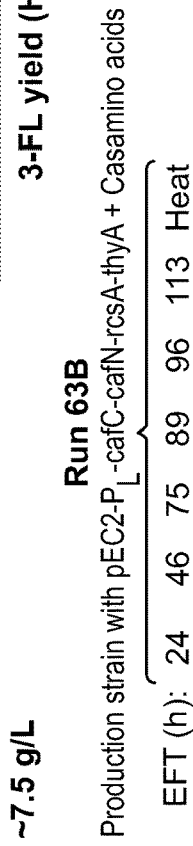
FIG. 22B Run 129
Production strain + pEC2-P$_L$-cafC-cafN-rcsA-thyA (pG420)
3-FL yield (HPLC): ~15 g/L
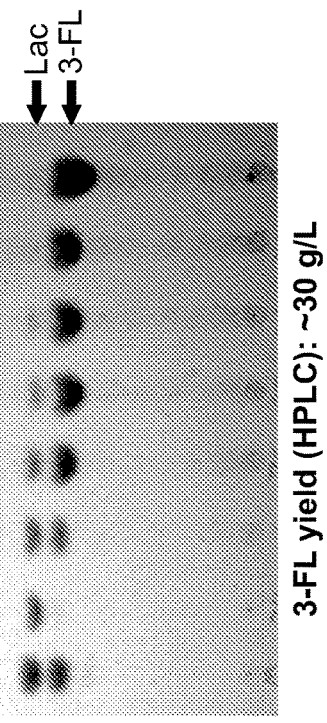
FIG. 22C Run 63B
Production strain with pEC2-P$_L$-cafC-cafN-rcsA-thyA + Casamino acids
3-FL yield (HPLC): ~30 g/L

SEQUENCE LISTING

```
<160> NUMBER OF SEQ ID NOS: 64

<210> SEQ ID NO 1
<211> LENGTH: 332
<212> TYPE: PRT
<213> ORGANISM: Akkermansia muciniphila

<400> SEQUENCE: 1

Met Lys Thr Leu Lys Ile Ser Phe Leu Gln Ser Thr Pro Asp Phe Gly
1               5                   10                  15

Arg Glu Gly Met Leu Gln Leu Leu Lys Ser Arg Tyr His Val Val Glu
                20                  25                  30

Asp Asp Ser Asp Phe Asp Tyr Leu Val Ala Thr Pro Trp Phe Tyr Val
            35                  40                  45

Asn Arg Glu Ala Phe Tyr Asp Phe Leu Gly Arg Ala Pro Gly His Ile
        50                  55                  60

Thr Val Met Tyr Gly Cys His Glu Ala Ile Ala Pro Asp Phe Met Leu
65                  70                  75                  80

Phe Asp Tyr Tyr Ile Gly Leu Asp Thr Val Pro Gly Ser Asp Arg Thr
                85                  90                  95

Val Lys Leu Pro Tyr Leu Arg His His Leu Glu Glu Val His Gly Gly
                100                 105                 110

Lys Glu Gly Leu Asp Ala His Ala Leu Leu Ala Ser Lys Thr Gly Phe
            115                 120                 125

Cys Asn Phe Ile Tyr Ala Asn Arg Lys Ser His Pro Asn Arg Asp Ala
130                 135                 140

Met Phe His Lys Leu Ser Ala Phe Arg Phe Val Asn Ser Leu Gly Pro
145                 150                 155                 160

His Leu Asn Asn Thr Pro Gly Asp Gly His Arg Ala Glu Asp Trp Tyr
                165                 170                 175

Ala Ser Ser Ile Arg Met Lys Lys Pro Tyr Lys Phe Ser Ile Ala Phe
            180                 185                 190

Glu Asn Ala Trp Tyr Pro Gly Tyr Thr Ser Glu Lys Ile Val Thr Ser
        195                 200                 205

Met Leu Ala Gly Thr Ile Pro Ile Tyr Trp Gly Asn Pro Asp Ile Ser
210                 215                 220

Arg Glu Phe Asn Ser Ala Ser Phe Ile Asn Cys His Asp Phe Pro Thr
225                 230                 235                 240

Leu Asp Asp Ala Ala Ala Tyr Val Lys Lys Val Asp Glu Asp Asp Asn
                245                 250                 255

Leu Trp Cys Glu Ile Met Ser Arg Pro Trp Lys Thr Pro Glu Gln Glu
            260                 265                 270

Ala Arg Phe Leu Glu Glu Thr Glu Arg Glu Thr Ala Lys Leu Tyr Lys
        275                 280                 285

Ile Phe Asp Gln Ser Pro Glu Glu Ala Arg Arg Lys Gly Asp Gly Thr
    290                 295                 300

Trp Val Ser Tyr Tyr Gln Arg Phe Leu Lys Arg Gly His Arg Met Gln
305                 310                 315                 320

Leu Ala Trp Arg Arg Leu Lys Asn Arg Leu Arg Arg
```

325                 330

<210> SEQ ID NO 2
<211> LENGTH: 315
<212> TYPE: PRT
<213> ORGANISM: Bacteroides nordii

<400> SEQUENCE: 2

Met Lys Thr Ile Lys Val Lys Phe Val Asp Phe Trp Glu Asn Phe Asp
1               5                   10                  15

Pro Gln His Asn Phe Ile Ala Asn Ile Ile Ser Lys Lys Tyr Arg Ile
            20                  25                  30

Glu Leu Ser Asp Thr Pro Asp Tyr Leu Phe Phe Ser Val Phe Gly Tyr
        35                  40                  45

Glu Asn Ile Asp Tyr His Asn Cys Thr Lys Ile Phe Tyr Ser Gly Glu
    50                  55                  60

Asn Ile Thr Pro Asp Phe Asn Ile Cys Asp Tyr Ala Ile Gly Phe Asn
65                  70                  75                  80

Phe Leu Ser Phe Gly Asp Arg Tyr Ile Arg Ile Pro Phe Tyr Thr Ala
                85                  90                  95

Tyr Gly Val Gln Gln Leu Ala Ala Pro Lys Val Ile Val Pro Glu Val
            100                 105                 110

Val Leu Asn Arg Lys Phe Cys Ser Phe Val Val Ser Asn Ala Lys Gly
        115                 120                 125

Ala Pro Glu Arg Glu Arg Phe Phe Gln Leu Leu Ser Glu Tyr Lys Gln
    130                 135                 140

Val Asp Ser Gly Gly Arg Tyr Lys Asn Asn Val Gly Gly Pro Val Pro
145                 150                 155                 160

Asp Lys Thr Ala Phe Ile Lys Asp Tyr Lys Phe Asn Ile Ala Phe Glu
                165                 170                 175

Asn Ser Met Cys Asp Gly Tyr Thr Thr Glu Lys Ile Met Glu Pro Met
            180                 185                 190

Leu Val Asn Ser Val Pro Ile Tyr Trp Gly Asn Lys Leu Ile Asp Arg
        195                 200                 205

Asp Phe Asn Pro Asp Ser Phe Ile Asn Val Ser Tyr Ser Ser Leu
    210                 215                 220

Glu Glu Ala Val Glu His Ile Val Arg Leu Asp Gln Asn Asp Asp Glu
225                 230                 235                 240

Tyr Leu Ser Leu Leu Ser Ala Pro Trp Phe Asn Glu Glu Asn Tyr Leu
                245                 250                 255

Asn Trp Glu Glu Gln Leu Ile Thr Phe Phe Asp Asn Ile Phe Glu Lys
            260                 265                 270

Pro Leu Ser Glu Ser Arg Tyr Ile Pro Thr His Gly Tyr Ile Gln Thr
        275                 280                 285

Tyr Gln Tyr Arg Leu His Arg Met Met Arg Asp Lys Leu Phe Arg Lys
    290                 295                 300

Arg Ile Asn Pro Leu Lys Trp Phe Ser Ser Lys
305                 310                 315

<210> SEQ ID NO 3
<211> LENGTH: 331
<212> TYPE: PRT
<213> ORGANISM: Bacteroides fragilis

<400> SEQUENCE: 3

Met Cys Asp Cys Leu Ser Ile Ile Leu Leu Val Lys Met Lys Lys Ile

```
                 1               5                  10                 15
       Tyr Leu Lys Phe Val Asp Phe Trp Asp Gly Phe Asp Thr Ile Ser Asn
                        20                  25                 30
       Phe Ile Val Asp Ala Leu Ser Ile Gln Tyr Glu Val Leu Ser Asn
                        35                  40                 45
       Glu Pro Asp Tyr Leu Phe Tyr Ser Cys Phe Gly Thr Ser His Leu Glu
                 50                  55                 60
       Tyr Asp Cys Ile Lys Ile Met Phe Ile Gly Glu Asn Ile Val Pro Asp
       65                  70                 75                 80
       Phe Asn Val Cys Asp Tyr Ala Ile Gly Phe Asn Tyr Ile Asp Phe Gly
                        85                  90                 95
       Asp Arg Tyr Leu Arg Leu Pro Leu Tyr Ala Ile Tyr Asp Gly Phe Ser
                        100                 105                110
       Asn Leu Gln Asn Lys Lys Ile Asp Val Asn Lys Ala Leu Asp Arg Lys
                        115                 120                125
       Phe Cys Ser Ile Val Val Ser Asn Asn Lys Trp Ala Asp Pro Ile Arg
                        130                 135                140
       Glu Thr Phe Phe Lys Leu Leu Ser Ser Tyr Lys Val Asp Ser Gly
       145             150                 155                160
       Gly Arg Ala Trp Asn Asn Ile Gly Gly Pro Val Asp Asn Lys Leu Asp
                        165                 170                175
       Phe Ile Ser Gln Tyr Lys Phe Asn Ile Ala Phe Glu Asn Ser Arg Val
                        180                 185                190
       Leu Gly Tyr Thr Thr Glu Lys Ile Met Glu Pro Met Gln Val Asn Ser
                        195                 200                205
       Ile Pro Val Tyr Trp Gly Asn Pro Leu Val Gly Lys Asp Phe Asn Val
                        210                 215                220
       Asp Ser Phe Val Asn Ala His Asp Phe Asp Ser Leu Glu Arg Leu Val
       225             230                 235                240
       Glu Tyr Ile Ile Glu Leu Asp Ser Ser Lys Asp Lys Tyr Leu Glu Met
                        245                 250                255
       Leu Glu Lys Pro Trp Leu Leu Asp Lys Thr Tyr Leu Asp Trp Lys Gln
                        260                 265                270
       Leu Leu Leu Asn Phe Ile Asn Asn Ile Met Met Lys Ser Tyr Lys Asp
                        275                 280                285
       Ala Lys Tyr Leu Val Asn Tyr Gly His Ala Gly Lys Tyr Arg Asn Glu
                        290                 295                300
       Gln Arg Phe Trp Gly Arg Cys Glu Arg Lys Phe Lys Leu Gln Arg Ile
       305             310                 315                320
       Ile Glu Tyr Tyr Ser Gln Leu Phe Asp Arg Lys
                        325                 330

<210> SEQ ID NO 4
<211> LENGTH: 296
<212> TYPE: PRT
<213> ORGANISM: Bacteroides fragilis

<400> SEQUENCE: 4

Met Asp Ile Leu Ile Leu Phe Tyr Asn Thr Met Trp Gly Phe Pro Leu
       1               5                   10                 15

Glu Phe Arg Lys Glu Asp Leu Pro Gly Gly Cys Val Ile Thr Thr Asp
                        20                  25                 30

Arg Asn Leu Ile Ala Lys Ala Asp Ala Val Val Phe His Leu Pro Asp
                        35                  40                 45
```

```
Leu Pro Ser Val Met Glu Asp Glu Ile Asp Lys Arg Glu Gly Gln Leu
 50                  55                  60

Trp Val Gly Trp Ser Leu Glu Cys Glu Glu Asn Tyr Ser Trp Thr Lys
 65                  70                  75                  80

Asp Pro Glu Phe Arg Glu Ser Phe Asp Leu Trp Met Gly Tyr His Gln
                 85                  90                  95

Glu Asp Asp Ile Val Tyr Pro Tyr Tyr Gly Pro Asp Tyr Gly Lys Met
                100                 105                 110

Leu Val Thr Ala Arg Arg Glu Lys Pro Tyr Lys Lys Ala Cys Met
                115                 120                 125

Phe Ile Ser Ser Asp Met Asn Arg Ser His Arg Gln Glu Tyr Leu Lys
130                 135                 140

Glu Leu Met Gln Tyr Thr Asp Ile Asp Ser Tyr Gly Lys Leu Tyr Arg
145                 150                 155                 160

Asn Cys Glu Leu Pro Val Glu Asp Arg Gly Arg Asp Thr Leu Leu Ser
                165                 170                 175

Val Ile Gly Asp Tyr Gln Phe Val Ile Ser Phe Glu Asn Ala Ile Gly
                180                 185                 190

Lys Asp Tyr Val Thr Glu Lys Phe Phe Asn Pro Leu Leu Ala Gly Thr
                195                 200                 205

Val Pro Val Tyr Leu Gly Ala Pro Asn Ile Arg Glu Phe Ala Pro Gly
210                 215                 220

Glu Asn Cys Phe Leu Asp Ile Cys Thr Phe Asp Ser Pro Glu Gly Val
225                 230                 235                 240

Ala Ala Phe Met Asn Gln Cys Tyr Asp Asp Glu Ala Leu Tyr Glu Arg
                245                 250                 255

Phe Tyr Ala Trp Arg Lys Arg Pro Leu Leu Leu Ser Phe Thr Asn Lys
                260                 265                 270

Leu Glu Gln Val Arg Ser Asn Pro Leu Ile Arg Leu Cys Gln Lys Ile
                275                 280                 285

His Glu Leu Lys Leu Gly Gly Ile
                290                 295

<210> SEQ ID NO 5
<211> LENGTH: 334
<212> TYPE: PRT
<213> ORGANISM: Helicobacter cinaedi

<400> SEQUENCE: 5

Met Gln Lys Pro Ile Lys Lys Val Tyr Phe Cys Asp Gly Ala Val Glu
 1               5                  10                  15

Gly Lys Ile Val Lys Ile Leu Lys Lys His Tyr Asn Leu Ile Phe Thr
                20                  25                  30

Asp Arg Asp Pro Asp Tyr Ile Phe Tyr Ser Val Met Gly Glu Lys His
                35                  40                  45

Ile Glu Tyr Asp Gly Ile Arg Ile Phe Ser Thr Gly Glu Asn Val Arg
 50                  55                  60

Ala Asp Phe Asn Phe Cys Asp Tyr Ala Ile Gly Phe Asp Tyr Ile Gln
 65                  70                  75                  80

Phe Asp Asp Arg Tyr Leu Arg Tyr Pro Leu Tyr Leu His Tyr Thr Lys
                 85                  90                  95

Asp Met Gln Lys Ala Lys Asn Lys His Leu Ala Ile Asn Thr Gln Thr
                100                 105                 110

Leu Gln Asn Lys Asp Arg Phe Cys Thr Phe Val Val Ser Asn Gly Lys
                115                 120                 125
```

```
Ala Asp Glu Leu Arg Thr Gln Phe Phe Asp Phe Leu Ser Gln Tyr Lys
            130                 135                 140

His Ile Asp Ser Gly Gly Lys Tyr Lys Asn Asn Ile Gly Lys Pro Ile
145                 150                 155                 160

Lys Asp Lys Ser Ser Phe Leu Ala Ile Gly Lys Phe Asn Ile Ala Phe
                165                 170                 175

Glu Asn Ser Asn Thr Asn Gly Tyr Thr Thr Glu Lys Leu Ile Gln Ala
            180                 185                 190

Leu Ser Ser Gln Thr Val Pro Ile Tyr Trp Gly Asp Glu Cys Val Ser
        195                 200                 205

Lys Pro Leu Asp Ser Ser Gly Gly Gly Gly Val Asn Pro Lys Ala
210                 215                 220

Phe Ile His Ile Lys Ser Val Asn Asp Phe Asp Thr Ala Leu Glu Lys
225                 230                 235                 240

Ile Gln Lys Leu Asp Asn Asp Glu Ala Tyr Leu Ser Met Leu Lys
                245                 250                 255

Glu Pro Ser Phe Leu Asp Ser Asn His Glu Glu Ile Phe Asp Glu Arg
            260                 265                 270

Leu Glu Asn Phe Leu Leu His Ile Phe Ser Gln Pro Ile Lys Lys Ala
        275                 280                 285

Tyr Arg Arg Gly Phe Gly Gln Trp Arg Tyr Asn Leu Glu Lys Arg Tyr
290                 295                 300

Lys Lys Phe Gln Arg Ala Arg Lys Ile Ala Asn Gly Phe Ala Asn Ile
305                 310                 315                 320

Phe Lys Ile Pro Ile Gln Lys Leu Arg Thr Tyr Ile Lys Tyr
                325                 330

<210> SEQ ID NO 6
<211> LENGTH: 343
<212> TYPE: PRT
<213> ORGANISM: Butyrivibrio fibrisolvens

<400> SEQUENCE: 6

Met Arg Arg Val Phe Ala Ile His Pro Ser Ile Lys Gly Ile Val Asp
1               5                   10                  15

Leu Ser Lys Tyr Leu Gly Phe Lys Ser Cys Ile Thr Glu Glu Ile Ile
            20                  25                  30

Trp Asp Ser Asn Ser Pro Glu Phe Ile Phe Val Ser Glu Arg Ile Tyr
        35                  40                  45

Thr Asp Ile Asn Glu Trp Glu Leu Phe Lys Lys Met Tyr Asn Pro Gln
50                  55                  60

Arg Ile Phe Ile Phe Val Ser Gly Glu Cys Met Thr Pro Asp Leu Asn
65                  70                  75                  80

Ile Phe Asp Tyr Ala Ile Val Phe Asp Arg Lys Leu Lys Asp Leu Asp
                85                  90                  95

Arg Ile Cys Arg Ile Pro Thr Asn Tyr Ile Arg His Arg Ser Leu Ile
                100                 105                 110

Lys Lys Val Asn Asp Met Ser Phe Glu Asn Ala Leu Ser Arg Val Lys
            115                 120                 125

Glu Leu Asp Phe Cys Ser Phe Ile Tyr Ser Asn Pro Lys Ala Asp Gln
        130                 135                 140

Ile Arg Glu Asp Ile Phe Trp Gly Leu Met Asn Tyr Lys His Val Asp
145                 150                 155                 160

Ser Leu Gly Glu Tyr Leu Asn Asn Ser Gly Val Lys Thr Thr Arg Asn
```

```
                    165                 170                 175
Asp Lys His Trp Arg Glu Leu Ser Ile Glu Met Lys Ser His Tyr Lys
            180                 185                 190

Phe Ser Ile Ala Val Glu Asn Ala Gln Tyr Glu Gly Tyr Ile Ser Glu
        195                 200                 205

Lys Leu Leu Thr Ser Phe Gln Ser His Ser Val Pro Ile Tyr Trp Gly
    210                 215                 220

Asp Pro Leu Val Val Asp Glu Tyr Asn Pro Lys Ala Phe Ile Asn Phe
225                 230                 235                 240

Asn Glu Met Ser Ser Ile Ser Glu Leu Val Asn His Val Lys Glu Ile
            245                 250                 255

Asp Glu Asn Asp Glu Leu Trp Ala Glu Met Val Ser Ala Asp Trp Gln
        260                 265                 270

Thr Ser Glu Gln Val Ala Arg Val Lys Lys Glu Thr Glu Glu Tyr Asp
    275                 280                 285

Leu Phe Ile Glu His Ile Leu Ser Gln Ser Val Ser Asp Ala Ile Arg
290                 295                 300

Arg Pro Arg Gly Cys Trp Pro Tyr Ile Tyr Thr Asn Arg Phe Phe Asp
305                 310                 315                 320

Glu Lys Trp Phe Leu Lys Ser Lys Ala Lys Arg Tyr Ile Arg Lys Ala
            325                 330                 335

Ile His Cys Phe Glu Glu Gln
            340

<210> SEQ ID NO 7
<211> LENGTH: 316
<212> TYPE: PRT
<213> ORGANISM: Butyrivibrio sp. AE2015

<400> SEQUENCE: 7

Met Lys Val Lys Phe Val Asp Ser Phe Phe Ala Arg Glu Gln Thr Met
1               5                   10                  15

Gly Val Leu Asn Glu Leu Phe Glu Asn Val Glu Ile Ser Asp Asp Pro
            20                  25                  30

Asp Phe Val Phe Cys Ser Val Asp Tyr Lys Ala Glu His Met Asn Tyr
        35                  40                  45

Asp Cys Pro Arg Ile Met Val Ile Gly Glu Asn Ile Val Pro Asp Phe
    50                  55                  60

Asn Cys Ile Asp Tyr Ala Val Gly Phe Asn Tyr Met Asn Phe Glu Asp
65                  70                  75                  80

Arg Tyr Leu Arg Val Pro Leu Tyr Asn Phe Tyr Leu Asp Tyr Lys
            85                  90                  95

Leu Ala Ile Arg Arg His Ile Asp Tyr Lys Arg Asp Ala Asn Lys Lys
            100                 105                 110

Phe Cys Asn Phe Val Tyr Ser Asn Gly Arg Asn Ala Ile Pro Glu Arg
        115                 120                 125

Asp Ser Phe Phe Ala Asp Leu Ser Lys Tyr Lys Gln Val Asp Ser Gly
    130                 135                 140

Gly Arg His Leu Asn Asn Ile Gly Gly Pro Val Asp Asp Lys Arg Glu
145                 150                 155                 160

Phe Gln Lys Gln Tyr Lys Phe Ser Ile Ala Phe Glu Asn Ala Val Ser
            165                 170                 175

Arg Gly Tyr Thr Thr Glu Lys Ile Ile Gln Ala Phe Ser Ala Gly Thr
        180                 185                 190
```

```
Ile Pro Ile Tyr Tyr Gly Asn Pro Leu Val Ala Lys Glu Phe Asn Ser
            195                 200                 205

Lys Ala Phe Ile Asn Cys His Glu Tyr Arg Ser Phe Asp Glu Val Ile
210                 215                 220

Glu Lys Val Lys Glu Leu Asp Asn Asp Pro Asp Leu Tyr Asp Ser Met
225                 230                 235                 240

Met Arg Glu Pro Ile Phe Thr Asp Ile Asp Glu Arg Gln Asp Pro Leu
                245                 250                 255

Lys Asp Tyr Arg Lys Phe Ile Tyr Asn Ile Cys Ser Gln Glu Ser Asp
                260                 265                 270

Lys Ala Ile Arg Arg Cys Asp Asp Cys Trp Gly Gly Lys Ile Gln Arg
                275                 280                 285

Glu Lys Lys Arg Cys Tyr Arg Phe Leu Thr Ser Thr Glu Gly Asn Gly
            290                 295                 300

Leu Lys Ala Arg Val Ile Arg Lys Leu Thr Glu Ile
305                 310                 315

<210> SEQ ID NO 8
<211> LENGTH: 357
<212> TYPE: PRT
<213> ORGANISM: Parabacteroides goldsteinii

<400> SEQUENCE: 8

Met Thr Val Thr Met Val Arg Ser Leu Tyr Phe Val His Pro Lys Val
1               5                   10                  15

His Asn Val Glu Ser Phe Leu Asn Tyr Val His Ile Cys Glu Leu Pro
            20                  25                  30

Gln Gly Leu Cys Leu Glu Trp Asn Asp Arg Asn Pro Glu Leu Leu Phe
        35                  40                  45

Ala Ser Glu Val Ile Tyr Ser Asp Lys Lys Ser Ser Glu Thr Phe Arg
    50                  55                  60

Arg Leu Tyr Cys Glu Ala Lys Val Val Tyr Tyr Gly Gly Glu Ala
65                  70                  75                  80

Ser Phe Thr Asp Phe Asn Ile Phe Asp Tyr Gly Val Gly Phe Asp His
                85                  90                  95

Thr Leu Lys Asn Gln Lys Tyr Ala Gln Ile Leu Ser Pro Ile Asp Phe
            100                 105                 110

Phe Asp Asn Phe Phe Tyr Pro Asp Arg Thr Asn Leu Ser Glu Glu Val
        115                 120                 125

Ala Gln Glu Lys Leu Arg Ser Gly Leu Lys Phe Cys Asn Phe Leu Tyr
130                 135                 140

Ser Asn Pro Val Ala His Pro Tyr Arg Asp Asn Leu Phe Tyr Lys Leu
145                 150                 155                 160

Ser Glu Tyr Lys Lys Val Asp Ala Leu Gly Arg His Leu Asn Asn Thr
                165                 170                 175

Gly Ile Gly Gly Thr Gly Phe Ala Gly His Ala Arg Glu Ser Val Asn
            180                 185                 190

Leu Lys Glu Asn Tyr Lys Phe Ser Ile Ala Ser Glu Asn Cys Gly Phe
        195                 200                 205

Gln Gly Tyr Thr Ser Glu Lys Ile Leu Thr Ser Leu Gln Ala His Thr
    210                 215                 220

Val Pro Ile Tyr Trp Gly Asp Pro Asp Val Asp Leu Val Asn Pro
225                 230                 235                 240

Lys Cys Phe Ile Asn Cys Asn Asp Phe Asp Thr Leu Asp Glu Val Leu
                245                 250                 255
```

Gln Lys Val Lys Glu Ile Asp Asn Asn Asp Leu Trp Cys Glu Met
        260                 265                 270

Val Ser Gln Pro Trp Phe Thr Glu Lys Gln Leu Glu Glu Arg Ile Gln
    275                 280                 285

Arg Asn Lys Asn Tyr His Lys Phe Met Leu Ser Leu Leu Cys Lys Ser
290                 295                 300

Ile Asp Ser Leu Thr Thr Arg Pro Asn Gly Thr Phe Gln Tyr Val Tyr
305                 310                 315                 320

Arg Ala Trp Phe Leu Asn Ala Ser Val Arg Asn Asp Ile Leu Tyr Arg
                325                 330                 335

Leu Lys Arg Lys Met Asn Phe Arg Arg Leu Arg Asn Phe Ser Leu Ser
            340                 345                 350

Gln Asn Arg Lys Asn
            355

<210> SEQ ID NO 9
<211> LENGTH: 314
<212> TYPE: PRT
<213> ORGANISM: Tannerella sp. CAG:118

<400> SEQUENCE: 9

Met Lys Thr Ile Lys Val Lys Phe Val Asp Phe Trp Lys Gly Phe Asp
1               5                   10                  15

Pro Arg Asn Asn Phe Leu Met Asp Ile Leu Lys Gln Arg Tyr His Ile
                20                  25                  30

Glu Leu Ser Glu Ser Pro Asp Tyr Leu Ile Phe Ser Val Phe Gly Phe
            35                  40                  45

Thr Asn Leu Asn Tyr Glu Arg Cys Val Lys Ile Phe Tyr Thr Gly Glu
    50                  55                  60

Asn Leu Thr Pro Asp Phe Asn Ile Cys Asp Tyr Ala Ile Gly Phe Asp
65                  70                  75                  80

Tyr Leu Ser Phe Gly Asp Arg Tyr Met Arg Leu Pro Leu Tyr Ala Val
                85                  90                  95

Tyr Gly Ile Glu Lys Leu Ala Ser Pro Lys Val Ile Asp Lys Glu Lys
            100                 105                 110

Val Leu Lys Arg Lys Phe Cys Ser Tyr Val Val Ser Asn Asn Ile Gly
        115                 120                 125

Ala Pro Glu Arg Ser Arg Phe Phe His Leu Leu Ser Glu Tyr Lys Lys
    130                 135                 140

Val Asp Ser Gly Gly Arg Trp Glu Asn Val Gly Gly Pro Val Pro
145                 150                 155                 160

Asn Lys Leu Asp Phe Ile Lys Asp Tyr Lys Phe Asn Ile Ala Phe Glu
                165                 170                 175

Asn Ser Met Tyr Asp Gly Tyr Thr Thr Glu Lys Ile Met Glu Pro Met
            180                 185                 190

Leu Val Asn Ser Leu Pro Ile Tyr Trp Gly Asn Arg Leu Ile Asn Lys
        195                 200                 205

Asp Phe Asn Pro Ala Ser Phe Ile Asn Val Ser Asp Phe Pro Ser Leu
    210                 215                 220

Glu Ala Ala Val Glu His Ile Val Met Leu Asp Asn Asn Asp Asp Met
225                 230                 235                 240

Tyr Leu Ser Ile Leu Ser Lys Pro Trp Phe Asn Asp Glu Asn Tyr Leu
                245                 250                 255

Asp Trp Lys Ala Arg Phe Phe His Phe Phe Asp Asn Ile Phe Asn Arg

```
              260                 265                 270
Pro Ile Asp Glu Cys Lys Tyr Leu Thr Pro Tyr Gly Phe Cys Arg His
            275                 280                 285

Tyr Arg Asn Gln Leu Arg Ser Ala Arg Leu Leu Lys Gln Arg Phe Arg
        290                 295                 300

Gln Leu Arg Asn Pro Leu Arg Trp Phe Arg
305                 310

<210> SEQ ID NO 10
<211> LENGTH: 336
<212> TYPE: PRT
<213> ORGANISM: Lachnospiraceae bacterium NK4A136

<400> SEQUENCE: 10

Met Ser Lys Lys Ile Lys Ile Asn Tyr Ile Asp Phe Trp Pro Gly
1               5                   10                  15

Phe Lys Lys Glu Asp Asn Phe Phe Ser Arg Ile Leu Asp Lys Tyr Tyr
                20                  25                  30

Asp Val Glu Ile Ser Asp Asn Pro Asp Tyr Val Phe Cys Ser Cys Phe
            35                  40                  45

Ser Arg Lys His Phe Lys Tyr Ala Asp Cys Val Lys Ile Phe Tyr Thr
        50                  55                  60

Gly Glu Asn Ile Ile Pro Asp Phe Asn Leu Tyr Asp Tyr Ser Met Gly
65                  70                  75                  80

Phe His Tyr Ile Asp Phe Glu Asp Arg Tyr Leu Arg Leu Pro His Tyr
                85                  90                  95

Ala Leu Tyr Asp Gln Cys Ile Lys Ala Ala Lys Glu Lys His Thr His
            100                 105                 110

Ser Asp Asp Tyr Tyr Leu Ala Lys Lys Lys Phe Cys Asn Tyr Val Ile
        115                 120                 125

Ser Asn Pro Tyr Ala Ala Pro Glu Arg Asp Leu Met Ile Asp Ala Leu
    130                 135                 140

Glu Lys Tyr Met Pro Val Asp Ser Gly Gly Arg Tyr Arg Asn Asn Val
145                 150                 155                 160

Gly Gly Pro Val Ala Asp Lys Val Glu Phe Ala Ser His Tyr Arg Phe
                165                 170                 175

Ser Met Ala Phe Glu Asn Ser Ala Met Ser Gly Tyr Thr Thr Glu Lys
            180                 185                 190

Ile Phe Asp Gly Phe Ala Ala Cys Thr Ile Pro Ile Tyr Trp Gly Ser
        195                 200                 205

Asp Arg Ile Lys Glu Glu Phe Asn Pro Glu Ser Phe Val Ser Ala Arg
    210                 215                 220

Asp Phe Glu Asn Phe Asp Gln Val Val Ala Arg Val Lys Glu Ile Tyr
225                 230                 235                 240

Glu Asn Asp Asp Leu Tyr Leu Lys Met Met Lys Ala Pro Ile Ala Pro
                245                 250                 255

Glu Gly Phe Gln Ala His Glu Cys Leu Lys Glu Asp Tyr Ala Asp Ala
            260                 265                 270

Phe Leu Arg Asn Ile Phe Asp Gln Asp Ile Asp Lys Ala Lys Arg Arg
        275                 280                 285

Asn Met Val Tyr Val Gly Arg Asp Tyr Gln Lys Lys Leu Lys Asp Ala
    290                 295                 300

Asn Lys Val Ile Glu Val Leu Asp Val Val Lys Lys Pro Met His Gln
305                 310                 315                 320
```

```
Phe Asn Lys Thr Lys Ser Gln Ile Ala Ser Lys Phe Arg Lys Lys Lys
                325                 330                 335
```

<210> SEQ ID NO 11
<211> LENGTH: 335
<212> TYPE: PRT
<213> ORGANISM: Methanobrevibacter ruminantium

<400> SEQUENCE: 11

```
Met Ser Glu Lys Lys Ile Lys Val Lys Phe Val Asp Phe Gln Asp
1               5                   10                  15

Ser Leu Lys Glu Asn Asp Asn Phe Phe Ile Asp Ser Leu Lys Lys Asn
                20                  25                  30

Phe Asp Val Glu Val Ser Asp Pro Asp Tyr Leu Phe Phe Gly Ala
            35                  40                  45

Tyr Gly Tyr Lys His Leu Asp Tyr Asp Cys Ile Arg Ile Met Trp Thr
        50                  55                  60

Ile Glu Asn Tyr Val Pro Asp Phe Asn Ile Cys Asp Tyr Ala Leu Ala
65                  70                  75                  80

Tyr Asp Ile Ile Glu Phe Gly Asp Arg Tyr Leu Arg Phe Pro Phe Phe
                85                  90                  95

Leu Asn Arg Pro Glu Ile Glu Asn Val Arg Lys Thr Ile Glu Arg Lys
                100                 105                 110

Pro Ile Asp Thr Ser Val Lys Thr Asp Phe Cys Ser Phe Val Val Ser
            115                 120                 125

Asn Glu Trp Gly Asp Asp Tyr Arg Ile Arg Leu Phe His Glu Leu Ser
        130                 135                 140

Lys Tyr Lys Lys Val Asp Ser Gly Gly Arg Ser Leu Asn Asn Ile Gly
145                 150                 155                 160

Gly Pro Ile Gly Met Gly Leu Asp Lys Lys Phe Glu Phe Asp Val Thr
                165                 170                 175

His Lys Phe Ser Phe Ala Leu Glu Asn Ala Gln Asn Arg Gly Tyr Thr
            180                 185                 190

Thr Glu Lys Ile Phe Asp Ala Phe Ala Ala Gly Cys Ile Pro Ile Tyr
        195                 200                 205

Trp Gly Asp Pro Asn Ile Glu Glu Glu Phe Asn Pro Lys Ser Phe Ile
210                 215                 220

Asn Cys Asn Asp Leu Thr Val Glu Glu Ala Val Glu Lys Ile Lys Glu
225                 230                 235                 240

Val Asp Gln Asn Asp Glu Leu Tyr His Ala Met Leu Asn Glu Pro Thr
                245                 250                 255

Phe Leu Gly Asp Leu Asp Lys Tyr Leu Gln Asp Phe Asp Asp Phe Leu
            260                 265                 270

Phe Asn Ile Cys Asn Gln Pro Leu Glu Lys Ala Tyr Arg Arg Asp Arg
        275                 280                 285

Ile Met Lys Gly Lys Thr Gln Glu His Gln Tyr Lys Leu Ile Asn Arg
290                 295                 300

Phe Tyr Tyr Lys Pro Tyr Phe Phe Leu Ile Lys Val Ala Gln Lys Leu
305                 310                 315                 320

His Ile Glu Phe Ile Gly Arg Lys Ile Tyr His Phe Ile Arg Asp
                325                 330                 335
```

<210> SEQ ID NO 12
<211> LENGTH: 329
<212> TYPE: PRT
<213> ORGANISM: Bacteroides salyersiae

<400> SEQUENCE: 12

| | | | | | | | | | | | | | | |
|---|---|---|---|---|---|---|---|---|---|---|---|---|---|---|
|Met|Lys|Lys|Val|Lys|Ile|Lys|Phe|Val|Asp|Phe|Phe|Asp|Gly|Phe|Asp|
|1| | | |5| | | | |10| | | | |15| |

Lys Gly Arg Asn Glu Phe Leu Glu Val Leu Lys Gln Arg Tyr Glu Ile
            20                 25               30

Asp Ile Ser Asp Glu Pro Asp Tyr Val Ile Tyr Ser Gly Phe Gly Tyr
        35                 40               45

Glu His Leu Lys Tyr Asn Cys Ile Arg Ile Phe Thr Gly Glu Cys
    50                 55               60

Gln Thr Pro Asp Phe Asn Glu Cys Asp Tyr Ala Ile Gly Phe Asp Arg
65               70               75               80

Leu Lys Phe Gly Asp Arg Tyr Val Arg Ile Pro Leu Tyr Asn Met Met
        85                 90               95

Gln Tyr Lys Leu Asp Tyr Lys Glu Leu Leu Asn Arg Lys Ser Ile Ile
       100             105             110

Ser Asp Asp Ile Lys Gly Arg Gly Phe Cys Ser Phe Val Val Ser Asn
       115             120             125

Cys Phe Ala Asn Asp Thr Arg Ala Ile Phe Tyr Glu Leu Leu Asn Gln
   130                 135             140

Tyr Lys Tyr Ile Ala Ser Gly Gly Arg Tyr Lys Asn Asn Ile Gly Gly
145              150             155             160

Ala Ile Lys Asp Lys Lys Thr Phe Leu Ser Lys Tyr Lys Phe Asn Ile
             165             170             175

Ala Phe Glu Asn Cys Ser His Asp Gly Tyr Ala Thr Glu Lys Ile Val
       180             185             190

Glu Ala Phe Ala Ala Gly Val Val Pro Ile Tyr Tyr Gly Asp Pro Arg
      195            200             205

Ile Ala Glu Asp Phe Asn Pro Lys Ala Phe Ile Asn Ala His Asp Tyr
   210                 215             220

Gln Ser Phe Glu Glu Met Val Glu Arg Ile Lys Glu Ile Asp Ala Asp
225              230             235             240

Asp Arg Leu Tyr Leu Thr Met Leu Asn Glu Pro Ile Ile Gln Pro Asn
             245             250             255

Ala Asp Val Thr Glu Leu Ala Asp Phe Leu Tyr Ser Ile Phe Asp Gln
       260             265             270

Pro Leu Ala Lys Ala Lys Arg Arg Ser Gln Ser Gln Pro Thr Gln Ala
      275            280             285

Met Glu Ala Met Lys Leu Arg His Glu Phe Phe Glu Met Lys Ile Tyr
   290                 295             300

Lys Tyr Tyr Lys Lys Gly Met Asn Gln Phe Thr Arg Leu Arg Lys Gly
305              310             315             320

Val Phe Leu Ser Ser Lys Arg Thr Lys
             325

<210> SEQ ID NO 13
<211> LENGTH: 335
<212> TYPE: PRT
<213> ORGANISM: Butyrivibrio fibrisolvens

<400> SEQUENCE: 13

Met Lys Lys Glu Ile Lys Ile Ala Tyr Val Asp Phe Trp Asn Gly Phe
1               5               10               15

Lys Pro Asp Ser Phe Phe Ile Thr Lys Thr Ile Ser Lys Lys Tyr Lys
         20                 25               30

-continued

```
Val Ile Ile Asp Asn Glu Asn Pro Asp Phe Val Ile Cys Gly Thr Phe
             35                  40                  45

Gly Asn Thr Phe Leu Ser Tyr Asp Cys Pro Arg Ile Leu Tyr Thr Gly
         50                  55                  60

Glu Ala Asn Cys Pro Asp Phe Asn Ile Tyr Asp Tyr Ala Ile Gly Phe
 65                  70                  75                  80

Glu Arg Met Val Tyr Glu Asp Arg Tyr Leu Arg Tyr Pro Leu Phe Leu
                 85                  90                  95

Val Asn Glu Asp Leu Leu Gln Asp Ala Leu Asn Lys His Lys Lys Ser
             100                 105                 110

Asp Asp Tyr Tyr Leu Arg Arg Asp Gly Phe Cys Ser Phe Val Val Ser
             115                 120                 125

Ala Ser Gly Gly Met Asp Gly Leu Arg Asn Trp Tyr Phe Asp Lys Ile
     130                 135                 140

Ser Glu Tyr Lys Gln Val Ala Ser Gly Gly Arg Phe Arg Asn Asn Leu
145                 150                 155                 160

Pro Asp Gly Lys Pro Val Pro Asp Lys Lys Ala Phe Gln Glu Asn Tyr
                165                 170                 175

Arg Phe Ser Leu Cys Phe Glu Asn Ala Gly Ile Ser Gly Tyr Ala Thr
            180                 185                 190

Glu Lys Ile Val Asp Ala Phe Ala Ala Gly Cys Ile Pro Ile Tyr Tyr
        195                 200                 205

Gly Asp Thr Asn Ile Glu Lys Asp Phe Asn Pro Lys Ser Phe Ile His
    210                 215                 220

Val Lys Ser Arg Glu Asp Leu Asp Ser Val Leu Ala Trp Val Lys Glu
225                 230                 235                 240

Leu Glu Glu Asn Gln Asn Lys Tyr Leu Glu Val Ile Arg Gln Pro Ala
                245                 250                 255

Ile Leu Pro Asp Ser Pro Ile Met Gly Met Leu Asn Asn Thr Tyr Ile
            260                 265                 270

Glu Glu Phe Leu Phe His Ile Phe Asp Gln Glu Pro Gln Glu Ala Ile
        275                 280                 285

Arg Arg His Ser Lys Leu Thr Met Trp Gly Gln Phe Tyr Glu Tyr Arg
    290                 295                 300

Leu Lys Lys Trp Asn Lys Ile Glu Asn Asn Met Phe Leu Lys Lys Ala
305                 310                 315                 320

Arg Ser Ile Lys Arg Lys Tyr Phe Gly Leu Lys Lys Ile Val Lys
                325                 330                 335
```

<210> SEQ ID NO 14
<211> LENGTH: 322
<212> TYPE: PRT
<213> ORGANISM: Parabacteroides goldsteinii dnLKV18

<400> SEQUENCE: 14

```
Met Lys Lys Lys Ile Tyr Cys Asn Phe Val Asp Phe Trp Leu Gly Phe
 1               5                  10                  15

Asn Tyr Lys Thr Tyr Phe Trp Tyr Leu Ser Asp Glu Tyr Asp Leu Gln
             20                  25                  30

Ile Asp Lys Glu His Pro Asp Tyr Leu Phe Tyr Ser Cys Phe Gly Asn
         35                  40                  45

Glu His Leu Phe Tyr Glu Asp Cys Ile Arg Ile Phe Trp Ser Asp Glu
 50                  55                  60

Asn Ile Met Pro Asp Leu Asn Ile Cys Asp Tyr Ala Leu Ser Leu Ser
```

```
                65                  70                  75                  80
Asn Leu Gln Cys Asp Asp Arg Thr Phe Arg Lys Tyr Ser Gly Phe Leu
                    85                  90                  95

Tyr Arg Lys Asp Ser His Leu Val Leu Pro Val Leu Lys Glu Glu Ala
                100                 105                 110

Leu Leu Asn Arg Lys Phe Cys Asn Phe Val Tyr Ser Asn Asn Thr Cys
                115                 120                 125

Ala Val Pro Tyr Arg Glu Leu Phe Phe Lys Ala Leu Ser Gly Tyr Lys
            130                 135                 140

Arg Ile Asp Ser Gly Gly Ala Phe Leu Asn Asn Met Gly Lys Lys Val
145                 150                 155                 160

Gly Asp Lys Arg Gln Phe Leu His Glu Tyr Lys Phe Thr Leu Ala Ile
                165                 170                 175

Glu Asn Ser Ser Met Pro Gly Tyr Val Thr Glu Lys Ile Leu Glu Pro
                180                 185                 190

Phe Met Ala Gln Ser Leu Pro Leu Tyr Trp Gly Ser Pro Thr Val Ser
                195                 200                 205

Ser Asp Tyr Asn Pro Asn Ser Phe Val Asn Leu Met Asn Tyr Ser Ser
            210                 215                 220

Met Glu Glu Ala Val Glu Val Ile Arg Leu Asp Lys Asp Asp Ala
225                 230                 235                 240

Ala Tyr Leu Asp Lys Met Met Thr Pro Phe Trp Leu Tyr Gly Ala Asn
                245                 250                 255

Phe Gln Glu Phe Arg Asp Ser Glu Ile Lys Lys Ile Lys Asp Phe Phe
                260                 265                 270

Ser Tyr Ile Phe Glu Gln Pro Leu Asp Lys Ala Gly Arg Arg Val Cys
                275                 280                 285

Tyr Gly Arg Asn Arg Ile Thr Ile Gln Lys Gln Arg Tyr Tyr Ala
            290                 295                 300

Pro Thr Phe Leu Glu Leu Ser Lys Ser Met Thr Lys Lys Leu Leu Lys
305                 310                 315                 320

Lys Lys

<210> SEQ ID NO 15
<211> LENGTH: 328
<212> TYPE: PRT
<213> ORGANISM: Clostridium bolteae

<400> SEQUENCE: 15

Met Lys Lys Ile Arg Leu Lys Tyr Val Asp Trp Trp Asp Gly Phe Gln
1               5                   10                  15

Pro Glu Gln Tyr Arg Phe His Gln Ile Leu Thr Lys His Phe Asp Ile
                20                  25                  30

Glu Ile Ser Asp Glu Pro Asp Tyr Ile Ile Ala Ser Val Tyr Ser Asp
            35                  40                  45

Glu Ala Lys Ser Tyr Asn Cys Val Arg Ile Leu Tyr Thr Gly Glu Asn
        50                  55                  60

Ile Cys Pro Asp Phe Asn Ile Tyr Asp Tyr Ala Ile Gly Phe Glu Tyr
65                  70                  75                  80

Leu Glu Phe Gly Asp Arg Tyr Ile Arg Ile Pro Asn Phe Ile Met Asn
                85                  90                  95

Pro Ala Tyr Asp Ile Asp Ile Gln Lys Ala Leu Ser Lys His Leu Leu
                100                 105                 110

Ser Ala Asp Asp Ile Lys Arg Glu Lys Lys Phe Cys Ser Phe Val Val
```

```
                115                 120                 125
Ser Asn Gly Asn Ala Ala Pro Ile Arg Glu Lys Met Phe Glu Leu
            130                 135                 140

Asn Lys Tyr Lys Arg Val Asp Ser Gly Gly Arg Tyr Leu Asn Asn Ile
145                 150                 155                 160

Gly Arg Pro Glu Gly Val Arg Asp Lys Phe Ala Phe Gln Ser Glu His
                165                 170                 175

Lys Phe Ser Leu Thr Phe Glu Asn Ser Ala His Leu Gly Tyr Thr Thr
            180                 185                 190

Glu Lys Leu Leu Gln Gly Phe Ser Ala Gly Thr Ile Pro Ile Tyr Trp
        195                 200                 205

Gly Asp Pro Ala Val Glu Asn Cys Phe Asn Pro Lys Ala Phe Ile Asn
    210                 215                 220

Ile Ser Gly Asn Asn Val Tyr Asp Ala Ile Glu Leu Val Lys Glu Val
225                 230                 235                 240

Asp Thr Gln Asp Leu Tyr Phe Ser Met Leu Arg Glu Pro Ala Phe
                245                 250                 255

Leu Asn Asn Asp Tyr Gln Thr Lys Leu Leu Glu Lys Leu Asp Asn Phe
            260                 265                 270

Leu Val His Ile Phe Asn Gln Pro Leu Glu Cys Ala Tyr Arg Arg Asn
        275                 280                 285

Ser Phe Glu His Ile Ser Asn Lys Ser Val Leu Asn Glu Phe Val Lys
    290                 295                 300

Glu Asp Arg Gly Arg Phe Ser Gln Trp Ile Ser Asn Lys Ala Arg Cys
305                 310                 315                 320

Phe Tyr Gly Lys Arg Lys Asn Lys
                325

<210> SEQ ID NO 16
<211> LENGTH: 347
<212> TYPE: PRT
<213> ORGANISM: Helicobacter canis NCTC 12740

<400> SEQUENCE: 16

Met Ser Lys Glu Lys Trp Lys Gln Glu Lys Arg Val His Phe Val Asp
1               5                   10                  15

Cys Cys Asp Asp Gly Ile Arg Asp Lys Val Cys Pro Ile Leu Glu Gln
            20                  25                  30

His Phe Thr Leu Ile Phe Asp Ser Val Asn Pro Glu Tyr Val Phe Tyr
        35                  40                  45

Ser Ala Tyr Gly Glu Glu His Leu Ala Tyr Asp Cys Ile Arg Ile Phe
    50                  55                  60

Ile Thr Gly Glu Asn Ile Thr Pro Asn Phe Thr Ile Cys Asp Tyr Ala
65                  70                  75                  80

Ile Gly Phe Asp His Leu His Phe Leu Asp Arg Tyr Leu Arg Tyr Pro
                85                  90                  95

Leu Tyr Leu Phe Tyr Glu Gln Asp Val Lys Arg Ala Ser Gln Lys His
            100                 105                 110

Lys Asp Ile Asp Glu Lys Leu Leu Ala Ser Lys Ser Arg Phe Cys Asn
        115                 120                 125

Phe Val Val Ser Asn Gly Asn Ala Asp Pro Tyr Arg Glu Gln Val Phe
    130                 135                 140

Tyr Ala Leu Asn Ala Tyr Lys Arg Val Asp Ser Gly Gly Arg Tyr Leu
145                 150                 155                 160
```

```
Asn Asn Ile Gly Gly Ser Val Ala Asp Lys Phe Ala Phe Gln Ser Glu
                165                 170                 175

Cys Arg Phe Ser Leu Cys Phe Glu Asn Ser Ser Thr Pro Gly Tyr Leu
            180                 185                 190

Thr Glu Lys Leu Ile Gln Ala Ala Ala Gln Thr Ile Pro Ile Tyr
        195                 200                 205

Trp Gly Asp Thr Leu Ala Thr Lys Pro Leu Phe Asp Gly Gly Gly
    210                 215                 220

Ile Asn Ala Lys Ala Phe Ile Asn Ala His Ser Phe Ser Ser Leu Glu
225                 230                 235                 240

Ser Leu Ile Ala His Ile Ala Glu Ile Glu Ala Asp Lys Thr Lys Gln
                245                 250                 255

Leu Ala Ile Leu Gln Glu Pro Leu Phe Leu Asp Ser Asn His Ile Glu
            260                 265                 270

Leu Phe Glu Lys Gln Phe Gln Phe Leu Leu Ser Ile Val Ser Gln
        275                 280                 285

Pro Tyr Glu Arg Ser Phe Arg Arg Gly Arg Val Met Trp Gln Ser Phe
    290                 295                 300

Val Glu Gln Arg Tyr Lys Arg Ala Met His Leu Leu Ala Leu Glu Asp
305                 310                 315                 320

Arg Ile Lys Ala Pro Tyr Arg Lys Leu Arg Gln Phe Leu Arg Ala Phe
                325                 330                 335

Trp Asp Ser Leu Lys Glu Lys Arg Ser His Thr
            340                 345

<210> SEQ ID NO 17
<211> LENGTH: 356
<212> TYPE: PRT
<213> ORGANISM: Helicobacter canis NCTC 12740

<400> SEQUENCE: 17

Met Gly Asp Glu Val Ala Met Gly Lys Glu Arg Lys Gln Ile Arg Val
1               5                   10                  15

His Phe Val Asp Phe Ser Asn Met Asp Asn Ile Ile Glu Lys Ile Cys
            20                  25                  30

Ser Ile Leu Ser Arg His Phe Ala Val Ile Ile Asp Gly Glu Asn Pro
        35                  40                  45

Glu Tyr Val Phe Tyr Ser Ala Phe Gly Ser Tyr Leu Lys Tyr Asp
    50                  55                  60

Cys Val Arg Ile Phe Tyr Thr Gly Glu Asn Ile Val Pro Asp Phe Asn
65                  70                  75                  80

Leu Cys Asp Tyr Ala Ile Gly Phe Asp His Ile Lys Phe Leu Asp Arg
                85                  90                  95

Tyr Leu Arg Tyr Pro Leu Tyr Leu Phe Tyr Glu Thr Asp Val Gln Lys
            100                 105                 110

Ala Ala Arg Lys His Gln Asn Leu Ser Leu Glu Val Val Arg Asn Lys
        115                 120                 125

Lys Arg Phe Cys Asn Phe Val Val Thr Asn Gly Lys Gly Asp Pro Tyr
    130                 135                 140

Arg Glu Lys Val Phe His Ala Leu Cys Ala Tyr Lys Arg Val Asp Ser
145                 150                 155                 160

Ala Gly Lys Phe Leu Asn Asn Val Gly Ala Arg Val Lys Asp Lys Phe
                165                 170                 175

Ala Phe Gln Ser Glu Cys Arg Phe Ser Leu Cys Phe Glu Asn Ser Ser
            180                 185                 190
```

```
Thr Pro Gly Tyr Leu Thr Glu Lys Leu Ile Gln Ala Ala Ala Ala Gln
            195                 200                 205

Thr Ile Pro Ile Tyr Trp Gly Asp Pro Leu Ala Thr Lys Pro Leu Phe
    210                 215                 220

Asp Gly Gly Gly Ile Asn Ala Lys Ala Phe Ile Asn Ala His Glu
225                 230                 235                 240

Phe Ala Asn Ile Ala Ser Leu Val Arg His Ile Glu Ser Ile Glu Asn
                245                 250                 255

Asp Glu Asn Lys Gln Leu Ala Ile Leu Gln Glu Pro Leu Phe Leu Asp
            260                 265                 270

Ser Asn His Ile Glu Leu Phe Glu Lys Gln Phe Glu Asp Phe Leu Val
        275                 280                 285

Tyr Ile Phe Ser Gln Pro Tyr Glu Arg Ser Phe Arg Arg Gly Lys Ile
    290                 295                 300

Met Trp Gln Ala His Leu Glu Gln Ile Ile Lys Lys Gly Val Gln Pro
305                 310                 315                 320

Thr Met Leu Glu Ile Trp Leu Arg Arg Pro Leu Arg Asn Phe Glu Arg
                325                 330                 335

Ala Ile Arg Ile Arg Val Lys Lys Ile Ile Gln Lys Val Lys Lys Pro
            340                 345                 350

Lys Asp Phe Met
        355

<210> SEQ ID NO 18
<211> LENGTH: 332
<212> TYPE: PRT
<213> ORGANISM: Akkermansia sp. CAG:344

<400> SEQUENCE: 18

Met Lys Thr Leu Lys Ile Ser Phe Leu Gln Ser Thr Pro Asp Phe Gly
1               5                   10                  15

Arg Glu Gly Ile Tyr Gln Leu Leu Lys Asp Arg Tyr Arg Val Val Glu
            20                  25                  30

Asp Asp Ser Asp Phe Asp Tyr Leu Ile Ala Thr Pro Trp Phe Tyr Val
        35                  40                  45

Asn Arg Glu Ala Phe Tyr Asp Phe Leu Glu Arg Ala Pro Gly His Ile
    50                  55                  60

Thr Val Met Tyr Gly Cys His Glu Ala Ile Ala Pro Asp Phe Met Leu
65                  70                  75                  80

Phe Asp Tyr Tyr Ile Gly Leu Asp Ala Val Pro Gly Ser Asp Arg Thr
                85                  90                  95

Val Lys Leu Pro Phe Leu Arg His His Leu Gln Glu Val His Gly Gly
            100                 105                 110

Lys Ala Gly Leu Asp Val Arg Ala Leu Leu Ala Ser Lys Thr Gly Phe
        115                 120                 125

Cys Asn Phe Ile Tyr Ala Asn Arg Lys Ser His Pro Asn Arg Asp Ala
    130                 135                 140

Ile Phe His Lys Leu Ser Ser Val Arg Phe Val Asn Ser Leu Gly Pro
145                 150                 155                 160

His Leu Asn Asn Thr Pro Gly Asp Gly His Arg Ser Glu Asp Trp Tyr
                165                 170                 175

Ala Ser Ser Ile Arg Met Lys Lys Pro Tyr Lys Phe Ser Ile Ala Phe
            180                 185                 190

Glu Asn Ala Trp Tyr Pro Gly Tyr Thr Ser Glu Lys Ile Val Thr Ser
```

```
            195                 200                 205
Met Leu Ala Gly Thr Ile Pro Ile Tyr Trp Gly Asn Pro Asp Ile Gly
210                 215                 220

Arg Glu Phe Asn Ser Ala Ala Phe Ile Asn Cys His Asp Phe Pro Thr
225                 230                 235                 240

Leu Asp Asp Ala Ala Tyr Val Lys Lys Val Asp Lys Asp Gly
                    245                 250                 255

Leu Trp Cys Glu Ile Met Ser Arg Pro Trp Lys Thr Leu Glu Gln Glu
                260                 265                 270

Ala Leu Phe Leu Glu Glu Thr Glu Arg Glu Thr Ala Lys Leu Tyr Arg
                275                 280                 285

Ile Phe Asp Gln Ser Pro Glu Glu Ala Arg Arg Lys Gly Asp Gly Thr
290                 295                 300

Trp Ile Ala Tyr Tyr Gln Arg Phe Leu Lys Arg Gly His Arg Leu Arg
305                 310                 315                 320

Leu Ala Trp Arg Arg Leu Lys Asn Arg Leu Arg His
                325                 330
```

<210> SEQ ID NO 19
<211> LENGTH: 338
<212> TYPE: PRT
<213> ORGANISM: Gillisia limnaea

<400> SEQUENCE: 19

```
Met Lys Thr Leu Lys Ile Trp Phe Thr Asp Phe Tyr Pro Gly Phe Glu
1               5                   10                  15

Pro Lys Asp Asn Leu Ile Thr Gln Leu Leu Phe Lys Ser Tyr Asn Ile
                20                  25                  30

Glu Phe Asp Lys Asn Lys Pro Asp Tyr Leu Ile Tyr Ser Cys His Gly
                35                  40                  45

His Glu Phe Leu Asn Tyr Asn Cys Val Arg Ile Phe Tyr Thr Gly Glu
            50                  55                  60

Asn Leu Lys Pro Asp Phe Asn Leu Cys Asp Tyr Ala Ile Gly Phe Asp
65                  70                  75                  80

Tyr Ile His Phe Asn Asn Arg Tyr Leu Arg Phe Pro Asn Phe Ala Phe
                85                  90                  95

Tyr Glu Ser Gln Phe Gln Gln Leu Ile Ile Ser Lys Asn Pro Gly Ser
                100                 105                 110

Leu Asp Leu Ser Ala Lys Lys His Phe Cys Asn Phe Ile Tyr Ala Asn
                115                 120                 125

Ser Asn Ala Asp Pro Thr Arg Asp Asn Phe Phe Tyr Leu Leu Asn Lys
130                 135                 140

Tyr Lys Lys Val Ala Ser Pro Gly Lys His Leu Asn Asn Ile Ser Met
145                 150                 155                 160

Asp Val Gly Glu Arg Tyr Ala Lys Asp Trp Met Phe Thr Lys Ile Glu
                165                 170                 175

Phe Gln Ser Ser Cys Lys Phe Ser Ile Ala Phe Glu Asn Thr Ser Ser
                180                 185                 190

Pro Gly Tyr Thr Thr Glu Lys Leu Leu His Ala Phe Ile Thr Gly Thr
                195                 200                 205

Ile Pro Ile Tyr Trp Gly Asn Pro Glu Val Met Lys Asp Phe Asn Pro
                210                 215                 220

Lys Ala Phe Ile Asn Cys His Asp Phe Glu Ser Phe Glu Asp Val Val
225                 230                 235                 240
```

```
Ser Lys Val Lys Glu Ile Asp Asn Asp Asp Glu Met Phe Leu Ser Met
                245                 250                 255

Leu Asn Glu Pro Pro Phe Arg Asn Asn Ile Ile Pro Glu Asn Leu Lys
            260                 265                 270

Lys Glu Pro Leu Leu Val Phe Leu Lys Asn Ile Phe Asp Gln Lys Arg
            275                 280                 285

Glu Asp Ala Phe Gln Arg Ser Phe Tyr Gly Thr Ser Ala Lys Tyr Glu
            290                 295                 300

Asn Asp Met Lys Glu Met Ile Leu Phe Arg Lys Lys Tyr Arg Ser Met
305                 310                 315                 320

Ile Gln Phe Leu Gly Leu Leu Lys Lys Thr Leu Lys Ile Met Lys Arg
                325                 330                 335

Asn Arg

<210> SEQ ID NO 20
<211> LENGTH: 335
<212> TYPE: PRT
<213> ORGANISM: Loktanella vestfoldensis

<400> SEQUENCE: 20

Met Lys Thr Ile Lys Leu His Tyr Thr Asp Met Trp Gly Thr Phe Asp
1               5                   10                  15

Pro Leu Ala Pro Ser Gln Ile Asp Arg Ile Leu Arg Lys His Phe His
            20                  25                  30

Val Val Leu Thr Asp Gln Asp Pro Asp Tyr Val Ile Cys Ser Val Phe
            35                  40                  45

Gly Asp Gly Ala Thr Arg Arg Arg Gly Val Arg Leu Arg Glu His His
        50                  55                  60

Leu Tyr Pro Asp Ala Ile Lys Ile Met Tyr Ser Gly Glu Asn Thr Leu
65                  70                  75                  80

Pro Asp Leu Asn Phe Cys Asp Tyr Gly Ile Gly Phe Asp His Leu Val
                85                  90                  95

Leu Gly Asp Arg Tyr Gln Arg Val Pro Leu Phe Ala Met Asn Asp Gly
            100                 105                 110

Tyr Gln Ala Leu Leu Gln Pro Arg Ala Pro Leu Thr Arg Asp Asp Ile
            115                 120                 125

Thr Ser Ser Val Glu Phe Cys Asn Phe Thr Phe Thr Asn Asn Met Ala
130                 135                 140

Met Pro Ala Arg Asp Gln Phe Phe His Leu Leu Asn Asp Arg Lys Pro
145                 150                 155                 160

Val Leu Ser Thr Gly Arg His Leu Arg Asn Ser Asp Ala Leu Asp Leu
                165                 170                 175

His Gln Gln Gln Thr Gly Leu Asp Pro Gln Gln Ala Lys Thr Asp Phe
            180                 185                 190

Leu Ala Arg Phe Lys Phe Thr Ile Ala Phe Glu Asn Ser Ser His Pro
            195                 200                 205

Gly Tyr Thr Thr Glu Lys Val Met Asp Pro Leu Val Ala Arg Ser Val
        210                 215                 220

Pro Ile Tyr Leu Gly Asn Pro Arg Ile Ala Asp Asp Phe Asn Thr Ala
225                 230                 235                 240

Ala Phe Ile Asn Gly His Asp Phe Pro Ser Leu Asp Ala Leu Ala Asp
                245                 250                 255

Glu Val Met Arg Ile Asp Ala Asp Ala Ala Tyr Leu Ala Ile Leu
            260                 265                 270
```

```
Asn Ala Pro Pro Leu Pro Pro Gly Gln Arg Glu Pro His Leu Cys
            275                 280                 285

Ala Leu Glu Arg Phe Leu Leu Gln Ile Phe Thr Pro Pro Lys Ala Glu
290                 295                 300

Ala Gln Arg Arg Gln Arg Tyr Gly Trp Ile Gly Arg Ile Asp Asp Glu
305                 310                 315                 320

Tyr Ser Ala Tyr Arg Arg Arg Thr Arg Arg Trp Arg Trp Phe
                325                 330                 335

<210> SEQ ID NO 21
<211> LENGTH: 325
<212> TYPE: PRT
<213> ORGANISM: Azospirillum brasilense

<400> SEQUENCE: 21

Met Leu Asp Gln Arg Thr Ser Ala Phe Leu Glu Glu Phe Leu Ala Lys
1               5                   10                  15

Pro Gly Gly Asp Pro Glu Arg Leu Asp Arg Phe Leu Leu His Gly Pro
            20                  25                  30

Tyr Arg Gly Arg Arg Gly Gly Arg Pro Arg Leu Lys Leu Ala Phe His
        35                  40                  45

Asp Phe Trp Pro Glu Phe Asp Thr Gly Thr Asn Phe Phe Ile Glu Ile
    50                  55                  60

Leu Ser Ser Arg Phe Asp Leu Ser Val Val Glu Asp Asp Ser Asp Leu
65                  70                  75                  80

Ala Ile Val Ser Val Phe Gly Gly Arg His Arg Glu Ala Arg Ser Cys
                85                  90                  95

Arg Thr Leu Phe Phe Thr Gly Glu Asn Val Arg Pro Pro Leu Asp Ser
            100                 105                 110

Phe Asp Met Ala Val Ser Phe Asp Arg Val Asp Asp Pro Cys His Tyr
        115                 120                 125

Arg Leu Pro Leu Tyr Val Met His Ala Tyr Glu His Met Arg Glu Gly
    130                 135                 140

Ala Val Pro His Phe Cys Ser Pro Val Leu Pro Val Pro Pro Thr
145                 150                 155                 160

Arg Ala Ala Phe Ala Glu Arg Gly Phe Cys Ala Phe Leu Tyr Lys Asn
                165                 170                 175

Pro Asn Gly Glu Arg Arg Asn Arg Phe Phe Pro Ala Leu Asp Gly Arg
            180                 185                 190

Arg Arg Val Asp Ser Val Gly Trp His Leu Asn Asn Thr Gly Ser Val
        195                 200                 205

Val Lys Met Gly Trp Leu Ser Lys Ile Arg Val Phe Glu Arg Tyr Arg
    210                 215                 220

Phe Ala Phe Ala Phe Glu Asn Ala Ser His Pro Gly Tyr Leu Thr Glu
225                 230                 235                 240

Lys Ile Leu Asp Val Phe Gln Ala Gly Ala Val Pro Leu Tyr Trp Gly
                245                 250                 255

Asp Pro Asp Leu Glu Arg Glu Val Ala Ala Gly Ser Phe Ile Asp Val
            260                 265                 270

Ser Arg Phe Ala Thr Asp Glu Glu Ala Val Asp His Ile Leu Ala Val
        275                 280                 285

Asp Asp Asp Tyr Asp Ala Tyr Cys Ala His Arg Ala Val Ala Pro Phe
    290                 295                 300

Leu Gly Thr Glu Glu Phe Tyr Phe Asp Ala Tyr Arg Leu Ala Asp Trp
305                 310                 315                 320
```

Ile Glu Ser Arg Leu
                325

<210> SEQ ID NO 22
<211> LENGTH: 722
<212> TYPE: PRT
<213> ORGANISM: Lachnospiraceae bacterium NK4A179

<400> SEQUENCE: 22

Met Leu Lys Thr Ala Ala Thr Gly Asn Ile Phe Ser Lys Ile Ser Asp
1               5                   10                  15

Ile Phe Phe Ile Leu Gly Ile Leu Cys Glu Leu Tyr Val Met Pro Ser
            20                  25                  30

Gly Tyr Ala Phe Gly Trp Tyr His Glu Lys Thr Phe Ile Ala Ala Gly
        35                  40                  45

Met Ala Cys Phe Cys Val Ser Ile Ile Phe Ser Met Asn Leu Lys Lys
    50                  55                  60

Asp Phe Pro Val Phe Ala Leu Leu Ala Ala Tyr Gly Ala Val Cys Tyr
65                  70                  75                  80

Arg Tyr Gln Gly Thr Ala Leu Val Leu Arg Ile Ile Leu Ala Leu Leu
                85                  90                  95

Ala Gly Arg Asp Lys Asn Arg Asp Arg Thr Val Lys Met Phe Phe Ala
            100                 105                 110

Gly Ser Met Phe Val Ile Val Leu Ala Ala Val Leu Ser Leu Leu Gly
        115                 120                 125

Ile His Asn Ser Val Met Gln Thr Gly Asn Thr Arg Ser Phe Thr Glu
    130                 135                 140

Thr Arg Leu Thr Leu Gly Phe Tyr Asn Pro Asn Gly Phe Ala Leu Phe
145                 150                 155                 160

Val Phe Arg Thr Tyr Val Leu Ala Val Phe Leu Leu Ile Thr Ala Leu
                165                 170                 175

Lys Asp Lys Lys Lys Gly Val Phe Ile Ala Ala Ala Val Ser Leu Pro
            180                 185                 190

Phe Leu Ile Leu Ile Leu Ser His Ser Lys Met Ala Ala Ala Ala
        195                 200                 205

Phe Val Ala Val Phe Ile Leu Thr Met Ile Cys Ile Gly Val Lys Gly
    210                 215                 220

Lys Ala Ala Asp Ile Thr Ala Tyr Ala Ala Ser Leu Gly Ala Val Ile
225                 230                 235                 240

Leu Gln Val Val Leu Leu Ile Val Phe Arg Phe Gln Leu Leu Pro Lys
                245                 250                 255

Met Arg Phe Gly Lys Asn Asp Thr Phe Phe Glu Lys Ile Asn Ser Leu
            260                 265                 270

Thr Thr Gly Arg Leu Met Met Thr Lys Ala Leu Phe Lys Ser Ala Val
        275                 280                 285

Pro Arg Pro Phe Gly Arg Pro Gln Gly Glu Met Ala Leu Thr Glu Met
    290                 295                 300

Gly Phe Glu Asn Ser Ala Phe Ala Gln Gly Tyr Ile Phe Ile Leu Leu
305                 310                 315                 320

Leu Leu Ala Cys Ile Phe Trp Leu Ser Ile Arg Phe Tyr Arg Lys Lys
                325                 330                 335

Asp Arg Ala Gly Leu Val Val Leu Ser Ala Thr Thr Leu Tyr Ala Leu
            340                 345                 350

Ala Glu Ser Tyr Leu Ala Tyr Phe Asn Lys Asn Ser Ile Trp Leu Met

```
            355                 360                 365
Met Ile Gly Ile Cys Ala Ala Gly Ala Ala Cys Arg Glu Arg Asn Glu
    370                 375                 380

Met Gly Lys Asp Gly Lys Lys Ile Arg Ile Asp Phe Ala Gly Phe
385                 390                 395                 400

Trp Pro Asp Phe Lys Asp Asn Tyr Phe Tyr Asn Arg Leu Lys
                405                 410                 415

Leu Tyr Tyr Asp Pro Glu Ile Cys Asp Asp Pro Asp Tyr Val Phe Cys
                420                 425                 430

Ser Gly Phe Ser Asp Glu His Phe Lys Tyr Met Asp Cys Val Lys Ile
            435                 440                 445

Phe Phe Thr Gly Glu Asn Ile Met Pro Asp Phe Asn Leu Phe Asp Tyr
        450                 455                 460

Ala Leu Gly Phe His Tyr Ile Asp Phe Glu Asp Arg Tyr Leu Arg Leu
465                 470                 475                 480

Pro Leu Tyr Ala Leu Tyr Asp Lys Glu Lys Ile Ile Pro Ala Leu
                485                 490                 495

Lys Lys His Thr His Glu Asp Glu Tyr Tyr Leu Ser Lys Lys Lys Phe
            500                 505                 510

Cys Asn Arg Val Val Ser Asn Pro Phe Gly Ala Gly Glu Arg Asp Glu
        515                 520                 525

Met Phe Asp Lys Leu Ser Ala Tyr Lys Gln Val Asp Ser Gly Gly Arg
    530                 535                 540

Tyr Arg Asn Asn Val Gly Gly Pro Val Asp Asp Lys Ile Ala Phe Glu
545                 550                 555                 560

Arg Asp Tyr Lys Phe Thr Leu Ala Phe Glu Asn Ser Ser Met Ser Gly
                565                 570                 575

Tyr Thr Thr Glu Lys Ile Leu Glu Ala Phe Ala Gly Asp Thr Ile Pro
            580                 585                 590

Val Tyr Phe Gly Ser Pro Arg Ile Lys Glu Glu Phe Asn Pro Glu Ser
        595                 600                 605

Phe Ile Asp Ala Ser Ser Phe Asp Ser Phe Asp Glu Val Val Glu Glu
    610                 615                 620

Ile Lys Lys Ile Asp Asn Asp Glu Leu Tyr Leu Lys Met Met Lys
625                 630                 635                 640

Ala Pro Ala Val Leu Pro Glu Ser Gln Ser Lys Pro Val Leu Glu Asp
                645                 650                 655

Asp Tyr Ile Asp Ala Phe Leu Lys Asn Ile Phe Asp Gln Asp Leu Ser
                660                 665                 670

Thr Ala Lys Arg Arg Asn Met Val Tyr Ile Gly His Asp Tyr Gln Lys
            675                 680                 685

Lys Leu Lys Asp Ala Asn Ala Leu Lys Arg Val Leu Asp Val Val Lys
        690                 695                 700

Arg Pro Val His Leu Met His Lys Ile Lys Trp Gln Ile Thr Ser Lys
705                 710                 715                 720

Asp Lys
```

<210> SEQ ID NO 23
<211> LENGTH: 335
<212> TYPE: PRT
<213> ORGANISM: Butyrivibrio sp. NC2007

<400> SEQUENCE: 23

Met Lys Lys Ile Thr Ile Gly Tyr Thr Asp Ile Tyr Pro Gly Phe Asp

```
           1               5                  10                 15
         Pro Thr Asn Asn Ile Ile Tyr Asn Cys Leu Lys Asp Arg Tyr Asp Val
                            20                 25                 30

Lys Ile Ala Asp Thr Ala Ala Leu Glu Ser Ser Glu Val Gln Tyr
                        35                 40                 45

Leu Phe Tyr Ser Ala Ser Asp Asn Arg Tyr Leu Asp Tyr Asn Cys Ile
                    50                 55                 60

Arg Ile Phe Val Thr Gly Glu Asn Leu Phe Pro Asn Phe Asn Leu Cys
         65                 70                 75                 80

Asp Tyr Ala Val Gly Phe Glu His Met Asp Val Gly Asp Arg Phe Tyr
                            85                 90                 95

Arg Leu Pro Ile Tyr Leu Trp Glu Gln Tyr Arg Glu Asp Tyr Asp Leu
                        100                105                110

Leu Leu Gln Asp Arg Leu Glu Leu Val Gly Val Ser Pro Glu Lys Arg
                        115                120                125

Lys Phe Cys Gly Ile Val Ala Thr Asn Asn Thr Phe Ala Asp Pro Val
                    130                135                140

Arg Glu Gln Phe Phe His Thr Leu Ser Arg Tyr Arg Gln Val Asp Ser
         145                150                155                160

Gly Gly Lys Ala Tyr Asn Asn Ile Gly Leu Pro Glu Gly Val Gly Asp
                        165                170                175

Lys Arg Ala Phe Leu Lys Asn Tyr Lys Phe Ser Ile Ala Phe Glu Asn
                        180                185                190

Ser Ala Tyr Pro Gly Tyr Cys Thr Glu Lys Leu Met Gln Ala Phe Ser
                        195                200                205

Ala Gly Thr Val Pro Ile Tyr Trp Gly Asp Glu Thr Ala Ile Ala Glu
                    210                215                220

Phe Asn Glu Lys Ala Phe Ile Asn Cys Cys Gly Leu Ser Met Glu Glu
         225                230                235                240

Ala Val Ala Arg Val Lys Glu Ile Asp Thr Asn Asp Glu Leu Tyr Leu
                        245                250                255

Lys Met Leu Gly Glu Gln Pro Leu Leu Asp Asn Glu Leu Arg Val Lys
                        260                265                270

Val Ile Ser Gly Leu Ser Lys Trp Leu Tyr His Ile Ile Asp Ser Asp
                    275                280                285

Tyr Glu Ser Ala Arg Arg Pro Ile His Gly Lys Met Ala Ala Tyr
                        290                295                300

Glu Glu Asn Tyr Lys Lys Arg Ile Arg Arg Glu Glu Lys Leu Lys Ser
         305                310                315                320

Asn Lys Leu Ile Ser Ala Met Val Trp Val Tyr Lys Lys Ile Arg
                        325                330                335

<210> SEQ ID NO 24
<211> LENGTH: 287
<212> TYPE: PRT
<213> ORGANISM: Anaeromyxobacter dehalogenans

<400> SEQUENCE: 24

Met Lys Pro Val Arg Val Asp Phe Val Asp Phe Trp Pro Gly Phe Asp
         1               5                  10                 15

Arg Arg Arg Asn Val Leu Leu Asp Val Leu Arg Ala Arg Phe Arg Val
                        20                 25                 30

Glu Val Val Asp Asp Pro Asp Phe Leu Phe Phe Ala Asn Phe Gly Arg
                        35                 40                 45
```

-continued

Arg His Arg Arg Tyr Arg Cys Thr Arg Val Phe Phe Thr Gly Glu Asn
    50                  55                  60

Val Arg Pro Asp Phe Arg Arg Cys Asp Phe Ala Leu Thr Phe Asp His
65                  70                  75                  80

Leu Pro Glu Glu Pro Arg His Leu Arg Trp Pro Leu Tyr Asn Leu Tyr
                85                  90                  95

Leu Asp Asp Pro Arg Phe Leu Leu Glu Arg Arg Arg Asp Val Asp Ala
            100                 105                 110

Leu Val Ala Glu Lys Thr Arg Phe Cys Asn Leu Val Cys Ser Asn Pro
            115                 120                 125

Ala Ala Thr Glu Arg Leu Arg Phe Phe Glu Lys Leu Ser Arg Tyr Lys
    130                 135                 140

Pro Val Asp Ser Gly Gly Arg Val Leu Asn Asn Val Gly Gly Pro Val
145                 150                 155                 160

Pro Asp Lys Leu Ala Phe Ile Arg Gln His Arg Phe Thr Ile Ala Phe
                165                 170                 175

Glu Asn Ala Ser Tyr Pro Gly Tyr Thr Thr Lys Ile Val Glu Pro
            180                 185                 190

Met Arg Val Gly Ser Ile Pro Ile Tyr Trp Gly Asn Pro Leu Val His
    195                 200                 205

Leu Asp Phe Asp Leu Arg Ser Ile Val Ser Trp His Glu His Gly Asn
210                 215                 220

Asp Glu Ala Thr Ile Glu Arg Val Ile Gln Ile Asp Arg Asp Glu Glu
225                 230                 235                 240

Leu Tyr Arg His Met Leu Leu Gln Pro Phe Leu Pro Asp Gly Arg Pro
                245                 250                 255

Thr Pro Tyr Ser Asp Pro Gly Val Leu Leu Asn Trp Leu Glu Arg Val
            260                 265                 270

Phe Ser Thr Pro Arg Arg Asp Ala Arg Pro Pro Arg Arg Trp Trp
            275                 280                 285

<210> SEQ ID NO 25
<211> LENGTH: 303
<212> TYPE: PRT
<213> ORGANISM: Azospirillum lipoferum

<400> SEQUENCE: 25

Met Leu Asp Arg Phe Leu Leu His Gly Pro Glu Arg Gly Gly Arg Ala
1               5                   10                  15

Ala Arg Pro Arg Leu Lys Ile Ala Phe Phe Asp Phe Trp Pro Glu Phe
            20                  25                  30

Asp Pro Ser Ala Asn Phe Phe Val Glu Ile Leu Ser Ser Arg Phe Asp
        35                  40                  45

Val Ser Val Val Asp Asn Asp Ser Asp Leu Ala Ile Leu Ser Val Phe
50                  55                  60

Gly Glu Arg His Arg Glu Ala Arg Thr Ala Arg Ala Leu Phe Phe Thr
65                  70                  75                  80

Gly Glu Asn Val Arg Pro Pro Leu Asp Gly Val Asp Met Ser Val Ser
                85                  90                  95

Phe Asp Arg Ile Asp His Pro Arg His Tyr Arg Leu Pro Leu Tyr Val
            100                 105                 110

Met His Ala Trp Asp His Arg Arg Glu Gly Ala Thr Pro His Phe Cys
        115                 120                 125

His Pro Val Leu Pro Pro Val Pro Pro Thr Arg Glu Glu Ala Ala Lys
    130                 135                 140

Arg Lys Phe Cys Ala Phe Leu Tyr Lys Asn Pro His Cys Ala Arg Arg
145                 150                 155                 160

Asn Asp Phe Phe Gln Met Leu Cys Ala Arg Arg His Val Glu Ser Val
            165                 170                 175

Gly Trp Leu Leu Asn Asn Thr Gly Ser Val Val Lys Met Gly Trp Leu
        180                 185                 190

Pro Lys Ile Arg Val Phe Ala Arg Tyr Arg Phe Ala Phe Ala Phe Glu
            195                 200                 205

Asn Ala Ala His Pro Gly Tyr Leu Thr Glu Lys Ile Leu Asp Ala Phe
210                 215                 220

Gln Ala Gly Thr Val Pro Leu Tyr Trp Gly Asp Ser Gly Val Leu Arg
225                 230                 235                 240

Asp Val Ala Ala Gly Ser Phe Ile Asp Val Ser Arg Tyr Ala Ser Asp
                245                 250                 255

Glu Glu Ala Ile Glu Ala Ile Leu Ala Ile Asp Asp Asp Tyr Asp Ser
            260                 265                 270

Tyr Arg Arg Tyr Arg Gly Thr Ala Pro Phe Leu Gly Thr Glu Asp Phe
            275                 280                 285

Tyr Phe Asp Ala Tyr Arg Leu Ala Glu Trp Ile Glu Ser Arg Leu
290                 295                 300

<210> SEQ ID NO 26
<211> LENGTH: 315
<212> TYPE: PRT
<213> ORGANISM: Algoriphagus sp. PR1

<400> SEQUENCE: 26

Met Val Leu Ile Lys Ile Lys Phe Val Asp His Tyr Asn Gly Phe Asn
1               5                   10                  15

Pro Glu Ser Asp Arg Ile Phe Thr Phe Leu Lys Arg His Phe Pro Val
            20                  25                  30

Val Leu Thr Glu Ser Asp Pro Asp Phe Ile Ile Tyr Ser Ser Trp Gly
        35                  40                  45

Ser Glu His Leu His Tyr Asp Cys Pro Lys Ile Phe Tyr Thr Gly Glu
    50                  55                  60

Asn His Arg Pro Asn Phe Phe Leu Cys Asp Tyr Ala Leu Gly Phe Asp
65                  70                  75                  80

Phe Leu Asn Arg Thr Asp Tyr Leu Arg Val Pro Leu Tyr Ser Ile Leu
                85                  90                  95

Trp Tyr Tyr Asp Phe Ser Thr Leu Leu Phe Pro Lys Gln Gln Gln Ile
            100                 105                 110

Leu Asp Gln Asn Pro Lys Thr Lys Phe Cys Cys Phe Val Ala Ser Asn
        115                 120                 125

Ala Gly Ala Met Glu Arg Asn Asn Phe Phe Lys Lys Leu Ser Asn Tyr
    130                 135                 140

Leu Pro Val Asp Ser Gly Gly Lys Val Leu Asn Asn Val Gly Gly Pro
145                 150                 155                 160

Val Pro Asp Lys Ile Gln Phe Met Lys Pro Tyr Lys Phe Cys Ile Ala
                165                 170                 175

Tyr Glu Asn Ser Ser Tyr Pro Gly Tyr Val Thr Glu Lys Ile Met Asp
            180                 185                 190

Cys Phe Ile Ala Gly Cys Ile Pro Ile Tyr Trp Gly Ser Thr Cys Ile
        195                 200                 205

Glu Lys Asp Phe Asn Pro Lys Arg Ile Leu Asn Arg Leu Asp Tyr Lys

```
                    210                 215                 220
Ser Asp Glu Glu Leu Ile Ala Glu Ile Lys Tyr Leu Asn Glu Asn His
225                 230                 235                 240

Ser Ala Tyr Asn Glu Phe Ile Ala Gln Pro Ile Phe Thr Asn Asn Gln
                245                 250                 255

Phe Thr Glu Tyr Phe Asp Glu Ser Arg Leu Val Lys Phe Phe Glu Lys
                    260                 265                 270

Ile Phe Asn Gly Pro Ser Glu Ser Arg Ser Lys Gly Ile Arg Lys Tyr
                275                 280                 285

Ile Gly Leu Ser Leu Arg Phe Asn Lys Met Ile Tyr Ser Arg Ile Lys
            290                 295                 300

Lys Lys Leu Gly Tyr Thr Gly Arg Val Trp Tyr
305                 310                 315
```

<210> SEQ ID NO 27
<211> LENGTH: 254
<212> TYPE: PRT
<213> ORGANISM: Helicobacter canis NCTC 12740

<400> SEQUENCE: 27

```
Met Gln Ser Pro His Pro Asn Lys Ser Pro Ile Arg Ile His Phe Cys
1               5                   10                  15

Asp Phe Gly Asp Met Gln Gly Ile Ala Lys Ala Ile Thr Ala Leu Leu
                20                  25                  30

Gln Arg His Tyr Thr Ile Thr Leu Asp Ser His Ser Pro Gln Tyr Leu
            35                  40                  45

Phe Tyr Ser Val Phe Gly Ser Glu His Ile Lys Tyr Asp Cys Val Arg
        50                  55                  60

Ile Phe Tyr Thr Gly Glu Asn Ile Thr Pro Asn Phe Thr Ile Cys Asp
65                  70                  75                  80

Tyr Ala Ile Gly Phe Asp His Leu His Phe Leu Asp Arg Tyr Leu Arg
                85                  90                  95

Tyr Pro Leu Tyr Leu Phe Tyr Glu Gln Asp Val Lys Arg Ala Ser Gln
            100                 105                 110

Lys His Lys Asp Ile Asp Glu Lys Leu Leu Ala Ser Lys Ser Arg Phe
        115                 120                 125

Cys Asn Phe Val Val Ser Asn Gly Asn Ala Asp Pro Tyr Arg Glu Gln
130                 135                 140

Val Phe Tyr Ala Leu Asn Ala Tyr Lys Arg Val Asp Ser Gly Gly Arg
145                 150                 155                 160

Tyr Leu Asn Asn Ile Gly Gly Ser Val Ala Asp Lys Phe Ala Phe Gln
                165                 170                 175

Ser Glu Cys Arg Phe Ser Leu Cys Phe Glu Asn Ser Ser Thr Pro Gly
            180                 185                 190

Tyr Leu Thr Glu Lys Leu Ile Gln Ala Ala Ala Gln Thr Ile Pro
        195                 200                 205

Ile Tyr Trp Gly Asp Pro Leu Ala Thr Lys Pro Leu Phe Asp Gly Gly
        210                 215                 220

Gly Gly Ile Asn Ala Lys Ala Phe Ile Asn Ala His Ser Phe Ser Ser
225                 230                 235                 240

Leu Glu Ser Leu Ile Glu His Ile Ala Glu Ile Glu Ala Asp
                245                 250
```

<210> SEQ ID NO 28
<211> LENGTH: 287

```
<212> TYPE: PRT
<213> ORGANISM: Anaeromyxobacter dehalogenans

<400> SEQUENCE: 28

Met Asn Pro Val Arg Leu Asp Phe Val Asp Phe Trp Pro Gly Phe Asp
1               5                   10                  15

Arg Arg Asn Asn Val Leu Leu Asp Val Leu Arg Thr Arg Phe Ala Val
                20                  25                  30

Glu Val Val Asp Asp Pro Asp Phe Val Phe Ala Asn Phe Gly Trp
            35                  40                  45

Arg His Trp Arg Tyr Arg Cys Thr Arg Val Phe Phe Thr Gly Glu Asn
        50                  55                  60

Val Arg Pro Asp Phe Arg His Cys Asp Phe Ala Leu Thr Phe Asp His
65                  70                  75                  80

Leu Pro Asp Glu Pro Arg His Leu Arg Trp Pro Leu Tyr Asn Leu Tyr
                85                  90                  95

Leu Gly Asp Pro Arg Phe Leu Leu Glu Arg Arg Arg Asp Val Asn Ala
            100                 105                 110

Ile Val Ala Glu Lys Thr Arg Phe Cys Asn Leu Val Cys Ser Asn Arg
        115                 120                 125

Ala Ala Arg Glu Arg Leu Arg Phe Phe Glu Lys Leu Ser Arg Tyr Lys
    130                 135                 140

Pro Val Asp Ser Gly Gly Arg Val Arg Asn Asn Val Gly Gly Pro Val
145                 150                 155                 160

Lys Asp Lys Leu Ala Phe Ile Arg Gln His Arg Phe Thr Ile Ala Phe
                165                 170                 175

Glu Asn Ala Ser Tyr Pro Gly Tyr Thr Thr Glu Lys Ile Val Glu Pro
            180                 185                 190

Met Arg Val Gly Ser Ile Pro Ile Tyr Trp Gly Asn Pro Leu Val His
        195                 200                 205

Leu Asp Phe Asp Leu Arg Ser Ile Val Ser Trp His Glu His Gly Ser
    210                 215                 220

Asp Glu Ala Ala Ile Glu Arg Val Ile Gln Ile Asp Arg Asp Glu Glu
225                 230                 235                 240

Leu Tyr Arg His Met Leu Leu Gln Pro Phe Leu Pro Glu Gly Arg Pro
                245                 250                 255

Thr Pro Tyr Ser Asp Pro Gly Val Leu Leu Asp Trp Leu Glu Arg Val
            260                 265                 270

Phe Ser Thr Pro Arg Arg Asp Ala Arg Pro Pro Arg Arg Trp Trp
        275                 280                 285

<210> SEQ ID NO 29
<211> LENGTH: 327
<212> TYPE: PRT
<213> ORGANISM: Coraliomargarita akajimensis

<400> SEQUENCE: 29

Met Lys Pro Thr Lys Arg Ile Ala Ile Val Asp Ala Gly Arg Thr Pro
1               5                   10                  15

Asp Ile Val His Ala Val Leu Pro Phe Ile Glu Glu Arg Tyr Asn Leu
                20                  25                  30

Glu Ile Thr Asp Asp Arg Asp Ala Asp Tyr Val Phe His Ser Cys Leu
            35                  40                  45

Gly His Glu Val Leu Lys Tyr Ser Gly Ile Arg Ile Phe Val Thr Gly
        50                  55                  60
```

Glu Cys Val Ser Pro Asp Phe Asn Ile Ser Asp Tyr Ala Leu Ala Phe
65                  70                  75                  80

Asp Pro Ile Asp Phe Gly Asp Arg Tyr Ile Arg Leu Pro Leu Ile Arg
            85                  90                  95

Leu Phe Thr Glu Ala Tyr Glu Ser Leu Cys Ala Pro Arg Ala Glu Pro
            100                 105                 110

Glu Gln Ile Leu Ala Lys Lys Asn Gly Phe Cys Ala Tyr Val Met Ser
            115                 120                 125

Asn Thr Lys Asn Ser Ala Pro Glu Arg Val Glu Leu Phe Glu Ala Leu
            130                 135                 140

Ser Arg Tyr Gln Pro Val Ala Ser Gly Gly Lys Trp Arg Asn Asn Val
145                 150                 155                 160

Gly Gly Pro Val Ala Asp Lys Ile Ala Phe Gln Ser Thr His Lys Phe
            165                 170                 175

Val Leu Ala Leu Glu Asn Glu Ser Tyr Pro Gly Tyr Leu Thr Glu Lys
            180                 185                 190

Phe Ala Gln Ala Ala Gln Ser Asn Ala Ile Pro Ile Tyr Trp Gly Asp
            195                 200                 205

Pro Thr Ile Thr Asp Ile Ile Asn Pro Arg Ala Phe Val Asn Val Arg
210                 215                 220

Asp Phe Gln Ser Thr Asp Ala Leu Val Ser His Ile Gln Ser Leu Asp
225                 230                 235                 240

Gln Asp Asp Ala Ala Tyr Leu Ser Met Leu Ser Glu Pro Trp Phe Arg
            245                 250                 255

Gly Gly Lys Glu Pro Glu Glu Trp Arg Ala Gln Gly Tyr Arg Asp Phe
            260                 265                 270

Leu Ala Asn Ile Phe Glu Gln Pro Lys Glu Arg Ala Tyr Arg Arg Asn
            275                 280                 285

Arg Ser Arg Trp Gly Lys Lys Tyr Glu Gly Arg Tyr Tyr Asp Met Ala
            290                 295                 300

Phe Arg Pro Gln Arg Gln Phe Ala Thr Leu Thr Lys Thr Ala Leu Arg
305                 310                 315                 320

Arg Leu Arg His Ser Gly Gln
                325

<210> SEQ ID NO 30
<211> LENGTH: 284
<212> TYPE: PRT
<213> ORGANISM: Helicobacter fennelliae MRY12-0050

<400> SEQUENCE: 30

Met Asp Trp Trp Glu Gln Asp Thr Lys Glu Asn Phe Tyr Lys Asn Pro
1               5                   10                  15

Phe Ile Gln Ala Leu Ser Gln Lys Tyr Asn Ile Glu Tyr Ser Asn Lys
                20                  25                  30

Pro Asp Phe Leu Leu Tyr Gly Pro Phe Gly Gln Asn Asn Leu Gln Phe
            35                  40                  45

Pro Lys Glu Val Val Arg Ile Phe Tyr Thr Gly Glu Asn Thr Arg Thr
        50                  55                  60

Asp Trp Asn Ile Ala Asp Tyr Gly Ile Asp Phe Asp Phe Met Asp Phe
65                  70                  75                  80

Gly Asp Arg His Leu Cys Met Pro Leu Phe Phe Leu Pro Gly Glu Cys
            85                  90                  95

Gly Ile Ser Ser Arg Ala Ile Thr Lys His Leu Arg Ala Glu Gln Ile
            100                 105                 110

Phe Gln Glu Lys Arg Glu Lys Phe Cys Ala Phe Leu Val Ser Asn Gly
                115                 120                 125

Ser Asn His Ile Arg Asn Thr Ala Phe Lys Lys Leu Cys Ala Tyr Lys
        130                 135                 140

Lys Val Asp Ser Gly Arg Tyr Leu Asn Asn Ile Gly Gly Arg Ile
145                 150                 155                 160

Gly Asp Arg Phe Lys Asp Phe Glu Lys Ser Lys Tyr Glu Trp Leu Leu
                165                 170                 175

Gly Tyr Lys Phe Asn Leu Cys Phe Glu Asn Ser Ser Tyr Pro Gly Tyr
            180                 185                 190

Val Thr Glu Lys Ile Leu Gln Ala Tyr Glu Ala Gly Cys Ile Pro Ile
            195                 200                 205

Tyr Trp Gly Asp Ser Thr Leu Cys Asp Val Arg Tyr Ala Lys Tyr Arg
    210                 215                 220

Pro Thr Phe Asn Pro Lys Ala Phe Val Asn Ala His Asp Phe Ala Asn
225                 230                 235                 240

Leu Asp Glu Leu Val Gln Glu Val Arg Arg Ile Asp Asn Asp Asn Glu
                245                 250                 255

Ala Tyr Leu Ala Met Leu Lys Glu Pro Ile Phe Leu Asp Ser Thr Ile
            260                 265                 270

Asp Thr His Val Leu Gly Gly Gly Ala Ser Thr Ser
            275                 280

<210> SEQ ID NO 31
<211> LENGTH: 322
<212> TYPE: PRT
<213> ORGANISM: Prevotella sp. CAG:873

<400> SEQUENCE: 31

Met Gly Asn Arg Thr Val Thr Val Lys Phe Val Asp Phe Trp Gln Ser
1               5                   10                  15

Phe Asp Trp Arg Asp Asn Arg Phe Val Arg Ala Leu Arg Ser Gln Arg
                20                  25                  30

Gln Val Thr Val Leu Glu Pro Ser Pro Glu Val Pro Asp Ile Leu
            35                  40                  45

Phe Tyr Ser Arg Gly Pro Gly Cys Asp His Leu Arg Tyr Asp Cys Leu
    50                  55                  60

Lys Val Tyr Phe Thr Gly Glu Asn Asp Phe Pro Asp Phe Asn Glu Cys
65                  70                  75                  80

Asp Tyr Ala Leu Ser Phe Tyr Glu Cys Asp Cys Gly Gly Arg Asn Leu
                85                  90                  95

Arg Tyr Pro Leu Tyr Met Leu Tyr Glu Cys Asp Glu Ala Ala Cys Pro
            100                 105                 110

Pro Val Leu Ser Asp Ala Glu Ala Leu Asp Arg Gly Phe Cys Ser Leu
        115                 120                 125

Val Met Ser Asn Ala Ser Asn Cys His Pro Arg Arg Leu Glu Ile Val
        130                 135                 140

Asp Ala Ile Glu Ala Tyr Arg Pro Leu Ala Tyr Gly Gly Ala Phe Arg
145                 150                 155                 160

Asn Asn Val Gly Ser Arg Val Glu Asp Lys Ile Ser Phe Ile Ser Gly
                165                 170                 175

Tyr Lys Phe Asn Leu Ala Leu Glu Asn Ser Val Met Pro Gly Tyr Val
            180                 185                 190

Thr Glu Lys Leu Leu Glu Pro Leu Ala Ala Ala Thr Val Pro Ile Tyr

```
                   195                 200                 205
Trp Gly Ala Asp Ala Ala Lys His Asp Phe Asn Pro Glu Ser Phe Val
            210                 215                 220

Cys Val Asn Asp Tyr Ala Thr Phe Asp Ser Leu Val Ala Glu Leu Arg
225                 230                 235                 240

Arg Leu Asp Asn Asp Ser Ala Ala Tyr Leu Ala Met Leu Arg Ala Pro
                245                 250                 255

Ser His Thr Gly Asp Thr Val Ala Arg Met Asp Thr Arg Leu Ala Glu
            260                 265                 270

Phe Leu Asn Ala Ile Ala Asp Arg Pro Glu Arg Arg Ile Ser Pro Tyr
                275                 280                 285

Gly Glu Ile His Asn Leu Gln Arg Arg Asn Arg Ala Leu Val Pro Leu
            290                 295                 300

Trp His Ser Arg Val Gly Arg Ala Ala Ala Arg Leu Leu Gly His Ile
305                 310                 315                 320

Ala Lys

<210> SEQ ID NO 32
<211> LENGTH: 301
<212> TYPE: PRT
<213> ORGANISM: Flavobacterium sp. ACAM 123

<400> SEQUENCE: 32

Arg Ile Phe Gly Leu Val Phe Asp Lys Thr Asn Asn Tyr Phe Tyr Asn
1               5                   10                  15

Leu Leu Val Gln Lys Tyr Ile Val Asn Ile Asp Glu Asn Pro Asp Phe
            20                  25                  30

Leu Phe Tyr Ser Cys Tyr Ser Asn Asp Tyr Leu Asn Tyr Asn Cys Thr
        35                  40                  45

Arg Ile Phe Phe Thr Gly Glu Asn Val Arg Pro Asp Phe Leu Ala Cys
50                  55                  60

Asp Phe Ala Phe Ser Cys Asp Tyr Asn Lys Gln Lys Asn His Phe Arg
65                  70                  75                  80

Leu Pro Leu Tyr Ser Leu Tyr Ile Asp His His Asn Leu Leu Asp Lys
                85                  90                  95

Leu Gln Ser Thr Leu Asn Lys Glu Glu Ala Arg Arg Val Trp Gln Ala
            100                 105                 110

Lys Ser Lys Phe Cys Cys Met Val Val Ser Asn Pro Lys Cys Val Glu
        115                 120                 125

Arg Ile Glu Phe Glu Asn Leu Ser Lys Val Lys Gln Val Asp Ser
130                 135                 140

Gly Gly Ser Val Leu Asn Asn Val Gly Gly Arg Val Ala Asp Lys Ala
145                 150                 155                 160

Glu Phe Ile Lys Asp Tyr Lys Phe Val Ile Ser Phe Glu Asn Glu Ser
                165                 170                 175

Tyr Asp Gly Tyr Thr Thr Glu Lys Ile Leu Glu Pro Ile Leu Met Asp
            180                 185                 190

Cys Ile Pro Ile Tyr Trp Gly Asn Lys Leu Val Asp Lys Asp Phe Asn
        195                 200                 205

Ala Lys Arg Phe Ile Asn Tyr Asn Thr Phe Lys Thr Glu Asn Lys Leu
            210                 215                 220

Ile Glu Arg Leu Leu Glu Ile Asp Gln Asn Glu Glu Leu Ala Ile Ala
225                 230                 235                 240

Met Leu Leu Glu Gln Pro Phe Asn Lys Asp Lys Lys Thr His Glu Glu
```

```
                245                 250                 255
Glu His Gln Gln Val Leu Asp Ile Ile Ser Asn Met Ile Glu Val Asp
                260                 265                 270
Lys Lys Pro Ile Ala Gln Gln Leu Trp Lys Tyr Val His Lys Ser Lys
                275                 280                 285
Leu Phe Ala Ala Lys Phe Lys Arg Phe Ile Lys Ile
            290                 295                 300

<210> SEQ ID NO 33
<211> LENGTH: 311
<212> TYPE: PRT
<213> ORGANISM: Azospirillum lipoferum

<400> SEQUENCE: 33

Met Lys Glu Ile Lys Ile Asn Phe Val Asp Phe Trp Pro Gly Phe Asn
1               5                   10                  15
Lys Thr Asn Asn Tyr Phe Tyr Asn Leu Leu Ile Gln Lys Tyr Lys Val
                20                  25                  30
Ser Ile Asp Ala Asn Pro Asp Leu Leu Phe Tyr Ser Cys Tyr Asn Asn
            35                  40                  45
Asp Tyr Leu Asn Phe Asp Cys Thr Arg Ile Phe Tyr Thr Ala Glu Asn
50                  55                  60
Ile Arg Pro Asp Phe Ser Ala Cys Asp Phe Ala Phe Ser Tyr Gly Tyr
65                  70                  75                  80
Asn Ala Lys Ile Asn His Phe Arg Leu Pro Leu Tyr Ser Met Tyr Ile
                85                  90                  95
Asp Leu Leu Asn Met Lys Asp Lys Ile Glu Ala Thr Leu Ser Arg Glu
                100                 105                 110
Glu Ala Gln Lys Ile Trp Lys Thr Lys Ser Lys Phe Cys Cys Met Val
            115                 120                 125
Val Ser Asn Ala Thr Gly Thr Lys Arg Leu Asp Phe Phe Lys Asn Leu
130                 135                 140
Ser Lys Ile Lys Gln Val Asp Ser Gly Gly Gly Ile Phe Asn Asn Ile
145                 150                 155                 160
Gly Gly Lys Val Val Asp Lys Leu Glu Phe Ile Lys Asp Tyr Lys Phe
                165                 170                 175
Val Ile Ser Phe Glu Asn Gly Gln Asn Asp Gly Tyr Thr Thr Glu Lys
                180                 185                 190
Ile Leu Glu Pro Ile Tyr Lys Asp Cys Ile Pro Ile Tyr Trp Gly Asn
            195                 200                 205
Lys Leu Val Asp Lys Asp Phe Asn Ser Lys Arg Phe Leu Asp Tyr Ser
210                 215                 220
Lys Phe Glu Cys Glu Lys Asp Leu Ile Asp Lys Leu Leu Glu Met Glu
225                 230                 235                 240
Leu Asp Asp Glu Leu Ala Ile Ser Met Leu Met Gln Pro Ala Phe Gly
                245                 250                 255
Glu Asn Lys Arg Pro His Glu Glu Arg Ala Glu Val Leu Arg Ile
                260                 265                 270
Leu Gly Arg Ile Ile Glu Asn Pro Glu Lys Pro Ile Ala Arg Gln Leu
            275                 280                 285
Trp Lys Tyr Ile His Leu Leu Lys Arg Lys Tyr Arg Lys Asn Lys Lys
            290                 295                 300
Arg Ile Lys Arg Ile Leu Asn
305                 310
```

<210> SEQ ID NO 34
<211> LENGTH: 324
<212> TYPE: PRT
<213> ORGANISM: Azospirillum lipoferum

<400> SEQUENCE: 34

Met Lys Lys Val Lys Val Lys Phe Val Asp Thr Tyr Gly Lys Gln Gln
1               5                   10                  15

Lys Tyr Leu Glu Lys Leu Leu Gly Asp Asp Ile Glu Leu Glu Tyr Ser
            20                  25                  30

Asp Glu Pro Asp Tyr Leu Phe Tyr Gly Val Phe Gly Ser Gly Met Glu
        35                  40                  45

His Tyr Lys Tyr Lys Asn Cys Val Lys Ile Phe Phe Ala Ser Glu Gly
    50                  55                  60

Val Ile Pro Asp Phe Asn Glu Cys Asp Tyr Ala Ile Ala Glu Tyr Pro
65                  70                  75                  80

Met Thr Val Gly Asp Arg Tyr Phe Cys Lys Pro Tyr Met Ala Pro Lys
                85                  90                  95

Glu Ala Asp Phe Ser Val Phe Asp Gly Lys Ala Asp Tyr Leu Gly Arg
            100                 105                 110

Lys Phe Cys Asn Phe Val Phe Ser Asn Glu Thr Asn Gly Arg Gly Ala
        115                 120                 125

Val Leu Arg Lys Gln Phe Cys Gln Lys Leu Met Glu Tyr Lys His Val
130                 135                 140

Asp Cys Pro Gly Lys Val Leu Asn Asn Met Lys Asp Ala Ile Glu Pro
145                 150                 155                 160

Arg Asn Gly Lys Trp Phe His Gly Lys Leu Asp Phe Ile Lys Asp Tyr
                165                 170                 175

Lys Phe Thr Ile Ala Phe Glu Asn Val Asn Thr Pro Gly Met Val Ser
            180                 185                 190

Glu Lys Ile Tyr Asn Ala Phe Gln Ala Arg Thr Val Pro Ile Tyr Trp
        195                 200                 205

Gly Pro Asp Asp Val Asn Lys Ile Tyr Asn Pro Lys Ser Phe Ile Asn
    210                 215                 220

Cys Ser Gly Leu Thr Ile Asp Glu Met Val Lys Lys Val Ala Glu Val
225                 230                 235                 240

Asp Ser Asn Asp Glu Leu Tyr Met Asp Met Leu Arg Gln Asn Pro Ile
                245                 250                 255

Ala Glu Gly Phe Asn Leu Asn Trp Glu Glu Asp Met Ala Arg Phe Leu
            260                 265                 270

Arg Gly Ile Ile Leu Glu Asn Lys Asp Tyr Tyr Asp Lys Asp Pro Leu
        275                 280                 285

Gly Trp Asp Ser Gly Asn Lys Ala Ala Lys Glu Leu Ile Ser Leu Glu
    290                 295                 300

Asp Thr Met Leu Tyr Lys Leu His Lys Gly Arg Glu Lys Val Ala Lys
305                 310                 315                 320

Lys Leu Lys Arg

<210> SEQ ID NO 35
<211> LENGTH: 369
<212> TYPE: PRT
<213> ORGANISM: Helicobacter pylori

<400> SEQUENCE: 35

Met Phe Gln Pro Leu Leu Asp Ala Phe Ile Glu Ser Ala Ser Ile Lys

```
1               5                   10                  15
Lys Lys Leu Pro Leu Asn Leu Pro Pro Leu Lys Ile Ala Val Ala
                20                  25                  30

Asn Trp Phe Asn Gly Ser Lys Glu Phe Lys Ala Ser Val Leu Tyr Phe
                35                  40                  45

Ile Leu Lys Gln Arg Tyr Lys Ile Ile Leu His Ser Asn Pro Asn Glu
        50                  55                  60

Pro Ser Asp Leu Val Phe Gly Asn Pro Leu Gly Gln Ala Arg Lys Ile
65                  70                  75                  80

Leu Ser Tyr Gln Asn Thr Lys Arg Val Phe Tyr Thr Gly Glu Asn Glu
                85                  90                  95

Ala Pro Asn Phe Asn Leu Phe Asp Tyr Ala Ile Gly Phe Asp Glu Leu
                100                 105                 110

Asp Phe Asn Asp Arg Tyr Leu Arg Met Pro Leu Tyr Tyr Ala Tyr Leu
            115                 120                 125

His Tyr Lys Ala Glu Ile Val Asn Asp Thr Thr Ser Pro Tyr Lys Leu
        130                 135                 140

Lys Ala Asp Ser Leu Tyr Thr Leu Lys Lys Pro Ser His Lys Phe Lys
145                 150                 155                 160

Glu Asn His Pro His Leu Cys Ala Leu Ile His Ser Glu Ser Asp Pro
                165                 170                 175

Leu Lys Arg Gly Phe Ala Ser Phe Val Ala Ser Asn Pro Asn Ala Pro
            180                 185                 190

Ile Arg Asn Ala Phe Tyr Asp Ala Leu Asn Ser Ile Glu Pro Val Ala
        195                 200                 205

Gly Gly Gly Ser Val Lys Asn Thr Leu Gly Tyr Lys Val Lys Asn Lys
210                 215                 220

Asn Glu Phe Leu Ser Gln Tyr Lys Phe Asn Leu Cys Phe Glu Asn Ser
225                 230                 235                 240

Gln Gly Tyr Gly Tyr Val Thr Glu Lys Ile Leu Asp Ala Tyr Phe Ser
                245                 250                 255

His Thr Ile Pro Ile Tyr Trp Gly Ser Pro Ser Val Ala Lys Asp Phe
                260                 265                 270

Asn Pro Lys Ser Phe Val Asn Val His Asp Phe Asn Asn Phe Asp Glu
            275                 280                 285

Ala Ile Asp Tyr Ile Arg Tyr Leu His Thr His Gln Asn Ala Tyr Leu
        290                 295                 300

Asp Met Leu Tyr Glu Asn Pro Leu Asn Thr Leu Asp Gly Lys Ala Ser
305                 310                 315                 320

Phe Tyr Gln Asp Leu Ser Phe Glu Lys Ile Leu Asp Phe Phe Lys Asn
                325                 330                 335

Ile Leu Glu Asn Asp Thr Ile Tyr His Cys Asn Asp Ala His Tyr Ser
            340                 345                 350

Ala Leu His Arg Asp Leu Asn Glu Pro Leu Val Ser Val Asp Asp Leu
        355                 360                 365

Arg

<210> SEQ ID NO 36
<211> LENGTH: 309
<212> TYPE: PRT
<213> ORGANISM: Verrucomicrobia bacterium SCGC AAA300-K03

<400> SEQUENCE: 36

Met Leu Asn Gln Ile Lys Ile Asn Tyr Thr Asp Phe Tyr Gly Asp Lys
```

1 5 10 15

Asn Tyr Glu Arg Asn Pro Phe His Asn Phe Leu Ser Ser His Phe Asn
20 25 30

Leu Glu Leu Ser Glu Glu Pro Asp Phe Leu Ile His Gly Val Tyr Gly
35 40 45

Gln Asp Tyr Leu Asn Tyr Asn Cys Val Arg Ile Leu Tyr Ser Ala Glu
50 55 60

Asn Met Ile Pro Asp Phe Lys Thr Tyr Asp Tyr Ser Leu Thr Phe Cys
65 70 75 80

Lys Ser Ser Phe Gln Asp Arg Asn Trp Arg Val Pro Leu Tyr Ala Val
85 90 95

Trp Asn Asp Leu Ser Ile Gln Leu Asp Ser His Leu Gly Phe Arg Asn
100 105 110

Ala Thr Asn Leu Ser Gln Asn Arg Asp Val Phe Cys Ser Phe Val Val
115 120 125

Ser Asn Pro Tyr Cys Ser Phe Arg Asn Asn Leu Phe Lys Arg Leu Glu
130 135 140

Lys Tyr Lys Phe Val His Ser Gly Gly Gly Val Phe Asn Asn Ser Gly
145 150 155 160

Gly Lys Thr Gly Asn Lys Leu His Phe Ile Arg Asn Ser Lys Phe Asn
165 170 175

Ile Ala Cys Glu Asn Gln Ser Tyr Pro Gly Tyr Thr Thr Glu Lys Ile
180 185 190

Leu Glu Ala Phe Leu Ala Gly Cys Ile Pro Val Tyr Trp Gly Asn Pro
195 200 205

Glu Ile Ala His Glu Phe Asn Glu Lys Ala Phe Ile Asn Cys His Asn
210 215 220

Tyr Lys Ser Ile Asn Glu Val Ala Asp Arg Ile Ile Glu Ile Asp Gln
225 230 235 240

Asn Lys Ala Leu Tyr Leu Asp Tyr Leu Ser Gln Pro Ile Phe Tyr Asn
245 250 255

Asp Thr Ile Pro Asp Asp Ala Ser His Ser Arg Ile Val Thr Ile Phe
260 265 270

Asn Asn Ile Phe Tyr Asn Thr Arg Pro Ser Arg Ile Ala Cys Ser Lys
275 280 285

Leu Pro Ser Lys Ile Phe Asn Ile Lys Lys Gln Leu Lys Lys Leu Ala
290 295 300

Gly Lys Tyr Ser Arg
305

<210> SEQ ID NO 37
<211> LENGTH: 737
<212> TYPE: PRT
<213> ORGANISM: Clostridium citroniae

<400> SEQUENCE: 37

Met Glu Lys Ile Lys Thr Lys Ile Ile Asn Lys Ile Thr Lys Ile Asn
1 5 10 15

Leu Ile Gly Ile Ala Leu Val Phe Tyr Thr Ser Val Trp Arg Gly Tyr
20 25 30

Lys Glu Tyr Cys Arg Leu Lys Lys Lys His Gly Asn Leu Pro Ile Ile
35 40 45

Thr Pro Thr Phe Lys Gly Thr Gly Asp Phe Tyr Met Val Ala Lys Tyr
50 55 60

```
Phe Pro Gln Trp Leu Lys Phe Lys Lys Ile Asp Lys Tyr Met Met Ile
 65                  70                  75                  80

Ala Gly Gly Ala Ser Glu Ile Arg Val Leu Glu Leu Phe Pro Gln Trp
                 85                  90                  95

Phe Ser Asn Ala Gln Tyr Glu Ile Leu Ser Trp Glu His Tyr Thr Tyr
            100                 105                 110

Leu Ile His Met Arg Leu Phe Trp Gly Val Glu Lys Ser Asp Ile Tyr
            115                 120                 125

Val Leu Asn His Ile Ala Asn Phe Gly Gly Glu His Thr Asn Tyr Leu
            130                 135                 140

Trp Ile Thr Trp Asn Leu Met Gly Tyr Lys Gly Leu Ser Leu Leu Asp
145                 150                 155                 160

Phe Tyr Leu Ile Tyr Gly Cys Lys Leu Ser Lys Leu Glu Lys Pro Leu
                165                 170                 175

Ile Pro Ile Phe Glu Thr Asp Ser Asn Lys Ile Asp Lys Ile Phe Lys
            180                 185                 190

Tyr Lys Lys Leu Lys Pro Gly Lys Thr Val Met Ile Ser Pro Tyr Ser
            195                 200                 205

Thr Gly Asn Gly Thr Phe His Val Ser Phe Trp Asn Ser Ile Val Lys
210                 215                 220

Gln Leu Gln Leu Ser Gly Tyr Ser Val Cys Thr Asn Cys Phe Gly Ser
225                 230                 235                 240

Glu Lys Pro Leu Ala Asn Thr Val Lys Leu Gly Leu Asp Tyr Arg Asp
                245                 250                 255

Leu Val Pro Phe Met Asp Lys Ala Gly Phe Ala Ile Gly Ile Arg Ser
            260                 265                 270

Gly Phe Phe Asp Ile Ile Ser Ser Thr Cys Lys Lys Ile Ile Ile
            275                 280                 285

His Thr Phe Lys Ala Asn His Trp Pro Asn Gly Asn Ser Leu Pro Tyr
            290                 295                 300

Thr Gly Leu Lys His Leu Gly Leu Cys Asn Asp Ala Ile Glu Tyr Glu
305                 310                 315                 320

Leu Asn Ser Asn Glu Ser Asn Phe Asp Val Ile Arg Arg Ser Ile Leu
                325                 330                 335

Gly Leu Phe Ala Ile His Val Ala Ser Ser Lys Lys Thr Ile Lys Ile
            340                 345                 350

Lys Tyr Val Asp Val Pro Pro Asp Phe Asn Lys Glu Lys Ile Trp Ile
            355                 360                 365

Thr Arg Val Leu Arg Glu Lys Tyr Asn Val Val Phe Ser Asp Asn Pro
370                 375                 380

Glu Phe Leu Phe Tyr Ser Val Phe Gly Leu Thr Phe Asp Gln Tyr Lys
385                 390                 395                 400

Asn Cys Ile Lys Ile Phe Phe Thr Gly Glu Asp Thr Ile Pro Asn Phe
                405                 410                 415

Asn Glu Cys Asp Tyr Ala Met Cys His Asp Arg Leu Glu Leu Gly Asp
            420                 425                 430

Arg Tyr Ile Arg Ala Asp Val Gly Glu Arg Tyr Gly Thr Pro Ile Gly
            435                 440                 445

Asn Leu Glu Pro Asp Trp Ile Glu Lys Gly Ile Ser Ile Ser Gly Trp
            450                 455                 460

Ile Asn Ser Ser Leu Ile Asp Ile Lys Asp Lys Ile Gln Asn Arg Ser
465                 470                 475                 480

Ile Val Ser Glu Lys Leu Ile Asn Arg Arg Phe Cys Asn Phe Ile Tyr
```

```
                    485                 490                 495
Ser Asn Glu Ser Phe Gly Glu Gly Ala Val Leu Arg Lys Lys Phe Cys
                500                 505                 510

Leu Glu Leu Met Lys Tyr Arg Arg Val Asp Cys Pro Gly Arg Val Leu
            515                 520                 525

Asn Asn Met Lys Asp Gly Leu Gly Ile Arg Trp Ser Val Lys Asp Gly
        530                 535                 540

Arg Asp Ser Ile Val Asp Asn Trp Thr Ser Thr Lys Leu Glu Phe Ile
545                 550                 555                 560

Lys Asn Tyr Lys Phe Thr Ile Ala Phe Glu Asn Thr Ala Ile Pro Gly
                565                 570                 575

His Thr Thr Glu Lys Leu Ile His Pro Phe Tyr Ala Tyr Ser Ile Pro
            580                 585                 590

Ile Tyr Trp Gly Asn Pro Asp Val Val Ala Asp Phe Asn Pro Lys Ala
        595                 600                 605

Phe Ile Asn Cys Asn Asp Tyr Asn Asn Asp Trp Arg Ala Val Cys Lys
610                 615                 620

Arg Ile Lys Glu Leu Asp Gln Asp His Glu Gln Tyr Leu Glu Met Leu
625                 630                 635                 640

Arg Gln Pro Pro Met Gln Pro Asp Phe Asp Phe Gly Ser Glu Glu Lys
                645                 650                 655

Ala Lys Gln Phe Leu Tyr Asn Ile Val Glu Lys Gly Tyr Lys Pro Tyr
            660                 665                 670

Thr Lys Ser Ser Leu Ala Phe Thr Ala Pro Asn Val Ala Arg Asn Ser
        675                 680                 685

Tyr His Glu Leu Met Glu Ile Lys Thr Ser Asn Ser Trp Lys Val Ala
690                 695                 700

Arg Arg Ile Gln Ala Phe Leu Gly Thr Lys Trp Gly Trp Phe Pro Arg
705                 710                 715                 720

Gln Leu Cys Leu Ala Leu Leu Asn Val Arg Asn Arg Leu Val Lys Lys
                725                 730                 735

Lys
```

<210> SEQ ID NO 38
<211> LENGTH: 386
<212> TYPE: PRT
<213> ORGANISM: Helicobacter bilis

<400> SEQUENCE: 38

```
Met Gln Lys Gln Val Lys Met Arg Val Leu Asp Trp Trp Asn Lys
1               5                   10                  15

Asp Cys Glu Glu Asn Phe Tyr Asn Asn Phe Ile Gln Ile Leu Gln
                20                  25                  30

Lys Lys Tyr Asp Val Val Tyr Ser Asp Lys Pro Asp Phe Ile Leu Tyr
            35                  40                  45

Gly Pro Phe Gly Tyr Glu His Leu Lys Tyr Asp Cys Val Arg Ile Phe
        50                  55                  60

His Thr Gly Glu Asn Ile Arg Pro Asp Tyr Asn Ile Ala Asp Tyr Ser
65                  70                  75                  80

Met Asp Phe Asp Tyr Ile Glu Phe Glu Asp Arg His Leu Arg Leu Pro
                85                  90                  95

His Met Phe Trp Val Phe Cys Asp Glu Met Arg Gln Lys Glu Met Asp
            100                 105                 110

Asn Arg Ile Ser Leu Leu Asp Lys Lys Glu Lys Phe Cys Gly Phe Met
```

```
            115                 120                 125
Val Ser Asn Asn Ala Leu Thr Asp Lys Arg Asp Met Phe Phe Glu Ala
            130                 135                 140

Leu Ser Lys Tyr Lys Arg Val Asp Ser Gly Gly Arg Trp Lys Asn Asn
145                 150                 155                 160

Met Gly Gly Asn Val Asp Asp Lys Ile Glu Trp Leu Lys Ser Tyr Lys
                165                 170                 175

Phe Asn Leu Cys Phe Glu Asn Ser Ser Tyr Pro Gly Tyr Leu Thr Glu
            180                 185                 190

Lys Leu Phe Asp Ala Phe Leu Ala Gly Cys Val Pro Ile Tyr Trp Gly
            195                 200                 205

Asp Thr Ser Leu Lys Ile His Lys Asn Thr Cys Ala Asp Ser Lys Asn
            210                 215                 220

Ser Glu Asn Ile Asn Asn Gln Gly Gly Ser Asn Asp Ala Phe Asp
225                 230                 235                 240

Met Arg Ile Pro Asn Ile Ser His Ser Leu Ile Asp Tyr Glu Ile Asn
                245                 250                 255

Pro Lys Ala Phe Ile Asn Ala His Asn Phe Pro Thr Phe Gln Asp Leu
            260                 265                 270

Ile Asp Glu Ile Lys Arg Ile Asp Asn Asp Ser Tyr Ala Phe Glu Ser
            275                 280                 285

Met Leu Arg Glu Pro Ile Phe Leu Asn Asp Phe Asn Pro His Glu Phe
            290                 295                 300

Tyr Ala Thr Lys Ile Ala Ala Phe Leu Asn Arg Ile Val Ser Gln Gly
305                 310                 315                 320

Ala Ile Gln Ala Lys Arg Arg Gly Asp Gly Phe Leu Leu Lys Ala Tyr
                325                 330                 335

Arg Glu Phe Gln Ser Ala Ile Ala Glu Asn Thr Gln Ile Ser Ser Gly
            340                 345                 350

Phe Phe Ser Tyr Cys Val Lys His Gly Arg Val Ile Gln Ala Ile Arg
            355                 360                 365

Asp Ser Ser Lys Leu Pro Lys Arg Phe Ser Arg Phe Ile Arg Arg Thr
            370                 375                 380

Arg Lys
385

<210> SEQ ID NO 39
<211> LENGTH: 319
<212> TYPE: PRT
<213> ORGANISM: Verrucomicrobia bacterium SCGC AAA300-N18

<400> SEQUENCE: 39

Met Val Ser Asn Gln Ile Lys Ile Gln Phe Thr Asp Phe Tyr Gln Ile
1               5                   10                  15

Pro Asn Glu Glu Glu Asn Tyr Leu Tyr Lys Tyr Leu Lys Gln Tyr Phe
                20                  25                  30

Asn Leu Glu Leu Ser Asp Asp Pro Asp Val Val Ile Tyr Ser Asn Tyr
            35                  40                  45

Gly Phe Glu Tyr Lys Gln Tyr Glu Cys Leu Arg Val Leu Phe Cys Ala
        50                  55                  60

Glu Tyr Ala Ile Pro Asp Ile Glu Asp Cys Asp Tyr Cys Phe Ser Gln
65                  70                  75                  80

His His Ala Ser Tyr Trp Gly Lys Asn Tyr Arg Leu Pro Met Tyr Val
                85                  90                  95
```

```
Phe Trp Gln Asn Phe Ser Leu Lys Phe Glu Leu Leu Arg Pro Val
                100                 105                 110

Asp Tyr Glu Glu Ile Arg Lys Gln Asp Arg Gly Phe Cys Ser Phe Val
            115                 120                 125

Val Ser Ser Pro Leu Gly Ser Gln Thr Arg Val Asn Phe Met His Glu
        130                 135                 140

Leu Ser Ser Tyr Lys Lys Val Asp Ser Gly Gly Lys Leu Leu Asn Asn
145                 150                 155                 160

Ile Gly Gly Pro Val Ala Asn Lys Arg Asp Phe Leu Lys Lys Tyr Lys
                165                 170                 175

Phe Asn Ile Ala Phe Ala Asn Gly Leu Ala Asp Gly Tyr Ala Asp Glu
            180                 185                 190

Lys Ile Val Asp Pro Met Phe Val Asp Ser Ile Pro Ile Phe Trp Gly
        195                 200                 205

Asn Pro Arg Ile Ala Glu Asp Phe Asn Pro Ala Ser Phe Val Asn Cys
        210                 215                 220

His Asp Tyr Asp Asn Phe Asp Ser Val Ile Lys Glu Val Ile Arg Ile
225                 230                 235                 240

Asp Lys Asn Glu Asp Val Tyr Arg Ser Tyr Leu Glu Gln Pro Trp Phe
                245                 250                 255

Pro Glu Asn Lys Leu Thr Arg Tyr Val Asp Leu Asp His Leu Gln Asn
            260                 265                 270

Arg Phe Arg Tyr Ile Phe Ser Gln Ile Gly Lys Lys Val Pro Ala Ala
        275                 280                 285

Arg Ser Lys Arg Arg Phe Tyr Lys Leu Leu Lys Lys Leu Lys Pro
        290                 295                 300

Leu Thr Pro Ile Val Gln Gln Trp Gly Asp Tyr Gln Pro Ser Asn
305                 310                 315

<210> SEQ ID NO 40
<211> LENGTH: 609
<212> TYPE: PRT
<213> ORGANISM: Moumouvirus goulette

<400> SEQUENCE: 40

Met Asp Lys Phe Lys Ile Val Cys Ile Asn Leu Ala Arg Arg Gln Asp
1               5                   10                  15

Arg Lys Asp Leu Ile Thr Asn Lys Leu Ile Asn Gln Asn Met Ser Asn
            20                  25                  30

Phe Glu Phe Phe Glu Ala Val Asp Gly Ser Gln Ile Asp Pro Tyr Asp
        35                  40                  45

Glu Arg Leu Asn Leu Phe Lys His Ser Val Ser Gly Leu Leu Arg Arg
50                  55                  60

Gly Val Thr Gly Cys Ala Leu Ser His Tyr Thr Ile Trp Lys Lys Leu
65                  70                  75                  80

Val Asn Asp Pro Asp Tyr Asn Thr Tyr Leu Val Ile Glu Asp Asp Ile
                85                  90                  95

Asn Phe Gly Pro Asp Phe Lys Phe Gly Leu Glu Lys Ile Leu Glu Lys
            100                 105                 110

Lys Pro Asn Tyr Gly Ile Ile Leu Leu Gly Met Thr Leu Glu Leu Glu
        115                 120                 125

Lys Lys Ala Glu Thr Lys His Leu Tyr Gln Tyr Asp Thr Ser Tyr Thr
        130                 135                 140

Ile His Asn Leu Asn Arg Asp Leu Tyr Cys Gly Gly Ala Phe Gly Tyr
145                 150                 155                 160
```

-continued

```
Ile Ile Ser Lys Ser Ala Ala Lys Tyr Leu Val Asp Tyr Ile Ser His
            165                 170                 175

Asn Gly Ile Arg Met Val Ile Asp Tyr Leu Met Phe Arg Ser Gly Val
        180                 185                 190

Pro Met Tyr Glu Ser His Pro His Leu Val Phe Thr Asp Ala Val Gln
            195                 200                 205

His Ser Ile His Tyr Val Asp Ser Asp Ile Gln His Asp His Glu Lys
210                 215                 220

Ile Lys Tyr Asn Lys Leu Pro Asn Asp Tyr Gln Phe Asp Asp Tyr Ile
225                 230                 235                 240

Phe Leu Ser Asn Arg Asp Ser Pro Arg Gly Asp Ile Arg Glu Ile Cys
            245                 250                 255

Ala Asp Ile Thr Thr Leu Lys Lys Ala Ala Asp Met Thr Ser Glu Cys
            260                 265                 270

Ile Ala Phe Asn Thr Tyr Gly Trp Leu Lys Asn Ile Leu Thr Asp Phe
        275                 280                 285

Asp Lys Phe Ile Val Leu His Asp Lys Phe Tyr Thr His Asp Gly Ile
        290                 295                 300

Tyr Ile Lys Lys Ser Tyr Phe Asn Leu Glu Asn Lys Leu Lys Asn Leu
305                 310                 315                 320

Arg Leu Leu Glu Arg Pro Ile Arg Ile Phe Leu Asn Lys Asn Thr Ile
            325                 330                 335

Asn Tyr Ser Gln His Leu Val Asn Ile Ile Leu Lys Asn Ile Pro Asn
            340                 345                 350

Tyr Asn Ile Val Lys Asp Asn Asp Ala Asp Ile Ile Asp Asn
        355                 360                 365

Ile Asn Asp Ser Asn Leu Tyr Tyr Asp Gln Thr Lys Ile Asn Met Ile
370                 375                 380

Ile Ser Gly Glu Pro Phe Asn Arg Lys Gln Lys Tyr Asp Ile Ala Ile
385                 390                 395                 400

Asp Thr Lys Lys Asn Ser Asn Ala Glu Cys Ile Ile Tyr His Pro Phe
            405                 410                 415

Leu Phe Ser Ser Leu His Glu His Lys Lys Ser Ile Asn Tyr Leu Asp
            420                 425                 430

Tyr Thr Asn Pro Lys Thr Lys Phe Cys Ala Tyr Met Phe His Met Ser
            435                 440                 445

Tyr Pro His Arg Ile Asn Tyr Phe Asn Ile Val Ser Ser Tyr Lys His
            450                 455                 460

Val Asp Ala Leu Gly Lys Cys Cys Asn Asn Val Asp Ile Lys Asn Thr
465                 470                 475                 480

Arg Tyr Val Leu Asn Asn Lys Glu Thr Tyr Asn Asp Ile Ala Val Glu
            485                 490                 495

Tyr Phe Ser Gln Tyr Lys Phe Val Leu Ala Ile Glu Asn Asn Met Ile
            500                 505                 510

Pro Gly Tyr Asn Thr Glu Lys Leu Ile Asn Pro Met Ile Ala Asn Ser
            515                 520                 525

Ile Pro Ile Tyr Trp Gly Asp Ser Glu Ile Phe Lys Tyr Ile Asn Lys
        530                 535                 540

Arg Arg Leu Val Tyr Ile Pro Asp Phe Ile Thr Asn Glu Asp Leu Ile
545                 550                 555                 560

Asn His Ile Lys Tyr Ile Asp Glu His Asp Asp Val Tyr Glu Asn Ile
            565                 570                 575
```

Ile Lys Glu Ser Ile Phe Thr Asp Pro Asp Phe Thr Leu Asp Val Ile
            580                 585                 590

Glu Gln Asn Leu Ser Gly Glu Ile Asp Asn Leu Leu Gly Phe Asn Lys
        595                 600                 605

Asn

<210> SEQ ID NO 41
<211> LENGTH: 1084
<212> TYPE: DNA
<213> ORGANISM: Artificial Sequence
<220> FEATURE:
<223> OTHER INFORMATION: Synthetic Sequence

<400> SEQUENCE: 41

| | | | | | |
|---|---|---|---|---|---|
| cagtcagtca | gaattcaaga | aggagatata | catatgcgtc | gtgtgtttgc | gatccaccca | 60 |
| tctattaaag | gcatcgttga | cctgtctaaa | tacctgggtt | tcaaatcttg | catcaccgaa | 120 |
| gagatcattt | gggattctaa | cagcccggag | ttcattttcg | tctctgagcg | tatttacact | 180 |
| gacatcaacg | aatgggaact | gtttaagaaa | atgtacaacc | cgcaacgtat | ctttattttt | 240 |
| gtttccggtg | aatgcatgac | cccggacctg | aacattttcg | actacgctat | tgtgttcgac | 300 |
| cgcaaactga | agacctggac | ccgtatttgc | cgcatcccga | ccaattacat | ccgtcaccgt | 360 |
| agcctgatca | aaaagtgaac | gacatgagc | ttcgaaaacg | cgctgtcccg | tgttaaagaa | 420 |
| ctggacttct | gctcttttat | ctacagcaat | ccgaaggcgg | accagatccg | cgaagacatt | 480 |
| ttctggggtc | tgatgaacta | caaacacgtt | gattctctgg | gcgaataccct | gaacaactct | 540 |
| ggtgtaaaaa | ctacccgtaa | tgacaaacat | tggcgtgagc | tgtctatcga | atgaaaagc | 600 |
| cactacaaat | tcagcatcgc | tgttgaaaac | gctcaatacg | aaggctacat | ttccgaaaaa | 660 |
| ctgctgactt | ccttccagag | ccattctgtc | cctatctact | ggggcgaccc | gctggtagtg | 720 |
| gatgaataca | acccgaaagc | gttcatcaac | ttcaacgaaa | tgtcctctat | ctctgaactg | 780 |
| gttaatcacg | tcaaagaaat | tgacgaaaat | gacgaactgt | gggcagaaat | ggtttccgcc | 840 |
| gactggcaga | cctccgaaca | ggtagctcgc | gtcaaaaagg | aaactgaaga | atatgatctg | 900 |
| tttatcgaac | acatcctgtc | tcagagcgtt | tccgatgcta | ttcgtcgccc | gcgtggctgt | 960 |
| tggccgtaca | tttacacgaa | ccgttttttc | gatgaaaaat | ggtttctgaa | gtccaaagca | 1020 |
| aagcgttata | ttcgtaaagc | catccactgt | ttcgaggaac | aatagtagct | cgagtgactg | 1080 |
| actg | | | | | | 1084 |

<210> SEQ ID NO 42
<211> LENGTH: 1002
<212> TYPE: DNA
<213> ORGANISM: Artificial Sequence
<220> FEATURE:
<223> OTHER INFORMATION: Synthetic Sequence

<400> SEQUENCE: 42

| | | | | | |
|---|---|---|---|---|---|
| agtcagtcag | aattcaagaa | ggagatatac | atatgaaagt | taagtttgtg | gatagctttt | 60 |
| ttgcacgtga | acagacgatg | ggcgtcctga | cgaactgtt | cgaaaacgtt | gagatttccg | 120 |
| acgacccgga | tttcgtgttt | tgctccgtag | attacaaagc | agaacacatg | aactacgact | 180 |
| gtccgcgtat | catggtgatc | ggtgaaaaca | ttgttccaga | ctttaactgc | atcgattacg | 240 |
| ctgttggttt | caactatatg | aacttcgagg | atcgctatct | gcgtgttccg | ctgtataact | 300 |
| tctacctgga | cgattataaa | ctggcaattc | gccgtcatat | cgattacaaa | cgtgacgaca | 360 |
| acaaaaaatt | ctgcaacttc | gtttactcca | acggtcgtaa | cgccattcct | gaacgtgatt | 420 |

```
ctttctttgc ggacctgagc aagtacaagc aagttgatag cggtggtcgt cacctgaaca    480
atatcggcgg tccggttgat gataaacgcg agttccagaa acagtacaag ttctccattg    540
ccttcgaaaa tgctgtttcc cgtggttaca ccaccgagaa aatcatccag gctttcagcg    600
ctggcactat cccgatttac tatggcaacc cgctggtagc taaagaattt aacagcaaag    660
cgttcattaa ttgccacgaa atcgtagctc tcgacgaagt tatcgaaaaa gtaaaagaac    720
tggataacga cccagacctg tatgattcta tgatgcgtga accgatcttc actgacatcg    780
acgagcgtca ggacccgctg aaggattatc gtaaattcat ctacaacatt tgctctcagg    840
agtctgataa agccattcgt cgttgtgacg attgctgggg tggtaaaatc cagcgtgaaa    900
agaaacgttg ttaccgcttc ctgacctcta ccgagggtaa cggtctgaaa gcacgtgtta    960
tccgtaaact gaccgaaatt tagtagctcg agtgactgac tg                      1002
```

<210> SEQ ID NO 43
<211> LENGTH: 1126
<212> TYPE: DNA
<213> ORGANISM: Artificial Sequence
<220> FEATURE:
<223> OTHER INFORMATION: Synthetic Sequence

<400> SEQUENCE: 43

```
cagtcagtca gaattcaaga aggagatata catatgaccg tgactatggt acgctctctg     60
tattttgtcc accctaaggt tcacaacgtc gaatccttcc tgaattatgt tcacatctgt    120
gaactgccgc agggcctgtg cctggaatgg aacgaccgta accctgaact gctgttcgct    180
tctgaggtaa tctattctga taaaaagtcc agcgaaacgt ttcgccgcct gtactgcgag    240
gccaaagtag ttgtttatta tggtggtgaa gcatctttta ctgattttaa tatcttcgac    300
tatggtgtcg gcttcgacca taccctgaaa aaccagaaat acgcgcagat cctgtctccg    360
attgattttt tcgacaactt cttctaccca gaccgcacga atctgagcga agaagtagca    420
caagaaaagc tgcgttctgg tctgaaattc tgcaacttcc tgtactccaa cccggttgcc    480
catccgtacc gtgacaatct gttctacaag ctgtctgaat acaagaaagt tgacgcgctg    540
ggccgtcacc tgaacaacac cggcatcggc ggcactggtt tcgcgggcca cgcccgtgaa    600
tccgtgaacc tgaaggaaaa ttacaaattt tccatcgcgt ctgaaaactg cggttttcag    660
ggttacacct ctgagaaaat cctgacctcc ctacaggccc acactgtacc gatctattgg    720
ggcgacccgg acgttgacct ggttgtaaat ccgaaatgct tcattaactg taacgacttc    780
gataccctga tgaagtact acagaaagtg aaagagattg acaacaacga cgatctgtgg    840
tgcgaaatgg tgtctcaacc gtggttcact gaaaaacaac tggaagaacg tatccagcgt    900
aacaaaaact atcataaatt tatgctgtcc ctgctgtgta atccattga cagcctgacc    960 acccgtccga acggcacgtt ccagtacgta tatcgtgcgt ggttcctgaa cgcgagcgta   1020
cgtaacgaca tcctgtaccg cctgaaacgt aaaatgaact tccgccgcct gcgcaatttt   1080
tctctgtctc aaaaccgtaa aaactagtag ctcgagtgac tgactg                  1126
```

<210> SEQ ID NO 44
<211> LENGTH: 997
<212> TYPE: DNA
<213> ORGANISM: Artificial Sequence
<220> FEATURE:
<223> OTHER INFORMATION: Synthetic Sequence

<400> SEQUENCE: 44

```
cagtcagtca gaattcaaga aggagatata catatgaaga ccatcaaggt aaaattcgtc    60
gatttctgga aaggtttcga cccgcgcaac aacttcctga tggacatcct gaaacagcgt   120
tatcacattg aactgagcga aagcccggac tacctgatct tctctgtctt cggtttcact   180
aacctgaact acgaacgctg cgttaaaatc ttctacaccg gtgaaaacct gaccccggat   240
ttcaacatct gcgactacgc gattggtttc gattatctga gcttcggtga tcgttacatg   300
cgtctgccac tgtacgcggt ctatggcatc gagaaactgg cttctccgaa agttatcgac   360
aaagaaaaag ttctgaagcg taaattctgt tcttacgtag taagcaataa catcggcgcg   420
ccggaacgtt ctcgtttctt ccatctgctg tctgaataca aaaaggttga ctccggtggt   480
cgttgggaaa acaacgtagg cggtccggtt ccgaataagc tggactttat caaagactac   540
aagttcaaca tcgcattcga aaactccatg tacgacggct acactactga aaaaatcatg   600
gaaccgatgc tggtgaacag cctgccgatt tattggggca accgcctgat caacaaagac   660
ttcaacccag cgtctttcat caacgtttcc gatttcccgt ctctggaagc ggcggtggag   720
cacattgtta tgctggacaa taacgatgat atgtacctga gcatcctgtc taaaccgtgg   780
tttaacgatg aaaactacct ggactggaaa gcgcgcttct ccactttttt cgataacatc   840
ttcaatcgtc cgatcgatga atgcaaatat ctgaccccgt acggcttttg tcgtcactat   900
cgtaaccaac tgcgtagcgc tcgtctgctg aaacagcgct ttcgccagct gcgtaacccg   960
ctgcgctggt tccgctagta gctcgagtga ctgactg                           997

<210> SEQ ID NO 45
<211> LENGTH: 1063
<212> TYPE: DNA
<213> ORGANISM: Artificial Sequence
<220> FEATURE:
<223> OTHER INFORMATION: Synthetic Sequence

<400> SEQUENCE: 45
cagtcagtca gaattcaaga aggagatata catatgtcta aaaaaaaaat caaaatcaac    60
tatatcgact tttggccggg cttcaaaaag gaagacaact tcttttcccg tatcctggac   120
aaatactacg atgtggaaat ttctgacaac ccggactatg tcttttgcag ctgcttctcc   180
cgcaagcact tcaaatatgc tgattgcgtt aaaatcttct acaccggtga gaacatcatc   240
cctgatttta acctgtatga ctactctatg ggtttccact acatcgattt tgaagatcgt   300
tacctgcgcc tgccgcatta cgcgctgtat gatcagtgta tcaaggccgc gaaagaaaag   360
cacacccact ctgatgacta ttacctggct aaaaaaaaat tctgtaacta tgttatttcc   420
aacccgtacg ccgccccgga acgtgacctg atgatcgatg cgctggagaa atacatgcct   480
gttgattctg gcggtcgtta tcgcaacaac gtcggtggtc ctgtagcaga taaagtagaa   540
tttgcgtccc actatcgctt ctctatggcg ttcgagaata gcgcgatgtc tggttacacc   600
actgaaaaaa tcttcgatgg tttcgccgcc tgtaccatcc gatctactg gggctctgat   660 cgcattaaag aggagttcaa tccggagagc tttgtaagcg cacgtgactt cgaaaacttc   720
gatcaggtgg tagcgcgtgt caaggaaatc tacgaaaatg atgacctgta cctgaaaatg   780
atgaaagcgc cgatcgcgcc ggaaggtttc caggcccacg aatgcctgaa ggaggattat   840
gccgacgcgt ttctgcgtaa cattttttgac caggacatcg acaaagctaa cgccgtaac    900 atggtttacg tcggtcgtga ttatcagaaa aagctgaagg atgctaacaa agtgattgag   960
gttctggatg tggtgaagaa accgatgcac cagtttaaca aaactaaatc tcagatcgcg  1020
tctaaattcc gtaagaaaaa atagtagctc gagtgactga ctg                   1063
```

<210> SEQ ID NO 46
<211> LENGTH: 1060
<212> TYPE: DNA
<213> ORGANISM: Artificial Sequence
<220> FEATURE:
<223> OTHER INFORMATION: Synthetic Sequence

<400> SEQUENCE: 46

| | |
|---|---|
| cagtcagtca gaattcaaga aggagatata catatgtccg aaaaaaaaaa aatcaaagtt | 60 |
| aaattcgtag atttccagga ctccctgaaa gaaaacgaca acttctttat tgactctctg | 120 |
| aaaaaaaact tcgacgttga agtttccgac gatccggact atctgttttt cggtgcttat | 180 |
| ggctacaaac acctggacta cgattgtatc cgtattatgt ggaccatcga aaactatgtg | 240 |
| ccggatttca acatttgcga ctatgctctg gcttatgaca tcattgagtt cggtgaccgt | 300 |
| tacctgcgct tcccgttctt cctgaaccgt ccggaaatcg aaaacgtgcg taaaaccatt | 360 |
| gaacgtaaac cgattgacac gtccgttaaa acggacttct gtagctttgt tgtaagcaac | 420 |
| gaatggggcg acgactaccg tattcgcctg ttccacgaac tgtccaaata caaaaaagtg | 480 |
| gactccggcg tcgttccct gaacaacatt ggcggtccga tcggcatggg cctggataaa | 540 |
| aaattcgagt tcgatgttac ccacaaattc tcctttgccc tggaaaacgc gcagaaccgc | 600 |
| ggttatacca ccgaaaaaat cttcgatgcg ttcgcggcgg gttgcattcc gatctattgg | 660 |
| ggtgatccga atattgagga agagttcaac ccgaaatcct tcatcaactg caacgacctg | 720 |
| accgttgagg aagccgttga gaaaatcaaa gaggttgacc agaacgatga actgtaccac | 780 |
| gcgatgctga acgaaccgac tttctgggc gacctggaca aatatctgca agacttcgac | 840 |
| gacttcctgt tcaacatttg caatcagccg ctggaaaaag cgtatcgtcg tgaccgcatc | 900 |
| atgaaaggca agactcagga acaccagtac aaactgatca accgtttcta ctacaagcca | 960 |
| tatttttttcc tgatcaaagt tgctcaaaaa ctgcacatcg agtttatcgg tcgtaagatt | 1020 |
| taccatttta tccgtgatta gtagctcgag tgactgactg | 1060 |

<210> SEQ ID NO 47
<211> LENGTH: 1042
<212> TYPE: DNA
<213> ORGANISM: Artificial Sequence
<220> FEATURE:
<223> OTHER INFORMATION: Synthetic Sequence

<400> SEQUENCE: 47

| | |
|---|---|
| cagtcagtca gaattcaaga aggagatata catatgaaaa aagttaagat caaatttgta | 60 |
| gacttcttcg atggtttcga caaaggccgt aacgagtttc tggaagttct gaaacagcgc | 120 |
| tatgaaatcg acatctctga tgagcctgat tatgtaatct acagcggctt cggttacgaa | 180 |
| cacctgaaat acaactgcat ccgtatcttc ttcaccggtg agtgccagac cccagacttc | 240 |
| aacgaatgcg attatgcaat cggctttgat cgcctgaaat tcggtgaccg ctatgtccgt | 300 |
| attccgctgt ataatatgat gcaatataaa ctggactata agaactgct gaaccgtaaa | 360 |
| tccatcattt ccgacgatat taaaggtcgt ggcttctgct cctttgtagt gtctaactgt | 420 |
| ttcgcgaatg atacccgtgc gatcttctac gaactgctga atcagtataa atatatcgct | 480 |
| agcggtggcc gttataaaaa caatatcggc ggtgccatta agataagaa gacgttcctg | 540 |
| agcaaataca aattcaacat cgcgttcgaa aactgttctc atgatggcta cgccaccgaa | 600 |
| aaaatcgtag aggcttttgc tgccggcgta gttccgatct actatggcga cccacgtatc | 660 |

```
gcagaagatt tcaacccgaa ggcatttatt aatgcacacg attatcagag cttcgaagaa    720
atggtggaac gcatcaaaga gatcgatgcc gatgaccgtc tgtacctgac catgctgaac    780
gaaccgatca ttcagccgaa cgcagacgtg actgaactgg cggatttcct gtatagcatc    840
ttcgaccagc cgctggccaa ggccaaacgc cgttcccagt cccagccgac tcaggctatg    900
gaggcaatga aactgcgcca cgagttcttc gaaatgaaaa tctacaaata ttataaaaaa    960
ggtatgaacc agttcacgcg tctgcgcaag ggcgtgttcc taagctctaa acgtaccaaa   1020
tagtagctcg agtgactgac tg                                            1042
```

<210> SEQ ID NO 48
<211> LENGTH: 1060
<212> TYPE: DNA
<213> ORGANISM: Artificial Sequence
<220> FEATURE:
<223> OTHER INFORMATION: Synthetic Sequence

<400> SEQUENCE: 48

```
cagtcagtca gaattcaaga aggagatata catatgaaaa aggaaatcaa aatcgcgtac     60
gtggatttct ggaacggctt caagcctgac tccttcttca tcaccaagac catcagcaaa    120
aaatacaagg ttatcatcga caatgaaaac ccggatttcg taatctgtgg taccttcggt    180
aataccttcc tgtcctatga ctgcccgcgt atcctgtata ccggtgaagc taactgcccg    240
gattttaata tctacgacta tgcaattggt ttcgaacgca tggtttacga agaccgctat    300
ctgcgctacc cgctgttcct ggtgaacgaa gacctgctac aggatgcgct gaacaaacac    360
aaaaaatctg atgactacta tctgcgtcgt gatggcttct gtagcttcgt ggtgtccgcg    420
tctggcggta tggacggtct gcgtaactgg tattttgata aaatcagcga atataagcag    480
gtagcttccg gtgccgtttt cgcaacaac ctgccggacg gcaaaccagt tccagataaa    540
aaggcattcc aggaaaacta ccgcttctcc ctgtgcttcg agaacgctgg catcagcggc    600
tatgctaccc aaaaaattgt tgacgcattc gcggctggtt gcatcccgat ctactacggt    660
gacaccaaca tcgaaaaaga cttcaacccg aaatcctta ttcacgtgaa atctcgtgaa    720
gacctggact ccgttctggc ttgggtgaag gagctggaag aaaaccagaa caaatatctg    780
gaggtgatcc gtcaacctgc aatcctgcct gacagcccga tcatgggtat gctgaacaac    840
acgtacatcg aagagttcct gttccatatc ttcgaccagg aacctcagga ggcaatccgt    900
cgtcacagca aactgactat gtggggccag ttctatgaat accgtctgaa aaaatggaac    960
aagatcgaga caacatgtt tctgaagaaa gcacgtagca ttaaacgtaa atactttggc   1020
ctgaaaaaaa tcgttaaata gtagctcgag tgactgactg                         1060
```

<210> SEQ ID NO 49
<211> LENGTH: 1021
<212> TYPE: DNA
<213> ORGANISM: Artificial Sequence
<220> FEATURE:
<223> OTHER INFORMATION: Synthetic Sequence

<400> SEQUENCE: 49

```
cagtcagtca gaattcaaga aggagatata catatgaaga aaaaaatcta ctgcaacttc     60
gtggactttt ggctgggttt taactataaa acctacttct ggtatctgtc cgacgagtac    120
gatctacaga tcgacaaaga acatccagat tacctgtttt actcctgctt cggtaacgaa    180
catctgttct acgaagactg cattcgcatt ttctggtctg acgagaacat catgccggac    240
ctgaacattt gcgactacgc tctgtctctg agcaacctac agtgcgacga ccgtaccttc    300
```

-continued

```
cgcaagtact ccggtttcct gtaccgtaag gattctcatc tggttctgcc ggtactgaaa      360
gaagaagcgc tgctgaatcg taaattttgc aacttcgtat actctaacaa cacctgtgct      420
gttccgtacc gtgaactgtt ctttaaagcg ctgtctggct acaaacgtat cgattctggt      480
ggtgcgtttc tgaataacat gggtaaaaaa gttggcgata agcgccagtt tctgcacgaa      540
tacaaattta ctctggctat cgaaaattcc tctatgccgg ttacgtgac cgaaaaaatc       600 ctggagcctt ttatggctca gagcctgcca ctgtactggg ttctccgac tgtttcctct       660 gactataacc ctaactcctt cgtaaatctg atgaactact cctctatgga agaagcggta      720
gaagaagtga ttcgcctgga caaagacgac gctgcgtatc tggacaaaat gatgacgcct      780
ttctggctgt acggtgcaaa cttccaagag ttccgtgact ccgagattaa aaaaattaaa      840
gatttcttct cttatatctt cgaacagccg ctggacaaag cgggccgtcg cgtttgttac      900
ggtcgtaatc gtatcaccat ccaaaaacag cgtcgttact acgccccgac ttttctggaa      960
ctgtctaaat ctatgactaa gaaactgctg aagaaaaaat agtagctcga gtgactgact      1020
g                                                                      1021
```

<210> SEQ ID NO 50
<211> LENGTH: 1039
<212> TYPE: DNA
<213> ORGANISM: Artificial Sequence
<220> FEATURE:
<223> OTHER INFORMATION: Synthetic Sequence

<400> SEQUENCE: 50

```
cagtcagtca gaattcaaga aggagatata catatgaaaa aaatccgtct gaaatacgtt      60
gattggtggg atggtttcca gccggaacaa tatcgctttc atcagatcct gactaaacat      120
ttcgacatcg aaattagcga tgaaccggat tacattatcg ctagcgtgta ctctgacgaa      180
gcaaaaagct acaactgtgt tcgcatcctg tataccggtg agaacatctg cccggatttc      240
aacatctatg actatgctat cggcttcgaa tacctggagt tcggtgatcg ctatatccgt      300
atcccgaact ttatcatgaa cccggcttac gacatcgaca tccagaaagc gctgtctaag      360
catctgctgt ctgctgatga tatcaaacgc gaaaaaaat tctgctcctt cgtcgtttct      420
aacggcaacg cagcgccaat ccgtgagaag atgttcgaag aactgaataa atataagcgt      480
gtggactccg gcggtcgcta cctgaacaac atcggtcgtc agaaggcgt tcgtgacaaa      540 ttcgctttcc aatctgaaca caagtttttct ctgaccttcg agaactccgc gcacctgggt      600
tacactacgg aaaaactgct acagggcttc tctgcgggca cgattccgat ctactgggggt      660 gacccggcgg tggaaaactg cttcaacccg aaagcgttca tcaacatttc cggcaacaac      720
gtttacgacg caatcgaact ggttaaagaa gttgatactc aggacgacct gtactttagc      780
atgttgcgtg aaccggcttt tctgaacaac gattaccaaa ctaaactgct ggagaagctg      840
gataacttcc tggtacacat ctttaatcag ccgctggagt gcgcctaccg tcgtaacagc      900
tttgagcata tcagcaacaa atctgttctg aatgagttcg tgaagaaga tcgtggccgt      960 ttctcccagt ggatctccaa caaggcgcgt tgtttctatg gcaaacgtaa aaacaagtag     1020
tagctcgagt gactgactg                                                  1039
```

<210> SEQ ID NO 51
<211> LENGTH: 1096
<212> TYPE: DNA
<213> ORGANISM: Artificial Sequence
<220> FEATURE:

<223> OTHER INFORMATION: Synthetic Sequence

<400> SEQUENCE: 51

| | | | | | |
|---|---|---|---|---|---|
| cagtcagtca | gaattcaaga | aggagatata | catatgagca | agaaaagtg | gaaacaggaa | 60 |
| aaacgcgttc | atttcgtaga | ttgttgcgac | gacggtatcc | gtgacaaagt | ttgcccgatc | 120 |
| ctggaacaac | actttactct | gatcttcgac | tctgtaaacc | cggaatacgt | gttctattct | 180 |
| gcctacggtg | aagaacatct | ggcttacgac | tgcatccgca | tttttatcac | tggcgaaaac | 240 |
| atcaccccga | acttcacgat | ttgcgactac | gctatcggtt | tcgaccacct | gcactttctg | 300 |
| gatcgttacc | tgcgctaccc | actgtacctg | ttctacgaac | aggatgtgaa | acgcgcatcc | 360 |
| cagaaacaca | aagatatcga | cgaaaagctg | ctggcttcta | atcccgtttt | ttgcaacttt | 420 |
| gtggtgagca | acggcaacgc | tgatccgtac | cgcgaacagg | tattctacgc | gctgaacgcc | 480 |
| tacaagcgtg | tggacagcgg | tggtcgttat | ctgaacaaca | ttggtggtag | cgtggccgat | 540 |
| aaattcgctt | ccagtctga | atgtcgtttt | agcctgtgct | cgaaaacag | ctctacgccg | 600 |
| ggttacctga | ccgagaaact | gattcaggcg | gcggctgctc | aaaccatccc | aatttattgg | 660 |
| ggcgacactc | tggcgactaa | accgctgttc | gatggcggtg | cggtatcaa | cgccaaggca | 720 |
| ttcatcaacg | cgcactcctt | ctcttctctg | gaatctctga | ttgctcacat | cgccgagatt | 780 |
| gaagcggata | agacgaaaca | gctggccatt | ctacaggaac | cactgttcct | ggactctaat | 840 |
| cacatcgagc | tgttcgaaaa | acagttcgaa | caatttctgc | tgagcattgt | gagccagccg | 900 |
| tatgaacgtt | ctttccgtcg | tggtcgtgtt | atgtggcagt | cttttgttga | acagcgctac | 960 |
| aaacgcgcca | tgcatctgct | ggctctggaa | gaccgcatca | aagctccgta | ccgtaagctg | 1020 |
| cgtcagttcc | tgcgcgcgtt | ctgggactcc | ctgaaagaaa | aacgttccca | cacttagtag | 1080 |
| ctcgagtgac | tgactg | | | | | 1096 |

<210> SEQ ID NO 52
<211> LENGTH: 1123
<212> TYPE: DNA
<213> ORGANISM: Artificial Sequence
<220> FEATURE:
<223> OTHER INFORMATION: Synthetic Sequence

<400> SEQUENCE: 52

| | | | | | |
|---|---|---|---|---|---|
| cagtcagtca | gaattcaaga | aggagatata | catatgggtg | acgaagttgc | tatgggtaaa | 60 |
| gagcgcaagc | agattcgcgt | tcacttcgta | gacttctcca | acatggataa | cattattgaa | 120 |
| aaaatttgct | ctattctgtc | ccgtcatttc | gcagttatca | ttgacggtga | aaacccggag | 180 |
| tatgtattct | actctgcttt | cggtagcgaa | tatctgaagt | acgattgtgt | tcgtatcttc | 240 |
| tacactggcg | aaaacattgt | accggatttt | aacctgtgcg | attacgctat | cggtttcgat | 300 |
| cacatcaagt | tcctggaccg | ttacctgcgc | taccctctgt | atctgttttta | tgaaaccgat | 360 |
| gtacagaaag | cggctcgtaa | acaccagaac | ctgtctctgg | aagttgtccg | caacaaaaaa | 420 |
| cgttttttgca | atttcgtagt | taccaacggc | aaaggtgacc | cgtatcgtga | aaaagttttt | 480 |
| catgctctgt | gcgcttacaa | acgtgtagat | agcgctggta | agtttctgaa | caacgttggt | 540 |
| gcacgcgtta | agataaaatt | tgcgttccag | agcgaatgcc | gttttttccct | gtgcttcgag | 600 |
| aactctagca | cccctggtta | tctgaccgaa | aaactgatcc | aggcagcggc | tgcgcaaact | 660 |
| atcccgatct | attggggcga | cccgctggcg | accaagccgc | tgtttgatgg | tggcggcggt | 720 |
| atcaacgcga | aagcgttcat | caacgctcac | gagttcgcca | catcgcgtc | cctggtgcgc | 780 |
| catattgaga | gcatcgaaaa | cgacgaaaac | aaacagctgg | ctatcctgca | agaaccgctg | 840 |

```
tttctggatt ccaatcatat tgaactgttc gaaaaacagt tcgaggattt cctggtgtat    900
atctttctc agccttacga gcgtagcttc cgtcgcggta aaatcatgtg gcaggcgcat     960
ctggaacaga tcatcaaaaa aggtgttcag ccgaccatgc tggaaatttg gctgcgtcgt   1020
ccactgcgca acttcgagcg cgcgatccgc atccgtgtga aaaaaattat tcagaaagtg   1080
aaaaaaccga agatttcat gtagtagctc gagtgactga ctg                      1123
```

<210> SEQ ID NO 53
<211> LENGTH: 320
<212> TYPE: PRT
<213> ORGANISM: Artificial Sequence
<220> FEATURE:
<223> OTHER INFORMATION: Synthetic Sequence

<400> SEQUENCE: 53

Met Lys Asp Asp Leu Val Ile Leu His Pro Asp Gly Gly Ile Ala Ser
1               5                   10                  15

Gln Ile Ala Phe Val Ala Leu Gly Leu Ala Phe Glu Gln Lys Gly Ala
            20                  25                  30

Lys Val Lys Tyr Asp Leu Ser Trp Phe Ala Glu Gly Ala Lys Gly Phe
        35                  40                  45

Trp Asn Pro Ser Asn Gly Tyr Asp Lys Val Tyr Asp Ile Thr Trp Asp
    50                  55                  60

Ile Ser Lys Ala Phe Pro Ala Leu His Ile Glu Ile Ala Asn Glu Glu
65                  70                  75                  80

Glu Ile Glu Arg Tyr Lys Ser Lys Tyr Leu Ile Asp Asn Asp Arg Val
                85                  90                  95

Ile Asp Tyr Ala Pro Pro Leu Tyr Cys Tyr Gly Tyr Lys Gly Arg Ile
            100                 105                 110

Phe His Tyr Leu Tyr Ala Pro Phe Phe Ala Gln Ser Phe Ala Pro Lys
        115                 120                 125

Glu Ala Gln Asp Ser His Thr Pro Phe Ala Ala Leu Leu Gln Glu Ile
    130                 135                 140

Glu Ser Ser Pro Ser Pro Cys Gly Val His Ile Arg Arg Gly Asp Leu
145                 150                 155                 160

Ser Gln Pro His Ile Val Tyr Gly Asn Pro Thr Ser Asn Glu Tyr Phe
                165                 170                 175

Ala Lys Ser Ile Glu Leu Met Cys Leu Leu His Pro Gln Ser Ser Phe
            180                 185                 190

Tyr Leu Phe Ser Asp Asp Leu Ala Phe Val Lys Glu Gln Ile Val Pro
        195                 200                 205

Leu Leu Lys Gly Lys Thr Tyr Arg Ile Cys Asp Val Asn Asn Pro Ser
    210                 215                 220

Gln Gly Tyr Leu Asp Leu Tyr Leu Leu Ser Arg Cys Arg Asn Ile Ile
225                 230                 235                 240

Gly Ser Gln Gly Ser Met Gly Glu Phe Ala Lys Val Leu Ser Pro His
                245                 250                 255

Asn Pro Leu Leu Ile Thr Pro Arg Tyr Arg Asn Ile Phe Lys Glu Val
            260                 265                 270

Glu Asn Val Met Cys Val Asn Trp Gly Glu Ser Val Gln His Pro Pro
        275                 280                 285

Leu Val Cys Ser Ala Pro Pro Pro Leu Val Ser Gln Leu Lys Arg Asn
    290                 295                 300

Ala Pro Leu Asn Ser Arg Leu Tyr Lys Glu Lys Asp Asn Ala Ser Ala

<210> SEQ ID NO 54
<211> LENGTH: 424
<212> TYPE: PRT
<213> ORGANISM: Artificial Sequence
<220> FEATURE:
<223> OTHER INFORMATION: Synthetic Sequence

<400> SEQUENCE: 54

Met Phe Gln Pro Leu Leu Asp Ala Phe Ile Glu Ser Ala Ser Ile Glu
1               5                   10                  15

Lys Met Ala Ser Lys Ser Pro Pro Pro Leu Lys Ile Ala Val Ala
            20                  25                  30

Asn Trp Trp Gly Asp Glu Glu Ile Lys Glu Phe Lys Lys Ser Val Leu
        35                  40                  45

Tyr Phe Ile Leu Ser Gln Arg Tyr Ala Ile Thr Leu His Gln Asn Pro
    50                  55                  60

Asn Glu Phe Ser Asp Leu Val Phe Ser Asn Pro Leu Gly Ala Ala Arg
65                  70                  75                  80

Lys Ile Leu Ser Tyr Gln Asn Thr Lys Arg Val Phe Tyr Thr Gly Glu
                85                  90                  95

Asn Glu Ser Pro Asn Phe Asn Leu Phe Asp Tyr Ala Ile Gly Phe Asp
            100                 105                 110

Glu Leu Asp Phe Asn Asp Arg Tyr Leu Arg Met Pro Leu Tyr Tyr Ala
        115                 120                 125

His Leu His Tyr Lys Ala Glu Leu Val Asn Asp Thr Thr Ala Pro Tyr
    130                 135                 140

Lys Leu Lys Asp Asn Ser Leu Tyr Ala Leu Lys Lys Pro Ser His His
145                 150                 155                 160

Phe Lys Glu Asn His Pro Asn Leu Cys Ala Val Val Asn Asp Glu Ser
                165                 170                 175

Asp Leu Leu Lys Arg Gly Phe Ala Ser Phe Val Ala Ser Asn Ala Asn
            180                 185                 190

Ala Pro Met Arg Asn Ala Phe Tyr Asp Ala Leu Asn Ser Ile Glu Pro
        195                 200                 205

Val Thr Gly Gly Gly Ser Val Arg Asn Thr Leu Gly Tyr Lys Val Gly
    210                 215                 220

Asn Lys Ser Glu Phe Leu Ser Gln Tyr Lys Phe Asn Leu Cys Phe Glu
225                 230                 235                 240

Asn Ser Gln Gly Tyr Gly Tyr Val Thr Glu Lys Ile Leu Asp Ala Tyr
                245                 250                 255

Phe Ser His Thr Ile Pro Ile Tyr Trp Gly Ser Pro Ser Val Ala Lys
            260                 265                 270

Asp Phe Asn Pro Lys Ser Phe Val Asn Val His Asp Phe Asn Asn Phe
        275                 280                 285

Asp Glu Ala Ile Asp Tyr Ile Lys Tyr Leu His Thr His Pro Asn Ala
    290                 295                 300

Tyr Leu Asp Met Leu Tyr Glu Asn Pro Leu Asn Thr Leu Asp Gly Lys
305                 310                 315                 320

Ala Tyr Phe Tyr Gln Asp Leu Ser Phe Lys Lys Ile Leu Asp Phe Phe
                325                 330                 335

Lys Thr Ile Leu Glu Asn Asp Thr Ile Tyr His Lys Phe Ser Thr Ser
            340                 345                 350

Phe Met Trp Glu Tyr Asp Leu His Lys Pro Leu Val Ser Ile Asp Asp

|  |  |  | 355 |  |  |  | 360 |  |  |  | 365 |  |  |
|--|--|--|--|--|--|--|--|--|--|--|--|--|--|

Leu Arg Val Asn Tyr Asp Asp Leu Arg Val Asn Tyr Asp Arg Leu Leu
            370                         375                         380

Gln Asn Ala Ser Pro Leu Leu Glu Leu Ser Gln Asn Thr Thr Phe Lys
385                         390                         395                         400

Ile Tyr Arg Lys Ala Tyr Gln Lys Ser Leu Pro Leu Leu Arg Ala Val
                    405                         410                         415

Arg Lys Leu Lys Lys Leu Gly Leu
            420

<210> SEQ ID NO 55
<211> LENGTH: 2070
<212> TYPE: DNA
<213> ORGANISM: Artificial Sequence
<220> FEATURE:
<223> OTHER INFORMATION: Synthetic Sequence

<400> SEQUENCE: 55

```
gttcggttat atcaatgtca aaaacctcac gccgctcaag ctggtgatca actccgggaa      60
cggcgcagcg ggtccggtgg tggacgccat tgaagcccgc tttaaagccc tcggcgcgcc     120
cgtggaatta atcaaagtgc acaacacgcc ggacggcaat tccccaacg gtattcctaa      180
cccactactg ccggaatgcc gcgacgacac ccgcaatgcg gtcatcaaac acggcgcgga     240
tatgggcatt gcttttgatg gcgattttga ccgctgtttc ctgtttgacg aaaaagggca     300
gtttattgag ggctactaca ttgtcggcct gttggcagaa gcattcctcg aaaaaaatcc     360
cggcgcgaag atcatccacg atccacgtct ctcctggaac accgttgatg tggtgactgc     420
cgcaggtggc acgccggtaa tgtcgaaaac cggacacgcc tttattaaag aacgtatgcg     480
caaggaagac gccatctatg gtggcgaaat gagcgcccac cattacttcc gtgatttcgc     540
ttactgcgac agcggcatga tcccgtggct gctggtcgcc gaactggtgt gcctgaaaga     600
taaaacgctg ggcgaactgg tacgcgaccg gatggcggcg tttccggcaa gcggtgagat     660
caacagcaaa ctggcgcaac ccgttgaggc gattaaccgc gtggaacagc attttagccg     720
tgaggcgctg gcggtggatc gcaccgatgg catcagcatg acctttgccg actggcgctt     780
taacctgcgc acctccaata ccgaaccggt ggtgcgcctg aatgtggaat cgcgcggtga     840
tgtgccgctg atggaagcgc gaacgcgaac tctgctgacg ttgctgaacg agtaatgtcg     900
gatcttccct taccccactg cgggtaaggg gctaataaca ggaacaacga tgattccggg     960
gatccgtcga cctgcagttc gaagttccta ttctctagaa agtataggaa cttcgaagca    1020
gctccagcct acagttaaca aagcggcata ttgatatgag cttacgtgaa aaaaccatca    1080
gcggcgcgaa gtggtcggcg attgccacgg tgatcatcat cggcctcggg ctggtgcaga    1140
tgaccgtgct ggcgcggatt atcgacaacc accagttcgg cctgcttacc gtgtcgctgg    1200
tgattatcgc gctggcagat acgctttctg acttcggtat cgctaactcg attattcagc    1260
gaaaagaaat cagtcacctt gaactcacca cgttgtactg gctgaacgtc gggctgggga    1320
tcgtggtgtg cgtggcggtg tttttgttga gtgatctcat cggcgacgtg ctgaataacc    1380
cggacctggc accgttgatt aaaacattat cgctggcgtt tgtggtaatc ccccacgggc    1440
aacagttccg cgcgttgatg caaaaagagc tggagttcaa caaaatcggc atgatcgaaa    1500
ccagcgcggt gctggcgggc ttcacttgta cggtggttag cgcccatttc tggccgctgg    1560
cgatgaccgc gatcctcggt tatctggtca atagtgcggt gagaacgctg ctgtttggct    1620
actttggccg caaaatttat cgccccggtc tgcatttctc gctggcgtcg gtggcaccga    1680
```

-continued

| | |
|---|---|
| acttacgctt tggtgcctgg ctgacggcgg acagcatcat caactatctc aataccaacc | 1740 |
| tttcaacgct cgtgctggcg cgtattctcg gcgcgggcgt ggcaggggga tacaacctgg | 1800 |
| cgtacaacgt ggccgttgtg ccaccgatga agctgaaccc aatcatcacc cgcgtgttgt | 1860 |
| ttccggcatt cgccaaaatt caggacgata ccgaaaagct gcgtgttaac ttctacaagc | 1920 |
| tgctgtcggt agtggggatt atcaactttc cggcgctgct cgggctaatg gtggtgtcga | 1980 |
| ataactttgt accgctggtc tttggtgaga agtggaacag cattattccg gtgctgcaat | 2040 |
| tgctgtgtgt ggtgggtctg ctgcgctccg | 2070 |

<210> SEQ ID NO 56
<211> LENGTH: 5046
<212> TYPE: DNA
<213> ORGANISM: Escherichia coli

<400> SEQUENCE: 56

| | |
|---|---|
| gtggatggaa gaggtggaaa aagtggttat ggaggagtgg gtaattgatg gtgaaaggaa | 60 |
| agggttggtg atttatggga aggggaagg ggaagaggga tgtggtgaat aattaaggat | 120 |
| tgggatagaa ttagttaagg aaaaaggggg gatttatgt gggtttaat ttttggtgta | 180 |
| ttgtggggt tgaatgtggg ggaaagatgg ggatatagtg aggtagatgt taatagatgg | 240 |
| ggtgaaggag agtggtgtga tgtgattagg tgggggaaat taaagtaaga gagaggtgta | 300 |
| tgattggggg gatgggtgga ggtggagttg gaagttggta ttgtgtagaa agtataggaa | 360 |
| gttgagaggg gttttgaagg tgaggtgggg ggaaggagtg agggggggaag gggtggtaaa | 420 |
| ggaaggggaa gaggtagaaa gggagtgggg agaaagggtg gtgagggggg atgaatgtga | 480 |
| ggtagtgggg tatgtggaga agggaaaagg gaaggggaaa gagaaaggag gtaggttgga | 540 |
| gtggggttag atggggatag gtagagtggg gggttttatg gagaggaagg gaaggggaat | 600 |
| tgggaggtgg ggggggggtgt ggtaaggttg ggaagggggtg gaaagtaaag tggatgggtt | 660 |
| tgttgggggg aaggatgtga tgggggaggg gatgaagatg tgatgaagag agaggatgag | 720 |
| gatggtttgg gatgattgaa gaagatggat tggaggaggg ttgtgggggg ggttgggtgg | 780 |
| agagggtatt ggggtatgag tggggagaag agagaatggg gtggtgtgat gggggggtgt | 840 |
| tgggggtgtg aggggagggg gggggggttg ttttttgtgaa gagggaggtg tgggggtgggg | 900 |
| tgaatgaagt ggaggaggag ggaggggggg tatggtgggt ggggaggagg ggggttggtt | 960 |
| gggggaggtgt ggtggaggtt gtgagtgaag ggggaaggga gtgggtggta ttgggggaag | 1020 |
| tgggggggga ggatgtggtg tgatgtgagg ttggtggtgg ggagaaagta tggatgatgg | 1080 |
| gtgatggaat gggggggggtg gatagggttg atgggggtag gtgggggattg gaggaggaag | 1140 |
| ggaaagatgg gatggaggga ggaggtagtg ggatggaagg gggtgttgtg gatgaggatg | 1200 |
| atgtggagga agaggatgag ggggtggggg gagggggaagt gttgggggagg gtgaagggggg | 1260 |
| gatggggggag ggggaggatg tggtggtgag ggatggggat gggtggttgg ggaatatgat | 1320 |
| ggtggaaaat gggggggtttt gtggattgat ggagtgtggg ggggtggggtg tggggagggg | 1380 |
| gtatgaggag ataggttgg gtaggggtga tattggtgaa gaggttgggg gggaatgggg | 1440 |
| tgaggggttg gtggtggttt agggtatggg gggtggggat tggagggga tggggttgta | 1500 |
| tggggttgtt gaggagttgt tgtaataagg ggatgttgaa gttggtattg ggaagttggt | 1560 |
| attgtgtaga aagtatagga agttggaagg aggtggaggg tagataaagg gggggttat | 1620 |
| ttttgagagg agaggaagtg gtaatggtag ggagggggggg tgaggtggaa ttgggggggat | 1680 |

```
agtgaggggg tggaggagtg gtgggggagga atggggatat ggaaagggtg gatattgagg    1740
gatgtgggtt gttggggtg gaggagatgg ggatgggtgg tttggatgag ttggtgttga     1800
gtgtaggggg tgatgttgaa gtggaagtgg ggggggagt ggtgtggggg ataattgaat     1860
tggggggtgg gggaggggag agggttttgg gtggggaaga ggtaggggt atagatgttg     1920 agaatgggag atgggagggg tgaaaagagg ggggagtaag ggggtgggga tagttttgtt    1980
gggggggtaa tgggagggag tttaggggt gtggtaggtg ggggaggtgg gagttgaggg    2040 gaatggggg gggatggggt gtatgggtgg ggagttgaag atgaagggta atgggatt     2100 gaggagtagg atgaatgggg taggttttgg gggtgataaa taaggttttg gggtgatggt    2160 gggagggtg agggtggta atgaggaggg gatgaggaag tgtatgtggg gtggagtgga     2220
agaagggtgg ttggggtgg taatggggg gggggttgga gggttggagg gaggggttag    2280
ggtgaatggg ggtgggttga gttagggaa tgtggttatg gagggtgga ggggtgaagt    2340 gatgggggag ggggtgagg agttgttttt tatggggaat ggagatgtgt gaaagaaagg    2400
gtgagtgggg gttaaattgg gaaggttat tagggaggtg gatggaaaaa tggatttggg    2460
tggtggtgag atggggatg gggtgggagg gggggggag ggtgagagtg aggttttggg    2520
ggagagggga gtggtgggag ggggtgatgt gggggggttg tgaggatggg gtggggttgg    2580
gttggagtag gggtagtgtg agggagagtt gggggggggt gtggggtgg ggtagttgag    2640 ggagttgaat gaagtgttta ggttgtggag ggagatggag agggagttga ggggttggga    2700
gggggttagg atggagggg aggatggagt ggaggaggtg gttatgggta tgagggaaga    2760
ggtattgggt ggtgagttgg atggtttggg gggataaagg gaagtggaaa aagtggtggt    2820
ggtgttttgg ttgggtgagg ggtggatggg gggtggggtg gggaaagagg agagggttga    2880
tagagaagtg gggatggttg ggggtatggg gaaaatgagg ggggtaaggg gaggaggggt    2940
tggggttttg atgatattta atgagggagt gatggaggga gtgggagagg aagggggggt    3000
gtaaaggggg atagtgagga aagggtgggg agtatttagg gaaaggggga agagtgttag    3060
ggatggggtg ggggtattgg gaaaggatga ggggggggt gtgtggaggt agggaaaggg    3120 atttttgat ggaggatttg gggagagggg ggaaggggtg gtgttgatgg agggggggt    3180 agatggggga aataatatgg gtggggtgg tgtggggtgg ggggggttga tagtggaggg    3240
ggggggaagg atggagagat ttgatggagg gatagagggg gtggtgatta gggggtggg    3300 gtgattgatt ggggagggag gagatgatga gagtgggtg attaggatgg gggtggagga    3360 ttgggttag gggttgggtg atgggggta gggaggggg atgatgggtg agaggattga    3420
ttgggaggat ggggtgggtt tgaatattgg gttgatggag gagatagagg gggtagggt    3480 gggagagggt gtaggagagg ggatggttgg gataatggga agaggggagg gggttaaagt    3540
tgttgtggtt gatgaggagg atatggtgga ggatggtgtg gtgatggatg aggtgaggat    3600
ggagaggatg atggtggtga gggttaaggg gtggaatgag gaaggggttg gggttgagga    3660
ggaggagagg attttgaatg gggaggtggg ggaaaggag atgggagggt tgtggttgaa    3720
tgagggtggg gtgggggtg tggagttgaa ggagggagg atagagattg gggatttggg    3780
gggtggagag tttgggggttt tggaggttga gaggtagtgt gagggatgg ggataaggag    3840 gagggtgatg gataatttga gggggaaag gggggtggg ggtgggaggg tgggtttgag    3900
ggtgggataa agaaagtgtt aggggtaggt agtgagggaa gtgggggag atgtgaagtt    3960 gagggtggag tagagggggg gtgaaatgat gattaaaggg agtgggaaga tggaaatggg    4020
tgatttgtgt agtgggttta tggaggaagg agaggtgagg gaaaatgggg gtgatggggg    4080
```

```
agatatggtg atgttggaga taagtgggt gagtggaggg gaggaggatg aggggaggg      4140 ggttttgtgg gggggtaaa aatgggtga ggtgaaattg agagggaaa ggagtgtggt       4200 gggggtaagg gagggagggg gggttggagg agagatgaaa ggggagtta aggggatgaa     4260 aaataattgg ggtgtggggt tggtgtaggg aggtttgatg aagattaaat gtgagggagt    4320
aagaaggggt gggattgtgg gtgggaagaa agggggatt gagggtaatg ggataggtga     4380
ggttggtgta gatggggga tggtaagggt ggatgtggga gtttgaggg aggaggagag      4440 tatgggggtg aggaagatgg gagggaggga ggtttgggg aggggttgtg gtggggaaa      4500 ggagggaaag ggggattggg gattgagggt gggaagtgt tgggaagggg gatgggtggg     4560
ggggtgttgg gtattagggg aggtgggaa aggggatgt ggtggaaggg gattaagttg      4620
ggtaagggga gggttttggg agtgaggagg ttgtaaaagg aggggagtg aatgggtaat     4680 gatggtgata gtaggtttgg tgaggttgtg agtggaaaat agtgaggtgg gggaaaatgg   4740
agtaataaaa agaggggtgg gagggtaatt gggggttggg agggtttttt tgtgtgggta   4800
agttagatgg gggatggggg ttgggttat taagggtgt tgtaagggga tgggtgggt      4860 gatataagtg gtggggttg gtaggttgaa ggattgaagt gggatataaa ttataaagag    4920
gaagagaaga gtgaataaat gtgaattgat ggagaagatt ggtggagggg gtgatatgtg   4980
taaaggtggg ggtgggggtg ggttagatgg tattattggt tgggtaagtg aatgtgtgaa   5040
agaagg                                                              5046
```

<210> SEQ ID NO 57
<211> LENGTH: 9
<212> TYPE: PRT
<213> ORGANISM: Artificial Sequence
<220> FEATURE:
<223> OTHER INFORMATION: Synthetic Sequence

<400> SEQUENCE: 57

Phe Val Asp Phe Trp Glu Asn Phe Asp
1               5

<210> SEQ ID NO 58
<211> LENGTH: 42
<212> TYPE: PRT
<213> ORGANISM: Artificial Sequence
<220> FEATURE:
<223> OTHER INFORMATION: Synthetic Sequence

<400> SEQUENCE: 58

Tyr His Asn Cys Thr Lys Ile Phe Tyr Ser Gly Glu Asn Ile Thr Pro
1               5                   10                  15

Asp Phe Asn Ile Cys Asp Tyr Ala Ile Gly Phe Asn Phe Leu Ser Phe
            20                  25                  30

Gly Asp Arg Tyr Ile Arg Ile Pro Phe Tyr
        35                  40

<210> SEQ ID NO 59
<211> LENGTH: 87
<212> TYPE: PRT
<213> ORGANISM: Artificial Sequence
<220> FEATURE:
<223> OTHER INFORMATION: Synthetic Sequence

<400> SEQUENCE: 59

Arg Lys Phe Cys Ser Phe Val Val Ser Asn Ala Lys Gly Ala Pro Glu
1               5                   10                  15

Arg Glu Arg Phe Phe Gln Leu Leu Ser Glu Tyr Lys Gln Val Asp Ser
            20                  25                  30

Gly Gly Arg Tyr Lys Asn Asn Val Gly Gly Pro Val Pro Asp Lys Thr
        35                  40                  45

Ala Phe Ile Lys Asp Tyr Lys Phe Asn Ile Ala Phe Glu Asn Ser Met
    50                  55                  60

Cys Asp Gly Tyr Thr Thr Glu Lys Ile Met Glu Pro Met Leu Val Asn
65                  70                  75                  80

Ser Val Pro Ile Tyr Trp Gly
                85

<210> SEQ ID NO 60
<211> LENGTH: 77
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (1)..(4)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid
<220> FEATURE:
<221> NAME/KEY: misc_feature
<222> LOCATION: (9)..(11)
<223> OTHER INFORMATION: Xaa can be any naturally occurring amino acid
<220> FEATURE:
<221> NAME/KEY: misc_feature
<222> LOCATION: (13)..(17)
<223> OTHER INFORMATION: Xaa can be any naturally occurring amino acid
<220> FEATURE:
<221> NAME/KEY: misc_feature
<222> LOCATION: (19)..(21)
<223> OTHER INFORMATION: Xaa can be any naturally occurring amino acid
<220> FEATURE:
<221> NAME/KEY: misc_feature
<222> LOCATION: (23)..(30)
<223> OTHER INFORMATION: Xaa can be any naturally occurring amino acid
<220> FEATURE:
<221> NAME/KEY: misc_feature
<222> LOCATION: (33)..(37)
<223> OTHER INFORMATION: Xaa can be any naturally occurring amino acid
<220> FEATURE:
<221> NAME/KEY: misc_feature
<222> LOCATION: (39)..(39)
<223> OTHER INFORMATION: Xaa can be any naturally occurring amino acid
<220> FEATURE:
<221> NAME/KEY: misc_feature
<222> LOCATION: (41)..(50)
<223> OTHER INFORMATION: Xaa can be any naturally occurring amino acid
<220> FEATURE:
<221> NAME/KEY: misc_feature
<222> LOCATION: (53)..(54)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (58)..(59)
<223> OTHER INFORMATION: Xaa can be any naturally occurring amino acid
<220> FEATURE:
<221> NAME/KEY: misc_feature
<222> LOCATION: (61)..(62)
<223> OTHER INFORMATION: Xaa can be any naturally occurring amino acid
<220> FEATURE:
<221> NAME/KEY: misc_feature
<222> LOCATION: (64)..(66)
<223> OTHER INFORMATION: Xaa can be any naturally occurring amino acid

```
<220> FEATURE:
<221> NAME/KEY: misc_feature
<222> LOCATION: (68)..(69)
<223> OTHER INFORMATION: Xaa can be any naturally occurring amino acid
<220> FEATURE:
<221> NAME/KEY: misc_feature
<222> LOCATION: (71)..(71)
<223> OTHER INFORMATION: Xaa can be any naturally occurring amino acid
<220> FEATURE:
<221> NAME/KEY: misc_feature
<222> LOCATION: (73)..(77)
<223> OTHER INFORMATION: Xaa can be any naturally occurring amino acid

<400> SEQUENCE: 60

Xaa Xaa Xaa Xaa Ser Xaa Pro Trp Xaa Xaa Xaa Glu Xaa Xaa Xaa Xaa
1               5                   10                  15

Xaa Leu Xaa Xaa Xaa Glu Xaa Xaa Xaa Xaa Xaa Xaa Xaa Xaa Ile Phe
            20                  25                  30

Xaa Xaa Xaa Xaa Xaa Glu Xaa Arg Xaa Xaa Xaa Xaa Xaa Xaa Xaa Xaa
        35                  40                  45

Xaa Xaa Tyr Gln Xaa Xaa Leu Xaa Arg Xaa Xaa Arg Xaa Xaa Leu Xaa
    50                  55                  60

Xaa Xaa Arg Xaa Xaa Asn Xaa Leu Xaa Xaa Xaa Xaa Xaa
65                  70                  75

<210> SEQ ID NO 61
<211> LENGTH: 113
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (6)..(7)
<223> OTHER INFORMATION: Xaa can be any naturally occurring amino acid
<220> FEATURE:
<221> NAME/KEY: misc_feature
<222> LOCATION: (12)..(15)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (21)..(21)
<223> OTHER INFORMATION: Xaa can be any naturally occurring amino acid
<220> FEATURE:
<221> NAME/KEY: misc_feature
<222> LOCATION: (36)..(39)
<223> OTHER INFORMATION: Xaa can be any naturally occurring amino acid
<220> FEATURE:
<221> NAME/KEY: misc_feature
<222> LOCATION: (43)..(64)
<223> OTHER INFORMATION: Xaa can be any naturally occurring amino acid
<220> FEATURE:
<221> NAME/KEY: misc_feature
<222> LOCATION: (66)..(68)
<223> OTHER INFORMATION: Xaa can be any naturally occurring amino acid
<220> FEATURE:
<221> NAME/KEY: misc_feature
<222> LOCATION: (71)..(74)
<223> OTHER INFORMATION: Xaa can be any naturally occurring amino acid
<220> FEATURE:
<221> NAME/KEY: misc_feature
<222> LOCATION: (76)..(89)
<223> OTHER INFORMATION: Xaa can be any naturally occurring amino acid
<220> FEATURE:
<221> NAME/KEY: misc_feature
<222> LOCATION: (91)..(91)
<223> OTHER INFORMATION: Xaa can be any naturally occurring amino acid
<220> FEATURE:
<221> NAME/KEY: misc_feature
```

```
<222> LOCATION: (100)..(104)
<223> OTHER INFORMATION: Xaa can be any naturally occurring amino acid
<220> FEATURE:
<221> NAME/KEY: misc_feature
<222> LOCATION: (106)..(106)
<223> OTHER INFORMATION: Xaa can be any naturally occurring amino acid
<220> FEATURE:
<221> NAME/KEY: misc_feature
<222> LOCATION: (110)..(113)
<223> OTHER INFORMATION: Xaa can be any naturally occurring amino acid

<400> SEQUENCE: 61

Asp Glu Asn Tyr Leu Xaa Xaa Phe Leu Lys Gln Xaa Xaa Xaa Xaa Phe
1               5                   10                  15

Asp Xaa Phe Leu Xaa Asn Ile Phe Ser Gln Pro Leu Asp Lys Ala Lys
            20                  25                  30

Arg Arg Pro Xaa Xaa Xaa Xaa Met Trp Gly Xaa Xaa Xaa Xaa Xaa Xaa
                35                  40                  45

Xaa Xaa Xaa Xaa Xaa Xaa Xaa Xaa Xaa Xaa Xaa Xaa Xaa Xaa Xaa Xaa
        50                  55                  60

Tyr Xaa Xaa Xaa Leu Lys Xaa Xaa Xaa Xaa Phe Xaa Xaa Xaa Xaa Xaa
65                  70                  75                  80

Xaa Xaa Xaa Xaa Xaa Xaa Xaa Xaa Arg Xaa Lys Gln Phe Leu Lys
            85                  90                  95

Leu Lys Ala Xaa Xaa Xaa Xaa Xaa Lys Xaa Lys Glu Lys Xaa Xaa Xaa
            100                 105                 110

Xaa

<210> SEQ ID NO 62
<211> LENGTH: 452
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (2)..(24)
<223> OTHER INFORMATION: Xaa can be any naturally occurring amino acid
<220> FEATURE:
<221> NAME/KEY: misc_feature
<222> LOCATION: (36)..(40)
<223> OTHER INFORMATION: Xaa can be any naturally occurring amino acid
<220> FEATURE:
<221> NAME/KEY: misc_feature
<222> LOCATION: (43)..(44)
<223> OTHER INFORMATION: Xaa can be any naturally occurring amino acid
<220> FEATURE:
<221> NAME/KEY: misc_feature
<222> LOCATION: (48)..(50)
<223> OTHER INFORMATION: Xaa can be any naturally occurring amino acid
<220> FEATURE:
<221> NAME/KEY: misc_feature
<222> LOCATION: (53)..(53)
<223> OTHER INFORMATION: Xaa can be any naturally occurring amino acid
<220> FEATURE:
<221> NAME/KEY: misc_feature
<222> LOCATION: (57)..(58)
<223> OTHER INFORMATION: Xaa can be any naturally occurring amino acid
<220> FEATURE:
<221> NAME/KEY: misc_feature
<222> LOCATION: (61)..(61)
<223> OTHER INFORMATION: Xaa can be any naturally occurring amino acid
<220> FEATURE:
<221> NAME/KEY: misc_feature
<222> LOCATION: (68)..(70)
<223> OTHER INFORMATION: Xaa can be any naturally occurring amino acid
<220> FEATURE:
<221> NAME/KEY: misc_feature
<222> LOCATION: (73)..(73)
<223> OTHER INFORMATION: Xaa can be any naturally occurring amino acid
```

```
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (82)..(83)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid
<220> FEATURE:
<221> NAME/KEY: misc_feature
<222> LOCATION: (91)..(97)
<223> OTHER INFORMATION: Xaa can be any naturally occurring amino acid
<220> FEATURE:
<221> NAME/KEY: misc_feature
<222> LOCATION: (122)..(122)
<223> OTHER INFORMATION: Xaa can be any naturally occurring amino acid
<220> FEATURE:
<221> NAME/KEY: misc_feature
<222> LOCATION: (132)..(134)
<223> OTHER INFORMATION: Xaa can be any naturally occurring amino acid
<220> FEATURE:
<221> NAME/KEY: misc_feature
<222> LOCATION: (138)..(138)
<223> OTHER INFORMATION: Xaa can be any naturally occurring amino acid
<220> FEATURE:
<221> NAME/KEY: misc_feature
<222> LOCATION: (140)..(140)
<223> OTHER INFORMATION: Xaa can be any naturally occurring amino acid
<220> FEATURE:
<221> NAME/KEY: misc_feature
<222> LOCATION: (142)..(144)
<223> OTHER INFORMATION: Xaa can be any naturally occurring amino acid
<220> FEATURE:
<221> NAME/KEY: misc_feature
<222> LOCATION: (148)..(148)
<223> OTHER INFORMATION: Xaa can be any naturally occurring amino acid
<220> FEATURE:
<221> NAME/KEY: misc_feature
<222> LOCATION: (156)..(184)
<223> OTHER INFORMATION: Xaa can be any naturally occurring amino acid
<220> FEATURE:
<221> NAME/KEY: misc_feature
<222> LOCATION: (187)..(187)
<223> OTHER INFORMATION: Xaa can be any naturally occurring amino acid
<220> FEATURE:
<221> NAME/KEY: misc_feature
<222> LOCATION: (200)..(200)
<223> OTHER INFORMATION: Xaa can be any naturally occurring amino acid
<220> FEATURE:
<221> NAME/KEY: misc_feature
<222> LOCATION: (204)..(205)
<223> OTHER INFORMATION: Xaa can be any naturally occurring amino acid
<220> FEATURE:
<221> NAME/KEY: misc_feature
<222> LOCATION: (215)..(215)
<223> OTHER INFORMATION: Xaa can be any naturally occurring amino acid
<220> FEATURE:
<221> NAME/KEY: misc_feature
<222> LOCATION: (230)..(236)
<223> OTHER INFORMATION: Xaa can be any naturally occurring amino acid
<220> FEATURE:
<221> NAME/KEY: misc_feature
<222> LOCATION: (242)..(242)
<223> OTHER INFORMATION: Xaa can be any naturally occurring amino acid
<220> FEATURE:
<221> NAME/KEY: misc_feature
<222> LOCATION: (245)..(245)
<223> OTHER INFORMATION: Xaa can be any naturally occurring amino acid
<220> FEATURE:
<221> NAME/KEY: misc_feature
<222> LOCATION: (257)..(258)
<223> OTHER INFORMATION: Xaa can be any naturally occurring amino acid
<220> FEATURE:
<221> NAME/KEY: misc_feature
<222> LOCATION: (267)..(267)
```

```
<223> OTHER INFORMATION: Xaa can be any naturally occurring amino acid
<220> FEATURE:
<221> NAME/KEY: misc_feature
<222> LOCATION: (269)..(269)
<223> OTHER INFORMATION: Xaa can be any naturally occurring amino acid
<220> FEATURE:
<221> NAME/KEY: misc_feature
<222> LOCATION: (288)..(294)
<223> OTHER INFORMATION: Xaa can be any naturally occurring amino acid
<220> FEATURE:
<221> NAME/KEY: misc_feature
<222> LOCATION: (306)..(306)
<223> OTHER INFORMATION: Xaa can be any naturally occurring amino acid
<220> FEATURE:
<221> NAME/KEY: misc_feature
<222> LOCATION: (308)..(309)
<223> OTHER INFORMATION: Xaa can be any naturally occurring amino acid
<220> FEATURE:
<221> NAME/KEY: misc_feature
<222> LOCATION: (318)..(318)
<223> OTHER INFORMATION: Xaa can be any naturally occurring amino acid
<220> FEATURE:
<221> NAME/KEY: misc_feature
<222> LOCATION: (328)..(328)
<223> OTHER INFORMATION: Xaa can be any naturally occurring amino acid
<220> FEATURE:
<221> NAME/KEY: misc_feature
<222> LOCATION: (333)..(333)
<223> OTHER INFORMATION: Xaa can be any naturally occurring amino acid
<220> FEATURE:
<221> NAME/KEY: misc_feature
<222> LOCATION: (337)..(338)
<223> OTHER INFORMATION: Xaa can be any naturally occurring amino acid
<220> FEATURE:
<221> NAME/KEY: misc_feature
<222> LOCATION: (341)..(346)
<223> OTHER INFORMATION: Xaa can be any naturally occurring amino acid
<220> FEATURE:
<221> NAME/KEY: misc_feature
<222> LOCATION: (351)..(351)
<223> OTHER INFORMATION: Xaa can be any naturally occurring amino acid
<220> FEATURE:
<221> NAME/KEY: misc_feature
<222> LOCATION: (353)..(354)
<223> OTHER INFORMATION: Xaa can be any naturally occurring amino acid
<220> FEATURE:
<221> NAME/KEY: misc_feature
<222> LOCATION: (361)..(361)
<223> OTHER INFORMATION: Xaa can be any naturally occurring amino acid
<220> FEATURE:
<221> NAME/KEY: misc_feature
<222> LOCATION: (364)..(366)
<223> OTHER INFORMATION: Xaa can be any naturally occurring amino acid
<220> FEATURE:
<221> NAME/KEY: misc_feature
<222> LOCATION: (368)..(368)
<223> OTHER INFORMATION: Xaa can be any naturally occurring amino acid
<220> FEATURE:
<221> NAME/KEY: misc_feature
<222> LOCATION: (372)..(373)
<223> OTHER INFORMATION: Xaa can be any naturally occurring amino acid
<220> FEATURE:
<221> NAME/KEY: misc_feature
<222> LOCATION: (376)..(378)
<223> OTHER INFORMATION: Xaa can be any naturally occurring amino acid
<220> FEATURE:
<221> NAME/KEY: misc_feature
<222> LOCATION: (381)..(410)
<223> OTHER INFORMATION: Xaa can be any naturally occurring amino acid
<220> FEATURE:
<221> NAME/KEY: misc_feature
<222> LOCATION: (413)..(413)
<223> OTHER INFORMATION: Xaa can be any naturally occurring amino acid
<220> FEATURE:
<221> NAME/KEY: misc_feature
<222> LOCATION: (416)..(416)
<223> OTHER INFORMATION: Xaa can be any naturally occurring amino acid
<220> FEATURE:
<221> NAME/KEY: misc_feature
```

```
<222> LOCATION: (419)..(420)
<223> OTHER INFORMATION: Xaa can be any naturally occurring amino acid
<220> FEATURE:
<221> NAME/KEY: misc_feature
<222> LOCATION: (422)..(422)
<223> OTHER INFORMATION: Xaa can be any naturally occurring amino acid
<220> FEATURE:
<221> NAME/KEY: misc_feature
<222> LOCATION: (427)..(428)
<223> OTHER INFORMATION: Xaa can be any naturally occurring amino acid
<220> FEATURE:
<221> NAME/KEY: misc_feature
<222> LOCATION: (436)..(447)
<223> OTHER INFORMATION: Xaa can be any naturally occurring amino acid
<220> FEATURE:
<221> NAME/KEY: misc_feature
<222> LOCATION: (449)..(452)
<223> OTHER INFORMATION: Xaa can be any naturally occurring amino acid

<400> SEQUENCE: 62

Met Xaa Xaa Xaa Xaa Xaa Xaa Xaa Xaa Xaa Xaa Xaa Xaa Xaa Xaa Xaa
1               5                   10                  15

Xaa Xaa Xaa Xaa Xaa Xaa Xaa Xaa Lys Thr Ile Lys Val Lys Phe Val
            20                  25                  30

Asp Phe Trp Xaa Xaa Xaa Xaa Xaa Phe Asp Xaa Xaa Arg Asn Phe Xaa
        35                  40                  45

Xaa Xaa Ile Leu Xaa Gln Arg Tyr Xaa Xaa Ile Glu Xaa Ser Asp Asn
    50                  55                  60

Pro Asp Tyr Xaa Xaa Xaa Val Phe Xaa Ser Val Xaa Phe Gly Tyr Glu
65                  70                  75                  80

His Xaa Xaa Leu Lys Xaa Asp Cys Val Arg Xaa Xaa Xaa Xaa Xaa Xaa
                85                  90                  95

Xaa Ile Phe Tyr Thr Gly Glu Asn Ile Thr Pro Asp Phe Asn Leu Cys
            100                 105                 110

Asp Tyr Ala Ile Gly Phe Asp Tyr Leu Xaa Phe Gly Asp Tyr Leu Arg
            115                 120                 125

Leu Pro Leu Xaa Xaa Xaa Leu Phe Tyr Xaa Tyr Xaa Val Xaa Xaa Xaa
        130                 135                 140

Lys Leu Ala Xaa Arg Lys His Ile Asp Ser Asp Xaa Xaa Xaa Xaa Xaa
145                 150                 155                 160

Xaa Xaa Xaa Xaa Xaa Xaa Xaa Xaa Xaa Xaa Xaa Xaa Xaa Xaa Xaa Xaa
                165                 170                 175

Xaa Xaa Xaa Xaa Xaa Xaa Xaa Lys Lys Xaa Phe Cys Asn Phe Val
            180                 185                 190

Val Ser Asn Gly Lys Ala Ala Xaa Pro Glu Arg Xaa Xaa Phe Phe His
        195                 200                 205

Ala Leu Ser Ala Tyr Lys Xaa Val Asp Ser Gly Gly Arg Tyr Leu Asn
    210                 215                 220

Asn Val Gly Gly Pro Xaa Xaa Xaa Xaa Xaa Xaa Val Ala Asp Lys
225                 230                 235                 240

Phe Xaa Gln Ser Xaa Tyr Lys Phe Ser Ile Ala Phe Glu Asn Ser Ser
                245                 250                 255

Xaa Xaa Gly Tyr Thr Thr Glu Lys Ile Ile Xaa Ala Xaa Ala Ala Gly
            260                 265                 270

Thr Ile Pro Ile Tyr Trp Gly Asn Pro Leu Ile Ala Lys Asp Phe Xaa
        275                 280                 285

Xaa Xaa Xaa Xaa Xaa Xaa Asn Pro Lys Ser Phe Ile Asn Ala His Asp
    290                 295                 300

Phe Xaa Ser Xaa Xaa Glu Ala Val Glu His Ile Lys Glu Xaa Asp Asn
```

```
                305                 310                 315                 320
Asp Asp Asp Leu Tyr Leu Ser Xaa Leu Ser Glu Pro Xaa Phe Asn Asp
                    325                 330                 335

Xaa Xaa Glu Asn Xaa Xaa Xaa Xaa Xaa Leu Lys Glu Lys Xaa Phe
            340                 345                 350

Xaa Xaa Phe Leu Tyr Asn Ile Phe Xaa Gln Pro Xaa Xaa Xaa Ala Xaa
                355                 360                 365

Arg Arg Gly Xaa Xaa Met Trp Xaa Xaa Xaa Leu Tyr Xaa Xaa Xaa Xaa
        370                 375                 380

Xaa Xaa Xaa Xaa Xaa Xaa Xaa Xaa Xaa Xaa Xaa Xaa Xaa Xaa Xaa Xaa
385                 390                 395                 400

Xaa Xaa Xaa Xaa Xaa Xaa Xaa Xaa Xaa Lys Arg Xaa His Arg Xaa
                405                 410                 415

Leu Thr Xaa Xaa Ile Xaa Arg Lys Arg Lys Xaa Xaa Pro Leu Arg Gln
                420                 425                 430

Phe Thr Arg Xaa Xaa Xaa Xaa Xaa Xaa Xaa Xaa Xaa Xaa Xaa Lys
                435                 440                 445

Xaa Xaa Xaa Xaa
    450

<210> SEQ ID NO 63
<211> LENGTH: 96
<212> TYPE: PRT
<213> ORGANISM: Artificial Sequence
<220> FEATURE:
<223> OTHER INFORMATION: Consensus Sequence
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: misc_feature
<222> LOCATION: (16)..(16)
<223> OTHER INFORMATION: Xaa can be any naturally occurring amino acid
<220> FEATURE:
<221> NAME/KEY: misc_feature
<222> LOCATION: (20)..(21)
<223> OTHER INFORMATION: Xaa can be any naturally occurring amino acid
<220> FEATURE:
<221> NAME/KEY: misc_feature
<222> LOCATION: (31)..(31)
<223> OTHER INFORMATION: Xaa can be any naturally occurring amino acid
<220> FEATURE:
<221> NAME/KEY: misc_feature
<222> LOCATION: (46)..(52)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (62)..(62)
<223> OTHER INFORMATION: Xaa can be any naturally occurring amino acid
<220> FEATURE:
<221> NAME/KEY: misc_feature
<222> LOCATION: (74)..(75)
<223> OTHER INFORMATION: Xaa can be any naturally occurring amino acid
<220> FEATURE:
<221> NAME/KEY: misc_feature
<222> LOCATION: (84)..(84)
<223> OTHER INFORMATION: Xaa can be any naturally occurring amino acid
<220> FEATURE:
<221> NAME/KEY: misc_feature
<222> LOCATION: (86)..(86)
<223> OTHER INFORMATION: Xaa can be any naturally occurring amino acid

<400> SEQUENCE: 63
```

-continued

```
Lys Lys Xaa Phe Cys Asn Phe Val Val Ser Asn Gly Lys Ala Ala Xaa
1               5                   10                  15

Pro Glu Arg Xaa Xaa Phe Phe His Ala Leu Ser Ala Tyr Lys Xaa Val
            20                  25                  30

Asp Ser Gly Gly Arg Tyr Leu Asn Asn Val Gly Gly Pro Xaa Xaa Xaa
            35                  40                  45

Xaa Xaa Xaa Xaa Val Ala Asp Lys Phe Xaa Phe Gln Ser Xaa Tyr Lys
    50                  55                  60

Phe Ser Ile Ala Phe Glu Asn Ser Ser Xaa Xaa Gly Tyr Thr Thr Glu
65                  70                  75                  80

Lys Ile Ile Xaa Ala Xaa Ala Ala Gly Thr Ile Pro Ile Tyr Trp Gly
            85                  90                  95
```

<210> SEQ ID NO 64
<211> LENGTH: 7225
<212> TYPE: DNA
<213> ORGANISM: Artificial Sequence
<220> FEATURE:
<223> OTHER INFORMATION: Synthetic Sequence

<400> SEQUENCE: 64

| | |
|---|---|
| caagaaggag atatacatat gaagaccatc aaggtaaaat tcgtcgattt ctggaaaggt | 60 |
| ttcgacccgc gcaacaactt cctgatggac atcctgaaac agcgttatca cattgaactg | 120 |
| agcgaaagcc cggactacct gatcttctct gtcttcggtt tcactaacct gaactacgaa | 180 |
| cgctgcgtta aaatcttcta caccggtgaa aacctgaccc cggatttcaa catctgcgac | 240 |
| tacgcgattg gtttcgatta tctgagcttc ggtgatcgtt acatgcgtct gccactgtac | 300 |
| gcggtctatg gcatcgagaa actggcttct ccgaaagtta tcgacaaaga aaaagttctg | 360 |
| aagcgtaaat tctgttctta cgtagtaagc aataacatcg gcgcgccgga acgttctcgt | 420 |
| ttcttccatc tgctgtctga atacaaaaag gttgactccg gtggtcgttg ggaaaacaac | 480 |
| gtaggcggtc cggttccgaa taagctggac tttatcaaag actacaagtt caacatcgca | 540 |
| tcgaaaaact ccatgtacga cggctacact actgaaaaaa tcatggaacc gatgctggtg | 600 |
| aacagcctgc cgatttattg gggcaaccgc ctgatcaaca agacttcaa cccagcgtct | 660 |
| ttcatcaacg tttccgattt cccgtctctg gaagcggcgg tggagcacat tgttatgctg | 720 |
| gacaataacg atgatatgta cctgagcatc ctgtctaaac cgtggtttaa cgatgaaaac | 780 |
| tacctggact ggaaagcgcg cttcttccac ttttttcgata acatcttcaa tcgtccgatc | 840 |
| gatgaatgca aatatctgac cccgtacggc ttttgtcgtc actatcgtaa ccaactgcgt | 900 |
| agcgctcgtc tgctgaaaca cgctttcgc cagctgcgta cccgctgcg ctggttccgc | 960 |
| tagtagctcg agctgcagta atcgtacagg gtagtacaaa taaaaaaggc acgtcagatg | 1020 |
| acgtgccttt tttcttgtga gcagtaagct tctacgaaca tcttccagga tactcctgca | 1080 |
| gcgaaatatt tgttttaagc tcactcacat atcgcaacat ttactttact ttaagacaat | 1140 |
| tccaggcaaa ttatacaaca ctttacggga tagtaagtcc gcctgaaaaa tcgcgagagt | 1200 |
| ggcgcattag gtgacccatg ttgttccgtt tagtcatgat gaaatattca ggtaagggga | 1260 |
| attatcgtta cgcattgagt gagggtatgc catgtcaacg attattatgg atttatgtag | 1320 |
| ttacacccga ctaggtttaa ccgggtatct gttgagtaga ggggttaaaa aagagaaat | 1380 |
| caacgacatt gaaaccgttg atgaccttgc catagcttgt gattcacagc gcccttcagt | 1440 |
| ggtgtttatt aatgaggact gtttcatcca cgatgcttct aacagtcagc gtatcaagct | 1500 |
| catcattaat caacatccca atacgttatt tatcgttttt atggcaattg ccaatgttca | 1560 |

```
ttttgatgaa tatctattgg tcagaaaaaa tttattgatc agttctaaat cgattaaacc    1620
ggaatctctc gacgatatcc ttggcgatat tctgaaaaaa gagacaacga taacctcgtt    1680
tttaaatatg ccgacgttat cattgagccg aaccgaatcg agtatgttgc gaatgtggat    1740
ggcaggtcag ggaaccattc aaatctctga ccaaatgaat atcaaagcca agaccgtttc    1800
atcgcataaa ggtaatatta aacgtaagat caaaacgcat aataaacagg ttatctacca    1860
tgtcgtccga ctgacggata atgtgactaa tggtattttt gtcaacatgc gctaacacat    1920
tctgactggt ggtttcccac cagtcaggct gaataagatt actctgcttt ctccacaaag    1980
ataccgtcct gatgccctgc ttcattaaag aaagcttggc actggccgtc gttttacaac    2040
gtcgtgactg ggaaaaccct ggcgttaccc aacttaatcg ccttgcagca catcccoctt    2100 tcgccagctg gcgtaatagc gaagaggccc gcaccgatcg cccttcccaa cagttgcgca    2160
gcctgaatgg cgaatggcgc cttcgggaag gcgtctcgaa gaatttaacg gagggtaaaa    2220
aaaccgacgc acactggcgt cggctctggc aggatgtttc gtaattagat agccaccggc    2280
gctttaatgc ccggatgcgg atcgtagcct tcaatctcaa agtcttcgaa acggtagtcg    2340
aagatggatt cgggtttacg tttgataatc aacttcggca gcggacgcgg ttcgcggctt    2400
aattgcagat gagtttgatc catatggttg ctgtacagat gcgtgtcgcc accggtccag    2460
acaaaatcac ccacttccag atcgcactgc tgcgccatca tatgcaccaa taacgcgtag    2520
ctggcaatgt tgaacggcag gccgaggaag acgtcacagg agcgctgata aagctggcaa    2580
gagagtttgc cgtctgccac atagaactgg aagaatgcat ggcacggtgc cagcgccatt    2640
ttatccagtt cgcctacgtt ccacgctgaa acaataatgc ggcgcgaatc cgggtcgttt    2700
ttcagctggt tcagtaccgt agtgatctgg tcaatatgac gaccatctgg cgttggccag    2760
gcgcgccact gtttaccata cactggcccg aggtcgccgt tttcatcggc ccattcgtcc    2820
cagatggtga cattgttttc gtgtagataa gcaatgttag tgtcgccctg cagaaaccac    2880
agcagttcat ggatgatgga acgcaggtgg caacgtttag ttgtcaccag cgggaatcca    2940
tcttgcaggt taaaacgcat ctgatgacca aaaatggaaa gcgttccggt tccggtacgg    3000 tcgttttttct gtgtgccttc gtcgagcact ttttgcatca gttctaaata ctgtttcatg    3060
gttcctcagg aaacgtgttg ctgtgggctg cgacgatatg cccagaccat catgatcaca    3120
cccgcgacaa tcatcgggat ggaaagaatt tgccccatgc tgatgtactg cacccaggca    3180
ccggtaaact gcgcgtcggg ctggcggaaa aactcaacaa tgatgcgaaa cgcgccgtaa    3240
ccaatcagga caaacctga gacagctccc attgggcgtg gttacgaat atacaggttg    3300 aggaggcgcc tgatgcggta ttttctcctt acgcatctgt gcggtatttc acaccgcata    3360
tatggtgcac tctcagtaca atctgctctg atgccgcata gttaagccag ccccgacacc    3420
cgccaacacc cgctgacgcg ccctgacggg cttgtctgct cccggcatcc gcttacagac    3480
aagctgtgac cgtctccggg agctgcatgt gtcagaggtt ttcaccgtca tcaccgaaac    3540
gcgcgagacg aaagggcctc gtgatacgcc tatttttata ggttaatgtc atgataataa    3600
tggtttctta gacgtcaggt ggcacttttc ggggaaatgt gcgcggaacc cctatttgtt    3660
tatttttcta aatacattca aatatgtatc cgctcatgag acaataaccc tgataaatgc    3720
ttcaataata ttgaaaaagg aagagtatga gtattcaaca tttccgtgtc gcccttattc    3780
ccttttttgc ggcattttgc cttcctgttt ttgctcaccc agaaacgctg gtgaaagtaa    3840
aagatgctga agatcagttg ggtgcacgag tgggttacat cgaactggat ctcaacagcg    3900
```

-continued

```
gtaagatcct tgagagtttt cgccccgaag aacgttttcc aatgatgagc acttttaaag    3960
ttctgctatg tggcgcggta ttatcccgta ttgacgccgg gcaagagcaa ctcggtcgcc    4020
gcatacacta ttctcagaat gacttggttg agtactcacc agtcacagaa aagcatctta    4080
cggatggcat gacagtaaga gaattatgca gtgctgccat aaccatgagt gataacactg    4140
cggccaactt acttctgaca acgatcggag gaccgaagga gctaaccgct tttttgcaca    4200
acatggggga tcatgtaact cgccttgatc gttgggaacc ggagctgaat gaagccatac    4260
caaacgacga gcgtgacacc acgatgcctg tagcaatggc aacaacgttg cgcaaactat    4320
taactggcga actacttact ctagcttccc ggcaacaatt aatagactgg atggaggcgg    4380
ataaagttgc aggaccactt ctgcgctcgg cccttccggc tggctggttt attgctgata    4440
aatctggagc cggtgagcgt gggtctcgcg gtatcattgc agcactgggg ccagatggta    4500
agccctcccg tatcgtagtt atctacacga cggggagtca ggcaactatg gatgaacgaa    4560
atagacagat cgctgagata ggtgcctcac tgattaagca ttggtaactg tcagaccaag    4620
tttactcata tatactttag attgatttaa aacttcattt ttaatttaaa aggatctagg    4680
tgaagatcct ttttgataat ctcatgacca aaatccctta acgtgagttt tcgttccact    4740
gagcgtcaga ccccgtagaa aagatcaaag gatcttcttg agatcctttt tttctgcgcg    4800
taatctgctg cttgcaaaca aaaaaaccac cgctaccagc ggtggtttgt ttgccggatc    4860
aagagctacc aactcttttt ccgaaggtaa ctggcttcag cagagcgcag ataccaaata    4920
ctgtccttct agtgtagccg tagttaggcc accacttcaa gaactctgta gcaccgccta    4980
catacctcgc tctgctaatc ctgttaccag tggctgctgc cagtggcgat aagtcgtgtc    5040
ttaccgggtt ggactcaaga cgatagttac cggataaggc gcagcggtcg ggctgaacgg    5100
ggggttcgtg cacacagccc agcttggagc gaacgaccta ccgaactg agataccta    5160 agcgtgagct atgagaaagc gccacgcttc ccgaagggag aaaggcggac aggtatccgg    5220
taagcggcag ggtcggaaca ggagagcgca cgagggagct tccaggggga acgcctggt    5280 atctttatag tcctgtcggg tttcgccacc tctgacttga gcgtcgattt tgtgatgct    5340 cgtcagggg gcggagccta tggaaaaacg ccagcaacgc ggcctttta cggttcctgg    5400 ccttttgctg gccttttgct cacatgttct ttcctgcgtt atccctgat tctgtggata    5460 accgtattac cgcctttgag tgagctgata ccgctcgccg cagccgaacg accgagcgca    5520
gcgagtcagt gagcgaggaa gcggaagagc gcccaatacg caaaccgcct ctccccgcgc    5580
gttggccgat tcattaatgc agaattgatc tctcacctac caaacaatgc cccctgcaa    5640 aaaataaatt catataaaaa acatacagat aaccatctgc ggtgataaat tatctctggc    5700
ggtgttgaca taaataccac tggcggtgat actgagcaca tcagcaggac gcactgacca    5760
ccatgaaggt gacgctctta aaattaagc cctgaagaag gcagcattc aaagcagaag    5820 gctttggggt gtgtgatacg aaacgaagca ttggccgtaa gtgcgattcc ggattagctg    5880
ccaatgtgcc aatcgcgggg ggttttcgtt caggactaca actgccacac accaccaaag    5940
ctaactgaca ggagaatcca gatggatgca caaacacgcc gccgcgaacg tcgcgcagag    6000
aaacaggctc aatggaaagc agcaaatccc ctgttggttg gggtaagcgc aaaaccagtt    6060
ccgaaagatt ttttaacta taaacgctga tggaagcgtt tatgcggaag aggtaaagcc    6120
cttcccgagt aacaaaaaaa caacagcata ataaccccg ctcttacaca ttccagccct    6180 gaaaagggc atcaaattaa accacaccta tggtgtatgc atttatttgc atacattcaa    6240 tcaatttta gaattctaga aagaaggaga tatacatatg aaaactatca agttaaatt    6300
```

```
cgttgatttc tgggaaaact tcgacccgca acacaacttt attgcaaaca ttatcagcaa    6360
aaaataccgt atcgaactgt ccgatacccc agactatctg ttcttttccg tgttcggtta    6420
tgaaaacatc gactaccata actgcaccaa aatcttctac tctggtgaaa acattactcc    6480
ggacttcaac atttgtgact atgcaattgg tttcaacttc ctgtcctttg gtgaccgtta    6540
tatccgtatc ccattttata ccgcgtacgg tgtgcagcag ctggccgcgc caaaagtaat    6600
cgttccggaa gttgttctga atcgtaagtt ctgtagcttc gttgtatcta atgccaaggg    6660
cgctccggag cgcgagcgtt tcttccaact gctgagcgaa tacaaacagg tggactctgg    6720
cggtcgttac aaaaataacg ttggcggtcc ggtaccagat aaaactgcat ttatcaaaga    6780
ctacaaattc aacattgcgt tcgaaaactc catgtgcgac ggttacacca cggaaaaaat    6840
catggaacct atgctggtca attccgttcc aatttactgg ggtaacaaac tgatcgaccg    6900
tgactttaac ccggactcct tcattaatgt atcctcttat tcttctctgg aagaagcagt    6960
tgagcacatc gtccgtctgg atcagaatga tgacgaatac ctgagcctgc tgtccgcccc    7020
gtggttcaac gaggaaaact acctgaactg ggaagaacag ctgatcactt tcttcgacaa    7080
catcttcgaa aaaccgctgt ctgaatcccg ttatatccca acccacggtt acatccagac    7140
ctatcagtac cgcctgcatc gtatgatgcg tgataaactg ttccgtaaac gtatcaaccc    7200
gctgaaatgg ttttcttcta agtaa                                          7225
```

US 11,453,900 B2

ALPHA (1,3) FUCOSYLTRANSFERASES FOR USE IN THE PRODUCTION OF FUCOSYLATED OLIGOSACCHARIDES

CROSS-REFERENCE TO RELATED APPLICATION

This application is a national stage application filed under 35 U.S.C. § 371, of International Patent Application No. PCT/US2015/049257, filed Sep. 9, 2015, which claims the benefit of and priority to U.S. Provisional Application No. 62/047,851 filed on Sep. 9, 2014, the contents of all of which are incorporated herein by reference in its entirety.

INCORPORATION BY REFERENCE

The content of the following submission on ASCII text file is incorporated herein by reference in its entirety: a computer readable form (CRF) of the Sequence Listing (file name: 37847516001WOSEQLIST.txt, date recorded: Sep. 9, 2015, size: 185,381 bytes).

FIELD OF THE INVENTION

The invention provides compositions and methods for producing purified oligosaccharides, in particular fucosylated oligosaccharides that are typically found in human milk.

BACKGROUND OF THE INVENTION

Human milk contains a diverse and abundant set of neutral and acidic oligosaccharides (Kunz, C., et al. (2000). Oligosaccharides in human milk: structural, functional, and metabolic aspects. Annu Rev Nutr 20, 699-722.; Bode, L., and Jantscher-Krenn, E. (2012). Structure-function relationships of human milk oligosaccharides. Adv Nutr 3, 383S-391S.). More than 130 different complex oligosaccharides have been identified in human milk, and their structural diversity and abundance is unique to humans. Although these molecules are likely not utilized by infants for nutrition, they nevertheless serve critical roles in the establishment of a healthy gut microbiome, in the prevention of disease, and in immune function (Gnoth, M. J., et al. (2000). Human milk oligosaccharides are minimally digested in vitro. J Nutr 130, 3014-020.; Newburg, D. S., and Walker, W. A. (2007). Protection of the neonate by the innate immune system of developing gut and of human milk. Pediatr Res 61, 2-8.; Bode, L., and Jantscher-Krenn, E. (2012). Structure-function relationships of human milk oligosaccharides. Adv Nutr 3, 383S-391S.; Rudloff, S., and Kunz, C. (2012). Milk oligosaccharides and metabolism in infants. Adv Nutr 3, 398S-405S.).

Human milk oligosaccharides (HMOS) include $\alpha(1,3)$ glycosylated oligosaccharides. For example, the human milk oligosaccharide (HMO) 3-fucosyllactose (3FL) is one of the most abundant fucosylated oligosaccharides present in human milk, and is thought to function with other HMOS to promote the growth of beneficial commensal bacteria in the infant gut. Additional $\alpha(1,3)$ fucosylated oligosaccharides include lactodifucotetraose (LDFT) and lacto-N-fucopentaose III (LNF III).

Prior to the invention described herein, the ability to produce human milk oligosaccharides (HMOS) inexpensively was problematic. For example, their production through chemical synthesis was limited by stereo-specificity issues, precursor availability, product impurities, and high overall cost. As an alternative to chemical synthesis, bacteria can be metabolically engineered to produce HMOS. A few glycosyltransferases derived from bacterial species have been identified and characterized in terms of their ability to catalyze the biosynthesis of HMOS in E. coli host strains. However, the high cost of reactants limits their utility for low-cost, large-scale production. Moreover, the previously available $\alpha(1,3)$ fucosyltransferases exhibit disadvantages including low yield and poor specificity for the location of $\alpha$-fucose linkage formation. As a result, purity as well as yield of the desired $\alpha(1,3)$ fucosylated product is therefore compromised As such, there exists a pressing need for new strategies to inexpensively manufacture large quantities of HMOS, in particular $\alpha(1,3)$ fucosylated oligosaccharides.

SUMMARY OF THE INVENTION

In a first aspect, the invention provides purified $\alpha(1,3)$ fucosyltransferase enzymes (also referred to herein as $\alpha(1,3)$ FTs) that utilize lactose and catalyze the transfer of an L-fucose sugar from a GDP-fucose donor substrate in an $\alpha1,3$ linkage. Preferably, the acceptor substrate is an oligosaccharide. The $\alpha(1,3)$ fucosyltransferases identified and described herein are useful for expressing in host bacteria for the production of human milk oligosaccharides (HMOS). The $\alpha(1,3)$ fucosyltransferases are heterologous with respect to a host organism in which they are expressed produced. For example, the nucleic acid and/or amino acid sequences of the fucosyltransferases are different from those that naturally occur in the host bacteria. Thus, the host bacteria are genetically-altered; for example, they have been altered to include heterologous fucosyltransferase encoding DNA such as cDNA. Exemplary fucosylated oligosaccharides produced by the methods of the invention include 3-fucosyllactose (3FL), lactodifucotetraose (LDFT) and lacto-N-fucopentaose III (LNF III).

For example, the invention provides a composition for use in the production of a fucosylated oligosaccharide. The composition includes a bacterium expressing at least one $\alpha(1,3)$ fucosyltransferase enzyme, wherein the amino acid sequence of the one or more enzymes comprises at least 25% identity up to 100% identity to full length CafC (SEQ ID NO: 2), an isolated nucleic acid (e.g., a cDNA) encoding the enzyme or enzymes, or the purified recombinant enzyme itself or combination of enzymes. In some examples, the bacterium expresses two or more $\alpha(1,3)$ fucosyltransferase enzymes, wherein the amino acid sequence of one of the enzymes has at least 25% identity up to 100% identity to full length CafC (SEQ ID NO: 2), and the amino acid sequence of the one or more additional enzymes comprises at least 25% identity up to 100% identity to full length SEQ ID NOS: 2 (CafC), 17 (CafV), 9 (CafN), 7 (CafL), 10 (CafO), 12 (CafQ), 16 (CafU) or 53 (CafD). In the latter case, an advantage of increased (e.g., 10%, 25%, 50%, 75%, 2-fold, 3-fold or more greater) enzyme production or activity is observed with at least 2 copies of a $\alpha(1,3)$ fucosyltransferase enzyme-encoding sequences. For example, the $\alpha(1,3)$ fucosyltransferase enzyme-encoding sequences are different heterologous sequences. Furthermore, the two or more $\alpha(1,3)$ fucosyltransferase enzymes may be under control of the $P_L$ promoter and the bacterium may harbor the expression vector pG420.

The invention further provides methods for producing a fucosylated oligosaccharide in any of the bacteria disclosed herein, in such methods a bacterium may fermented in the presence of a nitrogen-rich nutritional additives comprising casamino acids or yeast extract. Additional examples of nitrogen-rich nutritional additives include protein hydrolysates of meat, casein, whey, gelatin, soybean, yeast or grain.

The α(1,3) fucosyltransferases of the invention comprise an amino acid sequence comprising at least 10% sequence identity and up to 100% sequence identity to CafC (SEQ ID NO: 2). Preferably, the α(1,3) fucosyltransferases of the invention comprise at least 50% sequence identity to CafC, more preferably less than 60%, 75%, 90%, 95%, and 99% sequence identity to CafC (SEQ ID NO:2). The α(1,3) fucosyltransferases of the invention retain the functional characteristic of catalyzing the formation of an α(1,3) linkage at the 3 position of glucose or GlcNAc. Preferably, the enzyme comprises the amino acid sequence of "FVDF-WENFD" (SEQ ID NO: 57), "YHNCTKIFYSGEN-ITPDFNICDYAIGFNFLSFGDRYIRIPFY" (SEQ ID NO:58), and "RKFCSFVVSNAKGAPERERFFQLL-SEYKQVDSGGRYKNNVGGPVPDKTAFIKDYKF NIAFENSMCDGYTTEKIMEPMLVNSVPIYWG" (SEQ ID NO: 59), corresponding to the substrate binding and catalytic domains of CafC.

In a particularly preferred aspect, the α(1,3) fucosyltransferases of the invention comprise the amino acid sequence of SEQ ID NO: 2 (CafC), SEQ ID NO: 17 (CafV) and SEQ ID NO: 9 (CafN). Alternatively, the α(1,3) fucosyltransferases of the invention comprise SEQ ID NO: 7 (CafL), SEQ ID NO: 10 (CafO) and SEQ ID NO: 12 (CafQ).

In another particularly preferred aspect, the α(1,3) fucosyltransferase of the invention comprise the amino acid sequence of SEQ ID NO: 53 (CafD):

(SEQ ID NO: 53)
MKDDLVILHPDGGIASQIAFVALGLAFEQKGAKVKYDLSWFAEGAKGFW

NPSNGYDKVYDITWDISKAFPALHIEIANEEEIERYKSKYLIDNDRVID

YAPPLYCYGYKGRIFHYLYAPFFAQSFAPKEAQDSHTPFAALLQEIESS

PSPCGVHIRRGDLSQPHIVYGNPTSNEYFAKSIELMCLLHPQSSFYLFS

DDLAFVKEQIVPLLKGKTYRICDVNNPSQGYLDLYLLSRCRNIIGSQGS

MGEFAKVLSPHNPLLITPRYRNIFKEVENVMCVNWGESVQHPPLVCSAP

PPLVSQLKRNAPLNSRLYKEKDNASA

The amino acid sequence of the α(1,3) fucosyltransferase enzymes of the invention is at least 5%, at least 65, at least 10%, at least 15%, at least 20%, at least 25%, at least 30%, at least 35%, at least 40%, at least 45%, at least 50%, at least 55%, at least 60%, at least 65%, at least 70% at least 75%, at least 80%, at least 85%, at least 90%, at least 95% identical to the sequence of SEQ ID NO: 2, 9 or 17. Preferably the amino acid sequence is at least 50%, 55%, 60%, 65%, 70%, 75%, 80%, 85%, 90%, 95% or 99% identical to the sequence of SEQ ID NO: 2 (CafC).

Alternatively, the α(1,3) fucosyltransferase comprises at least at least 15%, at least 20%, at least 25%, at least 30%, at least 355, at least 40%, at least 45%, at least 50%, at least 55%, at least 60%, at least 65%, at least 70% at least 75%, at least 80%, at least 85%, at least 90%, at least 95% sequence identity to any one of the novel α(1,3) fucosyltransferases disclosed herein, for example having the amino acid sequences listed in Table 1. The fucosylated oligosaccharides are preferably isolated and purified.

The α(1,3) fucosyltransferases of the invention include the amino acid sequences of the α(1,3) fucosyltransferases as well as fragments and variants thereof that exhibit α(1,3) fucosyltransferase activity.

In a second aspect, the invention provides a method for producing fucosylated oligosaccharides, in particular for producing α(1,3)-fucosylated oligosaccharides. The method comprises providing a bacterium that expresses at least one exogenous lactose-utilizing α(1,3) fucosyltransferase according to the invention and culturing the bacterium in the presence of lactose so as to produce one or more α(1,3)-fucosylated oligosaccharides. The method preferably further comprises retrieving or purifying the fucosylated oligosaccharide from said bacterium or from a culture supernatant of said bacterium.

In a related aspect, the invention provides methods for producing α(1,3)-fucosylated oligosaccharides utilizing a bacterial strain harboring an expression plasmid containing two different different α(1,3) fucosyltransferases in a "tandem" arrangement. These tandem (1,3) fucosyltransferases may be under the control of the $P_L$ promoter. An example expression vector comprising tandem (1,3) fucosyltransferases and a $P_L$ promoter is pG420. In a preferred embodiment, these tandem α(1,3) fucosyltransferases are CafC and CafN.

Furthermore, methods of the invention provide for eliminating added tryptophan in culture of strains producing high levels of α(1,3) fucosyltransferases and thereby repressing a $P_L$ promoter and minimizing cellular toxicity.

Optionally, the bacterium also expresses one or more exogenous lactose-utilizing α(1,2) fucosyltransferase enzymes and/or one or more exogenous lactose-utilizing α(1,4) fucosyltransferase enzymes. The combination of fucosyltransferases expressed in the production bacterium is dependent upon the desired fucosylated oligosaccharide product Examples of suitable α(1,2) fucosyltransferase enzymes include those described in U.S. Ser. No. 61/993,742, filed on May 15, 2014 (hereby incorporated by reference), but are not limited to *Bacteroides vulgatus* ATCC 8482 FutN (Genbank accession: YP_001300461.1), *Parabacteroides johnsonii* CL02T12C29 FutX (Genbank accession: WP_008155883.1), *Lachnospiraceae bacterium* 3_1_57FAA_CT1 FutQ (Genbank accession: WP_009251343.1), *Prevotella melaninogenica* ATCC 25845 FutO (Genbank accession: YP_003814512.1), *Prevotella* sp. CAG:891 FutW (Genbank accession: WP_022481266.1) and *Bacteroides* sp. CAG:63 FutZA (Genbank accession: WP_022161880.1). Examples of suitable α(1,4) fucosyltransferase enzymes include, but are not limited to *H. pylori* UA948 FucTa (which has a relaxed acceptor specificity and is able to generate both α(1,3)- and α(1,4)-fucosyl linkages). An example of an enzyme possessing only α(1,4) fucosyltransferase activity is given by the FucT III enzyme from *Helicobacter pylori* strain DMS6709 (e.g., GenBank Accession Number AY450598.1 (GI:40646733), incorporated herein by reference) (S. Rabbani, V. Miksa, B. Wipf, B. Ernst, *Glycobiology* 15, 1076-83 (2005). Alternatively, the α(1,3) fucosyltransferase also exhibits α(1,2) fucosyltransferase and/or α(1,4) fucosyltransferase activity.

In a third aspect, nucleic acid sequences encoding the α(1,3) fucosyltransferases are provided.

In a fourth aspect, the invention provides a nucleic acid construct, or vector, comprising an isolated nucleic acid encoding a lactose-accepting α(1,3) fucosyltransferase enzyme or variant, or fragment thereof, said nucleic acid being operably linked to one or more heterologous control sequences that direct production of the enzyme in a host bacteria production strain. The vector can further include one or more regulatory elements, e.g., a heterologous promoter. By "heterologous" is meant that the control sequence and protein-encoding sequence originate from different bacterial strains. The regulatory elements can be operably linked to a gene encoding a protein, a gene construct encoding a fusion protein gene, or a series of genes linked in an operon in order to express the fusion protein.

In a fifth aspect, the invention comprises an isolated recombinant cell, e.g., a bacterial cell containing an aforementioned nucleic acid molecule, construct or vector. The nucleic acid is optionally integrated into the genome of the host bacterium.

The fucosylated oligosaccharide produced by the engineered bacterium is preferably 3-fucosyllactose (3FL), lactodifucotetraose (LDFT) or lacto-N-fucopentaose III (LNF III). For example, for expression of 3FL, the bacterium is engineered to express an α(1,3) fucosyltransferase according to the invention. For example, to produce LDFT, the host bacterium is engineered to express an exogenous α(1,2) fucosyltransferase that also possesses α(1,3) fucosyltransferase activity, or an exogenous α(1,2) fucosyltransferase and an exogenous α(1,3) fucosyltransferase. For the production of LNF III, the host bacterium is preferably engineered to express an α(1,3) fucosyltransferase that is *Helicobacter hepaticas* ATCC 51449 CafD (SEQ ID NO: 53) (Genbank accession: AAP76669) or an α(1,3) fucosyltransferase which has 95%, 90%, 85%, 80%, 75%, 70%, 65%, 60%, 55% or 50% sequence identity with CafD and which retains the ability to catalyze the attachment of fucose to the GlcNAc moiety of lacto-N-neohexaose (LNnT).

Large quantities of 3-fucosyllactose (3FL), lactodifucotetraose (LDFT) or lacto-N-fucopentaose III (LNF III) are produced in bacterial hosts, e.g., an *E. coli* bacterium comprising an exogenous α(1,3) fucosyltransferase gene.

As described in detail below, *E. coli* (or other bacteria) is engineered to produce selected fucosylated oligosaccharides (including 3-fucosyllactose (3FL), lactodifucotetraose and lacto-N-fucopentaose III (LNF III)) in commercially viable levels. For example, yields are >5 grams/liter in a bacterial fermentation process. In other embodiments, the yields are greater than 10 grams/liter, greater than 15 grams/liter, greater than 20 grams/liter, greater than 25 grams/liter, greater than 30 grams/liter, greater than 35 grams/liter, greater than 40 grams/liter, greater than 45 grams/liter, greater than 50 grams/liter, greater than 55 grams/liter, greater than 60 grams/liter, greater than 65 grams/liter, greater than 70 grams/liter, or greater than 75 grams/liter of fucosylated oligosaccharide products, such as 3-fucosyllactose (3 FL), lactodifucotetraose and lacto-N-fucopentaose III (LNF III).

A suitable production host bacterial strain is one that is not the same bacterial strain as the source bacterial strain from which the fucosyltransferase-encoding nucleic acid sequence was identified. The host organism or cell used to express the lactose-accepting fucosyltransferase gene is typically the enterobacterium *Escherichia coli* K-12 (*E. coli*). *E. coli* K-12 is not considered a human or animal pathogen nor is it toxicogenic. *E. coli* K-12 is a standard production strain of bacteria and is noted for its safety due to its poor ability to colonize the colon and establish infections (see, e.g., epa.gov/oppt/biotech/pubs/fragra004.htm). However, a variety of bacterial species may be used in the oligosaccharide biosynthesis methods, e.g., *Erwinia herbicola* (*Pantoea agglomerans*), *Citrobacter freundii, Pantoea citrea, Pectobacterium carotovorum*, or *Xanthomonas campestris*. Bacteria of the genus *Bacillus* may also be used, including *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus*, and *Bacillus circulans*. Similarly, bacteria of the genera *Lactobacillus* and *Lactococcus* may be modified using the methods of this invention, including but not limited to *Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii*, and *Lactococcus lactis*. *Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bifidobacterium* (e.g., *Bifidobacterium longum, Bifidobacterium infantis*, and *Bifidobacterium bifidum*), *Sporolactobacillus* spp., *Micromomospora* spp., *Micrococcus* spp., *Rhodococcus* spp., and *Pseudomonas* (e.g., *Pseudomonas fluorescens* and *Pseudomonas aeruginosa*).

The bacterium utilized in the production methods described herein is preferably genetically engineered to increase the efficiency and yield of fucosylated oligosaccharide products. For example, the host production bacterium is characterized as having one, two, three or four of a reduced level of β-galactosidase activity, a defective colanic acid synthesis pathway, an inactivated ATP-dependent intracellular protease, an inactivated lacA. Preferably, the host production bacterium is characterized as having a reduced level of β-galactosidase activity, a defective colanic acid synthesis pathway, an inactivated ATP-dependent intracellular protease and an inactivated lacA.

A host bacterium suitable for the production systems described herein exhibits an enhanced or increased cytoplasmic or intracellular pool of lactose and/or GDP-fucose. For example, the bacterium is *E. coli* and endogenous *E. coli* metabolic pathways and genes are manipulated in ways that result in the generation of increased cytoplasmic concentrations of lactose and/or GDP-fucose, as compared to levels found in wild type *E. coli*. Preferably, the bacterium accumulates an increased intracellular lactose pool and an increased intracellular GDP-fucose pool. For example, the bacteria contain at least 10%, 20%, 50%, or 200%, 500%, 1000% or more of the levels of intracellular lactose and/or intracellular GDP-fucose compared to a corresponding wild type bacteria that lacks the genetic modifications described herein.

Increased intracellular concentration of lactose in the host bacterium compared to wild-type bacterium is achieved by manipulation of genes and pathways involved in lactose import, export and catabolism. In particular, described herein are methods of increasing intracellular lactose levels in *E. coli* genetically engineered to produce a human milk oligosaccharide by simultaneous deletion of the endogenous β-galactosidase gene (lacZ) and the lactose operon repressor gene (lacI). During construction of this deletion, the lacIq promoter is placed immediately upstream of (contiguous with) the lactose permease gene, lacY, i.e., the sequence of the lacIq promoter is directly upstream and adjacent to the start of the sequence encoding the lacY gene, such that the lacY gene is under transcriptional regulation by the lacIq promoter. The modified strain maintains its ability to transport lactose from the culture medium (via LacY), but is deleted for the wild-type chromosomal copy of the lacZ (encoding β-galactosidase) gene responsible for lactose catabolism. Thus, an intracellular lactose pool is created when the modified strain is cultured in the presence of exogenous lactose.

Another method for increasing the intracellular concentration of lactose in *E. coli* involves inactivation of the lacA gene. An inactivating mutation, null mutation, or deletion of lacA prevents the formation of intracellular acetyl-lactose, which not only removes this molecule as a contaminant from subsequent purifications, but also eliminates *E. coli*'s ability to export excess lactose from its cytoplasm (Danchin A. Cells need safety valves. Bioessays 2009, July; 31(7):769-73.), thus greatly facilitating purposeful manipulations of the *E. coli* intracellular lactose pool.

In a further aspect, the invention also provides methods for increasing intracellular levels of GDP-fucose in a bacterium by manipulating the organism's endogenous colanic acid biosynthesis pathway. This increase is achieved through a number of genetic modifications of endogenous *E. coli* genes involved either directly in colanic acid precursor biosynthesis, or in overall control of the colanic acid synthetic regulon. Particularly preferred is inactivation of the genes or encoded polypeptides that act in the colanic acid synthesis pathway after the production of GDP-fucose (the donor substrate) and before the generation of colanic acid. Exemplary colanic acid synthesis genes include, but are not limited to: a wcaJ gene, (e.g., GenBank Accession Number (amino acid) BAA15900 (GI:1736749), incorporated herein by reference), a wcaA gene (e.g., GenBank Accession Number (amino acid) BAA15912.1 (GI:1736762), incorporated herein by reference), a wcaC gene (e.g., GenBank Accession Number (amino acid) BAE76574.1 (GI:85675203), incorporated herein by reference), a wcaE gene (e.g., GenBank Accession Number (amino acid) BAE76572.1 (GI:85675201), incorporated herein by reference), a wcaI gene (e.g., GenBank Accession Number (amino acid) BAA15906.1 (GI:1736756), incorporated herein by reference), a wcaL gene (e.g., GenBank Accession Number (amino acid) BAA15898.1 (GI:1736747), incorporated herein by reference), a wcaB gene (e.g., GenBank Accession Number (amino acid) BAA15911.1 (GI:1736761), incorporated herein by reference), a wcaF gene (e.g., GenBank Accession Number (amino acid) BAA15910.1 (GI:1736760), incorporated herein by reference), a wzxE gene (e.g., GenBank Accession Number (amino acid) BAE77506.1 (GI:85676256), incorporated herein by reference), a wzxC gene, (e.g., GenBank Accession Number (amino acid) BAA15899 (GI:1736748), incorporated herein by reference), a wcaD gene, (e.g., GenBank Accession Number (amino acid) BAE76573 (GI:85675202), incorporated herein by reference), a wza gene (e.g., GenBank Accession Number (amino acid) BAE76576 (GI:85675205), incorporated herein by reference), a wzb gene (e.g., GenBank Accession Number (amino acid) BAE76575 (GI: 85675204), incorporated herein by reference), and a wzc gene (e.g., GenBank Accession Number (amino acid) BAA15913 (GI:1736763), incorporated herein by reference).

Preferably, the host bacterium, such as *E. coli*, comprises, or more preferably comprises in addition to the above-discussed genetic manipulations, inactivation of the wcaJ gene, which encoding the UDP-glucose lipid carrier transferase. The inactivation of the wcaJ gene can be by deletion of the gene, a null mutation, or inactivating mutation of the wcaJ gene, such that the activity of the encoded wcaJ is reduced or eliminated compared to wild-type *E. coli*. In a wcaJ null background, GDP-fucose accumulates in the *E. coli* cytoplasm.

Over-expression of a positive regulator protein, RcsA (e.g., GenBank Accession Number M58003 (GI:1103316), incorporated herein by reference), in the colanic acid synthesis pathway results in an increase in intracellular GDP-fucose levels. Over-expression of an additional positive regulator of colanic acid biosynthesis, namely RcsB (e.g., GenBank Accession Number E04821 (GI:2173017), incorporated herein by reference), is also utilized, either instead of or in addition to over-expression of RcsA, to increase intracellular GDP-fucose levels. Therefore, the host cell alternatively or additionally over-expresses RcsB and/or over-expresses RcsA.

Alternatively, colanic acid biosynthesis is increased following the introduction of a mutation into the *E. coli* lon gene (e.g., GenBank Accession Number L20572 (GI: 304907), incorporated herein by reference). Lon is an adenosine-5'-triphosphate (ATP)-dependent intracellular protease that is responsible for degrading RcsA, mentioned above as a positive transcriptional regulator of colanic acid biosynthesis in *E. coli*. In a lon null background, RcsA is stabilized, RcsA levels increase, the genes responsible for GDP-fucose synthesis in *E. coli* are up-regulated, and intracellular GDP-fucose concentrations are enhanced. Mutations in lon suitable for use with the methods presented herein include null mutations or insertions that disrupt the expression or function of lon.

A functional lactose permease gene is preferably also present in the host bacterium. The lactose permease gene is an endogenous lactose permease gene or an exogenous lactose permease gene. For example, the lactose permease gene comprises an *E. coli* lacY gene (e.g., GenBank Accession Number V00295 (GI:41897), incorporated herein by reference). Many bacteria possess the inherent ability to transport lactose from the growth medium into the cell, by utilizing a transport protein that is either a homolog of the *E. coli* lactose permease (e.g., as found in *Bacillus licheniformis*), or a transporter that is a member of the ubiquitous PTS sugar transport family (e.g., as found in *Lactobacillus casei* and *Lactobacillus rhamnosus*). For bacteria lacking an inherent ability to transport extracellular lactose into the cell cytoplasm, this ability is conferred by an exogenous lactose transporter gene (e.g., *E. coli* lacY) provided on recombinant DNA constructs, and supplied either on a plasmid expression vector or as exogenous genes integrated into the host chromosome.

As described herein, the host bacterium preferably has a reduced level of β-galactosidase activity. When the bacterium is characterized by the deletion of the endogenous β-galactosidase gene, an exogenous β-galactosidase gene is introduced to the bacterium. For example, a plasmid expressing an exogenous β-galactosidase gene is introduced to the bacterium, or recombined or integrated into the host genome. For example, the exogenous β-galactosidase gene is inserted into a gene that is inactivated in the host bacterium, such as the lon gene.

The exogenous β-galactosidase gene is a functional β-galactosidase gene characterized by a reduced or low level of β-galactosidase activity compared to β-galactosidase activity in wild-type bacteria lacking any genetic manipulation. Exemplary β-galactosidase genes include *E. coli* lacZ and β-galactosidase genes from any of a number of other organisms (e.g., the lac4 gene of *Kluyveromyces lactis* (e.g., GenBank Accession Number M84410 (GI:173304), incorporated herein by reference) that catalyzes the hydrolysis of β-galactosides into monosaccharides. The level of β-galactosidase activity in wild-type *E. coli* bacteria is, for example, 1,000 units. Thus, the reduced β-galactosidase activity level encompassed by engineered host bacterium described herein includes less than 1,000 units, less than 900 units, less than 800 units, less than 700 units, less than 600 units, less than 500 units, less than 400 units, less than 300 units, less than 200 units, less than 100 units, or less than 50 units. Low, functional levels of β-galactosidase include β-galactosidase activity levels of between 0.05 and 1,000 units, e.g., between 0.05 and 750 units, between 0.05 and 500 units, between 0.05 and 400 units, between 0.05 and 300 units, between 0.05 and 200 units, between 0.05 and 100 units, between 0.05 and 50 units, between 0.05 and 10 units, between 0.05 and 5 units, between 0.05 and 4 units, between 0.05 and 3 units, or between 0.05 and 2 units of β-galactosidase activity. For unit definition and assays for determining β-galactosidase activity, see Miller J H, Laboratory CSH. Experiments in molecular genetics. Cold Spring Harbor Laboratory Cold Spring Harbor, N.Y.; 1972; (incorporated herein by reference). This low level of cytoplasmic β-galactosidase activity is not high enough to significantly diminish the intracellular lactose pool. The low level of β-galactosidase activity is very useful for the facile removal of undesired residual lactose at the end of fermentations. The art-recognized standard level of β-galactosidase activity in a wild-type bacterium is 1000 units. (See, Garcia et al., 2011, Biophysical J. 101:535-544). The art-recognized value for single copy wild type lac β-galactosidase activity is 1000 Miller units. By "low level" of β-galactosidase activity is meant less than 200 Miller units, i.e., less than 20% of wild type.

Optionally, the bacterium has, or additionally has, an inactivated thyA gene. Preferably, a mutation in a thyA gene in the host bacterium allows for the maintenance of plasmids that carry thyA as a selectable marker gene. Exemplary alternative selectable markers include antibiotic resistance genes such as BLA (beta-lactamase), or proBA genes (to complement a proAB host strain proline auxotropy) or purA (to complement a purA host strain adenine auxotrophy).

Most preferably, the host bacterium is an $E.$ $coli$ bacterium comprising the genotype $\Delta ampC::P_{trp}^{B}cI$, $\Delta(lacI-lacZ)::$FRT, $P_{lacIq}lacY^+$, $\Delta wcaJ::FRT$, thyA::Tn10, $\Delta lon:(npt3, lacZ^+)$, and also expressing at least one of the exogenous $\alpha(1,3)$ fucosyltransferases described herein.

The bacterium comprising the above characteristics, most preferably the above characteristics in combination, is cultured in the presence of lactose. In some cases, the method further comprises culturing the bacterium in the presence of tryptophan and in the absence of thymidine.

In some cases, the culture medium is supplemented with a nitrogen-rich nutritional additive. High level expression (e.g. as driven from the induced $P_L$ promoter) of nearly all $\alpha(1,3)$ fucosyltransferases can be toxic to $E.$ $coli$ strains, resulting in poor viability and low 3-FL yields in fermentation runs. In some embodiments, supplementation of fermentation media with a nitrogen-rich additive such as casamino acids (CAA) or yeast extract (YE) protect against the toxic properties of $\alpha(1,3)$ fucosyltransferase activity, leading to significantly improved 3-FL production yields. In particular, CAA supplementation doubles the yield of 3FL obtained. In alternative embodiments, other such nitrogen-rich nutritional additives could include any protein hydrolysate (peptone) from a variety of sources, including but not limited to meat, casein, whey, gelatin, soybean, yeast and grains and/or extracts thereof. The fucosylated oligosaccharide is retrieved from the bacterium (i.e., a cell lysate) or from a culture supernatant of the bacterium. The fucosylated oligosaccharide is purified for use in therapeutic or nutritional products, or the bacteria are used directly in such products.

In another aspect, the invention provides a purified $\alpha(1,3)$ fucosylated oligosaccharide produced by the methods described herein. A "purified oligosaccharide", e.g., 3-fucosyllactose (3FL), lactodifucotetraose (LDFT) or lacto-N-fucopentaose III (LNF III), is one that is at least 90%, 95%, 98%, 99%, or 100% (w/w) of the desired oligosaccharide by weight. Purity is assessed by any known method, e.g., thin layer chromatography or other chromatographic techniques known in the art. For example, an engineered bacterium, bacterial culture supernatant, or bacterial cell lysate according to the invention comprises 3-fucosyllactose (3FL), lactodifucotetraose (LDFT) or lacto-N-fucopentaose III (LNF III) produced by the methods described herein, and does not substantially comprise any other fucosylated oligosaccharides prior to purification of the fucosylated oligosaccharide products from the cell, culture supernatant, or lysate. As a general matter, the fucosylated oligosaccharide produced by the methods contains a negligible amount of 2'-FL in a 3-FL-containing cell, cell lysate or culture, or supernatant, e.g., less than 1% of the level of 3-FL or 0.5% of the level of 3-FL. Moreover, the fucosylated oligosaccharide produced by the methods described herein also have a minimal amount of contaminating lactose, which can often be co-purified with the fucosylated oligosaccharide product, such as 3-FL. This reduction in contaminating lactose results from the reduced level of β-galactosidase activity present in the engineered host bacterium. The fucosylated oligosaccharide is purified for use in therapeutic or nutritional products, or the bacterium is used directly in such products.

The invention includes a method of purifying a fucosylated oligosaccharide produced by the genetically engineered bacterium described above, which method comprises separating the desired fucosylated oligosaccharide (e.g., 3-FL) from contaminants in a bacterial cell lysate or bacterial cell culture supernatant of the bacterium.

The oligosaccharides are purified and used in a number of products for consumption by humans as well as animals, such as companion animals (dogs, cats) as well as livestock (bovine, equine, ovine, caprine, or porcine animals, as well as poultry). For example, a pharmaceutical composition comprises purified 3-fucosyllactose (3FL), lactodifucotetraose (LDFT) or lacto-N-fucopentaose III (LNF III) and a pharmaceutically-acceptable excipient that is suitable for oral administration.

In another aspect, the invention provides a method of producing a pharmaceutical composition comprising a purified human milk oligosaccharide (HMOS), said method comprising culturing the bacterium described above, purifying the HMOS produced by the bacterium, and combining the HMOS with an excipient or carrier to yield a dietary supplement for oral administration. These compositions are useful in methods of preventing or treating enteric and/or respiratory diseases in infants and adults. Accordingly, the compositions are administered to a subject suffering from or at risk of developing such a disease.

In yet another aspect, the invention also provides methods of identifying an $\alpha(1,3)$ fucosyltransferase gene capable of synthesizing fucosylated oligosaccharides in a host bacterium, e.g., 3-FL in $E.$ $coli$. An exemplary method of identifying novel, lactose-utilizing $\alpha(1,3)$fucosyltransferase enzyme comprises the following steps:
1) performing a computational search of sequence databases to define a broad group of simple sequence homologs of any single, known, lactose-utilizing $\alpha(1,3)$fucosyltransferase;
2) using the list of search hits from step (1) to derive a search profile containing common sequence and/or structural motifs shared by the members of the list;
3) searching sequence databases, using the derived search profile based on the common sequence or structural motif from step (2) as query, and identifying additional candidate sequences, wherein a sequence homology to a reference lactose-utilizing α(1,3)fucosyltransferase is a predetermined percentage threshold;

4) compiling a list of candidate organisms of interest, said organisms being characterized as either expressing α(1,3) fucosyl-glycans in a naturally-occurring state, or whose natural habitat is known to include processes and interactions involving α(1,3)fucosyl-glycans;

5) selecting candidate sequences that are derived from candidate organisms of interest to generate a list of candidate lactose-utilizing enzymes;

6) expressing the candidate lactose-utilizing enzyme in a host organism; and 7) testing for lactose-utilizing α(1,3)fucosyltransferase activity, wherein detection of the desired fucosylated oligosaccharide product in said organism indicates that the candidate sequence comprises a novel lactose-utilizing α(1,3) fucosyltransferase. In another embodiment, the search profile is generated from a multiple sequence alignment of the amino acid sequences of more than one enzyme with known α(1,3)fucosyltransferase activity. The database search can then be designed to refine and iteratively search for novel α(1,3)fucosyltransferases with significant sequence similarity to the multiple sequence alignment query.

The predetermined percentage threshold in step (3) above is for example 50% or less, preferably less than 50%, more preferably 45% or less, more preferably 42% or less, or 40% or less. A particularly preferred percentage threshold is a sequence homology, or identity, of between 6 and 50%, more preferably between 6 and 42%.

In another aspect, the invention provides a method of treating, preventing, or reducing the risk of infection in a subject comprising administering to said subject a composition comprising a purified recombinant human milk oligosaccharide, wherein the HMOS binds to a pathogen and wherein the subject is infected with or at risk of infection with the pathogen. In one aspect, the infection is caused by a Norwalk-like virus or *Campylobacter jejuni*. The subject is preferably a mammal in need of such treatment. The mammal is, e.g., any mammal, e.g., a human, a primate, a mouse, a rat, a dog, a cat, a cow, a horse, or a pig. In a preferred embodiment, the mammal is a human. For example, the compositions are formulated into animal feed (e.g., pellets, kibble, mash) or animal food supplements for companion animals, e.g., dogs or cats, as well as livestock or animals grown for food consumption, e.g., cattle, sheep, pigs, chickens, and goats. Preferably, the purified HMOS is formulated into a powder (e.g., infant formula powder or adult nutritional supplement powder, each of which is mixed with a liquid such as water or juice prior to consumption) or in the form of tablets, capsules or pastes or is incorporated as a component in dairy products such as milk, cream, cheese, yogurt or kefir, or as a component in any beverage, or combined in a preparation containing live microbial cultures intended to serve as probiotics, or in prebiotic preparations to enhance the growth of beneficial microorganisms either in vitro or in vivo.

Polynucleotides, polypeptides, and oligosaccharides of the invention are purified and/or isolated. Purified defines a degree of sterility that is safe for administration to a human subject, e.g., lacking infectious or toxic agents. Specifically, as used herein, an "isolated" or "purified" nucleic acid molecule, polynucleotide, polypeptide, protein or oligosaccharide, is substantially free of other cellular material, or culture medium when produced by recombinant techniques, or chemical precursors or other chemicals when chemically synthesized. For example, purified HMOS compositions are at least 60% by weight (dry weight) the compound of interest. Preferably, the preparation is at least 75%, more preferably at least 90%, and most preferably at least 99%, by weight the compound of interest. Purity is measured by any appropriate standard method, for example, by column chromatography, thin layer chromatography, or high-performance liquid chromatography (HPLC) analysis. For example, a "purified protein" refers to a protein that has been separated from other proteins, lipids, and nucleic acids with which it is naturally associated. Preferably, the protein constitutes at least 10, 20, 50, 70, 80, 90, 95, 99-100% by dry weight of the purified preparation.

Similarly, by "substantially pure" is meant an oligosaccharide that has been separated from the components that naturally accompany it. Typically, the oligosaccharide is substantially pure when it is at least 60%, 70%, 80%, 90%, 95%, or even 99%, by weight, free from the proteins and naturally-occurring organic molecules with which it is naturally associated.

By "isolated nucleic acid" is meant a nucleic acid that is free of the genes which, in the naturally-occurring genome of the organism from which the DNA of the invention is derived, flank the gene. The term covers, for example: (a) a DNA which is part of a naturally occurring genomic DNA molecule, but is not flanked by both of the nucleic acid sequences that flank that part of the molecule in the genome of the organism in which it naturally occurs; (b) a nucleic acid incorporated into a vector or into the genomic DNA of a prokaryote or eukaryote in a manner, such that the resulting molecule is not identical to any naturally occurring vector or genomic DNA; (c) a separate molecule such as a cDNA, a genomic fragment, a fragment produced by polymerase chain reaction (PCR), or a restriction fragment; and (d) a recombinant nucleotide sequence that is part of a hybrid gene, i.e., a gene encoding a fusion protein. Isolated nucleic acid molecules according to the present invention further include molecules produced synthetically, as well as any nucleic acids that have been altered chemically and/or that have modified backbones.

A "heterologous promoter" is a promoter which is different from the promoter to which a gene or nucleic acid sequence is operably linked in nature.

The term "overexpress" or "overexpression" refers to a situation in which more factor is expressed by a genetically-altered cell than would be, under the same conditions, by a wild type cell. Similarly, if an unaltered cell does not express a factor that it is genetically altered to produce, the term "express" (as distinguished from "overexpress") is used indicating the wild type cell did not express the factor at all prior to genetic manipulation.

As used herein, an "inactivated" or "inactivation of a" gene, encoded gene product (i.e., polypeptide), or pathway refers to reducing or eliminating the expression (i.e., transcription or translation), protein level (i.e., translation, rate of degradation), or enzymatic activity of the gene, gene product, or pathway. In the instance where a pathway is inactivated, preferably one enzyme or polypeptide in the pathway exhibits reduced or negligible activity. For example, the enzyme in the pathway is altered, deleted or mutated such that the product of the pathway is produced at low levels compared to a wild-type bacterium or an intact pathway. Alternatively, the product of the pathway is not produced. Inactivation of a gene is achieved by deletion or mutation of the gene or regulatory elements of the gene such that the gene is no longer transcribed or translated. Inactivation of a polypeptide can be achieved by deletion or mutation of the gene that encodes the gene product or mutation of the polypeptide to disrupt its activity. Inactivating mutations include additions, deletions or substitutions of one or more nucleotides or amino acids of a nucleic acid or amino acid sequence that results in the reduction or elimination of the expression or activity of the gene or polypeptide. In other embodiments, inactivation of a polypeptide is achieved through the addition of exogenous sequences (i.e., tags) to the N or C-terminus of the polypeptide such that the activity of the polypeptide is reduced or eliminated (i.e., by steric hindrance).

The terms "treating" and "treatment" as used herein refer to the administration of an agent or formulation to a clinically symptomatic individual afflicted with an adverse condition, disorder, or disease, so as to effect a reduction in severity and/or frequency of symptoms, eliminate the symptoms and/or their underlying cause, and/or facilitate improvement or remediation of damage. The terms "preventing" and "prevention" refer to the administration of an agent or composition to a clinically asymptomatic individual who is susceptible to a particular adverse condition, disorder, or disease, and thus relates to the prevention of the occurrence of symptoms and/or their underlying cause.

By the terms "effective amount" and "therapeutically effective amount" of a formulation or formulation component is meant a nontoxic but sufficient amount of the formulation or component to provide the desired effect.

The transitional term "comprising," which is synonymous with "including," "containing," or "characterized by," is inclusive or open-ended and does not exclude additional, unrecited elements or method steps. By contrast, the transitional phrase "consisting of" excludes any element, step, or ingredient not specified in the claim. The transitional phrase "consisting essentially of" limits the scope of a claim to the specified materials or steps "and those that do not materially affect the basic and novel characteristic(s)" of the claimed invention.

Other features and advantages of the invention will be apparent from the following description of the preferred embodiments thereof, and from the claims. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

All published foreign patents and patent applications cited herein are incorporated herein by reference. Genbank and NCBI submissions indicated by accession number cited herein are incorporated herein by reference. All other published references, documents, manuscripts and scientific literature cited herein are incorporated herein by reference. In the case of conflict, the present specification, including definitions, will control. In addition, the materials, methods, and examples are illustrative only and not intended to be limiting.

BRIEF DESCRIPTION OF THE DRAWINGS

FIG. 4A shows significant production of 3-FL by FutA, CafA, and CafB. FIG. 4B shows significant production of 3-FL by FutA and CafC. FIG. 4C shows significant production of 3-FL by CafF.

FIG. 5 is a series of photographs showing protein expression of Caf genes in an *E. coli* production strain.

FIG. 19 is a sequence alignment across "active site region 2" (corresponding to FutA residues 180-266) of CafC with 8 other lactose-utilizing "Caf" α(1,3) fucosyltransferases (i.e. CafV (SEQ ID NO: 17), CafN (SEQ ID NO: 9), CafL (SEQ ID NO: 7), CafO (SEQ ID NO: 10), CafQ (SEQ ID NO: 12), CafU (SEQ ID NO: 16), CafF (SEQ ID NO: 1) and FutA (SEQ ID NO: 54)). Conserved regions important for substrate binding and catalysis are delineated by thick bars above the sequences. Within those bars the white dots indicate three completely conserved residues at this region of the catalytic active site. Consensus sequences is SEQ ID NO: 63.

FIG. 20 is a pairwise comparison table of the alignment of FIG. 19, presenting percent identities across "active site region 2" (corresponding to FutA residues 180-266) of CafC with 8 other lactose-utilizing "Caf" α(1,3) fucosyltransferases (i.e. CafV, CafN, CafL, CafO, CafQ, CafU, CafF and FutA).

FIG. 22A-FIG. 22C are images of thin layer chromatography analysis of culture supernatants for various strains of the invention. FIG. 22A is an image of thin layer chromatography analysis of culture supernatants from a pEC2-$P_L$—CafC-rcsA-thyA (pG366) strain. FIG. 22B is an image of thin layer chromatography analysis of culture supernatants from a pEC2-$P_L$—CafC-CafN-rcsA-thyA (pG420) strain. FIG. 22C is an image of thin layer chromatography analysis of culture supernatants

DETAILED DESCRIPTION

Figure 1:
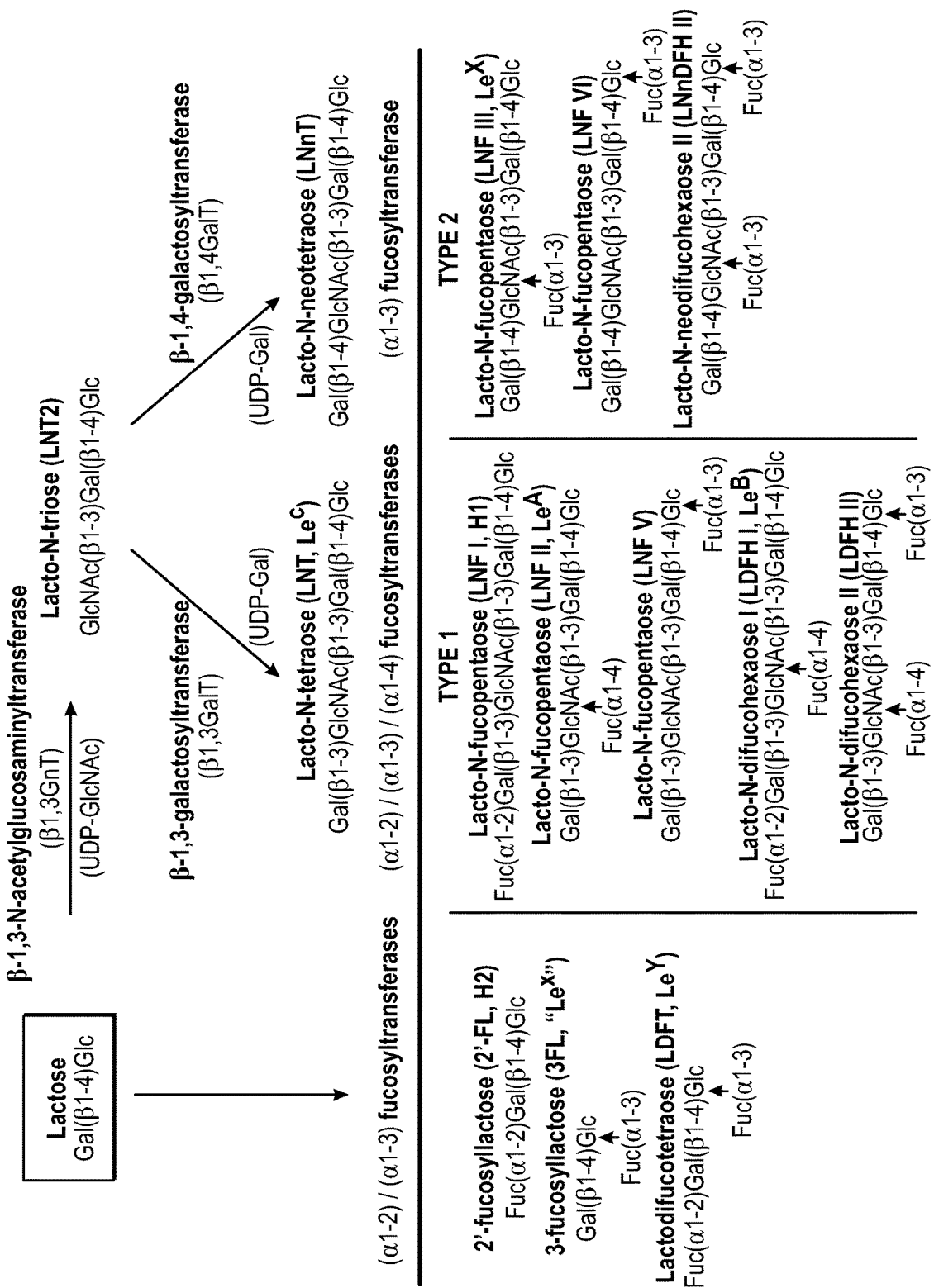
FIG. 1 is a schematic illustration showing the synthetic pathway of the major neutral fucosyl-oligosaccharides found in human milk.

While some studies suggest that human milk glycans could be used as antimicrobial anti-adhesion agents, the difficulty and expense of producing adequate quantities of these agents of a quality suitable for human consumption has limited their full-scale testing and perceived utility. What has been needed is a suitable method for producing the appropriate glycans in sufficient quantities at reasonable cost. Prior to the invention described herein, there were attempts to use several distinct synthetic approaches for glycan synthesis. Some chemical approaches can synthesize oligosaccharides (Flowers, H. M. Methods Enzymol 50, 93-121 (1978); Seeberger, P. H. Chem Commun (Camb) 1115-1121 (2003)), but reactants for these methods are expensive and potentially toxic (Koeller, K. M. & Wong, C. H. Chem Rev 100, 4465-4494 (2000)).

Enzymes expressed from engineered organisms (Albermann, C., Piepersberg, W. & Wehmeier, U. F. Carbohydr Res 334, 97-103 (2001); Bettler, E., Samain, E., Chazalet, V., Bosso, C., et al. Glycoconj J 16, 205-212 (1999); Johnson, K. F. Glycoconj J 16, 141-146 (1999); Palcic, M. M. Curr Opin Biotechnol 10, 616-624 (1999); Wymer, N. & Toone, E. J. Curr Opin Chem Biol 4, 110-119 (2000)) provide a precise and efficient synthesis (Palcic, M. M. Curr Opin Biotechnol 10, 616-624 (1999)); Crout, D. H. & Vic, G. Curr Opin Chem Biol 2, 98-111 (1998)), but the high cost of the reactants, especially the sugar nucleotides, limits their utility for low-cost, large-scale production. Microbes have been genetically engineered to express the glycosyltransferases needed to synthesize oligosaccharides from the bacteria's innate pool of nucleotide sugars (Endo, T., Koizumi, S., Tabata, K., Kakita, S. & Ozaki, A. Carbohydr Res 330, 439-443 (2001); Endo, T., Koizumi, S., Tabata, K. & Ozaki, A. Appl Microbiol Biotechnol 53, 257-261 (2000); Endo, T. & Koizumi, S. Curr Opin Struct Biol 10, 536-541 (2000); Endo, T., Koizumi, S., Tabata, K., Kakita, S. & Ozaki, A. Carbohydr Res 316, 179-183 (1999); Koizumi, S., Endo, T., Tabata, K. & Ozaki, A. Nat Biotechnol 16, 847-850 (1998)).

One strategy for efficient, industrial-scale synthesis of HMOS is the metabolic engineering of bacteria. This approach involves the construction of microbial strains overexpressing heterologous glycosyltransferases, membrane transporters for the import of precursor sugars into the bacterial cytosol, and possessing enhanced pools of regenerating nucleotide sugars for use as biosynthetic precursors (Dumon, C., Samain, E., and Priem, B. (2004). Biotechnol Prog 20, 412-19; Ruffing, A., and Chen, R. R. (2006). Microb Cell Fact 5, 25). A key aspect of this approach is the heterologous glycosyltransferase selected for overexpression in the microbial host. The choice of glycosyltransferase can significantly affect the final yield of the desired synthesized oligosaccharide, given that enzymes can vary greatly in terms of kinetics, substrate specificity, affinity for donor and acceptor molecules, stability and solubility. A few glycosyltransferases derived from different bacterial species have been identified and characterized in terms of their ability to catalyze the biosynthesis of HMOS in E. coli host strains (Dumon, C., et al. (2006). Chembiochem 7, 359-365; Dumon, C., Samain, E., and Priem, B. (2004). Biotechnol Prog 20, 412-19; Li, M., Liu, X. W., Shao, J., Shen, J., Jia, Q., Yi, W., Song, J. K., Woodward, R., Chow, C. S., and Wang, P. G. (2008). Biochemistry 47, 378-387). The identification of additional glycosyltransferases with faster kinetics, greater affinity for nucleotide sugar donors and/or acceptor molecules, or greater stability within the bacterial host significantly improves the yields of therapeutically useful HMOS. Prior to the invention described herein, chemical syntheses of HMOS were possible, but were limited by stereo-specificity issues, precursor availability, product impurities, and high overall cost (Flowers, H. M. Methods Enzymol 50, 93-121 (1978); Seeberger, P. H. Chem Commun (Camb) 1115-1121 (2003); Koeller, K. M. & Wong, C. H. Chem Rev 100, 4465-4494 (2000)). The invention overcomes the shortcomings of these previous attempts by providing new strategies to inexpensively manufacture large quantities of human milk oligosaccharides (HMOS) for use as dietary supplements.

Prior to the invention described herein, there was a growing need to identify and characterize additional glycosyltransferases that are useful for the synthesis of HMOS in metabolically engineered bacterial hosts.

Advantages provided by the invention include efficient expression of the enzyme, improved stability and/or solubility of the fucosylated oligosaccharide product β-FL, LDFT and LNF III,) and reduced toxicity to the host organism. The invention features novel α(1,3) FTs suitable for expression in production strains for increased efficacy and yield of fucosylated HMOS compared to α(1,3) FTs currently utilized in the field.

Human Milk Glycans

Human milk contains a diverse and abundant set of neutral and acidic oligosaccharides (Kunz, C., Rudloff, S., Baier, W., Klein, N., and Strobel, S. (2000). Annu Rev Nutr 20, 699-722; Bode, L. (2006). J Nutr 136, 2127-130). More than 130 different complex oligosaccharides have been identified in human milk, and their structural diversity and abundance is unique to humans. Although these molecules may not be utilized directly by infants for nutrition, they nevertheless serve critical roles in the establishment of a healthy gut microbiome (Marcobal, A., Barboza, M., Froehlich, J. W., Block, D. E., et al. J Agric Food Chem 58, 5334-5340 (2010)), in the prevention of disease (Newburg, D. S., Ruiz-Palacios, G. M. & Morrow, A. L. Annu Rev Nutr 25, 37-58 (2005)), and in immune function (Newburg, D. S. & Walker, W. A. Pediatr Res 61, 2-8 (2007)). Despite millions of years of exposure to human milk oligosaccharides (HMOS), pathogens have yet to develop ways to circumvent the ability of HMOS to prevent adhesion to target cells and to inhibit infection. The ability to utilize HMOS as pathogen adherence inhibitors promises to address the current crisis of burgeoning antibiotic resistance. Human milk oligosaccharides produced by biosynthesis represent the lead compounds of a novel class of therapeutics against some of the most intractable scourges of society.

Role of Human Milk Glycans in Infectious Disease

Human milk glycans, which comprise both unbound oligosaccharides and their glycoconjugates, play a significant role in the protection and development of the infant gastrointestinal (GI) tract. Neutral fucosylated oligosaccharides, including α(1,3) fucosylated oligosaccharides, protect infants against several important pathogens. Milk oligosaccharides found in various mammals differ greatly, and the composition in humans is unique (Hamosh M., 2001 Pediatr Clin North Am, 48:69-86; Newburg D. S., 2001 Adv Exp Med Biol, 501:3-10). Moreover, glycan levels in human milk change throughout lactation and also vary widely among individuals (Morrow A. L. et al., 2004 J Pediatr, 145:297-303; Chaturvedi P et al., 2001 Glycobiology, 11:365-372). Approximately 200 distinct human milk oligosaccharides have been identified and combinations of simple epitopes are responsible for this diversity (Newburg D. S., 1999 Curr Med Chem, 6:117-127; Ninonuevo M. et al., 2006 J Agric Food Chem, 54:7471-74801).

Human milk oligosaccharides are composed of 5 monosaccharides: D-glucose (Glc), D-galactose (Gal), N-acetylglucosamine (GlcNAc), L-fucose (Fuc), and sialic acid (N-acetyl neuraminic acid, Neu5Ac, NANA). Human milk oligosaccharides are usually divided into two groups according to their chemical structures: neutral compounds containing Glc, Gal, GlcNAc, and Fuc, linked to a lactose (Galβ1-4Glc) core, and acidic compounds including the same sugars, and often the same core structures, plus NANA (Charlwood J. et al., 1999 Anal Biochem, 273:261-277; Martin-Sosa et al., 2003 J Dairy Sci, 86:52-59; Parkkinen J. and Finne J., 1987 Methods Enzymol, 138:289-300; Shen Z. et al., 2001 J Chromatogr A, 921:315-321).

Approximately 70-80% of oligosaccharides in human milk are fucosylated, and their synthetic pathways are believed to proceed as shown in FIG. 1. A smaller proportion of the oligosaccharides are sialylated or both fucosylated and sialylated, but their synthetic pathways are not fully defined. Understanding of the acidic (sialylated) oligosaccharides is limited in part by the ability to measure these compounds. Sensitive and reproducible methods for the analysis of both neutral and acidic oligosaccharides have been designed. Human milk oligosaccharides as a class survive transit through the intestine of infants very efficiently, being essentially indigestible (Chaturvedi, P., Warren, C. D., Buescher, C. R., Pickering, L. K. & Newburg, D. S. Adv Exp Med Biol 501, 315-323 (2001)).

Human Milk Glycans Inhibit Binding of Enteropathogens to their Receptors

Human milk glycans have structural homology to cell receptors for enteropathogens and function as receptor decoys.

For example, 3-fucosyllactose (3FL) is one of the most abundant fucosylated oligosaccharides present in human milk and is thought to function with other HMOS to promote the growth of beneficial commensal bacteria in the infant gut, such as *Bifidobacterium* spp (Marcobal, A., et al. (2010). Consumption of human milk oligosaccharides by gut-related microbes. J Agric Food Chem 58, 5334-340.; Asakuma, S., et al. (2011). Physiology of the consumption of human milk oligosaccharides by infant-gut associated bifidobacteria. J Biol Chem; Sela, D. A., et al. (2012). *Bifidobacterium longum* subsp. *infantis* ATCC 15697 α-fucosidases are active on fucosylated human milk oligosaccharides. Appl Environ Microbiol 78, 795-803.; Garrido, D., et al. (2012). A molecular basis for bifidobacterial enrichment in the infant gastrointestinal tract. Adv Nutr 3, 415S-421S.). Indeed, it has been shown that 3FL can be utilized for growth by several different *Bifidobacterium* spp. In vitro when provided as the sole sugar source (Yu, Z. T., et al. (2012). The Principal Fucosylated Oligosaccharides of Human Milk Exhibit Prebiotic Properties on Cultured Infant Microbiota. Glycobiology). Furthermore, it has been demonstrated that 3FL was consumed in the context of an in vitro infant fecal microbiota culture system, providing further evidence that 3FL is a substrate for beneficial commensal microbes in the infant gut (Yu, Z. T., et al. (2012). The Principal Fucosylated Oligosaccharides of Human Milk Exhibit Prebiotic Properties on Cultured Infant Microbiota. Glycobiology). In addition, several bacterial and viral pathogens target host cell molecules with structural similarity to 3FL for cell-surface binding in the process of initiating infection. Several studies have shown that 3FL can prevent the binding of pathogens to their target molecules or host cells via a competition mechanism, suggesting that 3FL will also be useful as an anti-infective molecule (Huang et al, 2003; Coppa et al 2006; Chessa et al, 2008). Structurally, 3FL consists of a fucose molecule α1,3 linked to the glucose portion of lactose (Galβ1-4(Fucα1-3)Glc) (FIG. 1). This structure is highly similar to that of the Lewis x (Le$^x$) histo-blood group antigen (Galβ1,4(Fucα1,3)GlcNAcβ-R), a common epitope of glycoproteins and glycolipids that has a role in many different biological processes (Rudloff, S., and Kunz, C. (2012). Milk oligosaccharides and metabolism in infants. Adv Nutr 3, 398S-405S.).

LDFT is a di-fucosylated HMOS and has the structure Fucα1,2Galβ1,4(Fucα1,3)Glc. LDFT is one of the most abundant HMOS found in human milk (Newburg et al., 2000; Warren et al., 2001). LDFT has been shown to be utilized as a sugar source for growth in vitro by beneficial, commensal bacteria of the infant gut (i.e. *Bifidobacteria* spp.) and will therefore have utility as an important prebiotic, or "Bifidogenic" factor (Asakuma, S., et al. (2011). Physiology of the consumption of human milk oligosaccharides by infant-gut associated bifidobacteria. J Biol Chem; Yu, Z. T., et al. (2012). The Principal Fucosylated Oligosaccharides of Human Milk Exhibit Prebiotic Properties on Cultured Infant Microbiota. Glycobiology; Blank, D., et al. (2012). Human milk oligosaccharides and Lewis blood group: individual high-throughput sample profiling to enhance conclusions from functional studies. Adv Nutr 3, 440S-49S.). Furthermore, LDFT is structurally highly similar to the histo-blood group antigen Lewis Y (Le$^y$). Many bacterial and viral pathogens target molecules on the surface of host cells with structural similarity to the Lewis Y epitope for binding in the process of initiating infection, such as at the lining of the gut. Orally administered LDFT could serve as a structural mimic of host cell receptors and therefore prevent the binding of pathogens to the intestinal epithelium via a competition mechanism (Ruiz-Palacios, G. M., et al. (2003). *Campylobacter jejuni* binds intestinal H(O) antigen (Fuc alpha 1, 2Gal beta 1, 4GlcNAc), and fucosyloligosaccharides of human milk inhibit its binding and infection. J Biol Chem 278, 14112-120.; Morrow, A. L., et al. (2004).

Human milk oligosaccharide blood group epitopes and innate immune protection against *campylobacter* and calicivirus diarrhea in breastfed infants. Adv Exp Med Biol 554, 443-46.; Sharon, N. (2006). Carbohydrates as future anti-adhesion drugs for infectious diseases. Biochim Biophys Acta 1760, 527-537.; Bode, L., and Jantscher-Krenn, E. (2012). Structure-function relationships of human milk oligosaccharides. Adv Nutr 3, 383S-391S.).

LNF III has the structure Galβ1-4(Fucα1,3)GlcNacβ1-3Galβ1-4Glc, and contains the Le$^x$ antigen structure. LNF III is likely to serve as a prebiotic factor for the growth of commensal microbes in the infant gut, and also may prevent the binding of microbial pathogens to the intestinal epithelia via receptor mimicry.

Several pathogens utilize sialylated glycans as their host receptors, such as influenza (Couceiro, J. N., Paulson, J. C. & Baum, L. G. Virus Res 29, 155-165 (1993)), parainfluenza (Amonsen, M., Smith, D. F., Cummings, R. D. & Air, G. M. J Virol 81, 8341-8345 (2007), and rotoviruses (Kuhlenschmidt, T. B., Hanafin, W. P., Gelberg, H. B. & Kuhlenschmidt, M. S. Adv Exp Med Biol 473, 309-317 (1999)). The sialyl-Lewis X epitope is used by *Helicobacter pylori* (Mandavi, J., Sondén, B., Hurtig, M., Olfat, F. O., et al. Science 297, 573-578 (2002)), *Pseudomonas aeruginosa* (Scharfman, A., Delmotte, P., Beau, J., Lamblin, G., et al. Glycoconj J 17, 735-740 (2000)), and some strains of noroviruses (Rydell, G. E., Nilsson, J., Rodriguez-Diaz, J., Ruvoën-Clouet, N., et al. Glycobiology 19, 309-320 (2009)).

Identification of Novel α(1,3) Fucosyltransferases

The present invention provides novel α(1,3) fucosyltransferase enzymes (α(1,3) FTs). The α(1,3) FTs of the invention provide advantages over known α(1,3) fucosyltransferase enzymes, such advantages including improved yield, improved specificity, and reduced toxicity to host cells.

Not all α(1,3)fucosyltransferases can utilize lactose as an acceptor substrate. An acceptor substrate includes, for example, a carbohydrate, an oligosaccharide, a protein or glycoprotein, a lipid or glycolipid, e.g., N-acetylglucosamine, N-acetyllactosamine, galactose, fucose, sialic acid, glucose, lactose, or any combination thereof. A preferred alpha (1,3) fucosyltransferase utilizes GDP-fucose as a donor, and lactose is the acceptor for that donor.

A method of identifying novel α(1,2)fucosyltransferase enzymes capable of utilizing lactose as an acceptor was previously carried out (as described in PCT/US2013/051777, hereby incorporated by reference in its entirety) using the following steps: 1) performing a computational search of sequence databases to define a broad group of simple sequence homologs of any known, lactose-utilizing α(1,2)fucosyltransferase (e.g. in this case *Helicobacter pylori* 26695 FutC); 2) using the list of homologs from step 1 to derive a search profile containing common sequence and/or structural motifs shared by the members of the broad group, e.g. by using computer programs such as MEME (Multiple Em for Motif Elicitation. http://meme.sdsc.edu/meme/cgi-bin/meme.cgi (accessed Aug. 5, 2014)) or PSI-BLAST (Position-Specific Iterated BLAST) (Blast. http://ncbi.nlm.nih.gov/blast (accessed Aug. 4, 2014); with additional information at openstax CNX. http://cnx.org/content/m11040/latest/(accessed Aug. 5, 2014)); 3) searching sequence databases (e.g., using computer programs such as PSI-BLAST, or MAST (Motif Alignment Search Tool. http://meme.sdsc.edu/meme/cgi-bin/mast.cgi (accessed Aug. 5, 2014)); using this derived search profile as query, and identifying "candidate sequences" whose simple sequence homology to the original lactose-accepting α(1,2) fucosyltransferase is 50% or less; 4) scanning the scientific literature and developing a list of "candidate organisms" known to express α(1,2)fucosyl-glycans, or whose natural habitat is known to include processes and interactions involving α(1,2)fucosyl-glycans; 5) selecting only those "candidate sequences" that are derived from "candidate organisms" to generate a list of "candidate lactose-utilizing enzymes"; and 6) expressing each "candidate lactose-utilizing enzyme" and testing for lactose-utilizing α(1,2)fucosyltransferase activity.

The percentage sequence identity threshold in step (3) above is 50% or less, such as less than 50%. Preferably, the % sequence identity threshold is 45% or less, more preferably 42% or less. A preferred % sequence identity threshold is 6%-42%. The threshold was set to select candidate sequences which are more distantly-related to the query α(1,2)fucosyltransferase (e.g. in this case *Helicobacter pylori* 26695 FutC), and to exclude more closely related candidate sequences.

Example α(1,2) fucosyltransferases include but are not limited to: *Helicobacter pylori* FutC (GenBank Accession AAD29869.1; *Helicobacter mustelae* 12198 FutL (GenBank Accession YP_003517185.1); *Bacteroides* vulgatus ATCC 8482 FutN (GenBank Accession YP_001300461.1); *Escherichia coli* UMEA 3065-1 WbgL (GenBank Accession WP_021554465.1); *Escherichia coli* WbsJ (GenBank Accession AA037698.1); *Prevotella melaninogenica* ATCC 25845 FutO (GenBank Accession YP_003814512.1); *Clostridium bolteae* 90A9 FutP (GenBank Accession WP_002570768.1); *Lachnospiraceae bacterium* 3_1_57FAA_CT1 FutQ (GenBank Accession WP_009251343.1); *Methanosphaerula palustris* E1-9c FutR (GenBank Accession YP_002467213.1); *Tannerella* sp. CAG:118 FutS (GenbBank WP_021929367.1); *Bacteroides caccae* ATCC 43185 FutU (GenBank Accession WP_005675707.1); *Butyrivibrio* sp. AE2015 FutV (GenBank Accesion WP_022772718.1); *Prevotella* sp. CAG:891 FutW (GenBank Accession WP_022481266.1); *Parabacteroides johnsonii* CL02T12C29 FutX (GenBank Accession WP_008155883.1); *Salmonella enterica* subsp. *enterica* serovar Poona str. ATCC BAA-1673 FutZ (GenBank Accession WP_023214330.1); and *Bacteroides* sp. CAG:633 (GenBank Accesion WP_022161880.1).

The MEME suite of sequence analysis tools (MEME. http://meme.sdsc.edu/meme/cgi-bin/meme.cgi (accessed Aug. 5, 2014)) is optionally used as an alternative to PSI-BLAST. Sequence motifs are discovered using the program "MEME". These motifs can then be used to search sequence databases using the program "MAST". The BLAST and PSI-BLAST search algorithms are other well-known alternatives.

An α(1,3) FT from *H. pylori* strain 26695 termed FutA has been utilized by others to catalyze the synthesis of 3FL in metabolically engineered *E. coli* (Dumon, C. et al. (2006). Production of Lewis x tetrasaccharides by metabolically engineered *Escherichia coli*. Chembiochem 7, 359-365.; Dumon, C. et al. (2004). Assessment of the two *Helicobacter pylori* alpha-1,3-fucosyltransferase ortholog genes for the large-scale synthesis of LewisX human milk oligosaccharides by metabolically engineered *Escherichia coli*. Biotechnol Prog 20, 412-19.), however the overall yield of 3FL obtained using this enzyme is low. Moreover FutA is promiscuous in its specificity, i.e. the enzyme will not only form an α-fucose linkage at the 3-position of glucose at the reducing end of sugar acceptors, but additionally will form α-fucose linkages at the 3-position of internal N-acetylglucosamine (GlcNAc) moieties. Thus FutA cannot be utilized effectively for the production of lacto-N-fucopentaose III (LNF-III, Lewis X) using lacto-N-neotetraose (LNnT) as the acceptor sugar. In addition FutA also catalyzes, at a low level, the promiscuous insertion of an α-fucose linkage at the 2-position of the galactose moiety of lactose. This latter activity, although it may sometime compromise the purity of a desired product in a particular biosynthesis, can also sometimes be advantageous, leading to the production of useful oligosaccharides as side products. The compositions and methods described herein overcomes these problems by providing novel α(1,3) fucosyltransferases, which generate higher 3-fucosyllactose yields, enable the production of LNF-III, and/or possess properties leading to either enhanced or reduced levels of oligosaccharide side products. The novel α(1,3) fucosyltransferases of the present invention therefore provide advantages over known α(1,3) fucosyltransferases, including FutA.

FutA: SEQ ID NO: 54

(SEQ ID NO: 54)
MFQPLLDAFIESASIEKMASKSPPPPLKIAVANWWGDEEIKEFKKSVLY

FILSQRYAITLHQNPNEFSDLVFSNPLGAARKILSYQNTKRVFYTGENE

SPNFNLFDYAIGFDELDFNDRYLRMPLYYAHLHYKAELVNDTTAPYKLK

DNSLYALKKPSHHFKENHPNLCAVVNDESDLLKRGFASFVASNANAPMR

NAFYDALNSIEPVTGGGSVRNTLGYKVGNKSEFLSQYKFNLCFENSQGY

GYVTEKILDAYFSHTIPIYWGSPSVAKDFNPKSFVNVHDFNNFDEAIDY

IKYLHTHPNAYLDMLYENPLNTLDGKAYFYQDLSFKKILDFFKTILEND

TIYHKFSTSFMWEYDLHKPLVSIDDLRVNYDDLRVNYDRLLQNASPLLE

LSQNTTFKIYRKAYQKSLPLLRAVRKLKKLGL

Identification of Alternative α(1,3) Fucosyltransferases

Figure 3:
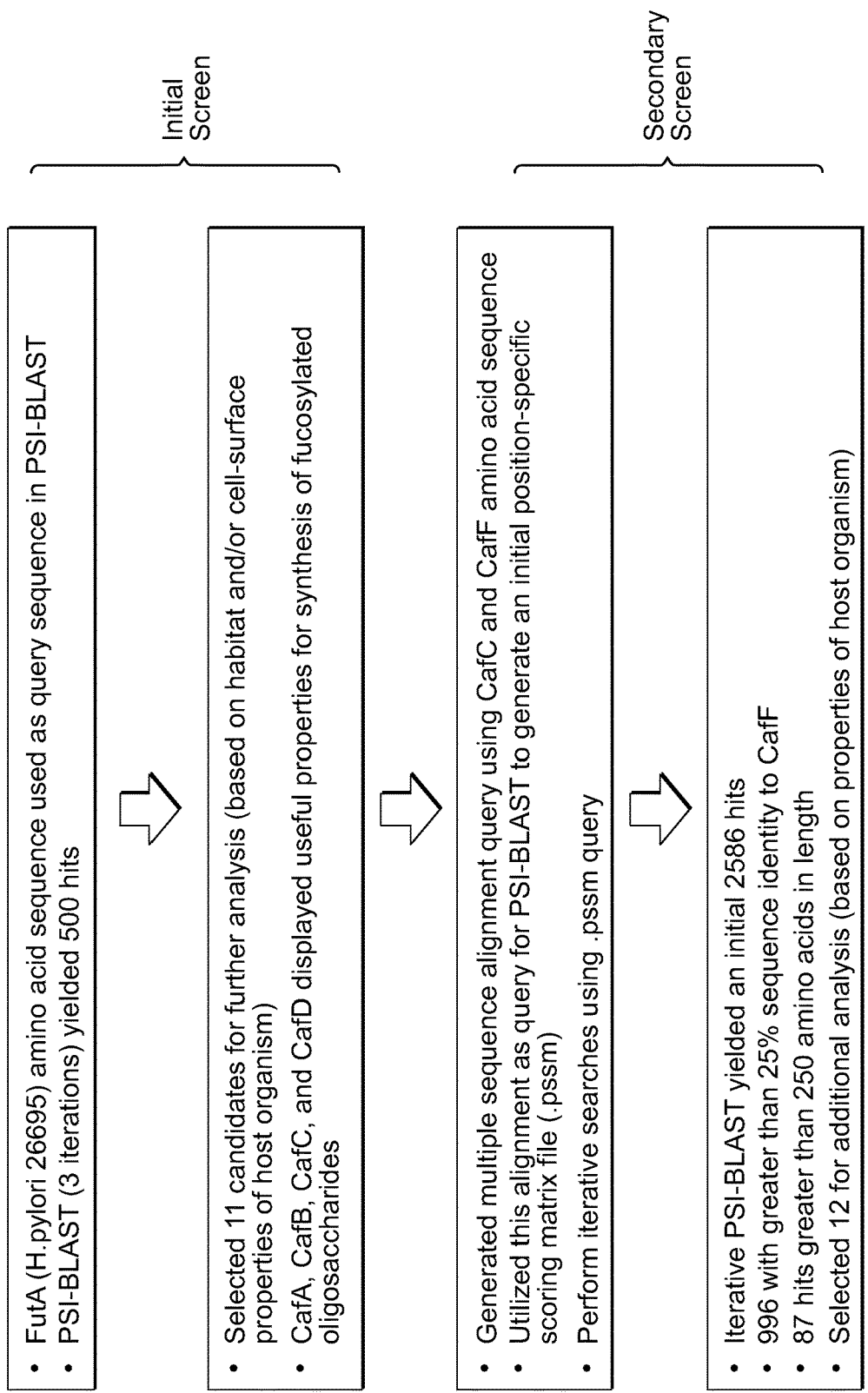
FIG. 3 is a scheme outlining the two sequential database screens that led to the discovery of the several novel α(1,3) fucosyltransferases of this invention.

To identify novel α(1,3)fucosyltransferases, two sequential database screens were performed. An outline of these two sequential screens is shown in FIG. 3.

First, the sequence of a single known lactose-accepting α(1,3)fucosyltransferase (i.e. *H. pylori* strain 26695 FutA) was used to search public databases to find simple homologs that might represent additional lactose-accepting α(1,3)fucosyltransferases. The amino acid sequence of FutA was used as a query in the search algorithm PSI-BLAST (Position Specific Iterated Basic Local Alignment Search Tool) in order to identify novel α(1,3) FTs. The PSI-BLAST program, using a given query protein sequence, generates a list of closely related proteins sequences based on a homology search of a database. These protein homolog hits are then used by the program to generate a profile reflecting their sequence similarities to the original query. The profile is then used by the algorithm to identify an expanded group of homolog proteins, and the process is iterated several times until the number of additional new candidates obtained after each iteration decreases. (Altschul et al., 1990, J. Mol. Bio. 215:403-410; Altschul et al., 1997, Nucleic Acids Res. 25:3389-3402).

The FutA amino acid sequence was used as a query for 3 iterations of the PSI-BLAST search algorithm. This approach yielded a group of 500 candidates with similarity to FutA, many of which were highly related to FutA (shared amino acid identity in the range of 50-90%) as well as a group that was more distantly related (shared amino acid identity less than 50%). Of note, FutA produces sub-optimal yields of 3FL when used in a metabolically engineered *E. coli* production strain. In addition, production of FutA appears to be moderately toxic in certain *E. coli* production strains, including the preferred strain for use herein. Therefore, candidates for further analysis were targeted from the more distantly related group identified via the PSI-BLAST search (shared amino acid identity to FutA of less than 50%) (Table 1). This group of candidates was similar to FutA, but primarily within the catalytic domain region of the respective proteins (Martin, S. L., et al. (1997). Lewis X biosynthesis in *Helicobacter pylori*. Molecular cloning of an alpha (1,3)-fucosyltransferase gene. J Biol Chem 272, 21349-356.; Breton, C., et al. (1998). Conserved structural features in eukaryotic and prokaryotic fucosyltransferases. Glycobiology 8, 87-94.; Rasko, A. (2000). Cloning and Characterization of the alpha (1,3/4) Fucosyltransferase of *Helicobacter pylori*. Journal of Biological Chemistry 275, 4988-994.). It is preferred that the α(1,3) fucosyltransferase of the invention, sharing 50% or less, preferably 45% or less, more preferably 42% or less overall sequence identity with FutA, at the same time possess a higher level of localized sequence identity to FutA within the catalytic domain (i.e. the regions covered by the thick black bars in FIG. 18). Without being bound by theory, it is believed that this group of candidates may include similar, better or distinct fucosyltransferase activities relative to FutA, but are different enough at the amino acid level to avoid the cryptic toxicity observed with FutA in production strains.

These more distantly related (less than 50% sequence identity to FutA) predicted α(1,3) fucoysyl transferases (FTs) were further screened to identify predicted α(1,3) FTs from bacterial species that incorporate fucose into the 0-antigen of their lipopolysaccharide (LPS) or into the polysaccharide subunits that compose the cell surface capsule. Predicted α(1,3) FTs from these types of organisms are more likely to utilize fucose as a substrate, given the presence of fucose in their surface carbohydrate structures. Predicted α(1,3) FTs from known enteric bacterial species, either commensals or pathogens, were also identified. Such organisms sometimes display carbohydrate structures on their cell-surface that contain fucose and mimic various 3-fucosyl containing Lewis antigen structures found in higher organisms (Coyne, M. J., et al. (2005). Human symbionts use a host-like pathway for surface fucosylation. Science 307, 1778-781.; Appelmelk, B. J., et al. (1998). Phase variation in *Helicobacter pylori* lipopolysaccharide. Infect Immun 66, 70-76.; Ma, B., et al. (2006). Fucosylation in prokaryotes and eukaryotes. Glycobiology 16, 158R-184R.). Again, candidate α(1,3) FTs from these types of organisms are believed to be more likely to utilize fucose as a substrate and also to catalyze the linkage of fucose to useful acceptor oligosaccharides.

11 predicted α(1,3) FTs with homology to FutA ranging from 6-42% at the amino acid level were identified from PSI-BLAST. All of these candidates are found in bacteria that are known to interact with the gastrointestinal system of higher organisms. In addition, 3 of these candidates are found in bacteria that have been shown to incorporate fucose into their cell surface glycans. For ease of description, the genes encoding these proteins were named cafA-K for candidate alpha (1,3) fucosyltransferase. The caf genes were cloned by standard molecular biological techniques into an expression plasmid.

This plasmid utilizes the strong leftwards promoter of bacteriophage λ (termed $P_L$) to direct expression of the candidate genes (Sanger, F., 1982, J. Mol. Bio. 162:729-773). The promoter is controllable, e.g., a trp-cI construct is stably integrated the into the *E. coli* host's genome (at the ampC locus), and control is implemented by adding tryptophan to the growth media. Gradual induction of protein expression is accomplished using a temperature sensitive cI repressor. Another similar control strategy (temperature independent expression system) has been described (Mieschendahl et al., 1986, Bio/Technology 4:802-808). The plasmid also carries the *E. coli* rcsA gene to up-regulate GDP-fucose synthesis, a critical precursor for the synthesis of fucosyl-linked oligosaccharides. In addition, the plasmid carries a β-lactamase (bla) gene for maintaining the plasmid in host strains by ampicillin selection (for convenience in the laboratory) and a native thyA (thymidylate synthase) gene as an alternative means of selection in thyA⁻ hosts. Alternative selectable markers include the proBA genes to complement proline auxotrophy (Stein et al., (1984), J Bacteriol 158:2, 696-700 (1984) or purA to complement adenine auxotrophy (S. A. Wolfe, J. M. Smith, *J Biol Chem* 263, 19147-53 (1988)). To act as plasmid selectable markers each of these genes are first inactivated in the host cell chromosome, then wild type copies of the genes are provided on the plasmid. Alternatively a drug resistance gene may be used on the plasmid, e.g. beta-lactamase (this gene is already on the expression plasmid described above, thereby permitting selection with ampicillin). Ampicillin selection is well known in the art and described in standard manuals such as Maniatis et al., (1982) Molecular cloning, a laboratory manual. Cold Spring Harbor Laboratory, Cold Spring, N.Y.

Figure 4:
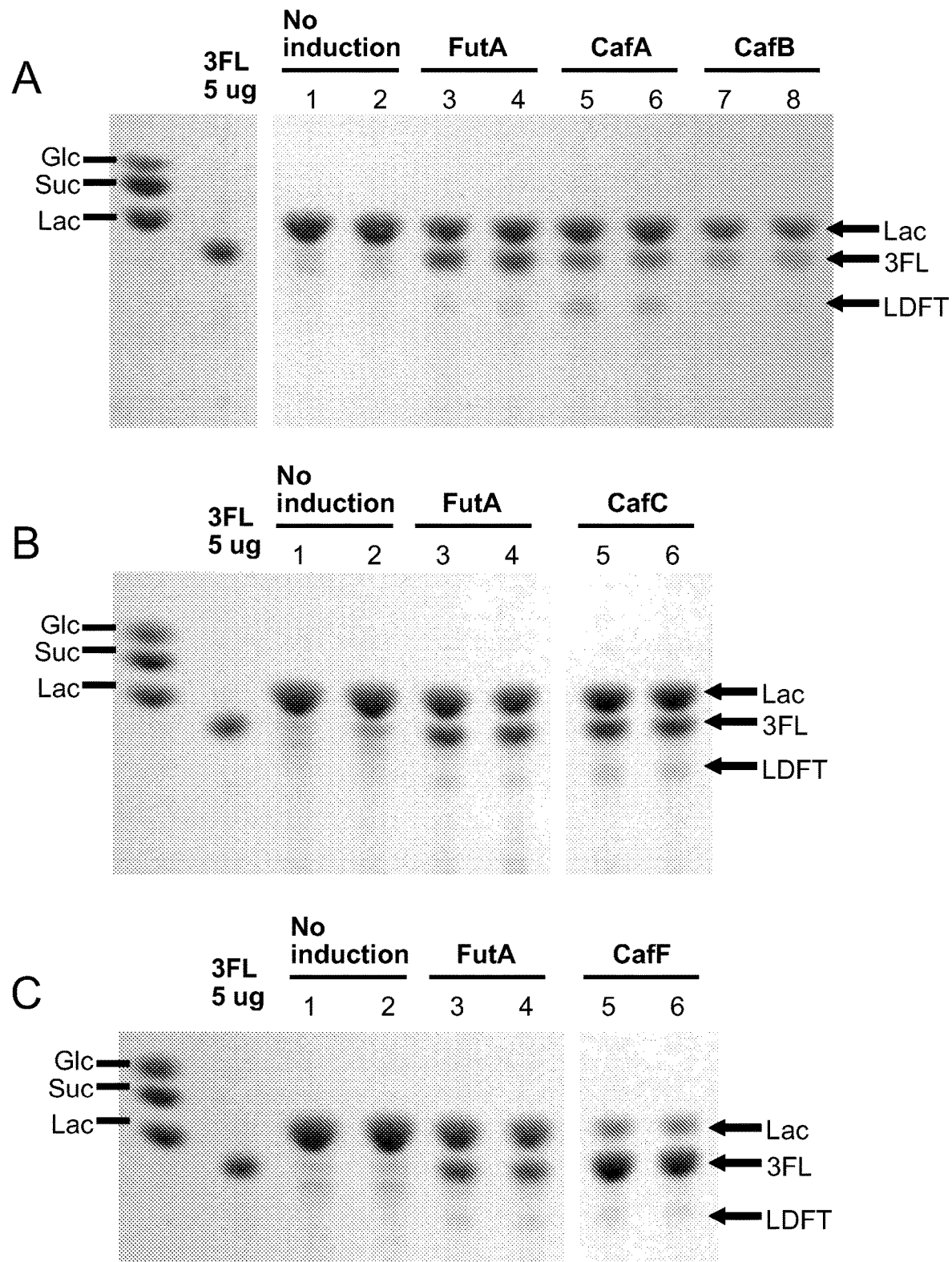
FIG. 4 is a series of photographs showing thin layer chromatography analysis of 3-FL produced in *E. coli* strains by candidate α(1,3) fucosyltransferases that were identified in an initial database screen utilizing the FutA sequence as the query.

The expression constructs were transformed into a host strain useful for the production of fucosylated oligosaccharides and the ability to direct the production of 3FL using lactose as an acceptor sugar was assessed. Candidate α(1,3) FTs CafC (SEQ ID NO: 2), CafF (SEQ ID NO: 1), CafA (SEQ ID NO: 4) and CafB (SEQ ID NO: 5) were found to be lactose-utilizing α(1,3) fucosyltransferases. (See Table 1 and FIG. 4).

TABLE 1

Summary of candidate α(1,3) fucosyltransferases analyzed in this study

| Gene Name | Accession No. | Organism | 3FL synthesis | LDFT synthesis[1] | LNF III synthesis[2] |
|---|---|---|---|---|---|
| futA | NP_207177.1 | *H. pylori* 26695 | +++ | ++ | |
| cafA | CAH09151.1 | *B. fragilis* NCTC 9343 | ++ | ++ | nt |
| cafB | CAH09495.1 | *B. fragilis* NCTC 9343 | ++ | nt | nt |
| cafC | WP_007483358.1 | *B. nordii* CL02T12CO5 | ++++ | +++ | nt |
| cafD | AAP76669.1 | *H. hepaticus* ATCC 51449 | − | nt | ++ |
| cafE | AAP78373.1 | *H. hepaticus* ATCC 51449 | − | nt | − |
| cafF | ACD04596.1 | *A. muciniphilia* ATCC BAA-835 | +++++ | ++++ | nt |
| cafG | WP_020995419.1 | *H. bilis* ATCC 43879 | − | nt | nt |
| cafH | WP_002956732.1 | *H. cinaedi* 18818 | − | nt | − |
| cafI | YP_004607881.1 | *H. bizzozeronii* CIII-I | − | nt | − |
| cafJ | YP_537673.1 | *R. bellii* RML369-C | − | nt | − |
| wbfL/cafK | BAA33600.1 | *V. cholerae* MO45 | − | nt | − | nt = not tested
[1]In combination with the α(1,2) fucosyltransferase WbgL (accession no. ADN43847.1)
[2]In combination with the β(1,3) N-acetylglucosaminyltransferase LgtA (*N. meningitidis* MC58, accession no. NP_274923.1) and the β(1,4) galactosyltransferase HP0826 (*H. pylori* 26695, accession no. NP_207619.1)

The second database screen to identify additional novel α(1,3)fucosyltransferases was then performed. A multiple sequence alignment was generated using the two strongest previously identified lactose-utilizing α(1,3)fucosyltransferase protein sequences from the first screen: i.e. CafC and CafF. The sequence alignment and percentage of sequence identity of these two sequences is shown in Table 2 below.

TABLE 2

| | | |
|---|---|---|
| Akkermansia muciniphila CafF | MKTLKISFLQSTPDFGREG--MLQLLKSRYHVVEDDSDFDYLVATPWFYVNREAFYDFLERAPGHITVMYGCHEAIAPDFMLFDYYI | 85 |
| Bacteroides nordii CafC | MKTIKVKFVDFWENFDPQHNFIANIISKKYRIELSDTP-DYLFFSVFGYEN----IDY-----HNCTKIFYSGENITPDFNICDYAI | 77 |
| Consensus | MKT.K..F......F....--........Y.....D...-DYL......Y.N----.D.-------...T......E.I.PDF...DY.I | |

TABLE 2-continued

| | | |
|---|---|---|
| Akkermansia muciniphila CafF | GLDTVPGSDRTVKLP-YLRHHLEEVHGGKEGLDAHALLASKTGFCNFIYANRKSHPNRDAMFHKLSAFRFVNSLGPHLNNTPGDGHR | 171 |
| Bacteroides nordii CafC | GFNFLSFGDRYIRIPFYTAYGVQQLAAPKV-IVPEVVLNRK--FCSFVVSNAKGAPERERFFQLLSEYKQVDSGGRYKNNVGGP--- | 158 |
| Consensus | G......DR....P-Y...........K.-......L..K--FC.F...N.K..P.R...F..LS....V.S.G...NN..G.--- | |
| Akkermansia muciniphila CafF | AEDWYASSIRMKKPYKFSIAFENAWYPGYTSEKIVTSMLAGTIPIYWGNPDISREFNSASFINCHDFPTLDDAAAYVKKVDEDDNLW | 258 |
| Bacteroides nordii CafC | ----VPDKTAFIKDYKFNIAFENSMCDGYTTEKIMEPMLVNSVPIYWGNKLIDRDFNPDSFINVSSYSSLEEAVEHIVRLDQNDDEY | 241 |
| Consensus | ----........K.YKF.IAFEN....GYT.EKI...ML....PIYWGN..I.R.FN..SFIN......L...A.......D..D... | |
| Akkermansia muciniphila CafF | CEIMSRPWKTPEQEARFLEETERETAKLYKIFDQSPEEARRKGDGTWVSYYQRFLKRGHRMQLAWRRLKNRLR----R | 332 |
| Bacteroides nordii CafC | LSLLSAPWFNEEN---YLNWEEQLITFFDNIFEKPLSESRYIPTHGYIQTYQYRLHRMMRDKLFRKRI-NPLKWFSSK | 315 |
| Consensus | ....S.PW...E.---.L...E........IF.....E.R..........YQ..L.R..R..L...R.-N.L.----. | |
| Akkermansia muciniphila CafF | (SEQ ID NO: 1) | |
| Bacteroides nordii CafC | (SEQ ID NO: 2) | |
| Consesus | (SEQ ID NO: 60) | |

A second iterative PSI-BLAST screen was then performed, this time using the FASTA-formatted CafC and CafF multiple sequence alignment as the query, with the NCBI PSI-BLAST program run on a local copy of NCBI BLAST+ version 2.2.29. An initial position-specific scoring matrix file (.pssm) was generated by PSI-BLAST, which the program then used to adjust the score of iterative homology search runs. The process is iterated to generate an even larger group of candidates, and the results of each run were used to further refine the matrix.

This PSI-BLAST search resulted in an initial 2586 hits. There were 996 hits with greater than 25% sequence identity to CafF. 87 hits were of greater than 250 amino acids in length. Additional analysis of the hits was performed, including comparing the sequences by BLAST to the existing inventory of known α(1,3) fucosyltransferases, (i.e. FutA, CafC, CafF, CafA and CafB), and manual annotation of hit sequences to identify those hits originating from bacteria that naturally exist in the gastrointestinal tract, as well as to remove eukaryotic and "*pylori*" sequences and duplicates. An annotated list of the novel α(1,3) fucosyltransferases identified by this screen (and subsequent filtering) are listed in Table 5. Table 5 provides the bacterial species from which the candidate enzyme is found, the GenBank Accession Number, GI Identification Number, amino acid sequence, and % sequence identity to CafF.

TABLE 5

| Bacteria species | GI number | Accession number | Protein name | % identity to CafF | | Sequence | SEQ ID NO |
|---|---|---|---|---|---|---|---|
| *Akkermansia muciniphila*; *Akkermansia muciniphila* ATCC BAA-835 | 187735265 | YP_001877377.1 | hypothetical protein Amuc_0760 [*Akkermansia muciniphila* ATCC BAA-835] | 100 | CafF | MKTLKISFLQSTPDFGREGMLQLLKSR YHVVEDDSDFDYLVATPWFYVNREAFY DFLERAPGHITVMYGCHEAIAPDFMLF DYYIGLDTVPGSDRTVKLPYLRHHLEE VHGGKEGLDAHALLASKTGFCNFIYAN RKSHPNRDAMFHKLSAFRFVNSLGPHL NNTPGDGHRAEDWYASSIRMKKPYKFS IAFENAWYPGYTSEKIVTSMLAGTIPI YWGNPDISREFNSASFINCHDFPTLDD AAAYVKKVDEDDNLWCEIMSRPWKTPE QEARFLEETERETAKLYKIFDQSPEEA RRKGDGTWVSYYQRFLKRGHRMQLAWR RLKNRLRR | 1 |
| *Bacteroides nordii*; *Bacteroides nordii* CL02T12C05 | 494747950 | WP_007483358.1 | glycosyl-transferase [*Bacteroides nordii*] | 30.24 | CafC | MKTIKVKFVDFWENFDPQHNFIANIIS KKYRIELSDTPDYLFFSVFGYENIDYH NCTKIFYSGENITPDFNICDYAIGFNF LSFGDRYIRIPFYTAYGVQQLAAPKVI VPEVVLNRKFCSFVVSNAKGAPERERF FQLLSEYKQVDSGGRYKNNVGGPVPDK TAFIKDYKFNIAFENSMCDGYTTEKIM EPMLVNSVPIYWGNKLIDRDFNPDSFI NVSSYSSLEEAVEHIVRLDQNDDEYLS LLSAPWFNEENYLNWEEQLITFFDNIF EKPLSESRYIPTHGYIQTYQYRLHRMM RDKLFRKRINPLKWFSSK | 2 |
| *Bacteroides fragilis*; *Bacteroides fragilis* NCTC 9343 | 60682921 | YP_213065.1 | LPS biosynthesis related glycosyl-transferase [*Bacteroides fragilis* NCTC 9343] | 26.49 | CafA | MCDCLSIILLVKMKKIYLKFVDFWDGF DTISNFIVDALSIQYEVVLSNEPDYLF YSCFGTSHLEYDCIKIMFIGENIVPDF NVCDYAIGFNYIDFGDRYLRLPLYAIY DGFSNLQNKKIDVNKALDRKFCSIVVS NNKWADPIRETFFKLLSSYKKVDSGGR AWNNIGGPVDNKLDFISQYKFNIAFEN SRVLGYTTEKIMEPMQVNSIPVYWGNP LVGKDFNVDSFVNAHDFDSLERLVEYI IELDSSKDKYLEMLEKPWLLDKTYLDW KQLLLNFINNIMMKSYKDAKYLVNYGH AGKYRNEQRFWGRCERKFKLQRIIEYY SQLFDRK | 3 |
| *Bacteroides fragilis*; *Bacteroides fragilis* NCTC 9343 | 60683260 | YP_213404.1 | putative fucosyl-transferase [*Bacteroides fragilis*] | 30.92 | CafB | MDILILFYNTMWGFPLEFRKEDLPGGC VITTDRNLIAKADAVVFHLPDLPSVME DEIDKREGQLWVGWSLECEENYSWTKD PEFRESFDLWMGYHQEDDIVYPYYGPD YGKMLVTARREKPYKKKACMFISSDMN RSHRQEYLKELMQYTDIDSYGKLYRNC ELPVEDRGRDTLLSVIGDYQFVISFEN AIGKDYVTEKFFNPLLAGTVPVYLGAP NIREFAPGENCFLDICTFDSPEGVAAF MNQCYDDEALYERFYAWRKRPLLLSFT NKLEQVRSNPLIRLCQKIHELKLGGI | 4 |
| *Helicobacter cinaedi*; *Helicobacter cinaedi* CCUG 18818 | 489046508 | WP_002956732.1 | alpha-1,3-fucosyl transferase [*Helicobacter cinaedi*] | 25.96 | CafH | MQKPIKKVYFCDGAVEGKIVKILKKHY NLIFTDRDPDYIFYSVMGEKHIEYDGI RIFSTGENVRADFNFCDYAIGFDYIQF DDRYLRYPLYLHYTKDMQKAKNKHLAI NTQTLQNKDRFCTFVVSNGKADELRTQ FFDFLSQYKHIDSGGKYKNNIGKPIKD KSSFLAIGKFNIAFENSNTNGYTTEKL IQALSSQTVPIYWGDECVSKPLDSSGG GGGVNPKAFIHIKSVNDFDTALEKIQK LDNDDEAYLSMLKEPSFLDSNHEEIFD ERLENFLLHIFSQPIKKAYRRGFGQWR YNLEKRYKKFQRARKIANGPANIFKIP IQKLRTYIKY | 5 |
| *Butyrivibrio fibrisolvens* | 551009204 | WP_022753767.1 | glycosyl-transferase [*Butyrivibrio fibrisolvens*] | 36.25 | CafK | MRRVFAIHPSIKGIVDLSKYLGFKSCI TEEIIWDSNSPEFIFVSERIYTDINEW ELFKKMYNPQRIFIFVSGECMTPDLNI FDYAIVFDRKLKDLDRICIRIPTNYIRH RSLIKKVNDMSFENALSRVKELDFCSF IYSNPKADQIREDIFWGLMNYKHVDSL GEYLNNSGVKTTRNDKHWRELSIEMKS HYKFSIAVENAQYEGYISEKLLTSFQS HSVPIYWGDPLVVDEYNPKAFINFNEM | 6 |

TABLE 5-continued

| Bacteria species | GI number | Accession number | Protein name | % identity to CafF | | Sequence | SEQ ID NO |
|---|---|---|---|---|---|---|---|
| | | | | | | SSISELVNHVKEIDENDELWAEMVSAD WQTSEQVARVKKETEEYDLFIEHILSQ SVSDAIRRPRGCWPYIYTNRFFDEKWF LKSKAKRYIRKAIHCFEEQ | |
| Butyrivibrio sp. AE2015 | 551028700 | WP_022772782.1 | glycosyl-transferase [Butyrivibrio sp. AE2015] | 32.92 | CafL | MKVKFVDSFFAREQTMGVLNELFENVE ISDDPDFVFCSVDYKAEHMNYDCPRIM VIGENIVPDFNCIDYAVGFNYMNFEDR YLRVPLYNFYLDDYKLAIRRHIDYKRD DNKKFCNFVYSNGRNAIPERDSFFADL SKYKQVDSGGRHLNNIGGPVDDKREFQ KQYKFSIAFENAVSRGYTTEKIIQAFS AGTIPIYYGNPLVAKEFNSKAFINCHE YRSFDEVIEKVKELDNDPDLYDSMMRE PIFTDIDERQDPLKDYRKFIYNICSQE SDKAIRRCDDCWGGKIQREKKRCYRFL TSTEGNGLKARVIRKLTEI | 7 |
| Parabac-teroides goldsteinii; Parabac-teroides goldsteinii CL02T12C30 | 494931837 | WP_007657871.1 | hypothetical protein [Parabac-teroides goldsteinii] | 32.59 | CafM | MTVTMVRSLYFVHPKVHNVESFLNYVH ICELPQGLCLEWNDRNPELLFASEVIY SDKKSSETFRRLYCEAKVVVYYGGEAS FTDFNIFDYGVGFDHTLKNQKYAQILS PIDFFDNFFYPDRTNLSEEVAQEKLRS GLKFCNFLYSNPVAHPYRDNLFYKLSE YKKVDALGRHLNNTGIGGTGFAGHARE SVNLKENYKFSIASENCGFQGYTSEKI LTSLQAHTVPIYWGDPDVDLVVNPKCF INCNDFDTLDEVLQKVKEIDNNDDLWC EMVSQPWFTEKQLEERIQRNKNYHKFM LSLLCKSIDSLTTRPNGTFQYVYRAWF LNASVRNDILYRLKRKMNFRRLRNFSL SQNRKN | 8 |
| Tannerella sp. CAG:118 | 547188760 | WP_021930564.1 | uncharac-terized protein [Tannerella sp. CAG:118] | 32.34 | CafN | MKTIKVKFVDFWKGFDPRNNFLMDILK QRYHIELSESPDYLIFSVFGFTNLNYE RCVKIFYTGENLTPDFNICDYAIGFDY LSFGDRYMRLPLYAVYGIEKLASPKVI DKEKVLRKKFCSYVVSNNIGAPERSRF FHLLSEYKKVDSGGRWENNVGGPVPNK LDFIKDYKFNIAFENSMYDGYTTEKIM EPMLVNSLPIYWGNRLINKDFNPASFI NVSDFPSLEAAVEHIVMLDNNDDMYLS ILSKPWFNDENYLDWKARFFHFFDNIF NRPIDECKYLTPYGFCRHYRNQLRSAR LLKQRFRQLRNPLRWFR | 9 |
| Lachno-spiraceae bacterium NK4A136 | 551037902 | WP_022781636.1 | glycosyl-transferase [Lachno-spiraceae bacterium NK4A136] | 29.34 | CafO | MSKKKIKINYIDFWPGFKKEDNFFSRI LDKYYDVEISDNPDYVFCSCFSRKHFK YADCVKIFYTGENIIPDFNLYDYSMGF HYIDFEDRYLRLPHYALYDQCIKAAKE KHTHSDDYYLAKKKFCNYVISNPYAAP ERDLMIDALEKYMPVDSGGRYRNNVGG PVADKVEFASHYRFSMAFENSAMSGYT TEKIFDGFAACTIPIYWGSDRIKEEFN PESFVSARDFENFDQVVARVKEIYEND DLYLKMMKAPIAPEGFQAHECLKEDYA DAFLRNIFDQDIDKAKRRNMVYVGRDY QKKLKDANKVIEVLDVVKKPMHQFNKT KSQIASKFRKKK | 10 |
| Methano-brevibacter ruminantium; Methano-brevibacter ruminantium M1 | 288560783 | YP_003424269.1 | glycosyl transferase [Methano-brevibacter ruminantium M1] | 29.11 | CafP | MSEKKKIKVKFVDFQDSLKENDNFFID SLKKNFDVEVSDDPDYLFFGAYGYKHL DYDCIRIMWTIENYVPDFNICDYALAY DIIEFGDRYLRFPFFLNRPEIENVRKT IERKPIDTSVKTDFCSFVVSNEWGDDY RIRLFHELSKYKKVDSGGRSLNNIGGP IGMGLDKKFEFDVTHKFSFALENAQNR GYTTEKIFDAFAAGCIPIYWGDPNIEE EFNPKSFINCNDLTVEEAVEKIKEVDQ NDELYHAMLNEPTFLGDLDKYLQDFDD FLFNICNQPLEKAYRRDRIMKGKTQEH QYKLINRFYYKPYFFLIKVAQKLHIEF IGRKIYHFIRD | 11 |

TABLE 5-continued

| Bacteria species | GI number | Accession number | Protein name | % identity to CafF | | Sequence | SEQ ID NO |
|---|---|---|---|---|---|---|---|
| Bacteroides salyersiae; Bacteroides salyersiae WAL 10018 = DSM 18765 = JCM 12988 | 492718747 | WP_005934126.1 | hypothetical protein [Bacteroides salyersiae] | 28.94 | CafQ | MKKVKIKFVDFFDGFDKGRNEFLEVLK QRYEIDISDEPDYVIYSGFGYEHLKYN CIRIFFTGECQTPDFNECDYAIGFDRL KFGDRYVRIPLYNMMQYKLDYKELLNR KSIISDDIKGRGFCSFVVSNCFANDTR AIFYELLNQYKYIASGGRYKNNIGGAI KDKKTFLSKYKFNIAFENCSHDGYATE KIVEAFAAGVVPIYYGDPRIAEDFNPK AFINAHDYQSFEEMVERIKEIDADDRL YLTMLNEPIIQPNADVTELADFLYSIF DQPLAKAKRRSQSQPTQAMEAMKLRHE FFEMKIYKYYKKGMNQFTRLRKGVFLS SKRTK | 12 |
| Lachnospiraceae bacterium NK4A136 | 551037432 | WP_022781173.1 | hypothetical protein [Lachnospiraceae bacterium NK4A136] | 27.08 | CafR | MKKEIKIAYVDFWNGFKPDSFFITKTI SKKYKVIIDNENPDFVICGTFGNTFLS YDCPRILYTGEANCPDFNIYDYAIGFE RMVYEDRYLRYPLFLVNEDLLQDALNK HKKSDDYYLRRDGFCSFVVSASGGMDG LRNWYFDKISEYKQVASGGRFRNNLPD GKPVPDKKAFQENYRFSLCFENAGISG YATEKIVDAFAAGCIPIYYGDTNIEKD FNPKSFIHVKSREDLDSVLAWVKELEE NQNKYLEVIRQPAILPDSPIMGMLNNT YIEEFLFHIFDQEPQEAIRRHSKLTMW GQFYEYRLKKWNKIENNMFLKKARSIK RKYFGLKKIVK | 13 |
| Parabacteroides; Parabacteroides goldsteinii dnLKV18; Parabacteroides sp. ASF519 | 498502734 | WP_010803436.1 | hypothetical protein [Parabacteroides] | 26.82 | CafS | MKKKIYCNFVDFWLGFNYKTYFWYLSD EYDLQIDKEHPDYLFYSCFGNEHLFYE DCIRIFWSDENIMPDLNICDYALSLSN LQCDDRTFRKYSGFLYRKDSHLVLPVL KEEALLNRKFCNFVYSNNTCAVPYREL FFKALSGYKRIDSGGAFLNNMGKKVGD KRQFLHEYKFTLAIENSSMPGYVTEKI LEPPFMAQSLPLYWGSPTVSSDYNPNSF VNLMNYSSMEEAVEEVIRLDKDDAAYL DKMMTPFWLYGANFQEFRDSEIKKIKD FFSYIFEQPLDKAGRRVCYGRNRITIQ KQRRYYAPTFLELSKSMTKKLLKKK | 14 |
| Clostridium bolteae; Clostridium bolteae 90A9; Clostridium bolteae 90133; Clostridium bolteae 90138 | 488634073 | WP_002570751.1 | hypothetical protein [Clostridium bolteae] | 26.43 | Caff | MKKIRLKYVDWWDGFQPEQYRFHQILT KHFDIEISDEPDYIIASVYSDEAKSYN CVRILYTGENICPDFNIYDYAIGFEYL EFGDRYIRIPNFIMNPAYDIDIQKALS KHLLSADDIKREKKFCSFVVSNGNAAP IREKMFEELNKYKRVDSGGRYLNNIGR PEGVRDKFAFQSEHKFSLTFENSAHLG YTTEKLLQGFSAGTIPIYWGDPAVENC FNPKAFINISGNNVYDAIELVKEVDTQ DDLYFSMLREPAFLNNDYQTKLLEKLD NFLVHIFNQPLECAYRRNSFEHISNKS VLNEFVKEDRGRFSQWISNKARCFYGK RKNK | 15 |
| Helicobacter canis NCTC 12740 | 564725892 | ETD25886.1 | hypothetical protein HMPREF2087_ 01720 [Helicobacter canis NCTC 12740] | 25.82 | CafU | MSKEKWKQEKRVHFVDCCDDGIRDKVC PILEQHFTLIFDSVNPEYVFYSAYGEE HLAYDCIRIFITGENITPNFTICDYAI GFDHLHFLDRYLRYPLYLFYEQDVKRA SQKHKDIDEKLLASKSRFCNFVVSNGN ADPYREQVFYALNAYKRVDSGGRYLNN IGGSVADKFAFQSECRFSLCFENSSTP GYLTEKLIQAAAAQTIPIYWGDTLATK PLFDGGGINAKAFINAHSFSSLESLI AHIAEIEADKTKQLAILQEPLFLDSNH IELFEKQFEQFLLSIVSQPYERSFRRG RVMWQSFVEQRYKRAMHLLALEDRIKA PYRKLRQFLRAFWDSLKEKRSHT | 16 |

TABLE 5-continued

| Bacteria species | GI number | Accession number | Protein name | % identity to CafF | Sequence | | SEQ ID NO |
|---|---|---|---|---|---|---|---|
| *Helicobacter canis* NCTC 12740 | 564725891 | ETD25885.1 | hypothetical protein HMPREF2087_ 01719 [*Helicobacter canis* NCTC 12740] | 25.44 | CafV | MGDEVAMGKERKQIRVHFVDFSNMDNI IEKICSILSRHFAVIIDGENPEYVFYS AFGSEYLKYDCVRIFYTGENIVPDFNL CDYAIGFDHIKFLDRYLRYPLYLFYET DVQKAARKHQNLSLEVVRNKKRFCNFV VTNGKGDPYREKVFHALCAYKRVDSAG KFLNNVGARVKDKFAFQSECRFSLCFE NSSTPGYLTEKLIQAAAAQTIPIYWGD PLATKPLFDGGGGINAKAFINAHEFAN IASLVRHIESIENDENKQLAILQEPLF LDSNHIELFEKQFEDFLVYIFSQPYER SFRRGKIMWQAHLEQIIKKGVQPTMLE IWLRRPLRNFERAIRIRVKKIIQKVKK PKDFM | 17 |
| *Akkermansia* sp. CAG:344 | 548174855 | WP_022396409.1 | putative uncharac- terized protein [*Akkermansia* sp. CAG:344] | 92.15 | | MKTLKISFLQSTPDFGREGIYQLLKDR YRVVEDDSDFDYLIATPWFYVNREAFY DFLERAPGHITVMYGCHEAIAPDFMLF DYYIGLDAVPGSDRTVKLPFLRHHLQE VHGGKAGLDVRALLASKTGFCNFIYAN RKSHPNRDAIFHKLSSVRFVNSLGPHL NNTPGDGHRSEDWYASSIRMKKPYKFS IAFENAWYPGYTSEKIVTSMLAGTIPI YWGNPDIGREFNSAAFINCHDFPTLDD AAAYVKKVDKDDGLWCEIMSRPWKTLE QEALFLEETERETAKLYRIFDQSPEEA RRKGDGTWIAYYQRFLKRGHRLRLAWR RLKNRLRH | 18 |
| *Gillisia limnaea*; *Gillisia limnaea* DSM 15749 | 494045634 | WP_006987752.1 | putative LPS biosynthesis related glycosyl- transferase [*Gillisia limnaea*] | 33.24 | | MKTLKIWFTDFYPGFEPKDNLITQLLF KSYNIEFDKNKPDYLIYSCHGHEFLNY NCVRIFYTGENLKPDFNLCDYAIGFDY IHFNNRYLRFPNFAFYESQFQQLIISK NPGSLDLSAKKHFCNFIYANSNADPTR DNFFYLLNKYKKVASPGKHLNNISMDV GERYAKDWMFTKIEFQSSCKFSIAFEN TSSPGYTTEKLLHAFITGTIPIYWGNP EVMKDFNPKAFINCHDFESFEDVVSKV KEIDNDDEMFLSMLNEPPFRNNIIPEN LKKEPLLVFLKNIFDQKREDAFQRSFY GTSAKYENDMKEMILFRKKYRSMIQFL GLLKKTLKIMKRNR | 19 |
| *Loktanella vestfoldensis* | 518799211 | WP_019955165.1 | hypothetical protein [*Loktanella vestfoldensis*] | 31.46 | | MKTIKLHYTDMWGTFDPLAPSQIDRIL RKHFHVVLTDQDPDYVICSVFGDGATR RRGVRLREHHLYPDAIKIMYSGENTLP DLNFCDYGIGFDHLVLGDRYQRVPLFA MNDGYQALLQPRAPLTRDDITSSVEFC NFTFTNNMAMPARDQFFHLLNDRKPVL STGRHLRNSDALDLHQQQTGLDPQQAK TDFLARFKFTIAFENSSHPGYTTEKVM DPLVARSVPIYLGNPRIADDFNTAAFI NGHDFPSLDALADEVMRIDADDAAYLA ILNAPPLPPGQREEPHLCALERFLLQI FTPPKAEAQRQRYGWIGRIDDEYSAY RRRRTRRWRWF | 20 |
| *Azospirillum brasilense*; *Azospirillum brasilense* Sp245 | 392378323 | YP_004985483.1 | putative glycosyl- transferase [*Azospirillum brasilense* Sp245] | 30.77 | | MLDQRTSAFLEEFLAKPGGDPERLDRF LLHGPYRGRRGGRPRLKLAFHDFWPEF DTGTNFFIEILSSRFDLSVVEDDSDLA IVSVFGGRHREARSCRTLFFTGENVRP PLDSFDMAVSFDRVDDPCHYRLPLYVM HAYEHMREGAVPHFCSPVLPPVPPTRA AFAERGFCAFLYKNPNGERRNRFFPAL DGRRRVDSVGWHLNNTGSVVKMGWLSK IRVFERYRFAFAFENASHPGYLTEKIL DVFQAGAVPLYWGDPDLEREVAAGSFI DVSRFATDEEEAVDHILAVDDDYDAYCA HRAVAPFLGTEEFYFDAYRLADWIESR L | 21 |

TABLE 5-continued

| Bacteria species | GI number | Accession number | Protein name | % identity to CafF | Sequence | SEQ ID NO |
|---|---|---|---|---|---|---|
| Lachnospiraceae bacterium NK4A179 | 551039804 | WP_022783468.1 | glycosyltransferase [Lachnospiraceae bacterium NK4A179] | 30.54 | MLKTAATGNIFSKISDIFFILGILCEL YVMPSGYAFGWYHEKTFIAAGMACFCV SIIFSMNLKKDFPVFALLAAYGAVCYR YQGTALVLRIILALLAGRDKNRDRTVK MFFAGSMFVIVLAAVLSLLGIHNSVMQ TGNTRSFTETRLTLGFYNPNGFALFVF RTYVLAVFLLITALKDKKKGVFIAAAV SLPFLILILLSHSKMAAAAFVAVFILT MICIGVKGKAADITAYAASLGAVILQV VLLIVFRFQLLPKMRFGKNDTFFEKIN SLTTGRLMMTKALFKSAVPRPFGRPQG EMALTEMGFENSAFAQGYIFILLLLAC IFWLSIRFYRKKDRAGLVVLSATTLYA LAESYLAYFNKNSIWLMMIGICAAGAA CRERNEMGKDGKKKIRIDFAGFWPDFK KDDNYFYNRLKLYYDPEICDDPDYVFC SGFSDEHFKYMDCVKIFFTGENIMPDF NLFDYALGPHYIDFEDRYLRLPLYALY DKEKIIIPALKKHTHEDEYYLSKKKFC NRVVSNPFGAGERDEMFDKLSAYKQVD SGGRYRNNVGGPVDDKIAFERDYKFTL AFENSSMSGYTTEKILEAFAGDTIPVY FGSPRIKEEFNPESFIDASSFDSFDEV VEEIKKIDNDDELYKMMKAPAVLPES QSKPVLEDDYIDAFLKNIFDQDLSTAK RRNMVYIGHDYQKKLKDANALKRVLDV VKRPVHLMHKIKWQITSKDK | 22 |
| Butyrivibrio sp. NC2007 | 551024122 | WP_022768256.1 | glycosyltransferase [Butyrivibrio sp. NC2007] | 29.08 | MKKITIGYTDIYPGFDPTNNIIYNCLK DRYDVKIADTAALESSSEVQYLFYSAS DNRYLDYNCIRIFVTGENLFPNFNLCD YAVGFEHMDVGDRFYRLPIYLWEQYRE DYDLLLQDRLELVGVSPEKRKFCGIVA TNNTFADPVREQFFHTLSRYRQVDSGG KAYNNIGLPEGVGDKRAFLKNYKFSIA FENSAYPGYCTEKLMQAFSAGTVPIYW GDETAIAEFNEKAFINCCGLSMEEAVA RVKEIDTNDELYKMLGEQPLLDNELR VKVISGLSKWLYHIIDSDYESARRRPI HGKMAAYEENYKKRIRREEKLKSNKLI SAMVWVYKKIR | 23 |
| Anaeromyxobacter dehalogenans; Anaeromyxobacter dehalogenans 2CP-1 | 220918351 | YP_002493655.1 | LPS biosynthesis glycosyltransferase [Anaeromyxobacter dehalogenans 2CP-1] | 29.01 | MKPVRVDFVDFWPGFDRRRNVLLDVLR ARFRVEVVDDPDFLFFANFGRRHRRYR CTRVFFTGENVRPDFRRCDFALTFDHL PEEPRHLRWPLYNLYLDDPRFLLERRR DVDALVAEKTRFCNLVCSNPAATERLR FFEKLSRYKPVDSGGRVLNNVGGPVPD KLAFIRQHRFTIAFENASYPGYTTEKI VEPMRVGSIPIYWGNPLVHLDFDLRSI VSWHEHGNDEATIERVIQIDRDEELYR HMLLQPFLPDGRPTPYSDPGVLLNWLE RVFSTPRRDARPPRRWW | 24 |
| Azospirillum lipoferum; Azospirillum sp. B510 | 288957550 | YP_003447891.1 | alpha-(1,3)-fucosyltransferase [Azospirillum sp. B510] | 28.84 | MLDRFLLHGPERGGRAARPRLKIAFFD FWPEFDPSANFFVEILSSRFDVSVVDN DSDLAILSVFGERHREARTARALFFTG ENVRPPLDGVDMSVSFDRIDHPRHYRL PLYVMHAWDHRREGATPHFCHPVLPPV PPTREEAAKRKFCAFLYKNPHCARRND FFQMLCARRHVESVGWLLNNTGSVVKM GWLPKIRVFARYRFAFAFENAAHPGYL TEKILDAFQAGTVPLYWGDSGVLRDVA AGSFIDVSRYASDEEAIEAILAIDDDY DSYRRYRGTAPFLGTEDFYFDAYRLAE WIESRL | 25 |
| Algoriphagus sp. PR1 | 495475427 | WP_008200114.1 | alpha (1,3)-fucosyltransferase [Algoriphagus machipongonensis] | 28.27 | MVLIKIKFVDHYNGFNPESDRIFTFLK RHFPVVLTESDPDFIIYSSWGSEHLHY DCPKIFYTGENHRPNFFLCDYALGFDF LNRTDYLRVPLYSILWYYDFSTLLFPK QQQILDQNPKTKFCCFVASNAGAMERN NFFKKLSNYLPVDSGGKVLNNVGGPVP DKIQFMKPYKFCIAYENSSYPGYVTEK IMDCFIAGCIPIYWGSTCIEKDFNPKR | 26 |

TABLE 5-continued

| Bacteria species | GI number | Accession number | Protein name | % identity to CafF | Sequence | SEQ ID NO |
|---|---|---|---|---|---|---|
| | | | | | ILNRLDYKSDEELIAEIKYLNENHSAY NEFIAQPIFTNNQFTEYFDESRLVKFF EKIFNGPSESRSKGIRKYIGLSLRFNK MIYSRIKKKLGYTGRVWY | |
| Helicobacter canis NCTC 12740 | 564725553 | ETD25547.1 | hypothetical protein HMPREF2087_01 375, partial [Helicobacter canis NCTC 12740] | 28.03 | MQSPHPNKSPIRIHFCDFGDMQGIAKA ITALLQRHYTITLDSHSPQYLFYSVFG SEHIKYDCVRIFYTGENITPNFTICDY AIGFDHLHFLDRYLRYPLYLFYEQDVK RASQKHKDIDEKLLASKSRFCNFVVSN GNADPYREQVFYALNAYKRVDSGGRYL NNIGGSVADKFAFQSECRFSLCFENSS TPGYLTEKLIQAAAAQTIPIYWGDPLA TKPLFDGGGGINAKAFINAHSFSSLES LIEHIAEIEAD | 27 |
| Anaeromyxo- bacter dehalogenans; Anaeromyxo- bacter dehalogenans 2CP-C | 86159477 | YP_466262.1 | LPS biosynthesis related glycosyl- transferase [Anaeromyxo- bacter dehalogenans 2CP-C] | 27.93 | MNPVRLDFVDFWPGFDRRNNVLLDVLR TRFAVEVVDDPDFVFFANFGWRHWRYR CTRVFFTGENVRPDFRHCDFALTFDHL PDEPRHLRWPLYNLYLGDPRFLLERRR DVNAIVAEKTRFCNLVCSNRAARERLR FFEKLSRYKPVDSGGRVRNNVGGPVKD KLAFIRQHRFTIAFENASYPGYTTEKI VEPMRVGSIPIYWGNPLVHLDFDLRSI VSWHEHGSDEAAIERVIQIDRDEELYR HMLLQPFLPEGRPTPYSDPGVLLDWLE RVFSTPRRDARPPRRWW | 28 |
| Coralio- margarita akajimensis; Coralio- margarita akajimensis DSM 45221 | 294056076 | YP_003549734.1 | alpha-1,3- fucosyl- transferase [Coralio- margarita akajimensis DSM 45221] | 27.41 | MKPTKRIAIVDAGRTPDIVHAVLPFIE ERYNLEITDDRDADYVFHSCLGHEVLK YSGIRIFVTGECVSPDFNISDYALAFD PIDFGDRYIRLPLIRLFTEAYESLCAP RAEPEQILAKKNGFCAYVMSNTKNSAP ERVELFEALSRYQPVASGGKWRNNVGG PVADKIAFQSTHKFVLALENESYPGYL TEKFAQAAQSNAIPIYWGDPTITDIIN PRAFVNVRDFQSTDALVSHIQSLDQDD AAYLSMLSEPWFRGGKEPEEWRAQGYR DFLANIFEQPKERAYRRNRSRWGKKYE GRYYDMAFRPQRQFATLTKTALRRLRH SGQ | 29 |
| Helicobacter fennelliae MRY12-0050 | 522684320 | GAD18300.1 | alpha (1,3)- Fucosyl- transferase [Helicobacter fennelliae MRY12-0050] | 27.31 | MDWWEQDTKENFYKNPFIQALSQKYNI EYSNKPDFLLYGPFGQNNLQFPKEVVR IFYTGENTRTDWNIADYGIDFDFMDFG DRHLCMPLFFLPGECGISSRAITKHLR AEQIFQEKREKFCAFLVSNGSNHIRNT AFKKLCAYKKVDSGGRYLNNIGGRIGD RFKDFEKSKYEWLLGYKFNLCFENSSY PGYVTEKILQAYEAGCIPIYWGDSTLC DVRYAKYRPTFNPKAFVNAHDFANLDE LVQEVRRIDNDNEAYLAMLKEPIFLDS TIDTHVLGGGASTS | 30 |
| Prevotella sp. CAG:873 | 548234549 | WP_022453039.1 | unchar- terized protein [Prevotella sp. CAG:873] | 26.9 | MGNRTVTVKFVDFWQSFDWRDNRFVRA LRSQRQVTVLEPSSPEVPDILFYSRGP GCDHLRYDCLKVYFTGENDFPDFNECD YALSFYECDCGGRNLRYPLYMLYECDE AACPPVLSDAEALDRGFCSLVMSNASN CHPRRLEIVDAIEAYRPLAYGGAFRNN VGSRVEDKISFISGYKFNLALENSVMP GYVTEKLLEPLAAATVPIYWGADAAKH DFNPESFVCVNDYATFDSLVAELRRLD NDSAAYLAMLRAPSHTGDTVARMDTRL AEFLNAIADRPERRISPYGEIHNLQRR NRALVPLWHSRVGRAAARLLGHIAK | 31 |
| Flavobacterium sp. ACAM 123 | 515556121 | WP_016989022.1 | hypothetical protein, partial [Flavo- bacterium sp. ACAM 123] | 26.5 | RIFGLVFDKTNNYFYNLLVQKYIVNID ENPDFLFYSCYSNDYLNYNCTRIFFTG ENVRPDFLACDFAFSCDYNKQKNHFRL PLYSLYIDHHNLLDKLQSTLNKEEARR VWQAKSKFCCMVVSNPKCVERIEFFEN LSKVKQVDSGGSVLNNVGGRVADKAEF IKDYKFVISFENESYDGYTTEKILEPI LMDCIPIYWGNKLVDKDFNAKRFINYN TFKTENKLIERLLEIDQNEELAIAMLL | 32 |

TABLE 5-continued

| Bacteria species | GI number | Accession number | Protein name | % identity to CafF | Sequence | SEQ ID NO |
|---|---|---|---|---|---|---|
| | | | | | EQPFNKDKKTHEEEHQQVLDIISNMIE VDKPIAQQLWKYVHKSKLFAAKFKKR FIKI | |
| Flavobacterium sp. ACAM 123 | 515558176 | WP_016991062.1 | hypothetical protein [Flavobacterium sp. ACAM 123] | 26.4 | MKEIKINFVDFWPGFNKTNNYFYNLLI QKYKVSIDANPDLLFYSCYNNDYLNFD CTRIFYTAENIRPDFSACDFAFSYGYN AKINHFRLPLYSMYIDLLNMKDKIEAT LSREEAQKIWKTKSKFCCMVVSNATGT KRLDFFKNLSKIKQVDSGGGIFNNIGG KVVDKLEFIKDYKFVISFENGQNDGYT TEKILEPIYKDCIPIYWGNKLVDKDFN SKRFLDYSKFECEKDLIDKLLEMELDD ELAISMLMQPAFGENKRPHEEERAEVL RILGRIIENPEKPIARQLWKYIHLLKR KYRKNKKRIKRILN | 33 |
| Butyrivibrio sp. AE3009 | 551033828 | WP_022777675.1 | hypothetical protein [Butyrivibrio sp. AE3009] | 26.38 | MKKVKVKFVDTYGKQQKYLEKLLGDDI ELEYSDEPDYLFYGVFGSGMEHYKYKN CVKIFFASEGVIPDFNECDYAIAEYPM TVGDRYFCKPYMAPKEADFSVFDEKAD YLGRKFCNFVFSNETNGRGAVLRKQFC QKLMEYKHVDCPGKVLNNMKDAIEPRN GKWFHGKLDFIKDYKFTIAFENVNTPG MVSEKIYNAFQARTVPIYWGPDDVNKI YNPKSFINCSGLTIDEMVKKVAEVDSN DELYMDMLRQNPIAEGFNLNWEEDMAR FLRGIILENKDYYDKDPLGWDSGNKAA KELISLEDTMLYKLHKGREKVAKKLKR | 34 |
| Helicobacter pylori; Helicobacter pylori FD577 | 537771103 | WP_020982055.1 | fucosyl-transferase, partial [Helicobacter pylori] | 26.38 | MFQPLLDAFIESASIKKKLPLNLPPPL KIAVANWFNGSKEFKASVLYFILKQRY KIILHSNPNEPSDLVFGNPLGQARKIL SYQNTKRVFYTGENEAPNFNLFDYAIG FDELDFNDRYLRMPLYYAYLHYKAEIV NDTTSPYKLKADSLYTLKKPSHKFKEN HPHLCALIHSESDPLKRGFASFVASNP NAPIRNAFYDALNSIEPVAGGGSVKNT LGYKVKNKNEFLSQYKFNLCFENSQGY GYVTEKILDAYFSHTIPIYWGSPSVAK DFNPKSFVNVHDFNNFDEAIDYIRYLH THQNAYLDMLYENPLNTLDGKASFYQD LSFEKILDFFKNILENDTIYHCNDAHY SALHRDLNEPLVSVDDLR | 35 |
| Verrucomicrobia bacterium SCGC AAA300-K03 | 518821759 | WP_019977713.1 | hypothetical protein [Verrucomicrobia bacterium SCGC AAA300-K03] | 26.16 | MLNQIKINYTDFYGDKNYERNPFHNFL SSHFNLELSEEPDFLIHGVYGQDYLNY NCVRILYSAENMIPDFKTYDYSLTFCK SSFQDRNWRVPLYAVWNDLSIQLDSHL GFRNATNLSQNRDVFCSFVVSNPYCSF RNNLFKRLEKYKFVHSGGGVFNNSGGK TGNKLHFIRNSKFNIACENQSYPGYTT EKILEAFLAGCIPVYWGNPEIAHEFNE KAFINCHNYKSINEVADRIIEIDQNKA LYLDYLSQPIFYNDTIPDDASHSRIVT IFNNIFYNTRPSRIACSKLPSKIFNIK KQLKKLAGKYSR | 36 |
| Clostridium citroniae; Clostridium citroniae WAL-17108 | 495144632 | WP_007869439.1 | hypothetical protein [Clostridium citroniae] | 25.88 | MEKIKTKIINKITKINLIGIALVFYTS VWRGYKEYCRLKKKHGNLPIITPTFKG TGDFYMVAKYFPQWLKFKKIDKYMMIA GGASEIRVLELFPQWFSNAQYEILSWE HYTYLIHMRLFWGVEKSDIYVLNHIAN FGGEHTNYLWITWNLMGYKGLSLLDFY LIYGCKLSKLEKPLIPIFETDSNKIDK IFKYKKLKPGKTVMISPYSTGNGTFHV SFWNSIVKQLQLSGYSVCTNCFGSEKP LANTVKLGLDYRDLVPFMDKAGFAIGI RSGFFDIISSSTCKKIIIHTFKANHWP NGNSLPYTGLKHLGLCNDAIEYELNSN ESNFDVIRRSILGLFAIHVASSKKTIK IKYVDPPDFNKEKIWITRVLREKYNV VFSDNPEFLFYSVFGLTFDQYKNCIKI FFTGEDTIPNFNECDYAMCHDRLELGD RYIRADVGERYGTPIGNLEPDWIEKGI SISGWINSSLIDIKDKIQNRSIVSEKL | 37 |

TABLE 5-continued

| Bacteria species | GI number | Accession number | Protein name | % identity to CafF | Sequence | SEQ ID NO |
|---|---|---|---|---|---|---|
| | | | | | INRRFCNFIYSNESFGEGAVLRKKFCL ELMKYRRVDCPGRVLNNMKDGLGIRWS VKDGRDSIVDNWTSTKLEFIKNYKFTI AFENTAIPGHTTEKLIHPFYAYSIPIY WGNPDVVADFNPKAFINCNDYNNDWRA VCKRIKELDQDHEQYLEMLRQPPMQPD FDFGSEEKAKQFLYNIVEKGYKPYTKS SLAFTAPNVARNSYHELMEIKTSNSWK VARRIQAFLGTKWGWFPRQLCLALLNV RNRLVKKK | |
| Helicobacter bilis; Helicobacter bilis WiWa | 490187781 | WP_004086382.1 | hypothetical protein [Helicobacter bilis] | 25.84 | MQKQQVKMRVLDWWNKDCEENFYNNFF IQILQKKYDVVYSDKPDFILYGPFGYE HLKYDCVRIFHTGENIRPDYNIADYSM DFDYIEFEDRHLRLPHMFWVFCDEMRQ KEMDNRISLLDKKEKFCGFMVSNNALT DKRDMFFEALSKYKRVDSGGRWKNNMG GNVDDKIEWLKSYKFNLCFENSSYPGY LTEKLFDAFLAGCVPIYWGDTSLKIHK NTCADSKNSENINNQGGGSNDAFDMRI PNISHSLIDYEINPKAFINAHNFPTFQ DLIDEIKRIDNDSYAFESMLREPIFLN DFNPHEFYATKIAAFLNRIVSQGAIQA KRRGDGFLLKAYREFQSAIAENTQISS GFFSYCVKHGRVIQAIRDSSKLPKRFS RFIRRTRK | 38 |
| Verrucomicrobia bacterium SCGC AAA300-N18 | 518996369 | WP_020152244.1 | hypothetical protein [Verrucomicrobia bacterium SCGC AAA300-N18] | 25.59 | MVSNQIKIQFTDFYQIPNEEENYLYKY LKQYFNLELSDDPDVVIYSNYGFEYKQ YECLRVLFCAEYAIPDIEDCDYCFSQH HASYWGKNYRLPMYVFWQNFSLKFEEL LRPVDYEEIRKQDRGFCSFVVSSPLGS QTRVNFMHELSSYKKVDSGGKLLNNIG GPVANKRDFLKKYKFNIAFANGLADGY ADEKIVDPMFVDSIPIFWGNPRIAEDF NPASFVNCHDYDNFDSVIKEVIRIDKN EDVYRSYLEQPWFPENKLTRYVDLDHL QNRFRYIFSQIGKKVPAARSKRRFFYK LLKKLKPLTPIVQQWGDYQPSN | 39 |
| Moumouvirus goulette | 451927149 | AGF85027.1 | family 10 protein [Moumouvirus goulette] | 25 | MDKFKIVCINLARRQDRKDLITNKLIN QNMSNFEFFEAVDGSQIDPYDERLNLF KHSVSGLLRRGVTGCALSHYTIWKKLV NDPDYNTYLVIEDDINFGPDFKFGLEK ILEKKPNYGIILLGMTLELEKKAETKH LYQYDTSYTIHNLNRDLYCGGAFGYII SKSAAKYLVDYISHNGIRMVIDYLMFR SGVPMYESHPHLVFTDAVQHSIHYVDS DIQHDHEKIKYNKLPNDYQFDDYIFLS NRDSPRGDIREICADITTLKKAADMTS ECIAFNTYGWLKNILTDFDKFIVLHDK FYTHDGIYIKKSYFNLENKLKNLRLLE RPIRIFLNKNTINYSQHLVNIILKNIP NYNIVKDNNDADIIIDNINDSNLYYDQ TKINMIISGEPFNRKQKYDIAIDTKKN SNAECIIYHPFLFSSLHEHKKSINYLD YTNPKTKFCAYMFHMSYPHRINYFNIV SSYKHVDALGKCCNNVDIKNTRYVLNN KETYNDIAVEYFSQYKFVLAIENNMIP GYNTEKLINPMIANSIPIYWGDSE1FK YINKRRLVYIPDFITNEDLINHIKYID EHDDVYENIIKESIFTDPDFTLDVIEQ NLSGEIDNLLGFNKN | 40 |

Figure 6:
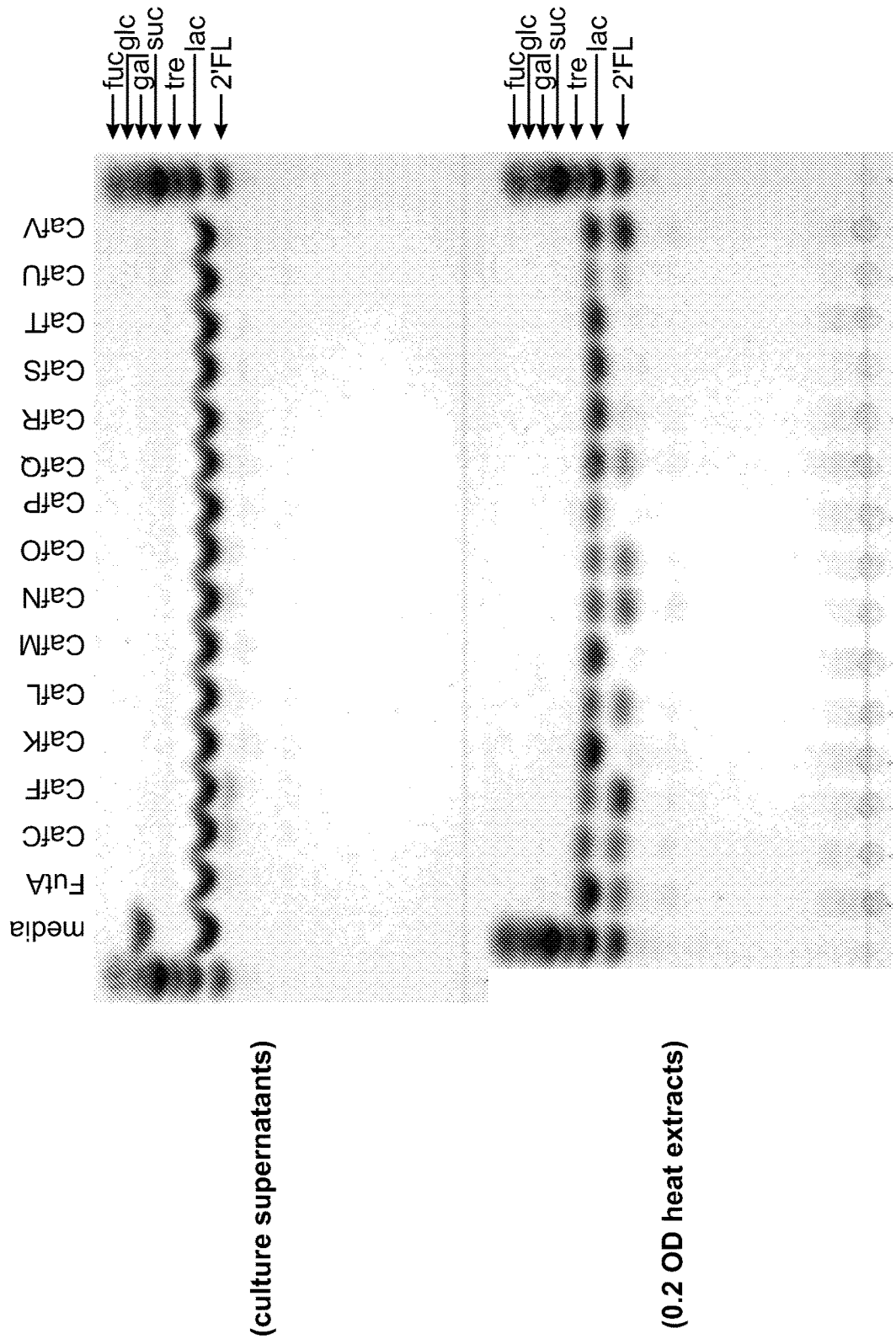
FIG. 6 is a photograph showing thin layer chromatography analysis of 3-FL produced in *E. coli* strains by 12 candidate α(1,3) fucosyltransferases identified in a second database screen that used a sequence alignment of CafC and CafF as the query. The figure shows significant production of 3-FL by FutA, CafC, CafF and also by the new candidate enzymes CafL, CafN, CafO, CafQ, CafU and CafV.

Of the identified hits, 12 novel α(1,3) fucosyltransferases were further analyzed for their functional capacity: *Butyrivibrio fibrisolvens* CafK, *Butyrivibri* sp. CafL, *Parabacteroides goldsteinii* CafM, *Tannerella* sp. CafN, *Lachnospiracae bacterium* CafO, *Methanobrevibacter ruminantium* CafP, *Bacteroides salyersiae* CafQ, *Lachnospiraceae bacterium* CafR, *Parabacteroides goldsteinii* CafS, *Clostridium bolteae* CafT, *Helicobacter canis* CafU and *Helicobacter canis* CafV. FIG. 6 demonstrates significant production of 3-FL by FutA, CafC, CafF and also by the new candidate α(1,3) fucosyltransferase enzymes derived from the second database screen; CafL, CafN, CafO, CafQ, CafU and CafV.

The sequence identity between the 12 novel α(1,3) fucosyltransferases identified in this second screen, the previously identified lactose-utilizing α(1,3) fucosyltransferases from the first screen, and FutA is shown in Tables 2 and 3 below.

TABLE 3

| | | \multicolumn{9}{c}{Sequence Identity} | | | | | | | | |
|---|---|---|---|---|---|---|---|---|---|---|
| | | 1 | 2 | 3 | 4 | 5 | 6 | 7 | 8 | 9 |
| *Bacteroides nordii* CafC | 1 | | 25.00 | 23.50 | 66.88 | 49.25 | 39.64 | 38.10 | 38.32 | 36.31 |
| *Akkermansia muciniphila* CafF | 2 | 25.00 | | 18.61 | 25.41 | 21.15 | 22.72 | 21.49 | 23.08 | 22.76 |
| *Helicobacter pylori* FutA | 3 | 23.50 | 18.61 | | 25.81 | 24.77 | 25.23 | 23.11 | 23.97 | 20.96 |
| *Tannerella* sp. CafN | 4 | 66.88 | 25.41 | 25.81 | | 53.45 | 39.23 | 35.82 | 35.82 | 36.42 |
| *Bacteroides fragilis* CafA | 5 | 49.25 | 21.15 | 24.77 | 53.45 | | 36.86 | 35.06 | 34.10 | 35.77 |
| *Bacteroides salyersiae* CafQ | 6 | 39.64 | 22.72 | 25.23 | 39.23 | 36.86 | | 35.36 | 42.43 | 40.75 |
| *Parabacteroides goldsteinii* CafS | 7 | 38.10 | 21.49 | 23.11 | 35.82 | 35.06 | 35.36 | | 32.27 | 31.64 |
| *Clostridium bolteae* CafT | 8 | 38.32 | 23.08 | 23.97 | 35.82 | 34.10 | 42.43 | 32.27 | | 41.91 |
| *Methanobrevibacter ruminantium* CafP | 9 | 36.31 | 22.76 | 20.96 | 36.42 | 35.77 | 40.75 | 31.64 | 41.91 | |
| *Lachnospiraceae bacterium* CafO | 10 | 35.91 | 24.08 | 24.54 | 37.39 | 35.73 | 38.95 | 33.91 | 40.94 | 37.82 |
| *Lachnospiraceae bacterium* CafR | 11 | 35.10 | 23.53 | 23.97 | 33.92 | 30.95 | 35.23 | 30.46 | 36.89 | 33.71 |
| *Butyrivibrio* sp. CafL | 12 | 34.76 | 25.67 | 23.22 | 35.37 | 36.95 | 39.35 | 32.54 | 41.96 | 39.83 |
| *Helicobacter canis* CafU | 13 | 32.87 | 20.00 | 23.08 | 32.59 | 32.60 | 37.33 | 32.04 | 37.88 | 34.71 |
| *Helicobacter canis* CafV | 14 | 31.40 | 19.30 | 23.30 | 31.96 | 31.23 | 32.51 | 32.51 | 36.91 | 32.97 |
| *Butyrivibrio fibrisolvens* CafK | 15 | 25.53 | 24.25 | 16.63 | 22.49 | 23.18 | 24.43 | 22.98 | 25.39 | 22.92 |
| *Parabacteroides goldsteinii* CafM | 16 | 22.99 | 24.62 | 16.85 | 23.94 | 23.47 | 24.27 | 20.37 | 25.54 | 23.14 |
| *Bacteroides fragilis* CafB | 17 | 14.44 | 14.21 | 8.67 | 14.40 | 13.81 | 15.09 | 13.16 | 13.99 | 13.00 |
| *Helicobacter hepaticus* CafD | 18 | 12.11 | 7.81 | 8.68 | 9.49 | 11.05 | 7.44 | 10.26 | 8.82 | 7.41 |

| | | 10 | 11 | 12 | 13 | 14 | 15 | 16 | 17 | 18 |
|---|---|---|---|---|---|---|---|---|---|---|
| *Bacteroides nordii* CafC | 1 | 35.91 | 35.10 | 34.76 | 32.87 | 31.40 | 25.53 | 22.99 | 14.44 | 12.11 |
| *Akkermansia muciniphila* CafF | 2 | 24.08 | 23.53 | 25.67 | 20.00 | 19.30 | 24.25 | 24.62 | 14.21 | 7.81 |
| *Helicobacter pylori* FutA | 3 | 24.54 | 23.97 | 23.22 | 23.08 | 23.30 | 16.63 | 16.85 | 8.67 | 8.68 |
| *Tannerella* sp. CafN | 4 | 37.39 | 33.92 | 35.37 | 32.59 | 31.96 | 22.49 | 23.94 | 14.40 | 9.49 |
| *Bacteroides fragilis* CafA | 5 | 35.73 | 30.95 | 36.95 | 32.60 | 31.23 | 23.18 | 23.47 | 13.81 | 11.05 |
| *Bacteroides salyersiae* CafQ | 6 | 38.95 | 35.23 | 39.35 | 37.33 | 32.51 | 24.43 | 24.27 | 15.09 | 7.44 |
| *Parabacteroides goldsteinii* CafS | 7 | 33.91 | 30.46 | 32.54 | 32.04 | 32.51 | 22.98 | 20.37 | 13.16 | 10.26 |
| *Clostridium bolteae* CafT | 8 | 40.94 | 36.89 | 41.96 | 37.88 | 36.91 | 25.39 | 25.54 | 13.99 | 8.82 |
| *Methanobrevibacter ruminantium* CafP | 9 | 37.82 | 33.71 | 39.83 | 34.71 | 32.97 | 22.92 | 23.14 | 13.00 | 7.41 |
| *Lachnospiraceae bacterium* CafO | 10 | | 38.57 | 37.90 | 30.66 | 31.69 | 22.82 | 24.34 | 13.74 | 8.96 |
| *Lachnospiraceae bacterium* CafR | 11 | 38.57 | | 33.24 | 33.51 | 33.15 | 22.25 | 19.37 | 13.70 | 8.12 |
| *Butyrivibrio* sp. CafL | 12 | 37.90 | 33.24 | | 35.85 | 33.80 | 26.98 | 26.33 | 14.78 | 9.49 |
| *Helicobacter canis* CafU | 13 | 30.66 | 33.51 | 35.85 | | 64.33 | 22.14 | 22.31 | 14.07 | 9.38 |
| *Helicobacter canis* CafV | 14 | 31.69 | 33.15 | 33.80 | 64.33 | | 22.96 | 21.26 | 14.25 | 7.90 |
| *Butyrivibrio fibrisolvens* CafK | 15 | 22.82 | 22.25 | 26.98 | 22.14 | 22.96 | | 26.88 | 11.78 | 9.23 |
| *Parabacteroides goldsteinii* CafM | 16 | 24.34 | 19.37 | 26.33 | 22.31 | 21.26 | 26.88 | | 13.12 | 7.43 |
| *Bacteroides fragilis* CafB | 17 | 13.74 | 13.70 | 14.78 | 14.07 | 14.25 | 11.78 | 13.12 | | 8.13 |
| *Helicobacter hepaticus* CafD | 18 | 8.96 | 8.12 | 9.49 | 9.38 | 7.90 | 9.23 | 7.43 | 8.13 | |

TABLE 4

Sequence alignments

| | | |
|---|---|---|
| Bacteroides nordii CafC | M--------------------KTIK--VKF-------VDFWENFDPQHNF----IANIISKKYR-IELSDTPDY--LFFSV-FG-Y--ENIDY-HNC---TKIFY-SGENITPDFNICD | 74 |
| Akkermansia muciniphila CafF | M--------------------KTLK--ISF-------LQSTPDFGREGMLQLLKSRYHVVE--DDSDFDYLVATPWFYVNREAFYDFLERAPGHITVMYGCHEAIAPDFMLFD | 82 |
| Helicobacter pylori FutA | MFQPILLDA-----PIESASIEKMASKSPPPPLKIAVANWWGDEIKEFKKSVLYFILSQRYAITLHQNPNEFSDLVFSNPLG-AARKILSY-QNTK---RVFY-TGENESPNNLFD | 106 |
| Tannerella sp. CafN | M--------------------KTIK--VKF-------VDFWKGFDPRNNF-----LMDILKQRYH-IELSESPDY--LIFSV-FG-F--TNLNY-ERC---VKIFY-TGENLTPDFNICD | 74 |
| Bacteroides fragilis CafA | MCDCLSII-------LLVKMKKIY---LKF-------VDFWDGFDTISNF-----IVDALSIQYE-VVLSNEPDY--LFYSC-FG-T--SHLEY-D-C---IKIMF-IGENIVPDFNVCD | 85 |
| Bacteroides salyersiae CafQ | M--------------------KKVK--IKF-------VDFFDGFDKGRNE----FLEVLKQRYE-IDISDEPDY--VIYSG-FG-Y--EHLKY-N-C---IRIFF-TGECQTPDFNECD | 73 |
| Parabacteroides goldsteinii CafS | M--------------------KKKIY--CNF-------VDFWLGFNVKTYF-----WY--LSDEYDLQIDKEHPDY--LFYSC-FG-N--EHLFY-EDC---IRIFW-SDENIMPDLNICD | 74 |
| Clostridium bolteae CafT | M--------------------KKIR--LKY-------VDWWDGFQPEQYR----FHQILTKHFD-DEISDEPDY--IIASV-YS-D--EAKSY-N-C---VRILY-TGENICPDFNIYD | 73 |
| Methanobrevibacter ruminantium CafP | MSE------------------KKKIK--VKF-------VDFQDSLKENDNF-----FIDSLKNFD-VEVSDDPDY--LFFGA-YG-Y--KHLDY-D-C---IRIMW-TIENYVPDFNICD | 76 |
| Lachnospiraceae bacterium CafO | MS-------------------KKKIK--INY-------IDFWPGFKKEDNF-----FSRILDKYYD-VEISDNPDY--VFSCS-FS-R--KHFKY-ADC---VKIFY-TGENIIPDFNLYD | 76 |
| Lachnospiraceae bacterium CafR | M--------------------KKEIK--IAY-------VDFWNGFKPDSFF-----ITKTISKKYKVIIDNENPDF--VICGT-FG-N--TFLSY-D-C---PRILY-TGEANCPDFNIYD | 75 |
| Butyrivibrio sp. CafL | M--------------------K---VKF-------VDSFFAREQT----------MGVLNELFENVEISDDPDF-VFCSVDYK-A--EHMNY-D-C---PRIMV-IGENIVPDFNCID | 68 |
| Heliobacter canis CafU | MSK--E---------KWKQEKR--VHF-------VDCCD--DGIRDK----VCPILEQHFTLIFDSVNPEY--VFYSA-YG-E--EHLAY-D-C---IRIFI-TGENITPNFTICD | 78 |
| Heliobacter canis CafV | MGD--EVA------MGKERKQIR--VHF-------VDFSN-MDNIIEK----ICSILSRHFAVIIDGENPEY--VFYSA-FG-S--EYLKY-D-C---VRIFY-TGENIVPDFNLCD | 83 |
| Butyrivibrio fibrisolvens CafK | MRRVFAI--------HPSIKGIVD--------LSKYLGFK---------SCITE--EIIWDSNSPEFIFVSERIYTDINEWELFKK-MYNPQRIFIFV-SGECMTPDLHIFD | 83 |
| Parabacteroides goldsteinii CafM | MTVTMVRS----LYFVHPKVHNVESF-------LNYVHICELPQGL----CLEWNDRNPELLFASE-----VIYSDKKS--S--ETFRR-LYCEAKVVYY-GGEASFTDFNIFD | 89 |

TABLE 4-continued

Sequence alignments

| Organism/Protein | Sequence | # |
|---|---|---|
| Bacteroides fragilis CafB | M-------------------DILLLFYNTMWGPPLEFRKE-DLPGGCVITTDRNLIAKADAVVF--HLPDLPSVMEDEIDKREGQLWVGWSLECEEN---YSWTKD---PEFRE-- | 86 |
| Helicobacter hepaticus CafD | MKDDLVILHPDGGIASQIAFVALGLAFEQKGAKVKYDLSWFAEGAKGFWNP--SNGYDKVYDITW-----DISKAFPALHIEIANEEEIERYK----------SKYLIDNDRVID | 98 |
| Consensus | M----------------------KKIK--VKF---------VDFWDGFPDI.NF-----.L.ILSKRY.-IEDSDNPDY--VFYSV-FG-N--EHLKY-D-C---IRIFY-TGENITPDFHICD | |
| Bacteroides nordii CafC | YAIGFNF-LSFGDRYIR-IPFYTAY-GVQ--------------------QLAAPK--------------VIVPEVLNRK-FCSFVVSN--AKGA-PERERFFQLLSEYKQVDSG-GRYK | 152 |
| Akkermansia muciniphila CafF | YYIGLD-TVPGSDRTVK-----------------------------------LPYLRHHLEEVHGGKEGLDAHALLASKTGFCNFIYAN--RK-SHPNRDAMFHKLSAFRFVNSL-GPHL | 162 |
| Helicobacter pylori FutA | YAIGFDE-LDFNDRYLR-MPLYYAHLHYKAELVNDTTAPYKLKDNSLYALKKPSHHFKENHPNLCAVVNDESDLLKRGFASFVASN--AN--APMRNAFYDALNSIEPVTGG-GSVR | 216 |
| Tannerella sp. CafN | YAIGFDY-LSFGDRYMR-LPLYAVY-GIE--------------------KLASPK--------------VIDKEKVLKRK-FCSYVVSN--NIGA-PERSRFPHLLSEYKKVDSG-GRWE | 152 |
| Bacteroides fragilis CafA | YAIGFNY-IDFGDRYLR-LPLYAIYDGFS----------------------NLQNKK--------------IDVNKALDRK-FCSIVVSN--NKWADPIRETFFKLLSSYKKVDSG-GRAW | 164 |
| Bacteroides salyersiae CafQ | YAIGFDR-LKFGDRYVR-IPLYNMMQ-YKLDYKE--------------LLNRKS--------------IISDDIKG-RG-FCSFVVSN--C-FANDTRAIFYELLNQYKYIASK-GRYK | 155 |
| Parabacteroides goldsteinii CafS | YALSLSN-LQCDDRTFRKYSGFL---YRKDSHL-----------------VL--P-------------VLKEEALLNRK-FCNFVYSN--NTCAVPYRELFFKALSGYKRIDSG-GAFL | 153 |
| Clostridium boltreae CafT | YAIGFEY-LEFGDRYIR-IPNFIMNPAYDIDIQK-------------------ALSKHL--------------LSADDIKREKK-FCSFVVSN--G-NAAPIREKMFEELNKYKRVDSG-GRYL | 157 |
| Methanobrevibacter ruminantium CafP | YALAYDI-IEFGDRYLR-FPFFLNRPEIE-NVRK--------------TIERKP--------------I---DTSVKTD-FCSFVVSN--E-WGDDYRIRLFHELSKYKKVDSG-GRSL | 156 |
| Lachnospiraceae bacterium CafO | YSMGPHY-IDFEDRYLR-LPHYALYDQCI----K-------------------AAKEKH--------------THSDDYYLAKKKRCNYVISN--P-YAAPERDLMIDALEKYMPVDSG-GRYR | 157 |
| Lachnospiraceae bacterium CafR | YAIGPER-MYEDRYLR-YPLFLVNEDLLQD------------------ALNKHK--------------K-SDDYYLRRDGFCSFVVSA--SGGMDGLRNWVFPDKISEYKQVASG-GRFR | 157 |
| Butyrivibrio sp. CafL | YAVGFNY-MNFEDRYLR-VPLYNF---YLDDYKL------------------AIRRHI--------------DYKRDDN--KK-FCNFVYSN--GRNAIPERDSFFADLSKYKQVDSG-GRHL | 148 |
| Helicobacter canis CafU | YAIGFDH-LHFLDRYLR-YPLYLF---YEQDVKR------------------ASQKHK--------------DIDEKLLASKSRFCNFVVSN--GN-ADPYREQVFYALHAYKRVDSG-GRYL | 160 |

TABLE 4-continued

Sequence alignments

| Name | Sequence | # |
|---|---|---|
| Helicobacter canis CafV | YAIGFDH-IKFLDRYLR-YPLYLF---YETDVQK---------AARKHQ--------NLSLEVRNKKRFCNFVVTN--GK-GDPYREKVFHALCAYKRVDSA-GKFL | 165 |
| Butyrivibrio fibrisolvens CafK | YAIVFDRKLKDLDRICRIPTNY------------IRHRSLIKKVNDMSFEMALSRVKELD---FCSFIYSN--PK-ADQIREDIFWGLMNYKHVDSL-GEYL | 166 |
| Parabacteroides goldsteinii CafM | YGVGFPDH-TLKNQKYAQILSPIDFFDNFYPDRT-------------VAQEKLRSGLKFCNFLYSN--PV-AHPYRDNLFYKLSEYKKVDAL-GRHL | 173 |
| Bacteroides fragilis CafB | ---SFDLWMGYHQEDDIVYPYY-----------GPDYGKMLVTARREKPYKKKACMFISSDMNR----SHRQEYLKELMQYTDIDS-YGKLY | 159 |
| Helicobacter hepaticus CafD | YAPPL-YCYGYKGRIFHYL------------------YAPFFAQSFAPKEAQDSHTPFAALLQEIESSPSPCCVHI | 155 |
| Consensus | YAIGFDY-L.FGDRYLR-.PLYL----YE----------ALRKHK----------VISD.KLL.KK.FCSFVVSN--.K-ADPYRERFFH.LSEYK.VDSG-GRYL | |
| Bacteroides nordii CafC | NN--VGGP-----VPD-KTAFIKDYKFHIAFENSMCDGYTTEKIMEPMLVNSVPIYWGNKLIDRDF------NPDSFINVSSYSSLEEAVEHIVRLDQNDDEYLSLLS--A-PWFN | 251 |
| Akkermansia muciniphila CafF | NNTPGDGHRAEDWYAS-SIRMKKPYKFSIAFENAWYPGYTSEKIVTSMLAGTIPIYWGNPDISREF------NSASFINCHDFPTLDDAAAYVKKVDEDDNLWCEIMS--R-PWKT | 268 |
| Helicobacter pylori FutA | NTLGY-------KVGN-KSEFLSQYKFNLCFENSQGVGVTVTEKILDAYFSHTIPIYWGSPSVAKDF------NPKSFVNVHDFNNFDEAIDYIKYLHTHPNAYIDMLY--ENPLNT | 316 |
| Tannerella sp. CafN | NN--VGGP-----VPN-KLDFIKDYKFNIAFENSMYDGYTTEKIMEPMLVNSLPIYWGNRLINKDF------NPASFINVSDFPSLEAAVEHIVMLDNNDDMVLSILS--K-PWFN | 251 |
| Bacteroides fragilis CafA | NN--IGGP-----VDN-KLDFISQYKFNIAFENSRVLGYTTEKIMEPMQVNSIPVYWGNPLVGKDF------NVDSFVNAHDFDSLERLVEYIIELDSSKDKYLEMLE--K-FWLL | 263 |
| Bacteroides salyersiae CafQ | NN--IGG----A-IKD-KKTFLSKYKFNIAFENCSHDGYATEKIVEAFAAGVPIYYGDPRIAEDF------NPKAFINAHDYQSFEEMVERIKEIDADDRLYLTMLN--E-PIIQ | 254 |
| Parabacteroides goldsteinii CafS | NN--MGKK-----VGD-KRQFLHEYKFTIAIENSSMPGVTVTEKILEPFMAQSLPLYWGSPTVSSDY------NPNSFVNLMNYSSMEEAVEEVIRLDKDDAAYLDKMM--T-PFWL | 252 |
| Clostridium bolteae CafT | NN--IGRP----EG-VRD-KFAFQSEHKFSLTFENSAHLGYTTEKLLQGFSAGTIPIYWGDPAVENCF------NPKAFTINISGNNVYDA--IELVKEVDTQDDLYFSMLR--E-PAFL | 257 |
| Methanobrevibacter ruminantium CafP | NN--IGGPIGMG-LDK-KFEFDVTHKFSPALENAQNRGYTTEKIFDAFAAGCIPIYWGDPNIEEEF------NPKSFINCMDLTV-IIAVEKIKEVDQNDELYHAMLN--E-PTFL | 258 |
| Lachnospiraceae bacterium CafO | NN--VGGP-----VAD-KVEFASHYRFSMAFENSAMSGYTTEKIFDGFAACTIPIYWGSDRIKEEF------NPESFVSARDFENFDQVVARVKEIYENDDLYLKMMK--A-PIAP | 256 |

TABLE 4-continued

Sequence alignments

| Organism/Protein | Sequence | Position |
|---|---|---|
| Lachnospiraceae bacterium CafR | NN--L--PDGKP-VPD-KKAFQENVRFSLCFENAGISGYATEKIVDAFAAGCIPIYYGDTNIEKDF------NPKSFIHVKSREDLDSVLAWVKELEENQNKYLEVIR--Q-PAIL | 258 |
| Butyrivibrio sp. CafL | NN--IGGP-----VDD-KREFQKQYKFSIAFENAVSRGYTTEKIIQAFSAGTIPIYYGNPLVAKEF------NSKAFINCHEYRSFDEVIEKVKELDNDPDLYDSMMR--E-PIFT | 247 |
| Helicobacter canis CafU | NN--IGGS-----VAD-KPAFQSECRFSLCFENSSTPGYLTEKLIQAAAAQTIPIYWGDTLATKPLFDGGGGINAKAFINAHSFSSLLESLIAHIAEIEADKTKQLAILQ--E-PLFL | 266 |
| Helicobacter canis CafV | NN--VGAR-----VKD-KPAFQSECRFSLCFENSSTPGYLTEKLIQAAAAQTIPIYWGDPLATKPLFDGGGGINAKAFINAHEFANIASLVRHIESIENDENKQLAILQ--E-PLFL | 271 |
| Butyrivibrio fibrosolvens CafK | NNSGVKTTRNDKHWRELSIEMKSHYKFSIAVENAQEGYISEKLLTSFQSHSVPIYWGDPLVVDEY------NPKAFINFNEMSSISELVNHVKEIDENDELWAEMVS--AD---W | 271 |
| Parabacteroides goldsteinii CafM | NNTGIGGTGFAGHARE-SVNCKENYKFSIASENCGFQGYTSEKILTSLQAHTVPIYWGDPDVD------LVVNPKCFINCNDFDTLDEVLQKVKEIDNNDDLWCEMVS--Q-PWFT | 279 |
| Bacteroides fragilis CafB | RNCELP--VEDRGRDTLLSVIGDYQFVISFENAIGKDYVTEKFFNPLLAGTVPVYLGAPNIRE------FAPGENCFLDICTFDSPEGVAAFMNQCYDDEALYERFYAWRKRPLLL | 267 |
| Helicobacter hepaticus CafD | RRGDLSQPHIVYGNPTSNEYFAKSIEL-MCLLHPQSSFYLFSDDLAFVKEQIVPLLKG-----KTYRICDVNNPSQGYLDLYLLSRCRNIIGSQGSMGE---FAKVLS-PHNPLLI | 261 |
| Consensus | NN--IGGP-----V.D-KF.FQSEVKFSIAFENS.YPGYTTEXIILEAFAAGTIPIYWGDPLI.KDF------NPKSFINAHDFSSLEEAVEH.KELDE.DDLYLEMLS--E-P.FL | |
| Bacteroides nordii CafC | EENYL-NWEEQ---LITFPDNIFEKPLSESRYIPT-HGYIQ------TY--QYRLHRMM------RDKLFRXRINPL--KWFSSK | 315 |
| Akkermansia muciniphila CafF | PEQEARFLEETERETAK--LYKIFDQSPEEARRKGDGTWV------SYYQRFLKRGHRMQLAWRRLKNRLRR | 332 |
| Helicobacter pylori FutA | LDGKAYFYQDLSFKKILDFFKTILEN--DTIYHKFSTSFMWEYDLHKPLVSIDDLRVNYDRLLQNASPLLELSQNTTFKIYRKAYQKSLPLLRAV---RKLVK-KLGL | 425 |
| Tannerella sp. CafN | DENYL-DWKAR---FFHFFDNIFNRPIDECKYLTP--YGFCR------HYRNQLRSARLL------KQR-FRQLRNPL--RWF--R--- | 314 |
| Bacteroides fragilis CafA | DKTYL-DWKQL---LLNFINNIMMKSYKDAKYLVN--YGHAG------KYRNEQRFWGRC------ERKPFKLQRIIEYYSQLFDRK---- | 331 |
| Bacteroides salyersiae CafQ | PNADVTELAD-------FLYSIFDQPLAKAKRRSQ--SQPTQ------AME-AMKLRHEFFEMKIY--KYYKKGMNQFTRLRKGVFLSSKRTK---- | 329 |
| Parabacteroides goldsteinii CafS | YGANPQEFRDSEIKKIKDFFSYIFEQPLDKAGRR---VCYGR------NRITIQKQRRYYAPT------FLELSKSMTKKLLKKK------ | 322 |
| Clostridium bolteae CafT | NNDYQTKLLEK---LDNFLVHIFNQPLECAYRRNS--FEHIS------NKS-VL--NEFV------KEDRGRFSQWISNKARCFYGKRKNK------ | 328 |

TABLE 4-continued

Sequence alignments

| Name | Sequence | # |
|---|---|---|
| Methanobrevibacter ruminantium CafP | --GDLDKYLQD-----FDDFLFNICNQPLEKAYRRDR--IMKGK---------TQEHQYKLINHRYYKPYFFLIKVAQKLHIEFIGRKIYHFI----RD---- | 335 |
| Lachnospirceae bacterium CafO | EGFQAHECLXEDY--ADAFLRNIFDQDIDKAKRRNM--VYVGR---------DYQKKLKDANKVIEV----LDVVKKPMHQFNKTKSQIASKFRKKK---- | 336 |
| Lachnospirceae bacterium CafR | PDSPIMGMLNNTY--IEEFLFHIFDQEPQEAIRRHSKLTMWGQ--------FYEYRLKKWNKI---------ENNMFLKKARSIKRKYFGLK-KIVK--- | 335 |
| Butyrivibrio sp. CafL | DIDERQDPLKD----YRKFIYNICSQESDKAIRRCD--DCWGG---------KIQREKKRCYRFL----------TSTEGNGLKARV-IRKLTEI---- | 316 |
| Helicobacter canis CafU | DSNKIELFEKQ----FEQFLSIVSQPYERSFRRGR--VMWQS--------FVEQRYK--RAMHLLALEDRIKAPYRKLRQFLRA---FWDSLKEK-RSHT | 347 |
| Helicobacter canis CafV | DSNHIELFEKQ----FEDFLVYIFSQPYERSFRRGK--IMWQA--------HLEQIIK--KGVQPTMLEIWLRRPLRNFERAIRIVKKIIQKVKKP-KDFM | 356 |
| Butyrivibrio fibrosolvens CafK | QTSEQVARVKKETEBYDLFIEHILSQSVSDAIRRPRGCWPYIYTNRFF----------------DEKWFLKSKAKRYIRKAIHC-FEEQ---- | 343 |
| Parabacteroides goldsteinii CafM | EKQLEERIQRN--KNYHKFMLSLLCKSIDSLTTRPNGTFQYVY--------RA---------WFLNASVRNDILYRLKRKMNFRRLRNFSLSQNRKN---- | 357 |
| Bacteroides fragilis CafB | S-------------FTNKLEQVRSNPLIRL--------------------------------CQKIHELKLGGI------------- | 296 |
| Helicobacter hepaticus CafD | TPRRNIFKEVENVMCVNWGESVQHPPLVCSAPPP------------------------LVSQLKRNAPLNSRLYEKDNASA--- | 320 |
| Consensus | DENYL-.FLKQ----FD.FL.NIFSQPLDKAKRP---MWG.-----------Y--LK--F--------------R.KQFLKLKA...K.KEK----- | |

Bacteroides nordii CafC (SEQ ID NO: 2)
Akkermansia muciniphila CafF (SEQ ID NO: 1)
Helicobacter pylori FutA (SEQ ID NO: 54)
Tannerella sp. CafN (SEQ ID NO: 9)
Bacteroides fragilis CafA (SEQ ID NO: 3)
Bacteroides Salyersiae CafQ (SEQ ID NO: 12)
Parabacteroides goisteinii CafS (SEQ ID NO: 14)
Clostridium bolteae CafT (SEQ ID NO: 15)
Methanobrevibacter ruminantium CafP (SEQ ID NO: 11)
Lachnospiraceae bacterium CafO (SEQ ID NO: 10)
Lachnospiraceae bacterium CafR (SEQ ID NO: 13)
Butyrivibrio sp. CafL (SEQ ID NO: 7)
Helicobacter Canis CafU (SEQ ID NO: 16)
Helicobacter Canis CafV (SEQ ID NO: 17)
Butyrivibrio fibrosolvens CafK (SEQ ID NO: 6)
Parabacteroides goldsteinii CafM (SEQ ID NO: 8)
Bacteroides fragilis CafB (SEQ ID NO: 4)
Helicobacter hepaticus CafD (SEQ ID NO: 53)
Consensus (SEQ ID NO: 61)

Based on the amino acid sequences of the identified α(1,3) fucosyltransferases (i.e., in Table 5), synthetic genes are designed and constructed by the skilled artisan using standard methods known in the art. For example, the synthetic genes include a ribosomal binding site, are codon-optimized for expression in a host bacterial production strain (i.e., *E. coli*), and have common 6-cutter restriction sites or sites recognized by endogenous restriction enzymes present in the host strain (i.e., EcoK restriction sites) removed to ease cloning and expression in the *E. coli* host strain. In a preferred embodiment, the synthetic genes are constructed with the following configuration: EcoRI site—T7g10 RBS—α(1,3) FT synthetic gene—XhoI site.

The nucleic acid sequences of sample synthetic genes for the 12 identified α(1,3) fucosyltransferases are shown in Table 6. Start and stop codons are underlined and bolded

TABLE 6

Nucleic acid sequences of 12 novel α(1,3) fucosyltransferase synthetic genes

| Gene Name | Sequence | SEQ ID NO |
|---|---|---|
| CafK | CAGTCAGTCAGAATTCAAGAAGGAGATATACATATGCGTCGTGTGTTTGCGATCCACC CATCTATTAAAGGCATCGTTGACCTGTCTAAATACCTGGGTTTCAAATCTTGCATCAC CGAAGAGATCATTTGGGATTCTAACGACCCGGAGTTCATTTTCGTCTCTGAGCGTATT TACACTGACATCAACGAATGGGAACTGTTTAAGAAAATGTACAACCCGCAACGTATCT TTATTTTTGTTTCCGGTGAATGCATGACCCCGGACCTGAACATTTTCGACTACGCTAT TGTGTTCGACCGCAAACTGAAAGACCTGGACCGTATTTGCCGCATCCCGACCAATTAC ATCCGTCACCGTAGCCTGATCAAAAAAGTGAACGACATGAGCTTCGAAAACGCGCTGT CCCGTGTTAAAGAACTGGACTTCTGCTCTTTTATCTACAGCAATCCGAAGGCGGACCA GATCCGCGAAGACATTTTCTGGGGTCTGATGAACTACAAACACGTTGATTCTCTGGGC GAATACCTGAACAACTCTGGTGTAAAAACTACCCGTAATGACAAACATTGGCGTGAGC TGTCTATCGAAATGAAAAGCCACTACAAATTCAGCATCGCTGTTGAAAACGCTCAATA CGAAGGCTACATTTCCGAAAAACTGCTGACTTCCTTCCAGAGCCATTCTGTCCCTATC TACTGGGGCGACCCGCTGGTAGTGGATGAATACAACCCGAAAGCGTTCATCAACTTCA ACGAAATGTCCTCTATCTCTGAACTGGTTAATCACGTCAAAGAAATTGACGAAAATGA CGAACTGTGGGCAGAAATGGTTTCCGCCGACTGGCAGACCTCCGAACAGGTAGCTCGC GTCAAAAAGGAAACTGAAGAATATGATCTGTTTATCGAACACATCCTGTCTCAGAGCG TTTCCGATGCTATTCGTCGCCCGCGTGGCTGTTGGCCGTACATTTACACGAACCGTTT TTTCGATGAAAAATGGTTTCTGAAGTCCAAAGCAAAGCGTTATATTCGTAAAGCCATC CACTGTTTCGAGGAACAATAGAGCTCGAGTGACTGACTG | 41 |
| CafL | AGTCAGTCAGAATTCAAGAAGGAGATATACATATGAAAGTTAAGTTTGTGGATAGCTT TTTTGCACGTGAACAGACGATGGGCGTCCTGAACGAACTGTTCGAAAACGTTGAGATT TCCGACGACCCGGATTTCGTGTTTTGCTCCGTAGATTACAAAGCAGAACACATGAACT ACGACTGTCCGCGTATCATGGTGATCGGTGAAAACATTGTTCCAGACTTTAACTGCAT CGATTACGCTGTTGGTTTCAACTATATGAACTTCGAGGATCGCTATCTGCGTGTTCCG CTGTATAACTTCTACCTGGACGATTATAAACTGGCAATTCGCCGTCATATCGATTACA AACGTGACGACAACAAAAAATTCTGCAACTTCGTTTACTCCAACGGTCGTAACGCCAT TCCTGAACGTGATTCTTTCTTTGCGGACCTGAGCAAGTACAAGCAAGTTGATAGCGGT GGTCGTCACCTGAACAATATCGGCGGTCCGGTTGATGATAAACGCGAGTTCCAGAAAC AGTACAAGTTCTCCATTGCCTTCGAAAATGCTGTTTCCCGTGGTTACACCACCGAGAA AATCATCCAGGCTTTCAGCGCTGGCACTATCCCGATTTACTATGGCAACCCGCTGGTA GCTAAAGAATTTAACAGCAAAGCGTTCATTAATTGCCACGAATATCGTAGCTTCGACG AAGTTATCGAAAAAGTAAAAGAACTGGATAACGACCCAGACCTGTATGATTCTATGAT GCGTGAACCGATCTTCACTGACATCGACGAGCGTCAGGACCCGCTGAAGGATTATCGT AAATTCATCTACAACATTTGCTCTCAGGAGTCTGATAAAGCCATTCGTCGTTGTGACG ATTGCTGGGGTGGTAAAATCCAGCGTGAAAAGAAACGTTGTTACCGCTTCCTGACCTC TACCGAGGGTAACGGTCTGAAAGCACGTGTTATCCGTAAACTGACCGAAATTTAGTAG CTCGAGTGACTGACTG | 42 |
| CafM | CAGTCAGTCAGAATTCAAGAAGGAGATATACATATGACCGTGACTATGGTACGCTCTC TGTATTTTGTCCACCCTAAGGTTCACAACGTCGAATCCTTCCTGAATTATGTTCACAT CTGTGAACTGCCGCAGGGCCTGTGCCTGGAATGGAACGACCGTAACCCTGAACTGCTG TTCGCTTCTGAGGTAATCTATTCTGATAAAAAGTCCAGCGAAACGTTTCGCCGCCTGT ACTGCGAGGCCAAAGTAGTTGTTTATTATGGTGGTGAAGCATCTTTTACTGATTTTAA TATCTTCGACTATGGTGTCGGCTTCGACCATACCCTGAAAAACCAGAAATACGCGCAG ATCCTGTCTCCGATTGATTTTTTCGACAACTTCTTCTACCCAGACCGCACGAATCTGA GCGAAGAAGTAGCACAAGAAAAGCTGCGTTCTGGTCTGAAATTCTGCAACTTCCTGTA CTCCAACCCGGTTGCCCATCCGTACCGTGACAATCTGTTCTACAAGCTGTCTGAATAC AAGAAAGTTGACGCGCTGGCCGTCACCTGAACAACACCGGCATCGGCGGCACTGGTT TCGCGGGCCACGCCCGTGAATCCGTGAACCTGAAGGAAAATTACAAATTTTCCATCGC GTCTGAAAACTGCGGTTTTCAGGGTTACACCTCTGAGAAAATCCTGACCTCCCTACAG GCCCACACTGTACCGATCTATTGGGGCGACCCGGACGTTGACCTGGTTGTAAATCCGA AATGCTTCATTAACTGTAACGACTTCGATACCCTGGATGAAGTACTACAGAAAGTGAA AGAGATTGACAACAACGACGATCTGTGGTGCGAAATGGTGTCTCAACCGTGGTTCACT GAAAAACAACTGGAAGAACGTATCCAGCGTAACAAAAACTATCATAAATTTATGCTGT CCCTGCTGTGTAAATCCATTGACAGCCTGACCACCCGTCCGAACGGCACGTTCCAGTA CGTATATCGTGCGTGGTTCCTGAACGCGAGCGTACGTAACGACATCCTGTACCGCCTG AAACGTAAAATGAACTTCCGCCGCCTGCGCAATTTTTCTCTGTCTCAAAACCGTAAAA ACTAGTAGCTCGAGTGACTGACTG | 43 |
| CafN | CAGTCAGTCAGAATTCAAGAAGGAGATATACATATGAAGACCATCAAGGTAAAATTCG TCGATTTCTGGAAAGGTTTCGACCCGCGCAACAACTTCCTGATGGACATCCTGAAACA GCGTTATCACATTGAACTGAGCGAAAGCCCGGACTACCTGATCTTCTCTGTCTTCGGT | 44 |

TABLE 6-continued

Nucleic acid sequences of 12 novel α(1,3) fucosyltransferase synthetic genes

| Gene Name | Sequence | SEQ ID NO |
|---|---|---|
| | TTCACTAACCTGAACTACGAACGCTGCGTTAAAATCTTCTACACCGGTGAAAACCTGA<br>CCCCGGATTTCAACATCTGCGACTACGCGATTGGTTTCGATTATCTGAGCTTCGGTGA<br>TCGTTACATGCGTCTGCCACTGTACGCGGTCTATGGCATCGAGAAACTGGCTTCTCCG<br>AAAGTTATCGACAAAGAAAAAGTTCTGAAGCGTAAATTCTGTTCTTACGTAGTAAGCA<br>ATAACATCGGCGCGCCGGAACGTTCTCGTTTCTTCCATCTGCTGTCTGAATACAAAAA<br>GGTTGACTCCGGTGGTCGTTGGGAAAACAACGTAGGCGGTCCGGTTCCGAATAAGCTG<br>GACTTTATCAAAGACTACAAGTTCAACATCGCATTCGAAAACTCCATGTACGACGGCT<br>ACACTACTGAAAAAATCATGGAACCGATGCTGGTGAACAGCCTGCCGATTTATTGGGG<br>CAACCGCCTGATCAACAAAGACTTCAACCCAGCGTCTTTCATCAACGTTTCCGATTTC<br>CCGTCTCTGGAAGCGGCGGTGGAGCACATTGTTATGCTGGACAATAACGATGATATGT<br>ACCTGAGCATCCTGTCTAAACCGTGGTTTAACGATGAAAACTACCTGGACTGGAAAGC<br>GCGCTTCTTCCACTTTTTCGATAACATCTTCAATCGTCCGATCGATAATGCAAATAT<br>CTGACCCCGTACGGCTTTGTCGTCACTATCGTAACCAACTGCGTAGCGCTCGTCTGC<br>TGAAACAGCGCTTTCGCCAGCTGCGTAACCCGCTGCGCTGGTTCCGTAGTAGCTCGA<br>GTGACTGACTG | |
| CafO | CAGTCAGTCAGAATTCAAGAAGGAGATATACATATGTCTAAAAAAAAAATCAAAATCA<br>ACTATATCGACTTTTGGCCGGGCTTCAAAAAGGAAGACAACTTCTTTTCCCGTATCCT<br>GGACAAATACTACGATGTGGAAATTTCTGACAACCCGGACTATGTCTTTTGCAGCTGC<br>TTCTCCCGCAAGCACTTCAAATATGCTGATTGCGTTAAAATCTTCTACACCGGTGAGA<br>ACATCATCCCTGATTTTAACCTGTATGACTACTCTATGGGTTTCCACTACATCGATTT<br>TGAAGATCGTTACCTGCGCCTGCCGCATTACGCGCTGTATGATCAGTGTATCAAGGCC<br>GCGAAAGAAAAGCACACCCACTCTGATGACTATTACCTGGCTAAAAAAAAATTCTGTA<br>ACTATGTTATTTCCAACCCGTACGCCGCCCGGAACGTGACCTGATGATCGATGCGCT<br>GGAGAAATACATGCCTGTTGATTCTGGCGGTCGTTATCGCAACAACGTCGGTGGTCCT<br>GTAGCAGATAAAGTAGAATTTGCGTCCCACTATCGCTTCTCTATGGCGTTCGAGAATA<br>GCGCGATGTCTGGTTACACCACTGAAAAAATCTTCGATGGTTTCGCCGCCTGTACCAT<br>CCCGATCTACTGGGGCTCTGATCGCATTAAAGAGGAGTTCAATCCGGAGAGCTTTGTA<br>AGCGCACGTGACTTCGAAAACTTCGATCAGGTGGTAGCGCGTGTCAAGGAAATCTACG<br>AAAATGATGACCTGTACCTGAAAATGATGAAAGCGCCGATCGCGCCGGAAGGTTTCCA<br>GGCCCACGAATGCCTGAAGGAGGATTATGCCGACGCGTTTCTGCGTAACATTTTTGAC<br>CAGGACATCGACAAAGCTAAGCGCCGTAACATGGTTTACGTCGGTCGTCGTGATTATCAGA<br>AAAAGCTGAAGGATGCTAACAAAGTGATTGAGGTTCTGGATGTGGTGAAGAAACCGAT<br>GCACCAGTTTAACAAAACTAAATCTCAGATCGCGTCTAAATTCCGTAAGAAAAAATAG<br>TAGCTCGAGTGACTGACTG | 45 |
| CafP | CAGTCAGTCAGAATTCAAGAAGGAGATATACATATGTCCGAAAAAAAAAAAATCAAAG<br>TTAAATTCGTAGATTTCCAGGACTCCCTGAAAGAAAACGACAACTTCTTTATTGACTC<br>TCTGAAAAAAACTTCGACGTTGAAGTTTCCGACGATCCGGACTATCTGTTTTTCGGT<br>GCTTATGGCTACAAACACCTGGACTACGATTGTATCCGTATTATGTGGACCATCGAAA<br>ACTATGTGCCGGATTTCAACATTTGCGACTATGCTCTGGCTTATGACATCATTGAGTT<br>CGGTGACCGTTACCTGCGCTTCCCGTTCTTCCTGAACCGTCCGGAAATCGAAAACGTG<br>CGTAAAACCATTGAACGTAAACCGATTGACACGTCCGTTAAAACGGACTTCTGTAGCT<br>TTGTTGTAAGCAACGAATGGGGCGACGACTACCGTATTCGCCTGTTCCACGAACTGTC<br>CAAATACAAAAAAGTGGACTCCGGCGGTCGTTCCCTGAACAACATTGGCGGTCCGATC<br>GGCATGGGCCTGGATAAAAAATTCGAGTTCGATGTTACCCACAAATTCTCCTTTGCCC<br>TGGAAAACGCGCAGAACCGCGGTTATACCACCGAAAAAATCTTCGATGCGTTCGCGGC<br>GGGTTGCATTCCGATCTATTGGGGTGATCCGAATATTGAGGAAGAGTTCAACCCGAAA<br>TCCTTCATCAACTGCAACGACCTGACCGTTGAGGAAGCCGTTGAGAAAATCAAAGAGG<br>TTGACCAGAACGATGAACTGTACCACGCGATGCTGAACGAACCGACTTTTCTGGGCGA<br>CCTGGACAAATATCTGCAAGACTTCGACGACTTCCTGTTCAACATTTGCAATCAGCCG<br>CTGGAAAAAGCGTATCGTCGTGACCGCATCATGAAAGGCAAGACTCAGGAACACCAGT<br>ACAAACTGATCAACCGTTTCTACTACAAGCCATATTTTTTCCTGATCAAAGTTGCTCA<br>AAAACTGCACATCGAGTTTATCGGTCGTAAGATTTACCATTTTATCCGTGATTAGTAG<br>CTCGAGTGACTGACTG | 46 |
| CafQ | CAGTCAGTCAGAATTCAAGAAGGAGATATACATATGAAAAAAGTTAAGATCAAATTTG<br>TAGACTTCTTCGATGGTTTCGACAAAGGCCGTAACGAGTTTCTGGAAGTTCTGAAACA<br>GCGCTATGAAATCGACATCTCTGATGAGCCTGATTATGTAATCTACAGCGGCTTCGGT<br>TACGAACACCTGAAATACAACTGCATCCGTATCTTCTTCACCGGTGAGTGCCAGACCC<br>CAGACTTCAACGAATGCGATTATGCAATCGGCTTTGATCGCTCGAAATTCGGTGACCG<br>CTATGTCCGTATTCCGCTGTATAATATGATGCAATATAAACTGGACTATAAAGAACTG<br>CTGAACCGTAAATCCATCATTTCCGACGATATTAAAGGTCGTGGCTTCTGCTCCTTTG<br>TAGTGTCTAACTGTTTCGCGAATGATACCCGTGCGATCTTCTACGAACTGCTGAATCA<br>GTATAAATATATCGCTAGCGGTGGCCGTTATAAAAACAATATCGGCGGTGCCATTAAA<br>GATAAGAAGACGTTCCTGAGCAAATACAAATTCAACATCGCGTTCGAAAACTGTTCTC<br>ATGATGGCTACGCCACCGAAAAAATCGTAGAGGCTTTTGCTGCCGGCGTAGTTCCGAT<br>CTACTATGGCGACCCACGTATCGCAGAAGATTTCAACCCGAAGGCATTTATTAATGCA<br>CACGATTATCAGAGCTTCGAAGAAATGGTGGAACGCATCAAAGAGATCGATGCCGATG<br>ACCGTCTGTACCTGACCATGCTGAACGAACCGATCATTCAGCCGAACGCAGACGTGAC<br>TGAACTGCGGATTTCCTGTATAGCATCTTCGACCAGCCGCTGGCCAAGGCCAAACGC<br>CGTTCCCAGTCCCAGCCGACTCAGGCTATGGAGGCAATGAAACTGCGCCACGAGTTCT<br>TCGAAATGAAAATCTACAAATATTATAAAAAAGGTATGAACCAGTTCACGCGTCTGCG<br>CAAGGGCGTGTTCCTAAGCTCTAAACGTACCAAATAGTAGCTCGAGTGACTGACTG | 47 |

TABLE 6-continued

Nucleic acid sequences of 12 novel α(1,3) fucosyltransferase synthetic genes

| Gene Name | Sequence | SEQ ID NO |
|---|---|---|
| CafR | CAGTCAGTCAGAATTCAAGAAGGAGATATACATATGAAAAAGGAAATCAAAATCGCGT<br>ACGTGGATTTCTGGAACGGCTTCAAGCCTGACTCCTTCTTCATCACCAAGACCATCAG<br>CAAAAAATACAAGGTTATCATCGACAATGAAAACCCGGATTTCGTAATCTGTGGTACC<br>TTCGGTAATACCTTCCTGTCCTATGACTGCCCGCGTATCCTGTATACCGGTGAAGCTA<br>ACTGCCCGGATTTTAATATCTACGACTATGCAATTGGTTTCGAACGCATGGTTTACGA<br>AGACCGCTATCTGCGCTACCCGCTGTTCCTGGTGAACGAAGACCTGCTACAGGATGCG<br>CTGAACAAACACAAAAAATCTGATGACTACTATCTGCGTCGTGATGGCTTCTGTAGCT<br>TCGTGGTGTCCGCGTCTGGCGGTATGGACGGTCTGCGTAACTGGTATTTTGATAAAAT<br>CAGCGAATATAAGCAGGTAGCTTCCGGTGGCCGTTTTCGCAACAACCTGCCGGACGGC<br>AAACCAGTTCCAGATAAAAAGGCATTCCAGGAAAACTACCGCTTCTCCCTGTGCTTCG<br>AGAACGCTGGCATCAGCGGCTATGCTACCGAAAAAATTGTTGACGCATTCGCGGCTGG<br>TTGCATCCCGATCTACTACGGTGACACCAACATCGAAAAAGACTTCAACCCGAAATCC<br>TTTATTCACGTGAAATCTCGTGAAGACCTGGACTCCGTTCTGGCTTGGGTGAAGGAGC<br>TGGAAGAAAACCAGAACAAATATCTGGAGGTGATCCGTCAACCTGCAATCCTGCCTGA<br>CAGCCCGATCATGGGTATGCTGAACAACACGTACATCGAAGAGTTCCTGTTCCATATC<br>TTCGACCAGGAACCTCAGGAGGCAATCCGTCGTCACAGCAAACTGACTATGTGGGGCC<br>AGTTCTATGAATACCGTCTGAAAAAATGGAACAAGATCGAGAACAACATGTTTCTGAA<br>GAAAGCACGTAGCATTAAACGTAAATACTTTGGCCTGAAAAAAATCGTTAAATAGTAG<br>CTCGAGTGACTGACTG | 48 |
| CafS | CAGTCAGTCAGAATTCAAGAAGGAGATATACATATGAAGAAAAAAATCTACTGCAACT<br>TCGTGGACTTTTGGCTGGGTTTTAACTATAAAACCTACTTCTGGTATCTGTCCGACGA<br>GTACGATCTACAGATCGACAAAGAACATCCAGATTACCTGTTTTACTCCTGCTTCGGT<br>AACGAACATCTGTTCTACGAAGACTGCATTCGCATTTTCTGGTCTGACGAGAACATCA<br>TGCCGGACCTGAACATTTGCGACTACGCTCTGTCTCTGAGCAACCTACAGTGCGACGA<br>CCGTACCTTCCGCAAGTACTCCGGTTTCCTGTACCGTAAGGATTCTCATCTGGTTCTG<br>CCGGTACTGAAAGAAGAAGCGCTGCTGAATCGTAAATTTTGCAACTTCGTATACTCTA<br>ACAACACCTGTGCTGTTCCGTACCGTGAACTGTTCTTTAAAGCGCTGTCTGGCTACAA<br>ACGTATCGATTCTGGTGGTGCGTTTCTGAATAACATGGGTAAAAAAGTTGGCGATAAG<br>CGCCAGTTTCTGCACGAATACAAATTTACTCTGGCTATCGAAAATTCCTCTATGCCGG<br>GTTACGTGACCGAAAAAATCCTGGAGCCTTTTATGGCTCAGAGCCTGCCACTGTACTG<br>GGGTTCTCCGACTGTTTCCTCTGACTATAACCCTAACTCCTTCGTAAATCTGATGAAC<br>TACTCCTCTATGGAAGAAGCGGTAGAAGAAGTGATTCGCCTGGACAAAGACGACGCTG<br>CGTATCTGGACAAAATGATGACGCCTTTCTGGCTGTACGGTGCAAACTTCCAAGAGTT<br>CCGTGACTCCGAGATTAAAAAAATTAAAGATTTCTTCTTATATCTTCGAACAGCCG<br>CTGGACAAAGCGGGCCGTCGCGTTTGTTACGGTCGTAATCGTATCACCATCCAAAAAC<br>AGCGTCGTTACTACGCCCCGACTTTTCTGGAACTGTCTAAATCTATGACTAAGAAACT<br>GCTGAAGAAAAAATAGTAGCTCGAGTGACTGACTG | 49 |
| CafT | CAGTCAGTCAGAATTCAAGAAGGAGATATACATATGAAAAAAATCCGTCTGAAATACG<br>TTGATTGGTGGGATGGTTTCCAGCCGGAACAATATCGCTTTCATCAGATCCTGACTAA<br>ACATTTCGACATCGAAATTAGCGATGAACCGGATTACATTATCGCTAGCGTGTACTCT<br>GACGAAGCAAAAAGCTACAACTGTGTTCGCATCCTGTATACCGGTGAGAACATCTGCC<br>CGGATTTCAACATCTATGACTATGCTATCGGCTTCGAATACCTGGAGTTCGGTGATCG<br>CTATATCCGTATCCCGAACTTTATCATGAACCCGGCTTACGACATCGACATCCAGAAA<br>GCGCTGTCTAAGCATCTGCTGTCTGCTGATGATATCAAACGCGAAAAAAAATTCTGCT<br>CCTTCGTCGTTTCTAACGGCAACGCAGCGCCAATCCGTGAAGAAGATGTTCGAAGAACT<br>GAATAAATATAAGCGTGTGGACTCCGGCGGTCGCTACCTGAACAACATCGGTCGTCCA<br>GAAGGCGTTCGTGACAAATTCGCTTTCCAATCTGAACAAGTTTTCTCTGACCTTCG<br>AGAACTCCGCGCACCTGGGTTACACTACGGAAAAACTGCTACAGGGCTTCTCTGCGGG<br>CACGATTCCGATCTACTGGGGTGACCCGGCGGTGGAAAACTGCTTCAACCCGAAAGCG<br>TTCATCAACATTTCCGGCAACAACGTTTACGACGCAATCGAACTGGTTAAAGAAGTTG<br>ATACTCAGGACGACCTGTACTTTAGCATGTTGCGTGAACCGGCTTTTCTGAACAACGA<br>TTACCAAACTAAACTGCTGGAGAAGCTGGATAACTTCCTGGTACACATCTTTAATCAG<br>CCGCTGGAGTGCGCCTACCGTCGTAACAGCTTTGAGCATATCAGCAACAAATCTGTTC<br>TGAATGAGTTCGTGAAAGAAGATCGTGGCCGTTTCTCCCAGTGGATCTCCAACAAGGC<br>GCGTTGTTTCTATGGCAAACGTAAAAACAAGTAGTAGCTCGAGTGACTGACTG | 50 |
| CafU | CAGTCAGTCAGAATTCAAGAAGGAGATATACATATGAGCAAAGAAAGTGGAAACAGG<br>AAAAACGCGTTCATTTCGTAGATTGTTGCGACGACGGTATCCGTGACAAGTTTGCC<br>GATCCTGGAACAACACTTTACTCTGATCTTCGACTCTGTAAACCCGGAATACGTGTTC<br>TATTCTGCCTACGGTGAAGAACATCTGGCTTACGACTGCATCCGCATTTTTATCACTG<br>GCGAAAACATCACCCCGAACTTCACGATTTGCGACTACGCTATCGGTTTCGACCACCT<br>GCACTTTCTGGATCGTTACCTGCGCTACCCACTGTACCTGTTCTACGAACAGGATGTG<br>AAACGCGCATCCCAGAAACACAAAGATATCGACGAAAAGCTGCTGGCTTCTAAATCCC<br>GTTTTTGCAACTTTGTGGTGAGCAACGGCAACGCTGATCCGTACCGCGAACAGGTATT<br>CTACGCGCTGAACGCCTACAAGCGTGTGGACAGCGGTGGTCGTTATCTGAACAACATT<br>GGTGGTAGCGTGGCCGATAAATTCGCTTTCCAGTCTGAATGTCGTTTTAGCCTGTGCT<br>TCGAAAACAGCTCTACGCGGGTTACCTGACCGAGAAACTGATTCAGGCGGCGGCTGC<br>TCAAACCATCCCAATTTATTGGGGCGACACTCTGGCGACTAAACCGCTGTTCGATGGC<br>GGTGGCGGTATCAACGCCAAGGCATTCATCAACGCGCACTCCTTCTCTTCTCTGGAAT<br>CTCTGATTGCTCACATCGCCGAGATTGAAGCGGATAAGACGAAACAGCTGGCCATTCT<br>ACAGGAACCACTGTTCCTGGACTCTAATCACATCGAGCTGTTCGAAAAACAGTTCGAA | 51 |

TABLE 6-continued

Nucleic acid sequences of 12 novel α(1,3) fucosyltransferase synthetic genes

| Gene Name | Sequence | SEQ ID NO |
|---|---|---|
| | CAATTTCTGCTGAGCATTGTGAGCCAGCCGTATGAACGTTCTTTCCGTCGTGGTCGTG<br>TTATGTGGCAGTCTTTTGTTGAACAGCGCTACAAACGCGCCATGCATCTGCTGGCTCT<br>GGAAGACCGCATCAAAGCTCCGTACCGTAAGCTGCGTCAGTTCCTGCGCGCGTTCTGG<br>GACTCCCTGAAAGAAAAACGTTCCCACACTTAGTAGCTCGAGTGACTGACTG | |
| CafV | CAGTCAGTCAGAATTCAAGAAGGAGATATACATATGGGTGACGAAGTTGCTATGGGTA<br>AAGAGCGCAAGCAGATTCGCGTTCACTTCGTAGACTTCTCCAACATGGATAACATTAT<br>TGAAAAAATTTGCTCTATTCTGTCCCGTCATTTCGCAGTTATCATTGACGGTGAAAAC<br>CCGGAGTATGTATTCTACTCTGCTTTCGGTAGCGAATATCTGAAGTACGATTGTGTTC<br>GTATCTTCTACACTGGCGAAAACATTGTACCGGATTTTAACCTGTGCGATTACGCTAT<br>CGGTTTCGATCACATCAAGTTCCTGGACCGTTACCTGCGCTACCCTCTGTATCTGTTT<br>TATGAAACCGATGTACAGAAAGCGGCTCGTAAACACCAGAACCTGTCTCTGGAAGTTG<br>TCCGCAACAAAAAACGTTTTTGCAATTTCGTAGTTACCAACGGCAAAGGTGACCCGTA<br>TCGTGAAAAAGTTTTTCATGCTCTGTGCGCTTACAAACGTGTAGATAGCGCTGGTAAG<br>TTTCTGAACAACGTTGGTGCACGCGTTAAAGATAAATTTGCGTTCCAGAGCGAATGCC<br>GTTTTTCCCTGTGCTTCGAGAACTCTAGCACCCCTGGTTATCTGACCGAAAAACTGAT<br>CCAGGCAGCGGCTGCGCAAACTATCCCGATCTATTGGGCGACCCGCTGGCGACCAAG<br>CCGCTGTTTGATGGTGGCGGCGGTATCAACGCGAAAGCGTTCATCAACGCTCACGAGT<br>TCGCCAACATCGCGTCCCTGGTGCGCCATATTGAGAGCATCGAAAACGACGAAAACAA<br>ACAGCTGGCTATCCTGCAAGAACCGCTGTTTCTGGATTCCAATCATATTGAACTGTTC<br>GAAAAACAGTTCGAGGATTTCCTGGTGTATATCTTTTCTCAGCCTTACGAGCGTAGCT<br>TCCGTCGCGGTAAAATCATGTGGCAGGCGCATCTGGAACAGATCATCAAAAAAGGTGT<br>TCAGCCGACCATGCTGGAAATTTGGCTGCGTCGTCCACTGCGCAACTTCGAGCGCGCG<br>ATCCGCATCCGTGTGAAAAAAATTATTCAGAAAGTGAAAAAACCGAAAGATTTCATGT<br>AGTAGCTCGAGTGACTGACTG | 52 |

In any of the methods described herein, the α(1,3) fucosyltransferase genes or gene products may be variants or functional fragments thereof. A variant of any of genes or gene products disclosed herein may have 50%, 55%, 60%, 65%, 70%, 75%, 80%, 85%, 90%, 95%, 96%, 97%, 98%, or 99% sequence identity to the nucleic acid or amino acid sequences described herein.

Variants as disclosed herein also include homolog, orthologs, or paralogs of the genes or gene products described herein that retain the same biological function as the genes or gene products specified herein. These variants can be used interchangeably with the genes recited in these methods. Such variants may demonstrate a percentage of homology or identity, for example, 50%, 55%, 60%, 65%, 70%, 75%, 80%, 85%, 90%, 95%, 96%, 97%, 98%, or 99% identity conserved domains important for biological function, preferably in a functional domain, e.g. catalytic domain.

The term "% identity," in the context of two or more nucleic acid or polypeptide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection. For example, % identity is relative to the entire length of the coding regions of the sequences being compared, or the length of a particular fragment or functional domain thereof.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Percent identity is determined using search algorithms such as BLAST and PSI-BLAST (Altschul et al., 1990, J Mol Biol 215:3, 403-410; Altschul et al., 1997, Nucleic Acids Res 25:17, 3389-402). For the PSI-BLAST search, the following exemplary parameters are employed: (1) Expect threshold was 10; (2) Gap cost was Existence:11 and Extension:1;

(3) The Matrix employed was BLOSUM62; (4) The filter for low complexity regions was "on".

Figure 18:
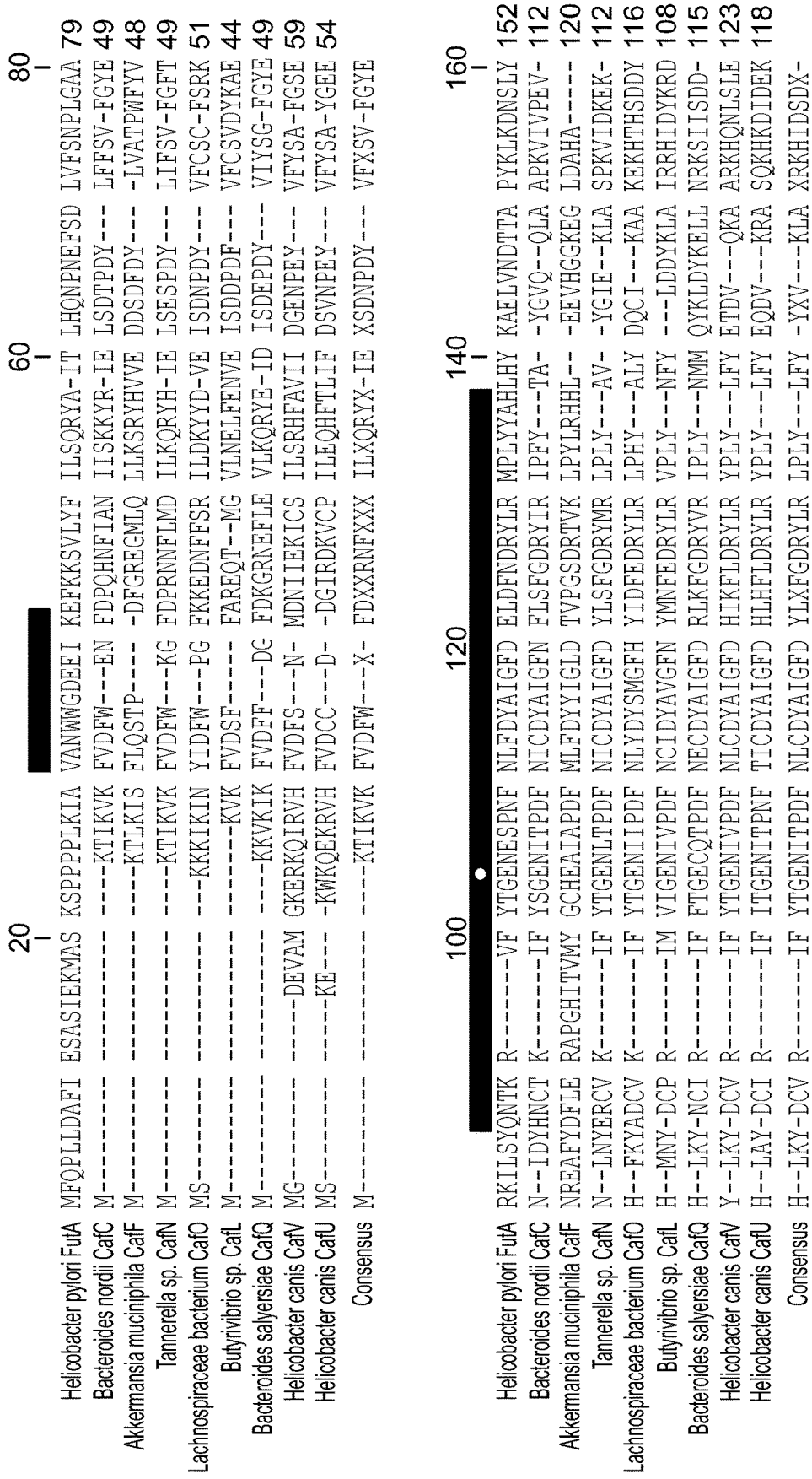
FIG. 18 is a sequence alignment of FutA (SEQ ID NO: 54) with 8 lactose-utilizing "Caf" α(1,3) fucosyltransferases (i.e. CafF (SEQ ID NO: 1), CafC (SEQ ID NO: 2), CafV (SEQ ID NO: 17), CafN (SEQ ID NO: 9), CafL (SEQ ID NO: 7), CafO (SEQ ID NO: 10), CafQ (SEQ ID NO: 12), and CafU (SEQ ID NO: 16)) discovered in the computational screens of this invention. Conserved regions important for substrate binding and catalysis are delineated by thick bars above the sequences. Within those bars the white dots indicate the four completely conserved residues at the catalytic active site. Consensus sequences is SEQ ID NO: 62.
Figure 18:
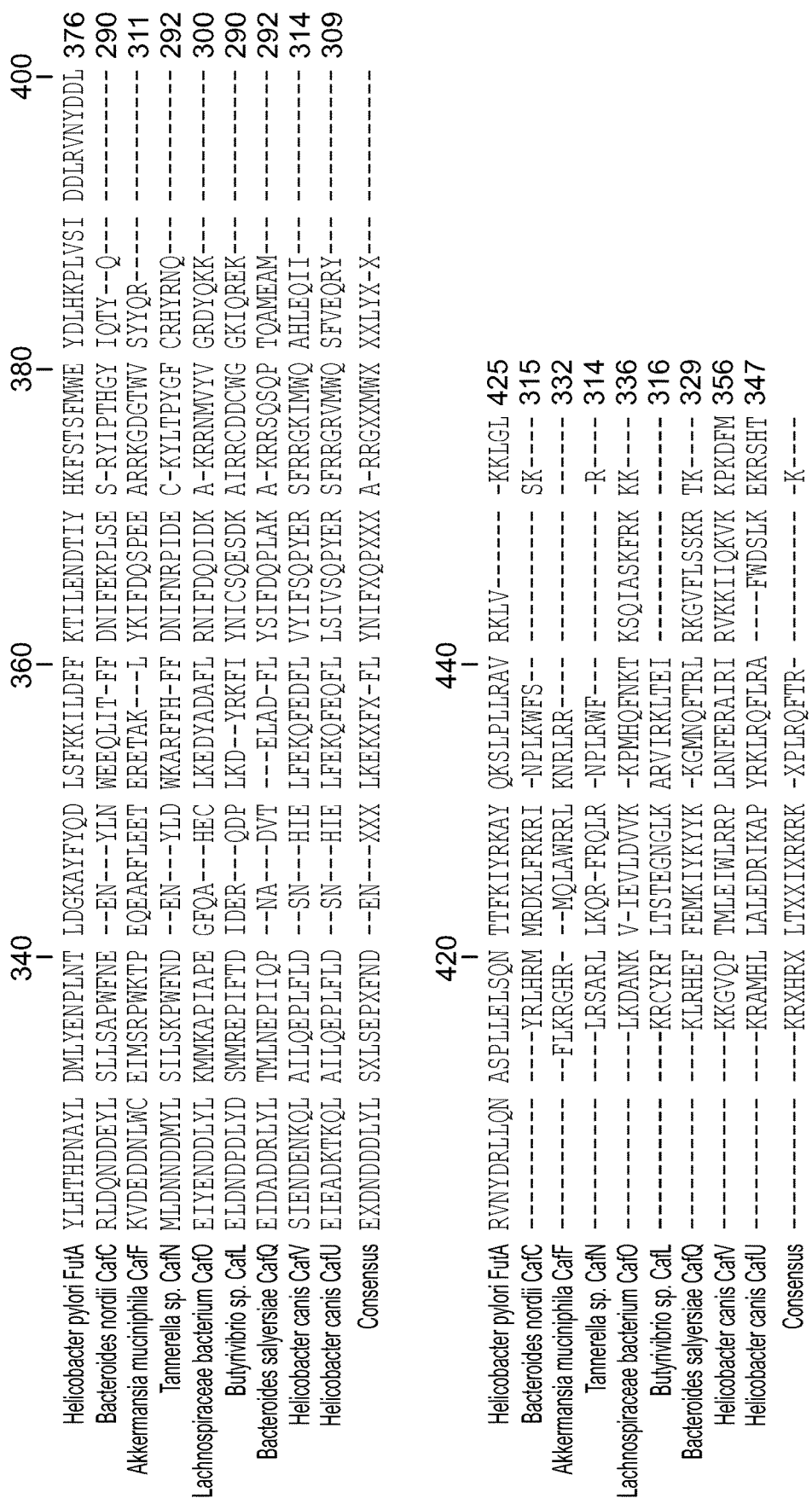

The three dimensional structure of the lactose-utilizing α(1,3) fucosyltransferase *Helicobacter pylori* FutA (FucT) is described in H. Y. Sun, S. W. Lin, T. P. Ko, J. F. Pan, et al., *J Biol Chem* 282, 9973-82 (2007). Here the amino acid residues essential for the substrate binding and the catalytic mechanism of the enzyme are discussed—in particular the sequences lying between FutA residues 31-42 (substrate binding), 85-129 (active site region 1) and 180-266 (active site region 2), with specific amino acid residues E96, R196, E250 and K251 are involved in catalysis. FIG. 18 is a sequence alignment of FutA with 8 lactose-utilizing "Caf" α(1,3) fucosyltransferases (i.e. CafF, CafC, CafV, CafN, CafL, CafO, CafQ, and CafU) discovered in the computational screens of this invention. It can readily be seen that the FutA regions known to be involved in substrate binding are well conserved in all 8 novel sequences. Moreover each of the 4 residues known to be involved at the catalytic site is completely conserved across all 8 enzymes.

Changes are introduced by mutation into the nucleic acid sequence or amino acid sequence of any of the genes or gene products described herein, leading to changes in the amino acid sequence of the encoded protein or enzyme, without altering the functional ability of the protein or enzyme. For example, nucleotide substitutions leading to amino acid substitutions at "non-essential" amino acid residues can be made in the sequence of any of sequences expressly disclosed herein. A "non-essential" amino acid residue is a residue at a position in the sequence that can be altered from the wild-type sequence of the polypeptide without altering the biological activity, whereas an "essential" amino acid residue is a residue at a position that is required for biological activity. For example, amino acid residues that are conserved among members of a family of proteins are not likely to be amenable to mutation. Other amino acid residues, however, (e.g., those that are poorly conserved among members of the protein family) may not be as essential for activity and thus are more likely to be amenable to alteration. Thus, another aspect of the invention pertains to nucleic acid molecules encoding the proteins or enzymes disclosed herein that contain changes in amino acid residues relative to the amino acid sequences disclosed herein that are not essential for activity (i.e., fucosyltransferase activity). Preferably, at least 0.1% of the activity of the reference enzyme is retained. In some embodiments, low α1,3 fucosyltransferase activity enzymes may be used in the production of large quantities of 3FL. For example, CafC is expressed very well in E. coli, leading to the easy generation of a vast excess of α1,3 fucosyltransferase enzymatic activity over that required for the production of large amounts of 3FL. Thus even variants of CafC enzyme with a relatively low level (e.g., 0.1, 1, 10%) of activity relative to the wildtype CafC enzyme, may produce useful levels of the product, 3FL.

An isolated nucleic acid molecule encoding a protein essentially retaining the functional capability compared to any of the genes described herein can be created by introducing one or more nucleotide substitutions, additions or deletions into the corresponding nucleotide sequence, such that one or more amino acid substitutions, additions or deletions are introduced into the encoded protein.

Mutations are introduced into a nucleic acid sequence by standard techniques such that the encoded amino acid sequence is altered, such as site-directed mutagenesis and PCR-mediated mutagenesis. Preferably, conservative amino acid substitutions are made at one or more predicted nonessential amino acid residues. A "conservative amino acid substitution" is one in which the amino acid residue is replaced with an amino acid residue having a similar side chain. Families of amino acid residues having similar side chains have been defined in the art. Certain amino acids have side chains with more than one classifiable characteristic. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, tryptophan, cysteine), nonpolar side chains (e.g., alanine, valine, leucine, isoleucine, proline, phenylalanine, methionine, tyrosine, tryptophan), beta-branched side chains (e.g., threonine, valine, isoleucine) and aromatic side chains (e.g., tyrosine, phenylalanine, tryptophan, histidine). Thus, a predicted nonessential amino acid residue in a given polypeptide is replaced with another amino acid residue from the same side chain family. Alternatively, in another embodiment, mutations can be introduced randomly along all or part of a given coding sequence, such as by saturation mutagenesis, and the resultant mutants can be screened for given polypeptide biological activity to identify mutants that retain activity. Conversely, the invention also provides for variants with mutations that enhance or increase the endogenous biological activity. Following mutagenesis of the nucleic acid sequence, the encoded protein can be expressed by any recombinant technology known in the art and the activity of the protein can be determined. An increase, decrease, or elimination of a given biological activity of the variants disclosed herein can be readily measured by the ordinary person skilled in the art, i.e., by measuring the capability for mediating oligosaccharide modification, synthesis, or degradation (via detection of the products).

The present invention includes functional fragments of the genes or gene products described herein, e.g., catalytic domain portions of the enzyme shown in FIGS. 18 and 19. A fragment, in the case of these sequences and all others provided herein, is defined as a part of the whole that is less than the whole. Moreover, a fragment ranges in size from a single nucleotide or amino acid within a polynucleotide or polypeptide sequence to one fewer nucleotide or amino acid than the entire polynucleotide or polypeptide sequence. Finally, a fragment is defined as any portion of a complete polynucleotide or polypeptide sequence that is intermediate between the extremes defined above.

For example, fragments of any of the proteins or enzymes disclosed herein or encoded by any of the genes disclosed herein can be 10 to 20 amino acids, 10 to 30 amino acids, 10 to 40 amino acids, 10 to 50 amino acids, 10 to 60 amino acids, 10 to 70 amino acids, 10 to 80 amino acids, 10 to 90 amino acids, 10 to 100 amino acids, 50 to 100 amino acids, 75 to 125 amino acids, 100 to 150 amino acids, 150 to 200 amino acids, 200 to 250 amino acids, 250 to 300 amino acids, 300 to 350 amino acids, 350 to 400 amino acids, 400 to 450 amino acids, or 450 to 500 amino acids. The fragments encompassed in the present invention comprise fragments that retain functional fragments. As such, the fragments preferably retain the catalytic domains that are required or are important for functional activity. Fragments can be determined or generated by using the sequence information herein, and the fragments can be tested for functional activity using standard methods known in the art. For example, the encoded protein can be expressed by any recombinant technology known in the art and the activity of the protein can be determined. The biological function of said fragment can be measured by measuring ability to synthesize or modify a substrate oligosaccharide, or conversely, to catabolize an oligosaccharide substrate.

Within the context of the invention, "functionally equivalent", as used herein, refers to a gene or the resulting encoded protein variant or fragment thereof capable of exhibiting a substantially similar activity as the wild-type fucosyltransferase. Specifically, the fucosyltransferase activity refers to the ability to transfer a fucose sugar to an acceptor substrate via an alpha-(1,3)-linkage. As used herein, "substantially similar activity" refers to an activity level within 5%, 10%, 20%, 30%, 40%, or 50% of the wild-type fucosyltransferase.

To test for lactose-utilizing fucosyltransferase activity, the production of α(1,3) fucosylated oligosaccharides is evaluated in a host organism that expresses a candidate enzyme synthetic gene and which contains both cytoplasmic GDP-fucose and lactose pools. The production of fucosylated oligosaccharides indicates that the candidate enzyme-encoding sequence functions as a lactose-utilizing α(1,3)fucosyltransferase.

The invention also provides nucleic acid constructs (i.e., a plasmid or vector) carrying the nucleic acid sequence of a novel α(1,3) fucosyltransferases for the expression of the novel α(1,3) fucosyltransferases in host bacterium.

The invention also provides methods for producing fucosylated oligosaccharides by expressing the novel α(1,3) fucosyltransferases in suitable host production bacterium, as further described herein.

Engineering of E. coli to Produce α(1,3) Fucosylated Human Milk Oligosaccharide

Described herein is a gene screening approach, which was used to validate the novel α(1,3) fucosyltransferases (α(1,3)

FTs) for the synthesis of fucosyl-linked oligosaccharides in metabolically engineered *E. coli*. Of particular interest are α(1,3) FTs that are capable of the synthesis of the HMOS 3-fucosyllactose (3-FL), lactodifucotetraose (LDFT), or lacto-N-fucopentaose III (LNF III). Of most interest are α(1,3) FTs that catalyze the synthesis of 3-FL. Preferably, the α(1,3) fucosyl-linked oligosaccharides are expressed in metabolically engineered *E. coli*.

In particular, therefore, the invention provides α(1,3) FTs that are capable of the synthesis of the HMO (human milk oligosaccharide) 3-fucosyllactose (3FL). As explained above, 3FL is one of the most abundant fucosylated oligosaccharide present in human milk, and is thought to function with other HMOS to promote the growth of beneficial commensal bacteria in the infant gut.

Production Host Strains

A suitable production host strain is one that is not the same bacterial strain as the source bacterial strain from which the fucosyltransferase-encoding nucleic acid sequence was identified.

*E. coli* K-12 is a well-studied bacterium which has been the subject of extensive research in microbial physiology and genetics and commercially exploited for a variety of industrial uses. The natural habitat of the parent species, *E. coli*, is the large bowel of mammals. *E. coli* K-12 has a history of safe use, and its derivatives are used in a large number of industrial applications, including the production of chemicals and drugs for human administration and consumption. *E. coli* K-12 was originally isolated from a convalescent diphtheria patient in 1922. Because it lacks virulence characteristics, grows readily on common laboratory media, and has been used extensively for microbial physiology and genetics research, it has become the standard bacteriological strain used in microbiological research, teaching, and production of products for industry and medicine. *E. coli* K-12 is now considered an enfeebled organism as a result of being maintained in the laboratory environment for over 70 years. As a result, K-12 strains are unable to colonize the intestines of humans and other animals under normal conditions. Additional information on this well-known strain is available at http://epa.gov/oppt/biotech/pubs/fra/fra004.htm. In addition to *E. coli* K-12, other bacterial strains are used as production host strains, e.g., a variety of bacterial species may be used in the oligosaccharide biosynthesis methods, e.g., *Erwinia herbicola (Pantoea agglomerans), Citrobacter freundii, Pantoea citrea, Pectobacterium carotovorum,* or *Xanthomonas campestris*. Bacteria of the genus *Bacillus* may also be used, including *Bacillus subtilis, Bacillus licheniformis, Bacillus coagulans, Bacillus thermophilus, Bacillus laterosporus, Bacillus megaterium, Bacillus mycoides, Bacillus pumilus, Bacillus lentus, Bacillus cereus,* and *Bacillus circulans*. Similarly, bacteria of the genera *Lactobacillus* and *Lactococcus* may be modified using the methods of this invention, including but not limited to *Lactobacillus acidophilus, Lactobacillus salivarius, Lactobacillus plantarum, Lactobacillus helveticus, Lactobacillus delbrueckii, Lactobacillus rhamnosus, Lactobacillus bulgaricus, Lactobacillus crispatus, Lactobacillus gasseri, Lactobacillus casei, Lactobacillus reuteri, Lactobacillus jensenii,* and *Lactococcus lactis. Streptococcus thermophiles* and *Proprionibacterium freudenreichii* are also suitable bacterial species for the invention described herein. Also included as part of this invention are strains, modified as described here, from the genera *Enterococcus* (e.g., *Enterococcus faecium* and *Enterococcus thermophiles*), *Bifidobacterium* (e.g., *Bifidobacterium longum, Bifidobacterium infantis,* and *Bifidobacterium bifidum*), *Sporo-lactobacillus* spp., *Micromomospora* spp., *Micrococcus* spp., *Rhodococcus* spp., and *Pseudomonas* (e.g., *Pseudomonas fluorescens* and *Pseudomonas aeruginosa*).

Suitable host strains are amenable to genetic manipulation, e.g., they maintain expression constructs, accumulate precursors of the desired end product, e.g., they maintain pools of lactose and GDP-fucose, and accumulate end product, e.g., 3FL. Such strains grow well on defined minimal media that contains simple salts and generally a single carbon source.

Figure 2:
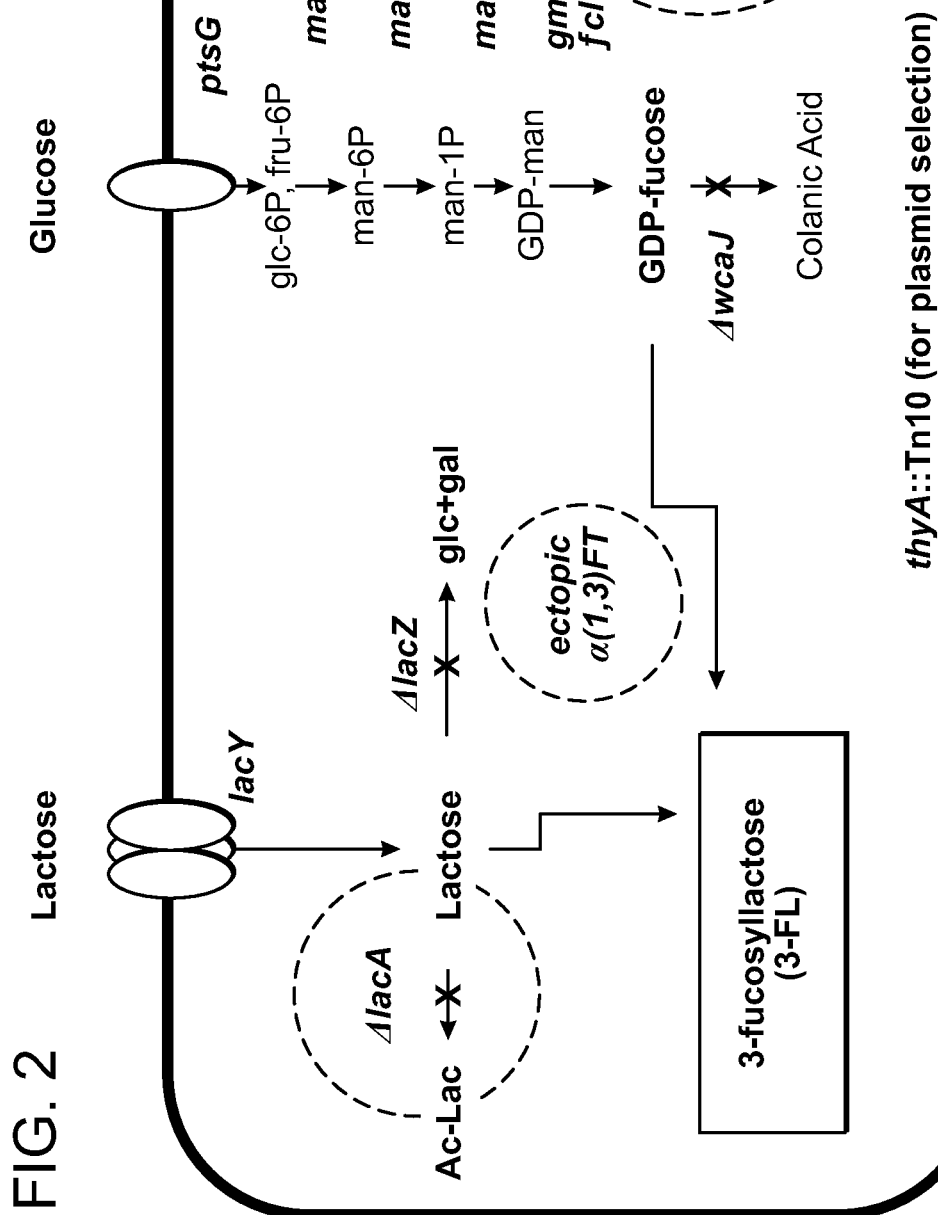
FIG. 2 is a schematic demonstrating metabolic pathways and the changes introduced into them to engineer 3-fucosyllactose (3-FL) synthesis in *Escherichia coli* (*E. coli*). Specifically, the lactose synthesis pathway and the GDP-fucose synthesis pathway are illustrated. In the GDP-fucose synthesis pathway: manA=phosphomannose isomerase (PMI), manB=phosphomannomutase (PMM), manC=mannose-1-phosphate guanylyltransferase (GMP), gmd=GDP-mannose-4,6-dehydratase, fcl=GDP-fucose synthase (GFS), and AwcaJ=mutated UDP-glucose lipid carrier transferase.

Biosynthesis of 3FL requires the generation of an enhanced cellular pool of both lactose and GDP-fucose (FIG. 2). Therefore, the host strain preferably has an enhanced cellular pool of lactose and/or GDP-fucose, preferably both lactose and gdp-fucose.

In the Examples provided herein, the wild-type *Escherichia coli* K-12 prototrophic strain W3110 was selected as the parent background host to test the ability of the candidates to catalyze 3FL production (Bachmann, 1972). The particular W3110 derivative employed was one that previously had been modified by the introduction (at the ampC locus) of a tryptophan-inducible $P_{trpB}$ CI+ repressor cassette, generating an *E. coli* strain known as GI724 (LaVallie et al., 2000). Other features of GI724 include lacIq and lacPL8 promoter mutations. *E. coli* strain GI724 affords economical production of recombinant proteins from the phage X $P_L$ promoter following induction with low levels of exogenous tryptophan (LaVallie et al., 1993; Mieschendahl et al., 1986). Additional genetic alterations (described below) were made to this strain to promote the biosynthesis of 3FL. This was achieved in strain GI724 through several manipulations of the chromosome using λ Red recombineering (Court et al., 2002) and generalized P1 phage transduction.

First: the ability of the *E. coli* host strain to accumulate intracellular lactose was engineered by simultaneous deletion of the endogenous β-galactosidase gene (lacZ) and the lactose operon repressor gene (lacI). During construction of this deletion the lacIq promoter was placed immediately upstream of the lactose permease gene, lacY. The strain thus modified maintains its ability to transport lactose from the culture medium (via LacY), but is deleted for the wild-type copy of the lacZ (β-galactosidase) gene responsible for lactose catabolism. An intracellular lactose pool is therefore created when the modified strain is cultured in the presence of exogenous lactose. In addition, the lacA gene was deleted in order to eliminate the production of acetyl-lactose from the enhanced pool of intracellular lactose.

Second: the ability of the host *E. coli* strain to synthesize colanic acid, an extracellular capsular polysaccharide, was eliminated by the deletion of the wcaJ gene, encoding the UDP-glucose lipid carrier transferase (Stevenson et al., 1996). In a wcaJ null background GDP-fucose accumulates in the *E. coli* cytoplasm (Dumon, C., et al. (2001). In vivo fucosylation of lacto-N-neotetraose and lacto-N-neohexaose by heterologous expression of *Helicobacter pylori* alpha-1,3 fucosyltransferase in engineered *Escherichia coli*. Glycoconj J 18, 465-474.)

The sequence of the chromosomal region of *E. coli* bearing the ΔwcaJ::FRT mutation is set forth below (SEQ ID NO: 55):

(SEQ ID NO: 55)
GTTCGGTTATATCAATGTCAAAAACCTCACGCCGCTCAAGCTGGTGATC

AACTCCGGGAACGGCGCAGCGGGTCCGGTGGTGGACGCCATTGAAGCCC

```
-continued
GCTTTAAAGCCCTCGGCGCGCCCGTGGAATTAATCAAAGTGCACAACAC
GCCGGACGGCAATTTCCCCAACGGTATTCCTAACCCACTACTGCCGGAA
TGCCGCGACGACACCCGCAATGCGGTCATCAAACACGGCGCGGATATGG
GCATTGCTTTTGATGGCGATTTTGACCGCTGTTTCCTGTTTGACGAAAA
AGGGCAGTTTATTGAGGGCTACTACATTGTCGGCCTGTTGGCAGAAGCA
TTCCTCGAAAAAAATCCCGGCGCGAAGATCATCCACGATCCACGTCTCT
CCTGGAACACCGTTGATGTGGTGACTGCCGCAGGTGGCACGCCGGTAAT
GTCGAAAACCGGACACGCCTTTATTAAAGAACGTATGCGCAAGGAAGAC
GCCATCTATGGTGGCGAAATGAGCGCCCACCATTACTTCCGTGATTTCG
CTTACTGCGACAGCGGCATGATCCCGTGGCTGCTGGTCGCCGAACTGGT
GTGCCTGAAAGATAAAACGCTGGGCGAACTGGTACGCGACCGGATGGCG
GCGTTTCCGGCAAGCGGTGAGATCAACAGCAAACTGGCGCAACCCGTTG
AGGCGATTAACCGCGTGGAACAGCATTTTAGCCGTGAGGCGCTGGCGGT
GGATCGCACCGATGGCATCAGCATGACCTTTGCCGACTGGCGCTTTAAC
CTGCGCACCTCCAATACCGAACCGGTGGTGCGCCTGAATGTGGAATCGC
GCGGTGATGTGCCGCTGATGGAAGCGCGAACGCGAACTCTGCTGACGTT
GCTGAACGAGTAATGTCGGATCTTCCCTTACCCCACTGCGGGTAAGGGG
CTAATAACAGGAACAACGATGATTCCGGGGATCCGTCGACCTGCAGTTC
GAAGTTCCTATTCTCTAGAAAGTATAGGAACTTCGAAGCAGCTCCAGCC
TACAGTTAACAAAGCGGCATATTGATATGAGCTTACGTGAAAAAACCAT
CAGCGGCGCGAAGTGGTCGGCGATTGCCACGGTGATCATCATCGGCCTC
GGGCTGGTGCAGATGACCGTGCTGGCGCGGATTATCGACAACCACCAGT
TCGGCCTGCTTACCGTGTCGCTGGTGATTATCGCGCTGGCAGATACGCT
TTCTGACTTCGGTATCGCTAACTCGATTATTCAGCGAAAAGAAATCAGT
CACCTTGAACTCACCACGTTGTACTGGCTGAACGTCGGGCTGGGGATCG
TGGTGTGCGTGGCGGTGTTTTTGTTGAGTGATCTCATCGGCGACGTGCT
GAATAACCCGGACCTGGCACCGTTGATTAAAACATTATCGCTGGCGTTT
GTGGTAATCCCCCACGGGCAACAGTTCCGCGCGTTGATGCAAAAGAGC
TGGAGTTCAACAAAATCGGCATGATCGAAACCAGCGCGGTGCTGGCGGG
CTTCACTTGTACGGTGGTTAGCGCCCATTTCTGGCCGCTGGCGATGACC
GCGATCCTCGGTTATCTGGTCAATAGTGCGGTGAGAACGCTGCTGTTTG
GCTACTTTGGCCGCAAAATTTATCGCCCCGGTCTGCATTTCTCGCTGGC
GTCGGTGGCACCGAACTTACGCTTTGGTGCCTGGCTGACGGCGGACAGC
ATCATCAACTATCTCAATACCAACCTTTCAACGCTCGTGCTGGCGCGTA
TTCTCGGCGCGGGCGTGGCAGGGGGATACAACCTGGCGTACAACGTGGC
CGTTGTGCCACCGATGAAGCTGAACCCAATCATCACCCGCGTGTTGTTT
CCGGCATTCGCCAAAATTCAGGACGATACCGAAAAGCTGCGTGTTAACT
TCTACAAGCTGCTGTCGGTAGTGGGGATTATCAACTTTCCGGCGCTGCT
CGGGCTAATGGTGGTGTCGAATAACTTTGTACCGCTGGTCTTTGGTGAG
AAGTGGAACAGCATTATTCCGGTGCTGCAATTGCTGTGTGTGGTGGGTC
TGCTGCGCTCCG
```

Third: The magnitude of the cytoplasmic GDP-fucose pool was enhanced by the introduction of a null mutation into the lon gene. Lon is an ATP-dependent intracellular protease that has been shown to be responsible for degrading RcsA, a positive transcriptional regulator of colanic acid biosynthesis in *E. coli* (Gottesman and Stout, 1991). In a lon null background RcsA is stabilized, RcsA levels increase, the genes responsible for GDP-fucose synthesis are up-regulated, and intracellular GDP-fucose concentrations are enhanced. The lon gene was almost entirely deleted in our production strain (E638) and replaced by an inserted functional, wild-type, but promoter-less *E. coli* lacZ$^+$ gene (Δlon::(kan, lacZ$^+$). λ Red recombineering was used to perform the construction.

Genomic DNA sequence surrounding the lacZ+ insertion into the lon region in the *E. coli* strain is set forth below (SEQ ID NO: 56):

```
                                           (SEQ ID NO: 56)
GTGGATGGAAGAGGTGGAAAAAGTGGTTATGGAGGAGTGGGTAATTGAT
GGTGAAAGGAAAGGGTTGGTGATTTATGGGAAGGGGGAAGGGAAGAGG
GATGTGGTGAATAATTAAGGATTGGGATAGAATTAGTTAAGGAAAAAGG
GGGGATTTTATGTGGGGTTTAATTTTTGGTGTATTGTGGGGGTTGAATG
TGGGGGAAAGATGGGGATATAGTGAGGTAGATGTTAATAGATGGGGTGA
AGGAGAGTGGTGTGATGTGATTAGGTGGGGAAATTAAAGTAAGAGAGA
GGTGTATGATTGGGGGATGGGTGGAGGTGGAGTTGGAAGTTGGTATTG
TGTAGAAAGTATAGGAAGTTGAGAGGGGTTTTGAAGGTGAGGGTGGGGG
AAGGAGTGAGGGGGAAGGGGTGGTAAAGGAAGGGGAAGAGGTAGAAAG
GGAGTGGGGAGAAAGGGTGGTGAGGGGGATGAATGTGAGGTAGTGGGG
TATGTGGAGAAGGGAAAAGGGAAGGGAAAGAGAAAGGAGGTAGGTTGG
AGTGGGGTTAGATGGGGATAGGTAGAGTGGGGGGTTTTATGGAGAGGAA
GGGAAGGGGAATTGGGAGGTGGGGGGGGGTGTGGTAAGGTTGGGAAGGG
GTGGAAAGTAAAGTGGATGGGTTTGTTGGGGGGAAGGATGTGATGGGGG
AGGGGATGAAGATGTGATGAAGAGAGAGGATGAGGATGGTTTGGGATGA
TTGAAGAAGATGGATTGGAGGGAGGTTGTGGGGGGGTTGGGTGGAGAG
GGTATTGGGGTATGAGTGGGGAGAAGAGAGAATGGGGTGGTGTGATGGG
GGGGTGTTGGGGGTGTGAGGGGAGGGGGGGGGGGTTGTTTTTGTGAAGA
GGGAGGTGTGGGTGGGGTGAATGAAGTGGAGGAGGAGGGAGGGGGGGT
ATGGTGGGTGGGAGGAGGGGGGTTGGTTGGGGAGGTGTGGTGGAGGTT
GTGAGTGAAGGGGGAAGGGAGTGGGTGGTATTGGGGGAAGTGGGGGGGG
AGGATGTGGTGTGATGTGAGGTTGGTGGTGGGGAGAAAGTATGGATGAT
GGGTGATGGAATGGGGGGGTGGATAGGGTTGATGGGGGTAGGTGGGGA
TTGGAGGAGGAAGGGAAAGATGGGATGGAGGGAGGAGGTAGTGGGATGG
AAGGGGGTGTTGTGGATGAGGATGATGTGGAGGAAGAGGATGAGGGGGT
GGGGGGAGGGGAAGTGTTGGGGAGGGTGAAGGGGGGATGGGGGAGGGGG
AGGATGTGGTGGTGAGGGATGGGATGGGTGGTTGGGGAATATGATGGT
GGAAAATGGGGGGTTTTGTGGATTGATGGAGTGTGGGGGGTGGGTGTG
GGGGAGGGGTATGAGGAGATAGGGTTGGGTAGGGGTGATATTGGTGAAG
```

-continued

```
AGGTTGGGGGGGAATGGGGTGAGGGGTTGGTGGTGGTTTAGGGTATGGG
GGGTGGGGATTGGGAGGGGATGGGGTTGTATGGGGTTGTTGAGGAGTTG
TTGTAATAAGGGGATGTTGAAGTTGGTATTGGGAAGTTGGTATTGTGTA
GAAAGTATAGGAAGTTGGAAGGAGGTGGAGGGTAGATAAAGGGGGGGT
TATTTTTGAGAGGAGAGGAAGTGGTAATGGTAGGGAGGGGGGTGAGGT
GGAATTGGGGGGATAGTGAGGGGGTGGAGGAGTGGTGGGGAGGAATGGG
GATATGGAAAGGGTGGATATTGAGGGATGTGGGTTGTTGGGGGTGGAGG
AGATGGGGATGGGTGGTTTGGATGAGTTGGTGTTGAGTGTAGGGGGTGA
TGTTGAAGTGGAAGTGGGGGGGGGAGTGGTGTGGGGGATAATTGAATTG
GGGGGTGGGGGAGGGGAGAGGGTTTGGGTGGGGAAGAGGTAGGGGGTA
TAGATGTTGAGAATGGGAGATGGGAGGGGTGAAAAGAGGGGGGAGTAAG
GGGGTGGGGATAGTTTTGTTGGGGGGGTAATGGGAGGGAGTTTAGGGGG
TGTGGTAGGTGGGGGAGGTGGGAGTTGAGGGGAATGGGGGGGGATGGG
GTGTATGGGTGGGGAGTTGAAGATGAAGGGTAATGGGGATTTGAGGAGT
AGGATGAATGGGGTAGGTTTTGGGGGTGATAAATAAGGTTTTGGGGTGA
TGGTGGGAGGGGTGAGGGGTGGTAATGAGGAGGGGATGAGGAAGTGTAT
GTGGGGTGGAGTGGAAGAAGGGTGGTTGGGGGTGGTAATGGGGGGGGG
GTTGGAGGGTTGGAGGGAGGGGTTAGGGTGAATGGGGGTGGGTTGAGTT
AGGGGAATGTGGTTATGGAGGGGTGGAGGGGTGAAGTGATGGGGAGGG
GGGTGAGGAGTTGTTTTTATGGGGAATGGAGATGTGTGAAAGAAAGGG
TGAGTGGGGGTTAAATTGGGAAGGGTTATTAGGGAGGTGGATGGAAAAA
TGGATTTGGGTGGTGGTGAGATGGGGGATGGGGTGGGAGGGGGGGGGA
GGGTGAGAGTGAGGTTTTGGGGGAGAGGGGAGTGGTGGGAGGGGGTGAT
GTGGGGGGGTTGTGAGGATGGGGTGGGGTTGGGTTGGAGTAGGGGTAGT
GTGAGGGAGAGTTGGGGGGGGGTGTGGGGGTGGGGTAGTTGAGGGAGTT
GAATGAAGTGTTTAGGTTGTGGAGGGAGATGGAGAGGGAGTTGAGGGGT
TGGGAGGGGTTAGGATGGAGGGGAGGATGGAGTGGAGGAGGTGGTTA
TGGGTATGAGGGAAGAGGTATTGGGTGGTGAGTTGGATGGTTTGGGGGG
ATAAAGGGAAGTGGAAAAAGTGGTGGTGGTGTTTTGGTTGGGTGAGGGG
TGGATGGGGGGTGGGGTGGGGAAAGAGGAGAGGGTTGATAGAGAAGTGG
GGATGGTTGGGGGTATGGGGAAAATGAGGGGGGTAAGGGGAGGAGGGGT
TGGGGTTTTGATGATATTTAATGAGGGGAGTGATGGAGGGAGTGGGAGAG
GAAGGGGGGGTGTAAAGGGGGATAGTGAGGAAAGGGGTGGGAGTATTTA
GGGAAAGGGGGAAGAGTGTTAGGGATGGGGTGGGGGTATTGGGAAAGGA
TGAGGGGGGGGGGTGTGTGGAGGTAGGGAAAGGGATTTTTTGATGGAGGA
TTTGGGGAGAGGGGGGAAGGGGTGGTGTTGATGGAGGGGGGGGTAGATG
GGGGAAATAATATGGGTGGGGGTGGTGTGGGGTGGGGGGGGTTGATAGT
GGAGGGGGGGGGAAGGATGGAGAGATTTGATGGAGGGATAGAGGGGGTG
GTGATTAGGGGGTGGGGTGATTGATTGGGAGGGAGGAGATGATGAGA
GTGGGGTGATTAGGATGGGGGTGGAGGATTGGGGTTAGGGGTTGGGTGA
TGGGGGGTAGGGAGGGGGGATGATGGGTGAGAGGATTGATTGGGAGGAT
GGGGTGGGTTTGAATATTGGGTTGATGGAGGAGATAGAGGGGGTAGGGG
TGGGAGAGGGTGTAGGAGAGGGGATGGTTGGGATAATGGGAAGAGGGGA
GGGGGTTAAAGTTGTTGTGGTTGATGAGGAGGATATGGTGGAGGATGGT
GTGGTGATGGATGAGGTGAGGATGGAGAGGATGATGGTGGTGAGGGTTA
AGGGGTGGAATGAGGAAGGGGTTGGGGTTGAGGAGGAGGAGAGGATTTT
GAATGGGGAGGTGGGGGAAAGGGAGATGGGAGGGTTGTGGTTGAATGAG
GGTGGGGTGGGGGGTGTGGAGTTGAAGGAGGGGAGGATAGAGATTGGGG
ATTTGGGGGGTGGAGAGTTTGGGGTTTTGGAGGTTGAGAGGTAGTGTGA
GGGGATGGGGATAAGGAGGAGGGTGATGGATAATTTGAGGGGGGAAAGG
GGGGGTGGGGTGGGAGGTGGGTTTGAGGGTGGGATAAAGAAAGTGTT
AGGGGTAGGTAGTGAGGGAAGTGGGGGGAGATGTGAAGTTGAGGGTGGA
GTAGAGGGGGGTGAAATGATGATTAAAGGGAGTGGGAAGATGGAAATG
GGTGATTTGTGTAGTGGGTTTATGGAGGAAGGAGAGGTGAGGGAAAATG
GGGGTGATGGGGGAGATATGGTGATGTTGGAGATAAGTGGGGTGAGTGG
AGGGGAGGAGGATGAGGGGGAGGGGTTTTGTGGGGGGGTAAAAATGG
GGTGAGGTGAAATTGAGAGGGGAAAGGAGTGTGGTGGGGGTAAGGGAGG
GAGGGGGGTTGGAGGAGAGATGAAAGGGGGAGTTAAGGGGATGAAAAA
TAATTGGGGTGTGGGGTTGGTGTAGGGAGGTTTGATGAAGATTAAATGT
GAGGGAGTAAGAAGGGTGGGATTGTGGGTGGGAAGAAAGGGGGGATTG
AGGGTAATGGGATAGGTGAGGTTGGTGTAGATGGGGGATGGTAAGGGT
GGATGTGGGAGTTTGAGGGGAGGAGGAGAGTATGGGGGTGAGGAAGATG
GGAGGGAGGGAGGTTTGGGGGAGGGGTTGTGGTGGGGGAAAGGAGGGAA
AGGGGGATTGGGGATTGAGGGTGGGGAAGTGTTGGGAAGGGGGATGGGT
GGGGGGGTGTTGGGTATTAGGGGAGGTGGGGAAAGGGGGATGTGGTGGA
AGGGGATTAAGTTGGGTAAGGGGAGGGTTTTGGGAGTGAGGAGGTTGTA
AAAGGAGGGGGAGTGAATGGGTAATGATGGTGATAGTAGGTTTGGTGAG
GTTGTGAGTGGAAAATAGTGAGGTGGGGAAAATGGAGTAATAAAAAGA
GGGGTGGGAGGGTAATTGGGGGTTGGGAGGGTTTTTTTGTGTGGGTAAG
TTAGATGGGGGATGGGGGTTGGGGTTATTAAGGGGTGTTGTAAGGGGAT
GGGTGGGGTGATATAAGTGGTGGGGGTTGGTAGGTTGAAGGATTGAAGT
GGGATATAAATTATAAAGAGGAAGAGAAGAGTGAATAAATGTGAATTGA
TGGAGAAGATTGGTGGAGGGGGTGATATGTGTAAAGGTGGGGGTGGGGG
TGGGTTAGATGGTATTATTGGTTGGGTAAGTGAATGTGTGAAAGAAGG
```

The inserted lacZ⁺ cassette not only knocks out lon, but also converts the lacZ⁻ host back to both a lacZ⁺ genotype and phenotype. The modified strain produces a minimal (albeit still readily detectable) level of β-galactosidase activity (1-2 units), which has very little impact on lactose consumption during production runs, but which is useful in removing residual lactose at the end of runs, and as an easily scorable phenotypic marker for moving the lon mutation into other lacZ⁻ *E. coli* strains by P1 transduction.

Fourth: A thyA (thymidylate synthase) mutation was introduced into the strain by P1 transduction. In the absence of exogenous thymidine, thyA strains are unable to make DNA and die. The defect can be complemented in trans by supplying a wild-type thyA gene on a multicopy plasmid (Belfort et al., 1983). This complementation is used here as a means of plasmid maintenance.

An additional modification that is useful for increasing the cytoplasmic pool of free lactose (and hence the final yield of 3-FL) is the incorporation of a lacA mutation. LacA is a lactose acetyltransferase that is only active when high levels of lactose accumulate in the *E. coli* cytoplasm. High intracellular osmolarity (e.g., caused by a high intracellular lactose pool) can inhibit bacterial growth, and *E. coli* has evolved a mechanism for protecting itself from high intra cellular osmolarity caused by lactose by "tagging" excess intracellular lactose with an acetyl group using LacA, and then actively expelling the acetyl-lactose from the cell (Danchin, A. Bioessays 31, 769-773 (2009)). Production of acetyl-lactose in *E. coli* engineered to produce 3-FL or other human milk oligosaccharides is therefore undesirable: it reduces overall yield. Moreover, acetyl-lactose is a side product that complicates oligosaccharide purification schemes. The incorporation of a lacA mutation resolves these problems. Sub-optimal production of fucosylated oligosaccharides occurs in strains lacking either or both of the mutations in the colanic acid pathway and the lon protease. Diversion of lactose into a side product (acetyl-lactose) occurs in strains that do not contain the lacA mutation. A schematic of the lacA deletion and corresponding genomic sequence is provided above.

The strain used in the Examples to test the different α(1,3) FT candidates incorporates all the above genetic modifications and has the following genotype:
ΔampC::$P_{trp}^{B}$ cI, Δ(lacI-lacZ)::FRT, $P_{lacIq}$lacY$^+$, ΔlacA, ΔwcaJ::FRT, thyA::Tn10, Δlon::(npt3, lacZ$^+$)

The strains engineered as described above to produce the desired fucosylated oligosaccharide(s) are grown in a minimal media. An exemplary minimal medium used in a bioreactor, minimal "FERM" medium, is detailed below.

Ferm (10 liters): Minimal medium comprising:
40 g $(NH_4)_2HPO_4$
100 g $KH_2PO_4$
10 g $MgSO_4 \cdot 7H_2O$
40 g NaOH
1× Trace elements:
1.3 g NTA (nitrilotriacetic acid)
5 g $FeSO_4 \cdot 7H_2O$
0.09 g $MnCl_2 \cdot 4H_2O$
0.09 g $ZnSO_4 \cdot 7H_2O$
0.01 g $CoCl_2 \cdot 6H_2O$
0.01 g $CuCl_2 \cdot 2H_2O$
0.02 g $H_3BO_3$
0.01 g $Na_2MoO_4 \cdot 2H_2O$ (pH 6.8)
Water to 10 liters
DF204 antifoam (0.1 ml/L)
150 g glycerol (initial batch growth), followed by fed batch mode with a 90% glycerol-1% $MgSO_4$-1× trace elements feed, at various rates for various times.

Bacteria comprising the characteristics described herein are cultured in the presence of lactose, and a fucosylated oligosaccharide is retrieved, either from the bacterium itself or from a culture supernatant of the bacterium. The fucosylated oligosaccharide is purified for use in therapeutic or nutritional products, or the bacteria are used directly in such products.

Post-Fermentation Purification

Fucosylated oligosaccharides produced by metabolically engineered *E. coli* cells are purified from culture broth post-fermentation. An exemplary procedure comprises five steps. (1) Clarification: Fermentation broth is harvested and cells removed by sedimentation in a preparative centrifuge at 6000×g for 30 min. Each bioreactor run yields about 5-7 L of partially clarified supernatant. (2) Product capture on coarse carbon: A column packed with coarse carbon (Calgon 12×40 TR) of ~1000 ml volume (dimension 5 cm diameter× 60 cm length) is equilibrated with 1 column volume (CV) of water and loaded with clarified culture supernatant at a flow rate of 40 ml/min. This column has a total capacity of about 120 g of sugar. Following loading and sugar capture, the column is washed with 1.5 CV of water, then eluted with 2.5 CV of 50% ethanol or 25% isopropanol (lower concentrations of ethanol at this step (25-30%) may be sufficient for product elution.) This solvent elution step releases about 95% of the total bound sugars on the column and a small portion of the color bodies. In this first step capture of the maximal amount of sugar is the primary objective. Resolution of contaminants is not an objective. (3) Evaporation: A volume of 2.5 L of ethanol or isopropanol eluate from the capture column is rotary-evaporated at 56 C.° and a sugar syrup in water is generated. Alternative methods that could be used for this step include lyophilization or spray-drying. (4) Flash chromatography on fine carbon and ion exchange media: A column (GE Healthcare HiScale50/40, 5×40 cm, max pressure 20 bar) connected to a Biotage Isolera One FLASH Chromatography System is packed with 750 ml of a Darco Activated Carbon G60 (100-mesh): Celite 535 (coarse) 1:1 mixture (both column packings were obtained from Sigma). The column is equilibrated with 5 CV of water and loaded with sugar from step 3 (10-50 g, depending on the ratio of 3-FL to contaminating lactose), using either a celite loading cartridge or direct injection. The column is connected to an evaporative light scattering (ELSD) detector to detect peaks of eluting sugars during the chromatography. A four-step gradient of isopropanol, ethanol or methanol is run in order to separate 3-FL from monosaccharides (if present), lactose and color bodies. Fractions corresponding to sugar peaks are collected automatically in 120-ml bottles, pooled and directed to step 5. In certain purification runs from longer-than-normal fermentations, passage of the 3-FL-containing fraction through anion-exchange and cation exchange columns can remove excess protein/DNA/caramel body contaminants. Resins tested successfully for this purpose include Dowex 22.

The gene screening approach described herein was successfully utilized to identify new α(1,3) FTs for the efficient biosynthesis of 3FL and other α(1,3) fucosylated oligosaccharides in metabolically engineered *E. coli* host strains. The results of the screen are summarized in Tables 1 and 4.

A directed screening approach was used to identify and characterize alternative bacterial α(1,3) FTs with different and desirable properties, (e.g. possessing higher specific activity, higher expression level, lower cellular toxicity, higher protease stability and/or different acceptor substrate specificity) that are useful for the large scale production of α(1,3)-linked fucosylated oligosaccharides. Specifically, the enzymes CafC, CafL, CafN, CafO, CafQ, CafU and CafV have utility for the production of 3FL and LDFT, two HMOS that are abundant in human milk that possess important and useful therapeutic properties. In addition, CafD is capable of promoting synthesis of LNF III, an HMOS that possesses the bona fide Le$^x$ epitope that is likely to possess therapeutic properties similar to that of 3FL and LDFT. The Le$^x$ epitope is involved in a myriad of biological recognition processes, and the ability to produce molecules containing this epitope on large-scale is useful as a tool to elucidate their modes of action (McEver et al., 1995; McEver and Cummings, 1997).

Example 1: α(1,3) Fucosyltransferase Expression in E. coli

The strain used to test the different α(1,3) FT candidates incorporates all the above genetic modifications and has the following genotype:
ΔampC::P$_{trp}^{B}$cI, Δ(lacI-lacZ)::FRT, P$_{lacIq}$lacY$^{+}$, ΔlacA, ΔwcaJ::FRT, thyA::Tn10, Δlon::(npt3, lacZ$^{+}$)

The E. coli strains harboring the different α(1,3) FT candidate expression plasmids were analyzed in small-scale experiments. Strains were grown in selective media (lacking thymidine) to early exponential phase. Lactose was then added to a final concentration of 1%, and tryptophan (200 µM) was added to induce expression of each candidate α(1,3) FT from the P$_L$ promoter. At the end of the induction period (~20 h) equivalent OD 600 units of each strain were harvested. Lysates were prepared and analyzed for the presence of 3FL by thin layer chromatography (TLC). As shown in FIG. 4A-C, a control strain producing FutA was capable of the biosynthesis of 3FL and also produced a smaller amount of the tetrasaccharide lactodifucotetraose (LDFT). Interestingly, the strains producing CafA, CafC and CafF synthesized a significant amount of 3FL as compared to the control strain producing FutA. Specifically, the strain producing CafA synthesized approximately ~50% as much 3FL compared to the control strain, but produced significantly more LDFT (FIG. 4A). Importantly, CafC and CafF reproducibly catalyzed the formation of greater levels of 3FL as compared to FutA (FIGS. 4A and 4B). Strains producing CafC and CafF also secreted a significant amount of 3FL into the culture supernatant. CafB was also able to catalyze the biosynthesis of 3FL, although at levels significantly less than that of the FutA control strain. Polypeptides of the predicted molecular weight for CafA, B, C and F were detected in protein lysates of the respective strains by SDS-PAGE analysis, indicating these proteins are robustly synthesized in our E. coli production strain (FIG. 5A-C). Thus, CafA, CafC and CafF are α(1,3) FTs that are useful for the large-scale production of fucosylated oligosaccharides. CafC and CafF are of particular interest, as strains synthesizing these enzymes routinely produced greater levels of 3FL as compared to the FutA control strain (Table 1). Of note, the remaining candidates (CafD, E, G, H, I, J and K) were unable to utilize lactose as an acceptor for the production of 3FL, despite the observation that most of these enzymes were robustly synthesized in E. coli. Therefore, the fact that only 3 of the 11 candidates tested were able to synthesize 3FL in the engineered E. coli strain indicates the uniqueness and surprising aspect of these findings.

In a related aspect of the invention, the bacterial production strain may harbor an expression plasmid containing two or more different α(1,3) fucosyltransferases in a "tandem" or "stringed" arrangement under control of a promoter, e.g., a fortuitous promoter. A relatively low level of constitutive expression of 2 different α(1,3) fucosyltransferases was found to yield a net increase of enzyme activity without a drawback of undesirable or unacceptable cell toxicity has been observed with high, e.g., inducible/induced, expression of a single heterologous α(1,3) fucosyltransferase. An exemplary promoter comprises the P$_L$ promoter (e.g. pG420 shown in FIG. 21.) SEQ ID NO: 64 below provides the nucleic acid sequence for the pG420 expression plasmid.

(SEQ ID NO: 64)
caagaaggagatataCATATGAAGACCATCAAGGTAAAATTCGTCGATT

TCTGGAAAGGTTTCGACCCGCGCAACAACTTCCTGATGGACATCCTGAA

ACAGCGTTATCACATTGAACTGAGCGAAAGCCCGGACTACCTGATCTTC

TCTGTCTTCGGTTTCACTAACCTGAACTACGAACGCTGCGTTAAAATCT

TCTACACCGGTGAAAACCTGACCCCGGATTTCAACATCTGCGACTACGC

GATTGGTTTCGATTATCTGAGCTTCGGTGATCGTTACATGCGTCTGCCA

CTGTACGCGGTCTATGGCATCGAGAAACTGGCTTCTCCGAAAGTTATCG

ACAAAGAAAAAGTTCTGAAGCGTAAATTCTGTTCTTACGTAGTAAGCAA

TAACATCGGCGCGCCGGAACGTTCTCGTTTCTTCCATCTGCTGTCTGAA

TACAAAAAGGTTGACTCCGGTGGTCGTTGGGAAAACAACGTAGGCGGTC

CGGTTCCGAATAAGCTGGACTTTATCAAAGACTACAAGTTCAACATCGC

ATTCGAAAACTCCATGTACGACGGCTACACTACTGAAAAAATCATGGAA

CCGATGCTGGTGAACAGCCTGCCGATTTATTGGGGCAACCGCCTGATCA

ACAAAGACTTCAACCCAGCGTCTTTCATCAACGTTTCCGATTTCCCGTC

TCTGGAAGCGGCGGTGGAGCACATTGTTATGCTGGACAATAACGATGAT

ATGTACCTGAGCATCCTGTCTAAACCGTGGTTTAACGATGAAAACTACC

TGGACTGGAAAGCGCGCTTCTTCCACTTTTTCGATAACATCTTCAATCG

TCCGATCGATGAATGCAAATATCTGACCCCGTACGGCTTTTGTCGTCAC

TATCGTAACCAACTGCGTAGCGCTCGTCTGCTGAAACAGCGCTTTCGCC

AGCTGCGTAACCCGCTGCGCTGGTTCCGCTAGtagcTCGAGCTGCAGTA

ATCGTACAGGGTAGTACAAATAAAAAAGGCACGTCAGATGACGTGCCTT

TTTTCTTGTGAGCAGTaagcttCTACGAACATCTTCCAGGATACTCCTG

CAGCGAAATATTTGTTTTAAGCTCACTCACATATCGCAACATTTACTTT

ACTTTAAGACAATTCCAGGCAAATTATACAACACTTTACGGGATAGTAA

GTCCGCCTGAAAAATCGCGAGAGTGGCGCATTAGGTGACCCATGTTGTT

CCGTTTAGTCATGATGAAATATTCAGGTAAGGGGAATTATCGTTACGCA

TTGAGTGAGGGTATGCCATGTCAACGATTATTATGGATTTATGTAGTTA

CACCCGACTAGGTTTAACCGGGTATCTGTTGAGTAGAGGGGTTAAAAAA

AGAGAAATCAACGACATTGAAACCGTTGATGACCTTGCCATAGCTTGTG

ATTCACAGCGCCCTTCAGTGGTGTTTATTAATGAGGACTGTTTCATCCA

CGATGCTTCTAACAGTCAGCGTATCAAGCTCATCATTAATCAACATCCC

AATACGTTATTTATCGTTTTTATGGCAATTGCCAATGTTCATTTTGATG

AATATCTATTGGTCAGAAAAAATTTATTGATCAGTTCTAAATCGATTAA

ACCGGAATCTCTCGACGATATCCTTGGCGATATTCTGAAAAAAGAGACA

ACGATAACCTCGTTTTTAAATATGCCGACGTTATCATTGAGCCGAACCG

AATCGAGTATGTTGCGAATGTGGATGGCAGGTCAGGGAACCATTCAAAT

CTCTGACCAAATGAATATCAAAGCCAAGACCGTTTCATCGCATAAAGGT

AATATTAAACGTAAGATCAAAACGCATAATAAACAGGTTATCTACCATG

TCGTCCGACTGACGGATAATGTGACTAATGGTATTTTTGTCAACATGCG

CTAACACATTCTGACTGGTGGTTTCCCACCAGTCAGGCTGAATAAGATT

ACTCTGCTTTCTCCACAAAGATACCGTCCTGATGCCCTGCTTCATTAAA

GAAAGCTTGGCACTGGCCGTCGTTTTACAACGTCGTGACTGGGAAAACC

CTGGCGTTACCCAACTTAATCGCCTTGCAGCACATCCCCCTTTCGCCAG

CTGGCGTAATAGCGAAGAGGCCCGCACCGATCGCCCTTCCCAACAGTTG
CGCAGCCTGAATGGCGAATGGCGCCTTCGGGAAGGCGTCTCGAAGAATT
TAACGGAGGGTAAAAAAACCGACGCACACTGGCGTCGGCTCTGGCAGGA
TGTTTCGTAATTAGATAGCCACCGGCGCTTTAATGCCCGGATGCGGATC
GTAGCCTTCAATCTCAAAGTCTTCGAAACGGTAGTCGAAGATGGATTCG
GGTTTACGTTTGATAATCAACTTCGGCAGCGGACGCGGTTCGCGGCTTA
ATTGCAGATGAGTTTGATCCATATGGTTGCTGTACAGATGCGTGTCGCC
ACCGGTCCAGACAAAATCACCCACTTCCAGATCGCACTGCTGCGCCATC
ATATGCACCAATAACGCGTAGCTGGCAATGTTGAACGGCAGGCCGAGGA
AGACGTCACAGGAGCGCTGATAAAGCTGGCAAGAGAGTTTGCCGTCTGC
CACATAGAACTGGAAGAATGCATGGCACGGTGCCAGCGCCATTTTATCC
AGTTCGCCTACGTTCCACGCTGAAACAATAATGCGGCGCGAATCCGGGT
CGTTTTTCAGCTGGTTCAGTACCGTAGTGATCTGGTCAATATGACGACC
ATCTGGCGTTGGCCAGGCGCGCCACTGTTTACCATACACTGGCCCGAGG
TCGCCGTTTTCATCGGCCCATTCGTCCCAGATGGTGACATTGTTTTCGT
GTAGATAAGCAATGTTAGTGTCGCCCTGCAGAAACCACAGCAGTTCATG
GATGATGGAACGCAGGTGGCAACGTTTAGTGTCACCAGCGGGAATCCA
TCTTGCAGGTTAAAACGCATCTGATGACCAAAAATGGAAAGCGTTCCGG
TTCCGGTACGGTCGTTTTTCTGTGTGCCTTCGTCGAGCACTTTTTGCAT
CAGTTCTAAATACTGTTTCATGGTTCCTCAGGAAACGTGTTGCTGTGGG
CTGCGACGATATGCCCAGACCATCATGATCACACCCGCGACAATCATCG
GGATGGAAAGAATTTGCCCCATGCTGATGTACTGCACCCAGGCACCGGT
AAACTGCGCGTCGGGCTGGCGGAAAAACTCAACAATGATGCGAAACGCG
CCGTAACCAATCAGGAACAAACCTGAGACAGCTCCCATTGGGCGTGGTT
TACGAATATACAGGTTGAGGAGGCGCCTGATGCGGTATTTTCTCCTTAC
GCATCTGTGCGGTATTTCACACCGCATATATGGTGCACTCTCAGTACAA
TCTGCTCTGATGCCGCATAGTTAAGCCAGCCCCGACACCCGCCAACACC
CGCTGACGCGCCCTGACGGGCTTGTCTGCTCCCGGCATCCGCTTACAGA
CAAGCTGTGACCGTCTCCGGGAGCTGCATGTGTCAGAGGTTTTCACCGT
CATCACCGAAACGCGCGAGACGAAAGGGCCTCGTGATACGCCTATTTTT
ATAGGTTAATGTCATGATAATAATGGTTTCTTAGACGTCAGGTGGCACT
TTTCGGGGAAATGTGCGCGGAACCCCTATTTGTTTATTTTTCTAAATAC
ATTCAAATATGTATCCGCTCATGAGACAATAACCCTGATAAATGCTTCA
ATAATATTGAAAAAGGAAGAGTATGAGTATTCAACATTTCCGTGTCGCC
CTTATTCCCTTTTTTGCGGCATTTTGCCTTCCTGTTTTTGCTCACCCAG
AAACGCTGGTGAAAGTAAAAGATGCTGAAGATCAGTTGGGTGCACGAGT
GGGTTACATCGAACTGGATCTCAACAGCGGTAAGATCCTTGAGAGTTTT
CGCCCCGAAGAACGTTTTCCAATGATGAGCACTTTTAAAGTTCTGCTAT
GTGGCGCGGTATTATCCCGTATTGACGCCGGGCAAGAGCAACTCGGTCG
CCGCATACACTATTCTCAGAATGACTTGGTTGAGTACTCACCAGTCACA
GAAAAGCATCTTACGGATGGCATGACAGTAAGAGAATTATGCAGTGCTG

CCATAACCATGAGTGATAACACTGCGGCCAACTTACTTCTGACAACGAT
CGGAGGACCGAAGGAGCTAACCGCTTTTTTGCACAACATGGGGGATCAT
GTAACTCGCCTTGATCGTTGGGAACCGGAGCTGAATGAAGCCATACCAA
ACGACGAGCGTGACACCACGATGCCTGTAGCAATGGCAACAACGTTGCG
CAAACTATTAACTGGCGAACTACTTACTCTAGCTTCCCGGCAACAATTA
ATAGACTGGATGGAGGCGGATAAAGTTGCAGGACCACTTCTGCGCTCGG
CCCTTCCGGCTGGCTGGTTTATTGCTGATAAATCTGGAGCCGGTGAGCG
TGGGTCTCGCGGTATCATTGCAGCACTGGGGCCAGATGGTAAGCCCTCC
CGTATCGTAGTTATCTACACGACGGGGAGTCAGGCAACTATGGATGAAC
GAAATAGACAGATCGCTGAGATAGGTGCCTCACTGATTAAGCATTGGTA
ACTGTCAGACCAAGTTTACTCATATATACTTTAGATTGATTTAAAACTT
CATTTTTAATTTAAAAGGATCTAGGTGAAGATCCTTTTTGATAATCTCA
TGACCAAAATCCCTTAACGTGAGTTTTCGTTCCACTGAGCGTCAGACCC
CGTAGAAAAGATCAAAGGATCTTCTTGAGATCCTTTTTTTCTGCGCGTA
ATCTGCTGCTTGCAAACAAAAAAACCACCGCTACCAGCGGTGGTTTGTT
TGCCGGATCAAGAGCTACCAACTCTTTTTCCGAAGGTAACTGGCTTCAG
CAGAGCGCAGATACCAAATACTGTCCTTCTAGTGTAGCCGTAGTTAGGC
CACCACTTCAAGAACTCTGTAGCACCGCCTACATACCTCGCTCTGCTAA
TCCTGTTACCAGTGGCTGCTGCCAGTGGCGATAAGTCGTGTCTTACCGG
GTTGGACTCAAGACGATAGTTACCGGATAAGGCGCAGCGGTCGGGCTGA
ACGGGGGGTTCGTGCACACAGCCCAGCTTGGAGCGAACGACCTACACCG
AACTGAGATACCTACAGCGTGAGCTATGAGAAAGCGCCACGCTTCCCGA
AGGGAGAAAGGCGGACAGGTATCCGGTAAGCGGCAGGGTCGGAACAGGA
GAGCGCACGAGGGAGCTTCCAGGGGGAAACGCCTGGTATCTTTATAGTC
CTGTCGGGTTTCGCCACCTCTGACTTGAGCGTCGATTTTTGTGATGCTC
GTCAGGGGGGCGGAGCCTATGGAAAAACGCCAGCAACGCGGCCTTTTTA
CGGTTCCTGGCCTTTTGCTGGCCTTTTGCTCACATGTTCTTTCCTGCGT
TATCCCCTGATTCTGTGGATAACCGTATTACCGCCTTTGAGTGAGCTGA
TACCGCTCGCCGCAGCCGAACGACCGAGCGCAGCGAGTCAGTGAGCGAG
GAAGCGGAAGAGCGCCCAATACGCAAACCGCCTCTCCCCGCGCGTTGGC
CGATTCATTAATGCAGAATTGATCTCTCACCTACCAAACAATGCCCCCC
TGCAAAAAATAAATTCATATAAAAAACATACAGATAACCATCTGCGGTG
ATAAATTATCTCTGGCGGTGTTGACATAAATACCACTGGCGGTGATACT
GAGCACATCAGCAGGACGCACTGACCACCATGAAGGTGACGCTCTTAAA
AATTAAGCCCTGAAGAAGGGCAGCATTCAAAGCAGAAGGCTTTGGGGTG
TGTGATACGAAACGAAGCATTGGCCGTAAGTGCGATTCCGGATTAGCTG
CCAATGTGCCAATCGCGGGGGGTTTTCGTTCAGGACTACAACTGCCACA
CACCACCAAAGCTAACTGACAGGAGAATCCAGATGGATGCACAAACACG
CCGCCGCGAACGTCGCGCAGAGAAACAGGCTCAATGAAAGCAGCAAAT
CCCCTGTTGGTTGGGGTAAGCGCAAAACCAGTTCCGAAAGATTTTTTA

-continued
ACTATAAACGCTGATGGAAGCGTTTATGCGGAAGAGGTAAAGCCCTTCC

CGAGTAACAAAAAAACAACAGCATAAATAACCCCGCTCTTACACATTCC

AGCCCTGAAAAAGGGCATCAAATTAAACCACACCTATGGTGTATGCATT

TATTTGCATACATTCAATCAATTtTTAGAAttcTAGaAAGAAGGAGATA

TACATATGAAAACTATCAAAGTTAAATTCGTTGATTTCTGGGAAAACTT

CGACCCGCAACACAACTTTATTGCAAACATTATCAGCAAAAAATACCGT

ATCGAACTGTCCGATACCCCAGACTATCTGTTCTTTTCCGTGTTCGGTT

ATGAAAACATCGACTACCATAACTGCACCAAAATCTTCTACTCTGGTGA

AAACATTACTCCGGACTTCAACATTTGTGACTATGCAATTGGTTTCAAC

TTCCTGTCCTTTGGTGACCGTTATATCCGTATCCCATTTTATACCGCGT

ACGGTGTGCAGCAGCTGGCCGCGCCAAAAGTAATCGTTCCGGAAGTTGT

TCTGAATCGTAAGTTCTGTAGCTTCGTTGTATCTAATGCCAAGGGCGCT

CCGGAGCGCGAGCGTTTCTTCCAACTGCTGAGCGAATACAAACAGGTGG

ACTCTGGCGGTCGTTACAAAAATAACGTTGGCGGTCCGGTACCAGATAA

AACTGCATTTATCAAAGACTACAAATTCAACATTGCGTTCGAAAACTCC

ATGTGCGACGGTTACACCACGGAAAAAATCATGGAACCTATGCTGGTCA

ATTCCGTTCCAATTTACTGGGGTAACAAACTGATCGACCGTGACTTTAA

CCCGGACTCCTTCATTAATGTATCCTCTTATTCTTCTCTGGAAGAAGCA

GTTGAGCACATCGTCCGTCTGGATCAGAATGATGACGAATACCTGAGCC

TGCTGTCCGCCCCGTGGTTCAACGAGGAAAACTACCTGAACTGGGAAGA

ACAGCTGATCACTTTCTTCGACAACATCTTCGAAAAACCGCTGTCTGAA

TCCCGTTATATCCCAACCCACGGTTACATCCAGACCTATCAGTACCGCC

TGCATCGTATGATGCGTGATAAACTGTTCCGTAAACGTATCAACCCGCT

GAAATGGTTTTCTTCTAAGTAA

Example 2: Synthesis of LDFT

Figure 7:
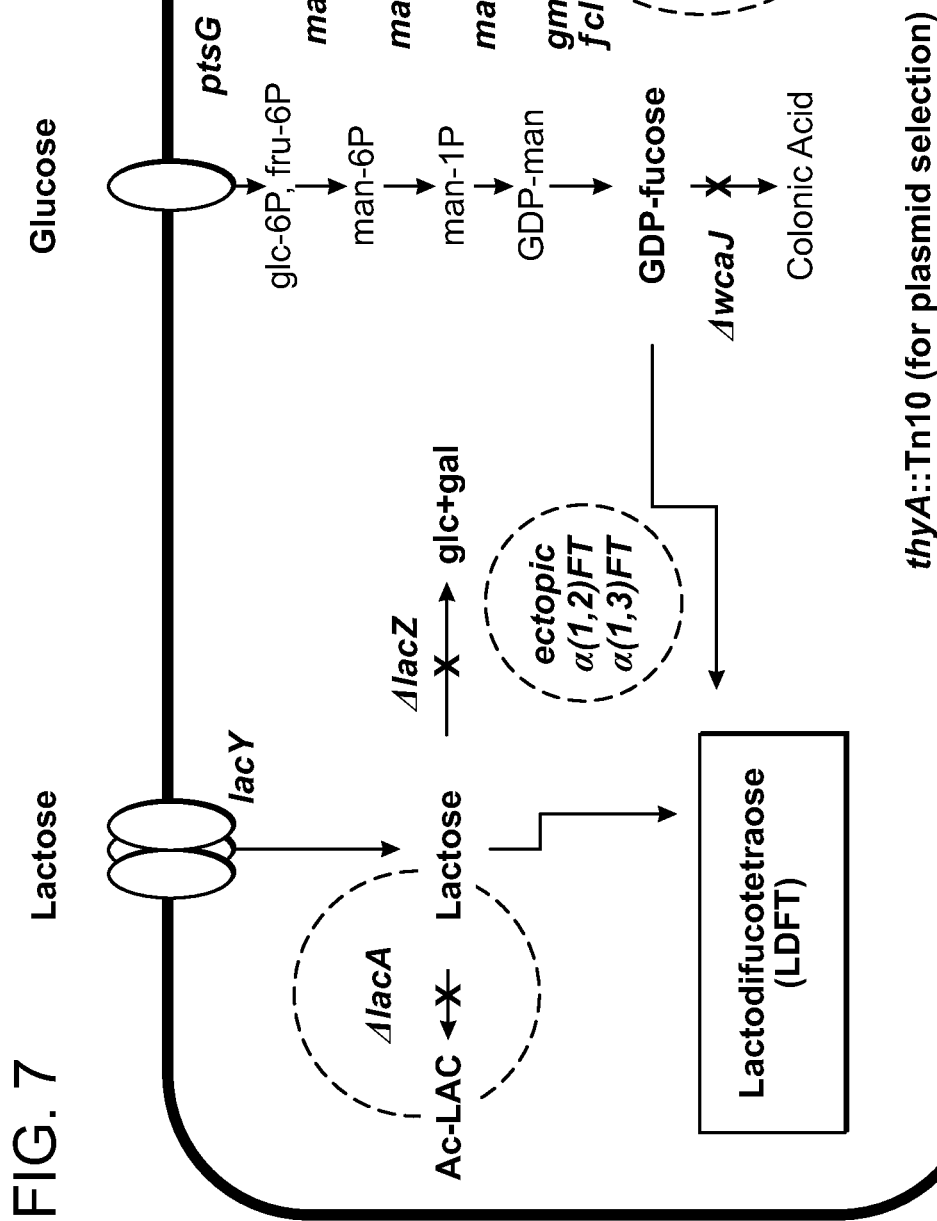
FIG. 7 is a schematic demonstrating metabolic pathways and the changes introduced into them to engineer lactodifucotetraose (LDFT) synthesis in *Escherichia coli* (*E. coli*).

CafA, C and F were tested for utilization in combination with an α(1,2) fucosyltransferase produced in the same strain to catalyze the synthesis of Lactodifucotetraose (LDFT) (FIG. 7). The genes encoding CafA, C and F were inserted into plasmid pG297 (harboring wbgL encoding an α(1,2) fucosyltransferase from E. coli 0126) using standard molecular biology techniques. Thus, a series of "mini-operons" consisting of wbgL in combination with cafA, cafC or cafF under control of the $P_L$ promoter were constructed. The resulting plasmids were then transformed into an engineered E. coli production strain.

Figure 8:
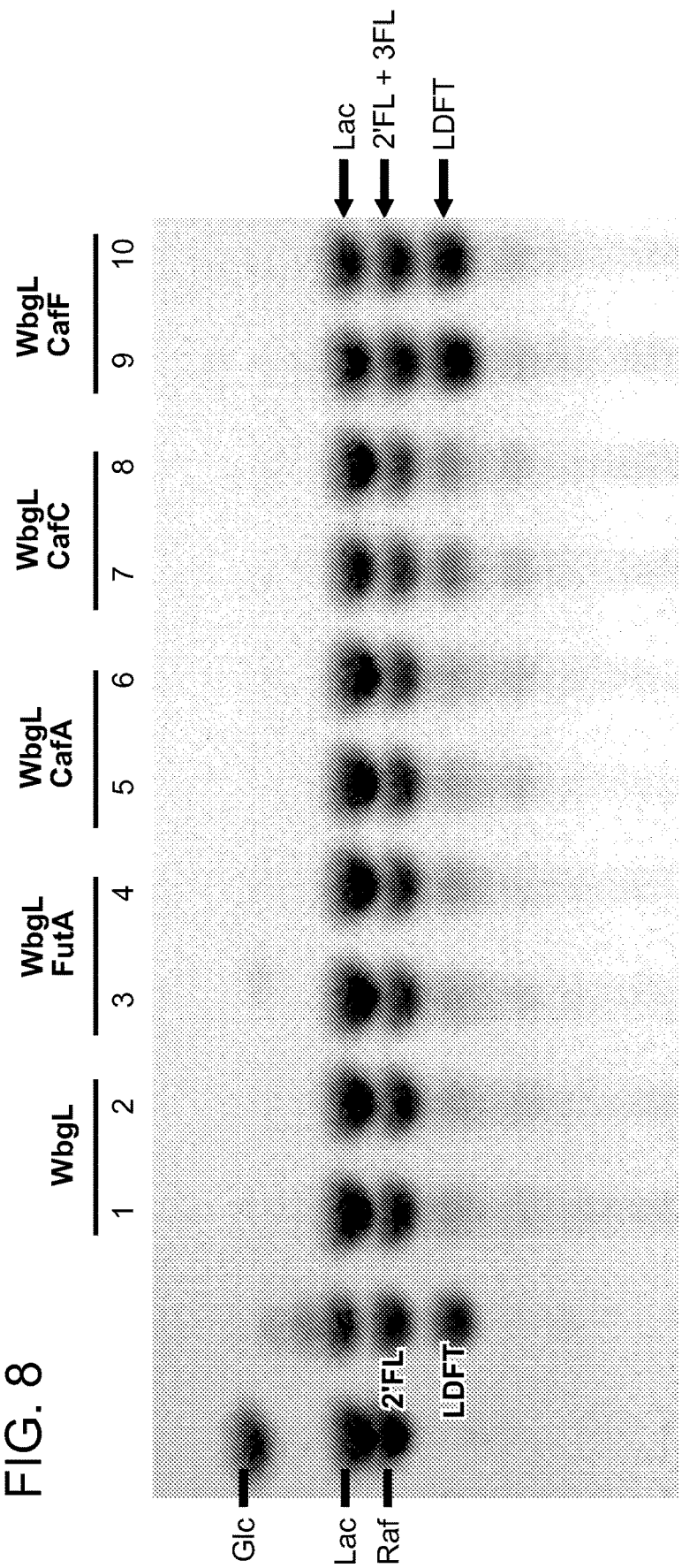
FIG. 8 shows the expression of LDFT in host bacteria expressing an α(1,3) fucosyltransferase (CafA, CafC, CafF) in combination with an α(1,2) fucosyltransferase (wbgL).

The E. coli strains harboring the different LDFT expression plasmids were analyzed in small-scale experiments. Strains were grown in selective media (lacking thymidine) to early exponential phase. Lactose was then added to a final concentration of 1%, and tryptophan (200 μM) was added to induce expression of the α(1,2) and α(1,3) FTs from the $P_L$ promoter. At the end of the induction period (~20 h) equivalent OD 600 units of each strain were harvested. Cell lysates were prepared and analyzed for the presence of intracellular LDFT by thin layer chromatography (TLC). As shown in FIG. 8, a control strain producing only the α(1,2) FT WbgL synthesized primarily 2'-FL and a relatively small amount of LDFT. In comparison, a strain producing WbgL in combination with the α(1,3) FT FutA or CafA synthesized an estimated 20-30% more LDFT. Strains producing WbgL in combination with CafC or CafF synthesized significantly more LDFT than strains producing WbgL alone or WbgL in combination with FutA. This effect was particularly pronounced for the WbgL plus CafF combination. Furthermore, we observed significant amounts of LDFT in the culture supernatant for the WbgL plus CafC and WbgL plus CafF combinations (data not shown) (Table 1). Therefore, these observations indicate that CafA, CafC and CafF will be useful for the large-scale synthesis of LDFT, another HMOS with high potential therapeutic value.

Example 3: Expression of LNF III

Figure 9:
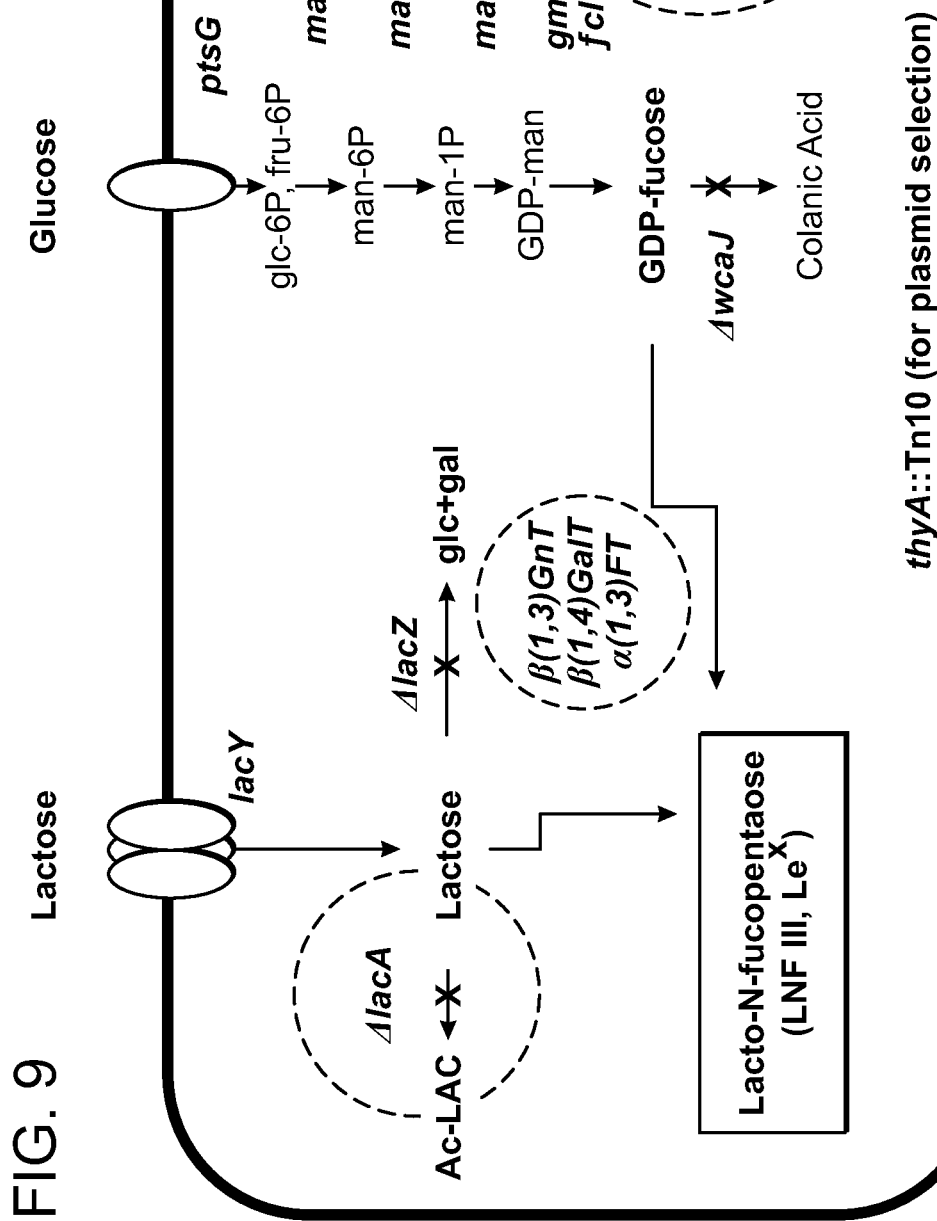
FIG. 9 is a schematic demonstrating metabolic pathways and the changes introduced into them to engineer lacto-N-fucopentaose (LNF III, Le$^x$) synthesis in *Escherichia coli* (*E. coli*).

The majority of the α(1,3) FT candidates tested from the first database screen (CafD, E, G, H, I, J, K) were unable to utilize lactose as a donor substrate and could not promote the synthesis of 3FL, despite the fact that most of these enzymes were well-expressed in E. coli (Table 1). One explanation for this observation is that some bacterial and higher eukaryotic α(1,3) FTs prefer N-acetylglucosamine (GlcNAc) rather than glucose (Glc) as an acceptor for the attachment of fucose (Breton, C., et al. (1998). Conserved structural features in eukaryotic and prokaryotic fucosyltransferases. Glycobiology 8, 87-94.; Ma, B., et al. (2003). C-terminal amino acids of *Helicobacter pylori* alpha 1,3/4 fucosyltransferases determine type I and type II transfer. J Biol Chem 278, 21893-1900.; Ma, B., et al. (2006). Fucosylation in prokaryotes and eukaryotes. Glycobiology 16, 158R-184R.). Therefore, studies were carried out to determine whether CafD, E, G, H, I, J or K catalyze the attachment of fucose to a GlcNAc moiety present within the HMOS LNnT (Lacto-N-neotetraose) to generate a fucosylated oligosaccharide found in human milk termed LNF III (Lacto-N-fucopentaose) (FIG. 9). To this end, these candidate α(1,3) FT genes were inserted into plasmid pG222 using standard molecular biology techniques. pG222 harbors genes encoding a β(1,3) N-acetylglucosaminyltransferase (lgtA) from *N. meningitidis* (Genbank Accession NP 274923.1) and a β(1,4) galactosyltransferase (JHP0765) from *H. pylori* (Genbank Accession NP_207619.1). In an alternative embodiment, *Helicobacter pylori* β(1,3) N-acetylglucosaminyltransferase JHP0563, (Genbank Accession YP_002301261.1) could be used. In another example, *Neisserria meningitidis* β(1,4) galactosyltransferase LgtB, (Genbank Accession NP_274922.1) could be used.

LgtA catalyzes the attachment of GlcNAc to the galactose in lactose to produce Lacto-N-triose (LNT2), a precursor of many HMOS that has the structure GlcNAcβ1-3Galβ1-4Glc. JHP0765 (a β(1,4) galactosyltransferase) can then utilize LNT2 as an acceptor to generate LNnT, an abundant HMOS of human milk. LNnT has the structure Galβ1-4GlcNacβ1-3Galβ1-4Glc and is an important Bifidogenic prebiotic factor in human milk (Marcobal, A., et al. (2010). Consumption of human milk oligosaccharides by gut-related microbes. J Agric Food Chem 58, 5334-340.; Garrido, D., et al. (2012). A molecular basis for bifidobacterial enrichment in the infant gastrointestinal tract. Adv Nutr 3, 415S-421S.; Sela, D. A., et al. (2012). *Bifidobacterium longum* subsp. *infantis* ATCC 15697 α-fucosidases are active on fucosylated human milk oligosaccharides. Appl Environ Microbiol 78, 795-803.). Attachment of fucose in an α1,3 linkage to the GlcNAc in LNnT generates LNF III, another HMOS found in human milk.

Figure 10:
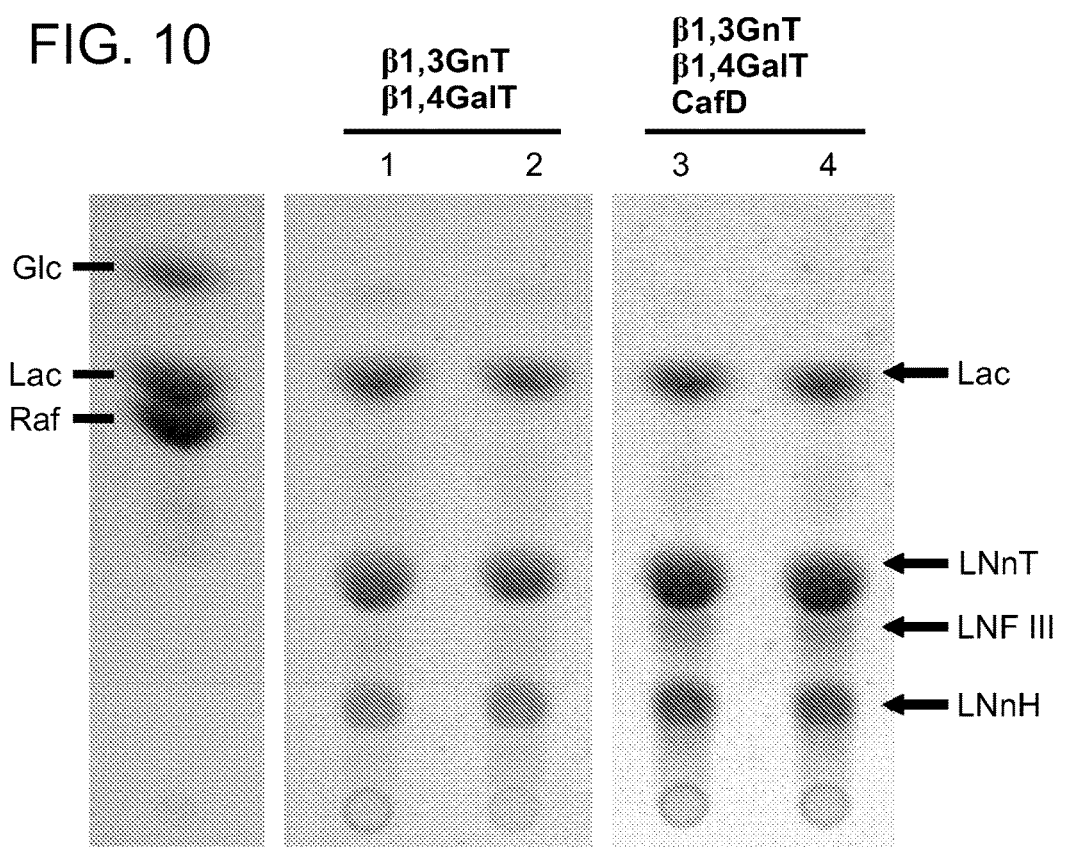
FIG. 10 shows synthesis of LNF III by attachment of fucose to LNnT.
Figure 11:
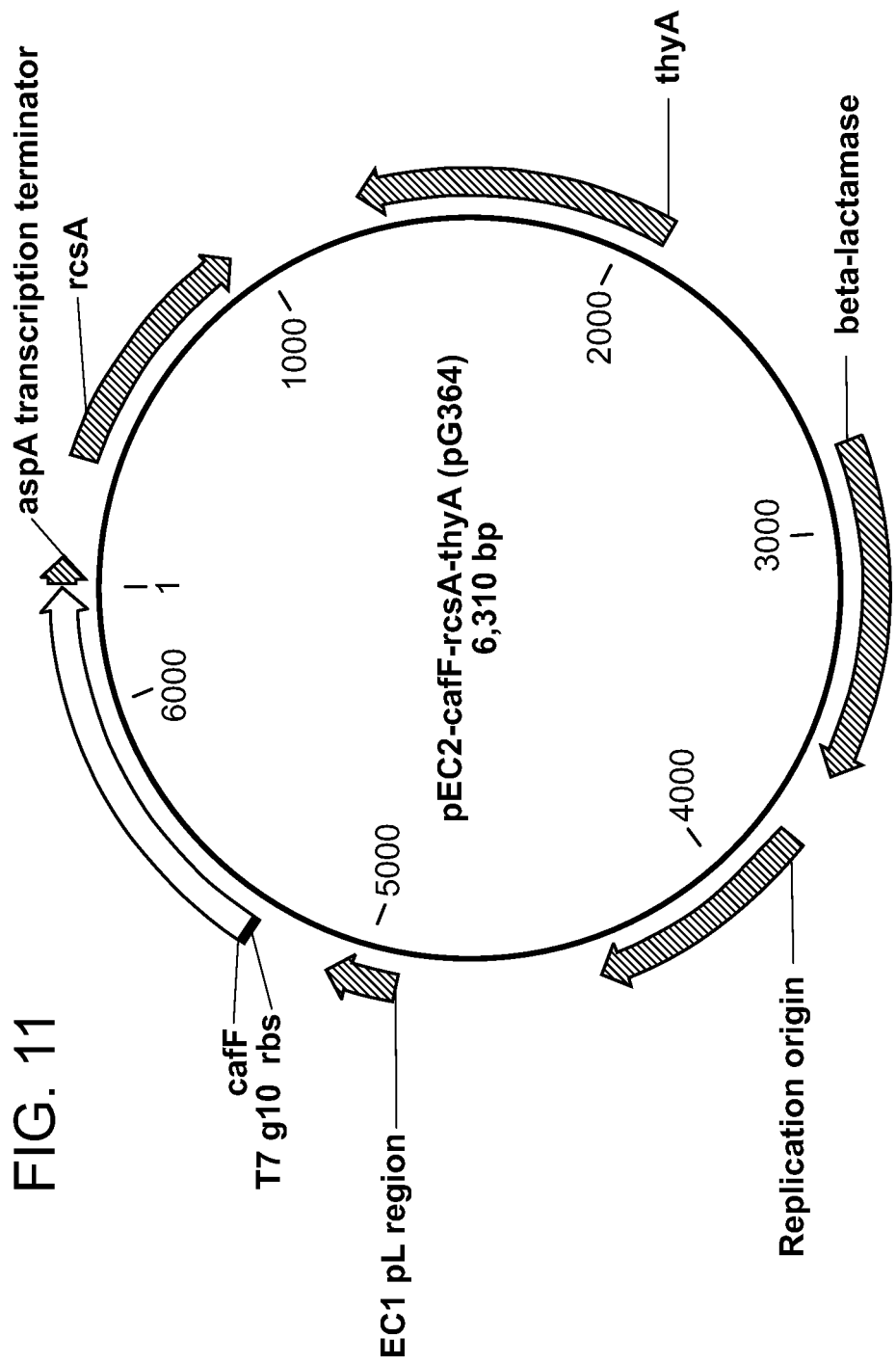
FIG. 11 is a diagram of plasmid pG364 (pEC2-cafF-rcsA-thyA).
Figure 12:
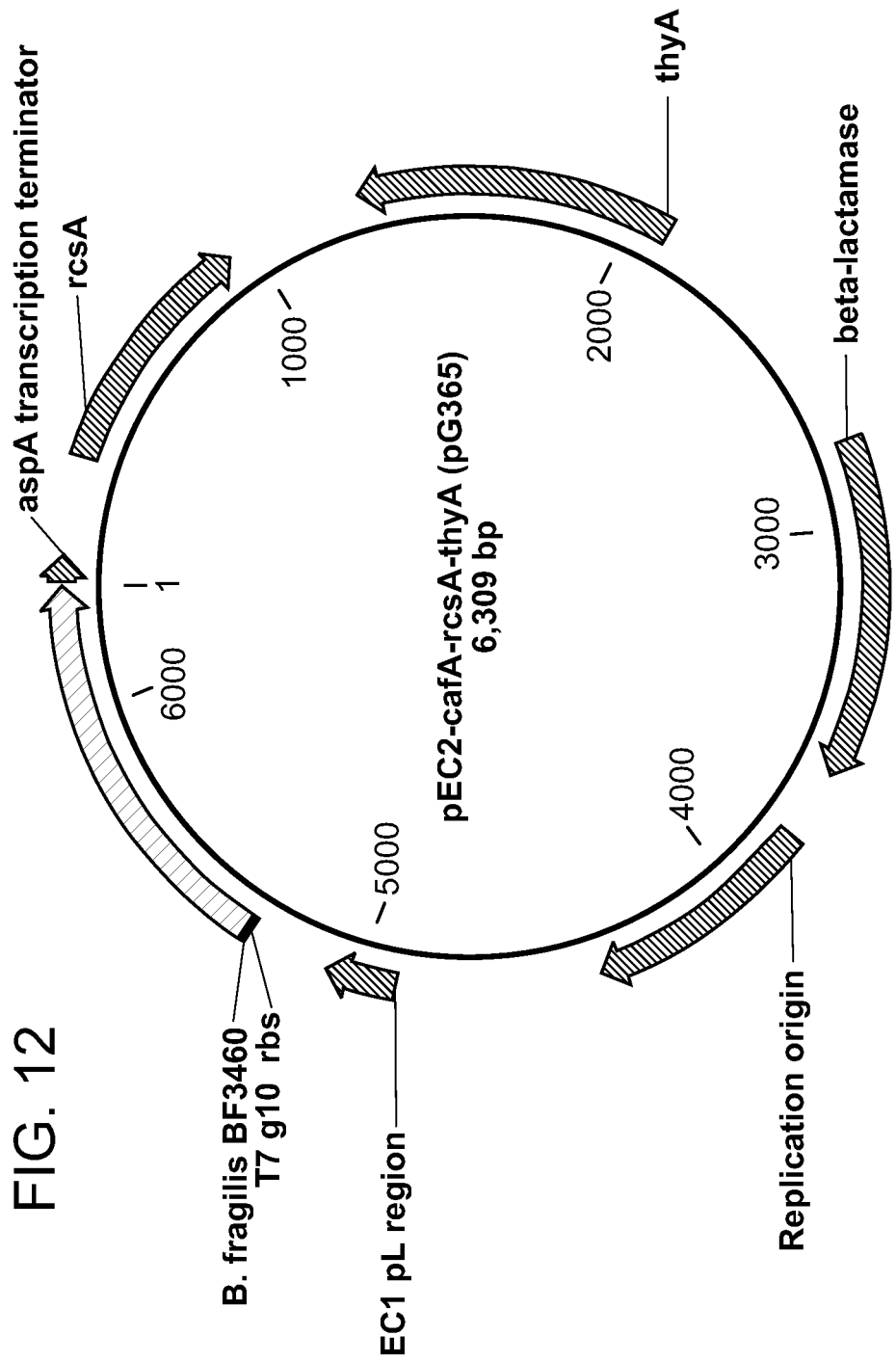
FIG. 12 is a diagram of plasmid pG365 (pEC2-cafA-rcsA-thyA).
Figure 13:
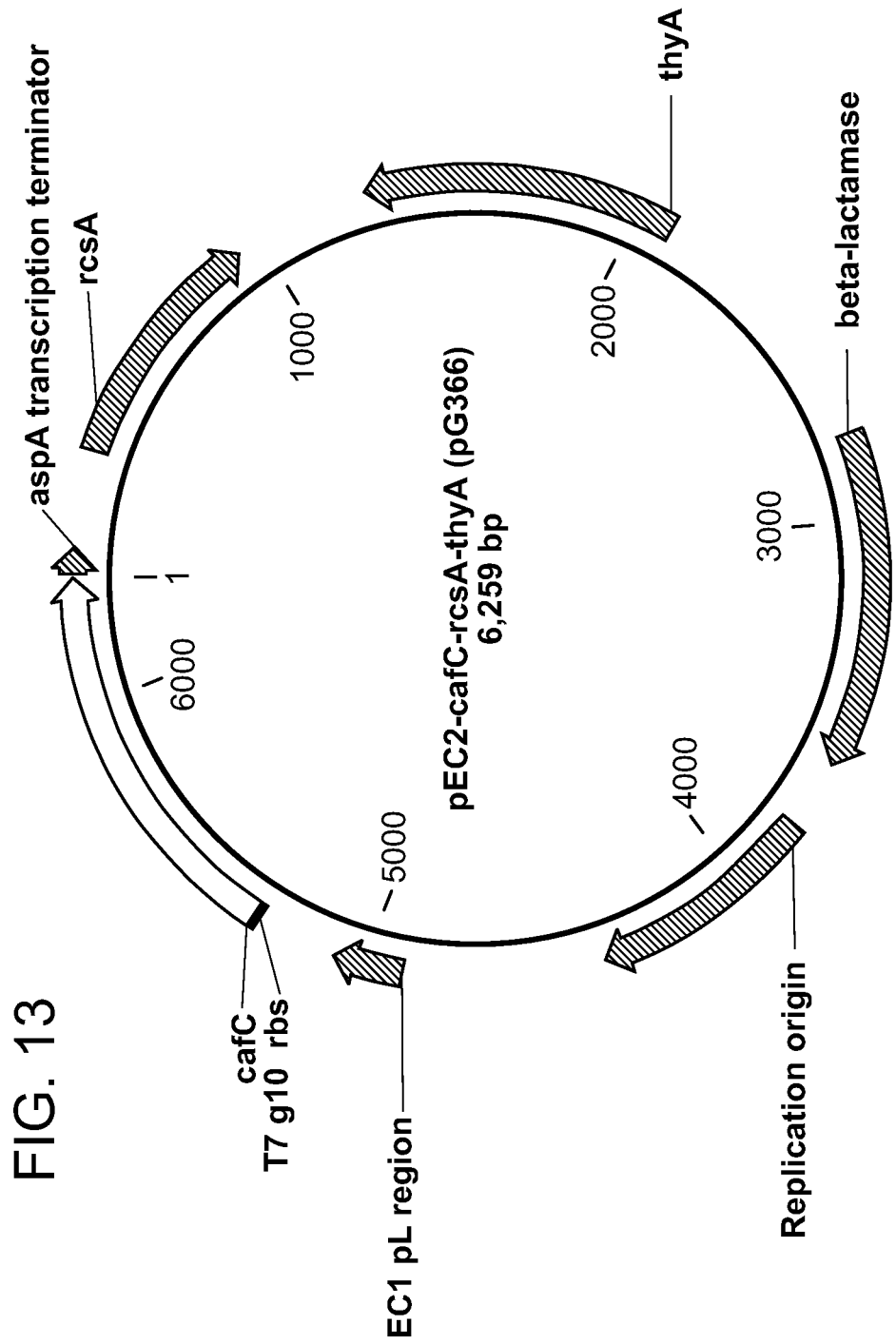
FIG. 13 is a diagram of plasmid pG366 (pEC2-cafC-rcsA-thyA).
Figure 14:
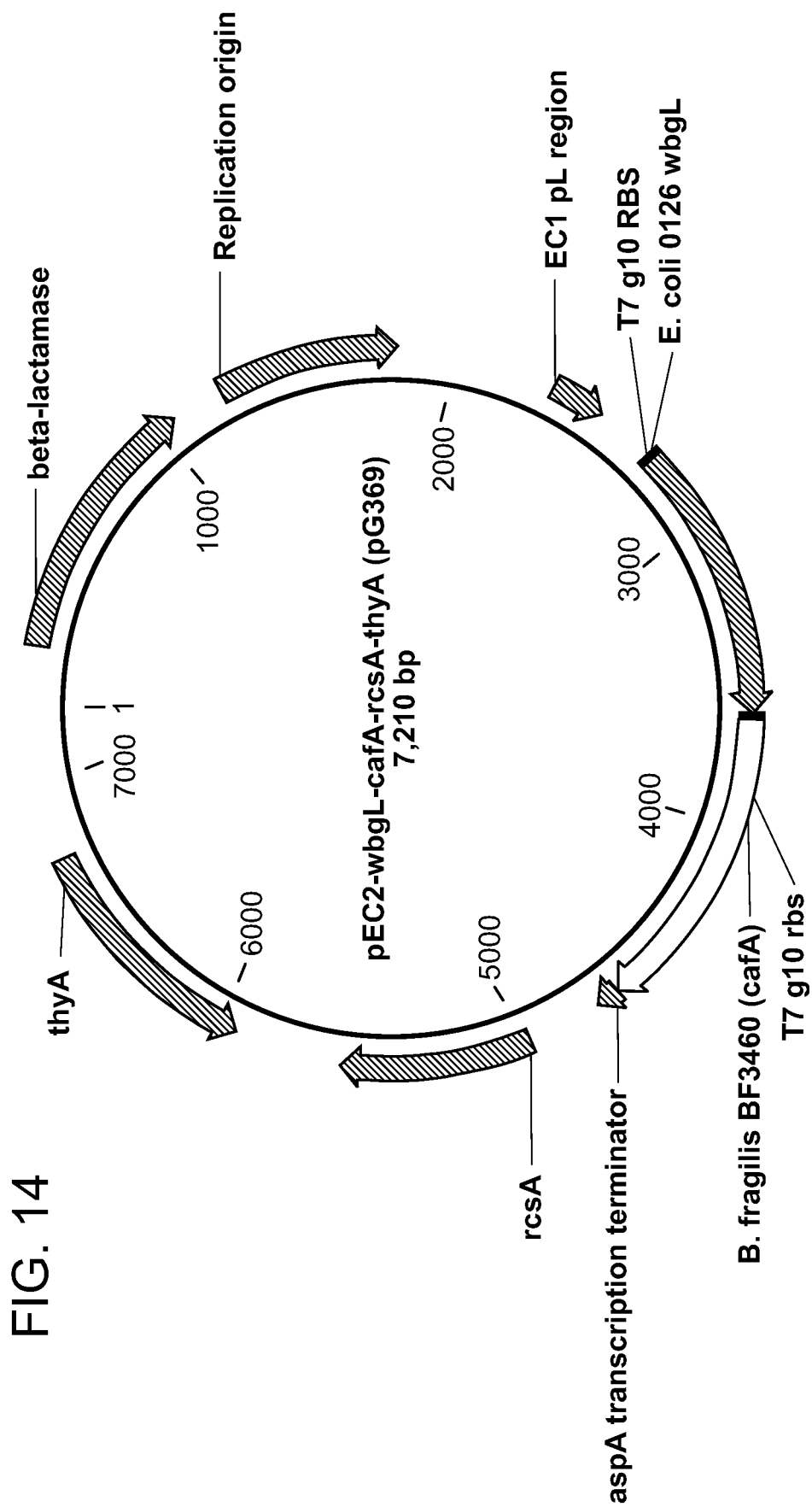
FIG. 14 is a diagram of plasmid pG369 (pEC2-wbgL-cafA-rcsA-thyA).
Figure 15:
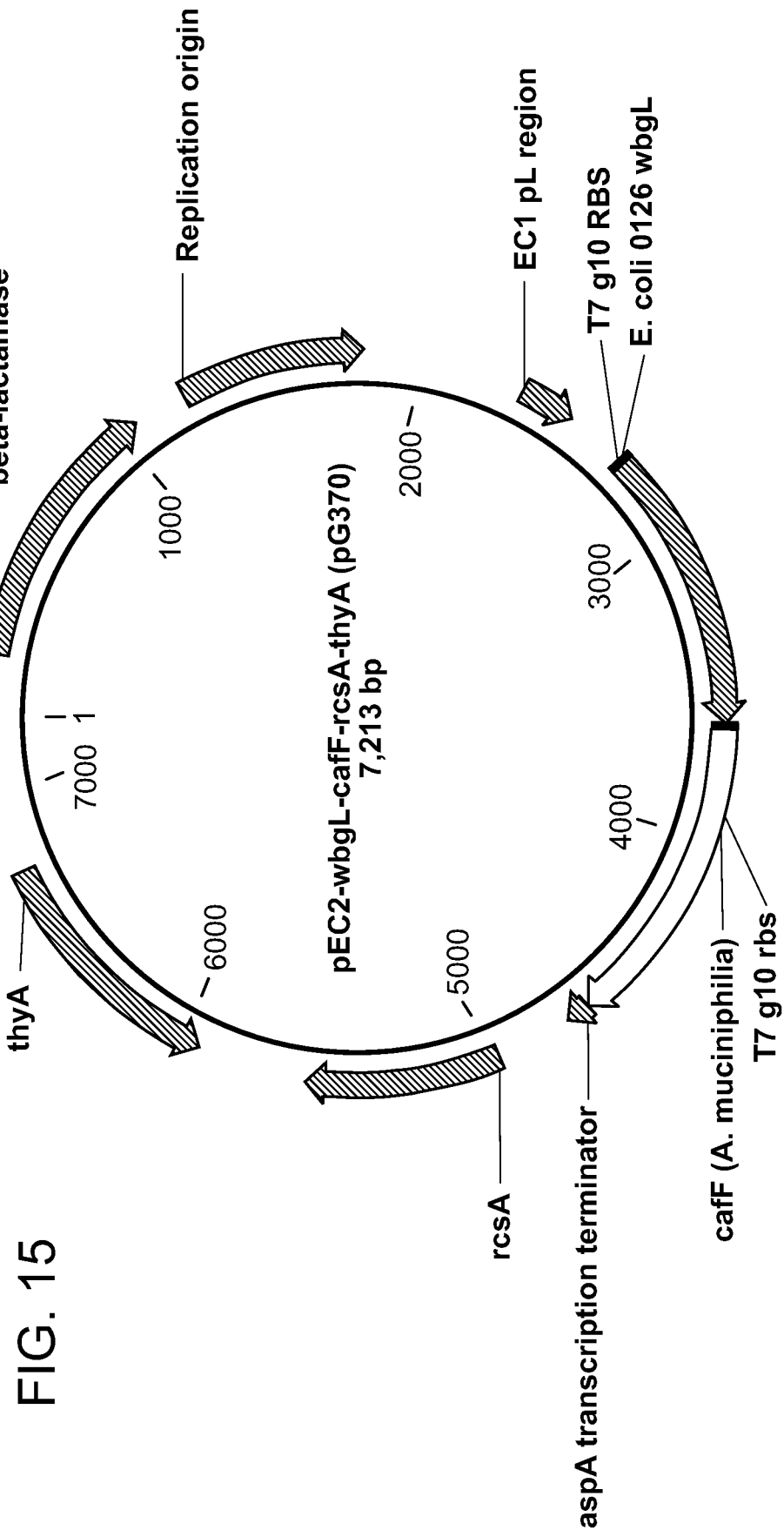
FIG. 15 is a diagram of plasmid pG370 (pEC2-wbgL-cafF-rcsA-thyA).
Figure 16:
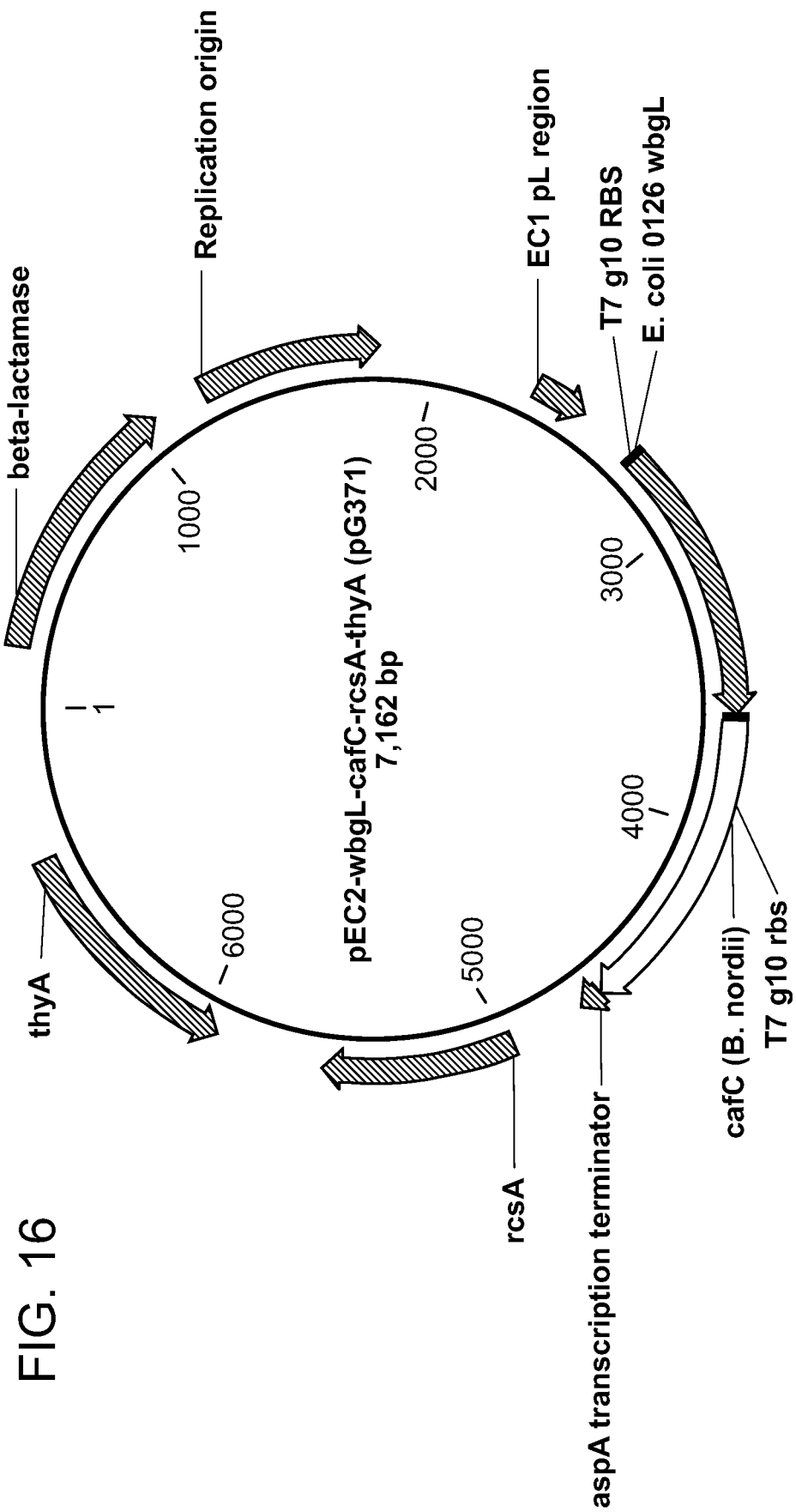
FIG. 16 is a diagram of plasmid pG371 (pEC2-wbgL-cafC-rcsA-thyA).
Figure 17:
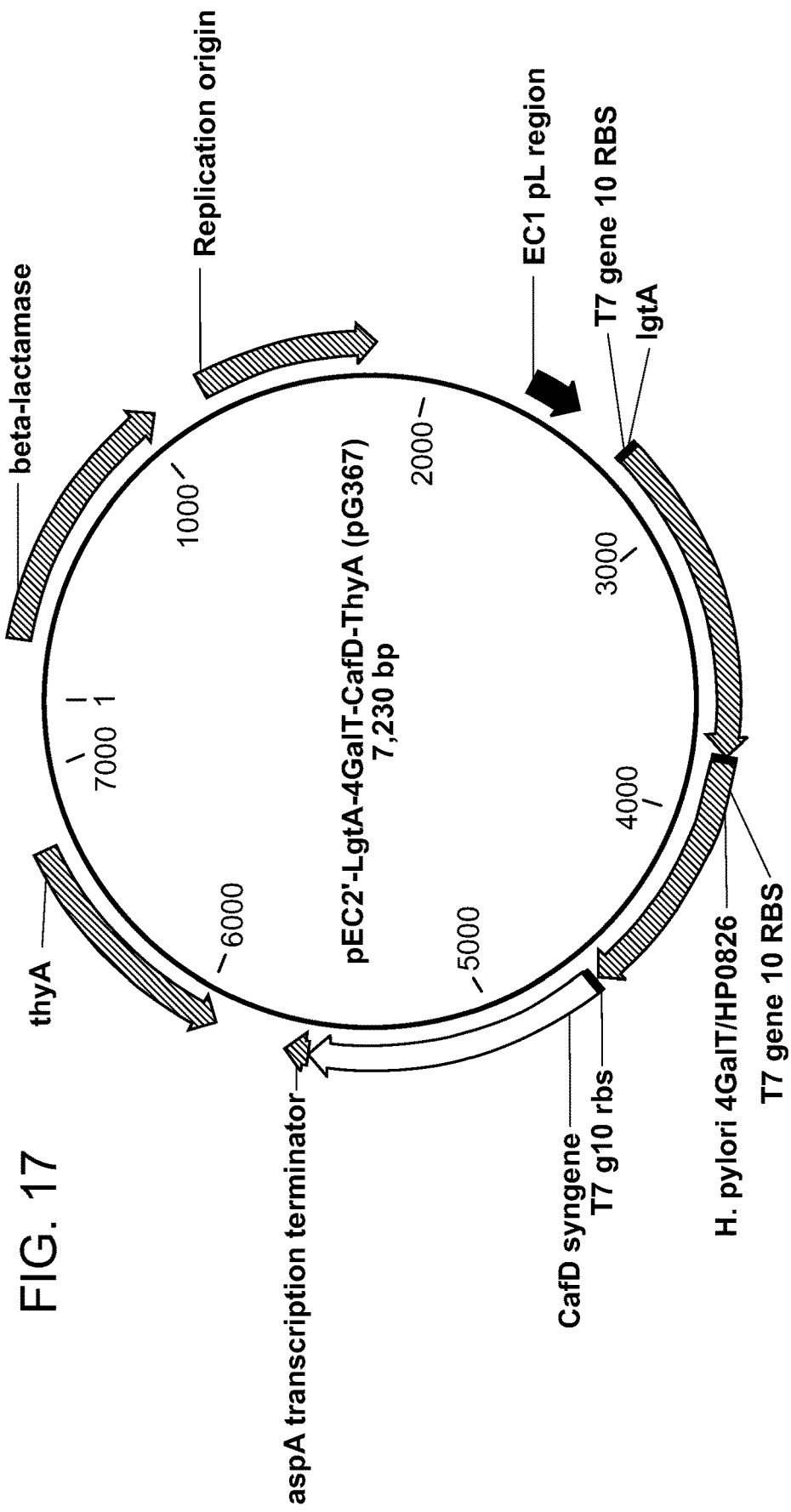
FIG. 17 is a diagram of plasmid pG367 (pEC2'-LgtA-4GalT-cafD-ThyA).

Derivatives of plasmid pG222 harboring each α(1,3) FT candidate were transformed into the E. coli production strain using standard techniques. The *E. coli* strains harboring the different LNF III expression plasmids were then analyzed in small-scale experiments. Strains were grown in selective media (lacking thymidine) to early exponential phase. Lactose was then added to a final concentration of 1%, and tryptophan (200 μM) was added to induce expression of the glycosyltransferases. At the end of the induction period (~20 h) equivalent OD 600 units of each strain were harvested. Cell lysates were prepared and analyzed for the presence of intracellular LNF III by thin layer chromatography (TLC). As shown in FIG. 10, a strain producing both LgtA and JHP0765 synthesized LNnT as well as a larger oligosaccharide, e.g., having the structure Galβ1-4GlcNacβ1-3Galβ1-4GlcNacβ1-3Galβ1-4Glc (Lacto-N-neohexaose). Of the 7 α(1,3) FTs tested only CafD was capable of catalyzing the attachment of fucose to LNnT (FIG. 10, see lanes 3 and 4). Liquid chromatography coupled with mass spectrometry revealed that this fucosylated molecule possessed a mass consistent with that of LNF III indicating that CafD catalyzes the biosynthesis of bona fide LNF III in our *E. coli* production strain.

Example 4: α(1,3) Fucosyltransferases in Tandem or in a String Configuration

Figure 21:
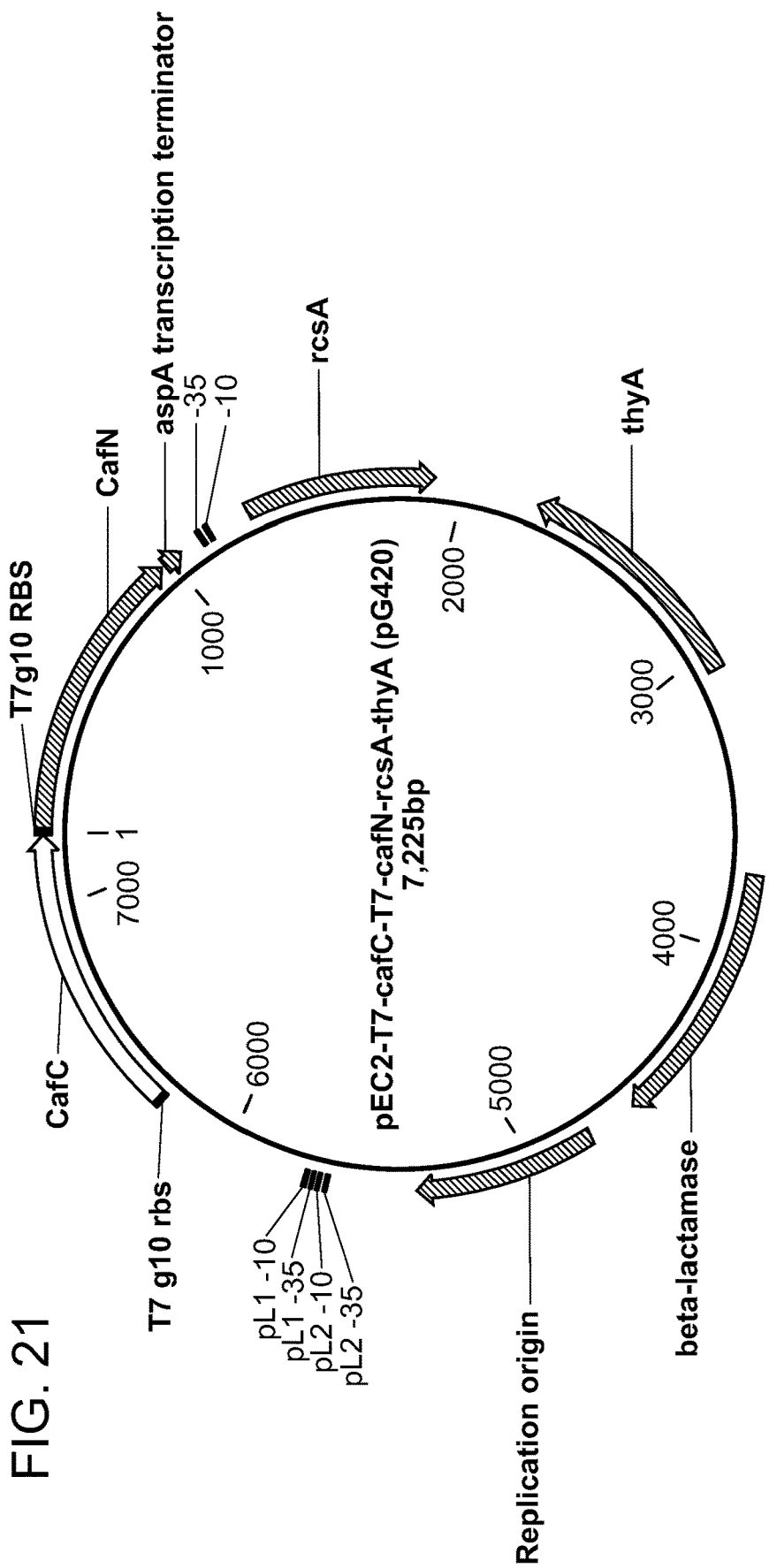
FIG. 21 is a diagram of plasmid pG420 (pEC2-cafC-cafN-rcsA-thyA).

Bacterial strains were constructed that harbor an expression plasmid containing two different α(1,3) fucosyltransferases in a "tandem" arrangement or in a string (three or more genes) configuration under control of the $P_L$ promoter. FIG. 21 provides a map of such a plasmid, pG420 (nucleic acid sequence SEQ ID NO: 64), that carries genes encoding two different α(1,3) fucosyltransferases; CafC (amino acid sequence SEQ ID NO: 2) and CafN (amino acid sequence SEQ ID NO: 44), arranged in an operon driven from the $P_L$ promoter.

FIG. 22A-B demonstrates enhanced fermentor production of 3-fucosyllactose using an expression plasmid expressing dual α(1,3) fucosyltransferases. Specifically, FIG. 22A shows thin layer chromatography analysis of culture supernatants from fermentation run 126. In this experiment, an engineered *E. coli* production strain harboring plasmid pG366 (pEC2-$P_L$-cafC-rcsA-thyA) was grown under fed-batch conditions with a defined linear lactose feed (50 g final lactose added per liter initial culture volume). A significant amount of 3-FL was produced under these conditions and exported to the culture medium. At the end of the process, the cells were heated at 65° C. for 20 minutes to release any remaining intracellular 3-FL to the culture medium. Analysis of product yield by HPLC in the final sample revealed that ~7.5 g/L 3-FL was produced under these conditions. Surprisingly, the yield of 3-FL could be improved to ~15 g/L when a second α(1,3) fucosyltransferase (cafN) was introduced into the parental plasmid pG366 to generate pG420 (pEC2-$P_L$-cafC-cafN-rcsA-thyA, SEQ ID NO: 64) (FIG. 22B), and the cells were grown under the same fed-batch process regimen.

Cellular toxicity and consequent lowered product yields were observed in 3-FL bioreactor runs such strains expressing high levels of α(1,3) fucosyltransferases driven by the fully-induced $P_L$ promoter. However, by keeping the $P_L$ promoter repressed (e.g. by eliminating the addition of tryptophan to the culture and relying on the low-level of constitutive transcription that originates from the promoter region) and by constructing a tandem arrangement of the α(1,3) fucosyltransferases CafC and CafN downstream of the promoter, the culture maintains good viability for the duration of the run and 3-FL yields are significantly improved.

Example 5: Enhanced Fermentor Production of 3-Fucosyllactose Using Casamino Acid Supplementation (CAA)

High level expression (e.g. as driven from the induced $P_L$ promoter) of nearly all α(1,3) fucosyltransferases tested to date can be toxic to *E. coli* production strains, resulting in poor viability and low 3-FL yields in fermentation runs. One explanation is that many α(1,3) fucosyltransferases may possess an off-target activity in which an endogenous *E. coli* molecule essential for cell viability is inappropriately fucosylated rendering it non-functional and/or toxic. Of note, some α(1,3) fucosyltransferases have been shown to use N-acetylglucosamine as an acceptor. Therefore, the identity of the secondary endogenous *E. coli* target may be a molecule containing N-acetylglucosamine, such as the lipid II precursor for cell wall peptidoglycan. Thus, cells producing high levels of α(1,3) fucosyltransferase activity displayed aberrant cell envelope morphology (swelling, membrane blebbing), suggesting a defect in cell wall/membrane structure or biogenesis. Interestingly, supplementation of fermentation media with a nitrogen-rich additive such as casamino acids (CAA) or yeast extract (YE) protected against the toxic properties of α(1,3) fucosyltransferase activity, leading to significantly improved 3-FL production yields. In particular, CAA supplementation increased, e.g., doubled, the yield of 3FL obtained in fermentation runs. This yield-boosting activity is associated with any rich nutritional additive containing amino acids, peptides, minerals, vitamins, and other micronutrients. In addition to CAA and YE, such additives may include any protein hydrolysate (e.g., peptone) from a variety of sources, including but not limited to meat, casein, whey, gelatin, soybean, yeast and grains.

FIG. 22C demonstrates enhanced fermentor production of 3-fucosyllactose using casamino acid supplementation (CAA). Specifically, an engineered *E. coli* production strain harboring plasmid pG420 (pEC2-$P_L$-cafC-cafN-rcsA-thyA, SEQ ID NO: 64) was grown under identical conditions as described above in relation to FIGS. 22A-B, except 50 g final CAA was added per liter initial culture volume and delivered in a linear feed over the course of the run. The addition of CAA significantly boosted product formation, resulting in ~30 g/L 3-FL as assessed by HPLC.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following claims.

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. Genbank and NCBI submissions indicated by accession number cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

The invention claimed is:

1. A method for producing a fucosylated oligosaccharide in a bacterium comprising expressing a lactose-accepting α(1,3) fucosyltransferase enzyme in a host bacterium, wherein the amino acid sequence of said enzyme comprises at least 90% identity to full length CafC (SEQ ID NO: 2), thereby producing an α(1,3) fucosylated oligosaccharide.

2. The method of claim 1, wherein the amino acid sequence of said enzyme comprises at least 95% sequence identity to full length CafC (SEQ ID NO: 2).

3. The method of claim 1, wherein said amino acid sequence comprises at least 50% or at least 80% identity to the CafC active site region 2 (residues 116-202 of SEQ ID NO:2).

4. The method of claim 1, wherein
(a) said α(1,3) fucosyltransferase enzyme comprises CafC, or a functional variant or fragment thereof; or
(b) said α(1,3) fucosyltransferase enzyme comprises the amino acid sequence of SEQ ID NO: 2 (CafC), or a functional fragment thereof.

5. The method of claim 1, further comprising providing the bacterium a nucleic acid construct comprising an isolated nucleic acid encoding the α(1,3) fucosyltransferase enzyme.

6. The method of claim 5, wherein said nucleic acid is operably linked to one or more heterologous control sequences that direct the production of the enzyme in the bacterium.

7. The method of claim 6, wherein said heterologous control sequence comprises a bacterial promoter and operator, a bacterial ribosome binding site, a bacterial transcriptional terminator, or a plasmid selectable marker.

8. The method of claim 1, further comprising retrieving the fucosylated oligosaccharide from said bacterium or from a culture supernatant of said bacterium.

9. The method of claim 1, wherein said fucosylated oligosaccharide comprises 3-fucosyllactose (3-FL) or lactodifucotetraose (LDFT).

10. The method of claim 1, wherein said bacterium is *E. coli*.

11. The method of claim 10, further comprising culturing said bacterium in the presence of tryptophan and in the absence of thymidine.

12. The method of claim 10, wherein an endogenous lacZ gene and an endogenous lacI gene of said bacterium are deleted.

13. The method of claim 12, wherein said bacterium comprises a lacIq gene promoter immediately upstream of a lacY gene.

14. The method of claim 10, wherein an endogenous wcaJ gene of said bacterium is deleted.

15. The method of claim 10, wherein said bacterium comprises a null mutation in a lon gene.

16. The method of claim 10, wherein said bacterium accumulates intracellular lactose in the presence of exogenous lactose.

17. The method of claim 10, wherein said bacterium accumulates intracellular guanosine diphosphate (GDP)-fucose.

18. The method of claim 10, wherein said bacterium further expresses an α(1,2) fucosyltransferase enzyme, an α(1,4) fucosyltransferase enzyme, and/or an additional α(1,3) fucosyltransferase enzyme.

19. The method of claim 5, wherein the nucleic acid construct further comprises an isolated nucleic acid encoding an α(1,2) fucosyltransferase enzyme and/or an additional α(1,3) fucosyltransferase enzyme.

20. The method of claim 10, further comprising culturing said bacterium in the presence of a nitrogen-rich additive.

21. The method of claim 20, wherein the nitrogen-rich additive comprises casamino acids (CAA), yeast extract (YE), or a protein hydrolysate.

22. The method of claim 1, wherein said α(1,3) fucosyltransferase enzyme comprises the amino acid sequence of SEQ ID NO: 2 (CafC).

23. The method of claim 1, wherein the method further comprises culturing the bacterium in the presence of lactose to produce the fucosylated oligosaccharide.

* * * * *